US012428661B2

United States Patent
Lavoie et al.

(10) Patent No.: US 12,428,661 B2
(45) Date of Patent: Sep. 30, 2025

(54) INFLUENZA VIRUS HEMAGGLUTININ MUTANTS

(71) Applicant: ARAMIS BIOTECHNOLOGIES INC., Quebec (CA)

(72) Inventors: Pierre-Olivier Lavoie, Quebec (CA); Aurelien Lorin, Quebec (CA); Alain Doucet, Quebec (CA); Marc-Andre D'Aoust, Quebec (CA); Manon Couture, Quebec (CA)

(73) Assignee: ARAMIS BIOTECHNOLOGIES INC., Quebec (CA)

( * ) Notice: Subject to any disclaimer, the term of this patent is extended or adjusted under 35 U.S.C. 154(b) by 1023 days.

(21) Appl. No.: 17/255,517

(22) PCT Filed: Jun. 27, 2019

(86) PCT No.: PCT/CA2019/050891
§ 371 (c)(1),
(2) Date: Dec. 23, 2020

(87) PCT Pub. No.: WO2020/000099
PCT Pub. Date: Jan. 2, 2020

(65) Prior Publication Data
US 2021/0340184 A1  Nov. 4, 2021

Related U.S. Application Data

(60) Provisional application No. 62/690,780, filed on Jun. 27, 2018.

(51) Int. Cl.
| | | |
|---|---|---|
| *C12P 21/02* | (2006.01) | |
| *A61K 38/00* | (2006.01) | |
| *A61K 39/00* | (2006.01) | |
| *A61K 39/145* | (2006.01) | |
| *A61P 31/16* | (2006.01) | |
| *A61P 37/04* | (2006.01) | |
| *C07K 14/005* | (2006.01) | |
| *C07K 14/11* | (2006.01) | |
| *C07K 16/10* | (2006.01) | |
| *C12N 7/00* | (2006.01) | |
| *C12N 15/82* | (2006.01) | |

(52) U.S. Cl.
CPC ............ *C12P 21/02* (2013.01); *A61K 39/145* (2013.01); *A61P 31/16* (2018.01); *A61P 37/04* (2018.01); *C07K 14/005* (2013.01); *C07K 14/11* (2013.01); *C07K 16/10* (2013.01); *C07K 16/1018* (2013.01); *C12N 7/00* (2013.01); *C12N 15/8257* (2013.01); *C12N 15/8258* (2013.01); *A61K 38/00* (2013.01); *A61K 2039/5258* (2013.01); *C12N 2760/16023* (2013.01); *C12N 2760/16033* (2013.01); *C12N 2760/16122* (2013.01); *C12N 2760/16123* (2013.01); *C12N 2760/16134* (2013.01); *C12N 2760/16152* (2013.01)

(58) Field of Classification Search
CPC ...... C07K 14/005; C07K 14/11; C07K 16/10; C07K 16/1018; A61K 39/145; A61K 38/00; A61K 2039/5258; A61K 39/12; A61P 31/16; A61P 37/04; C12N 7/00; C12N 15/8257; C12N 15/8258; C12N 2760/16023; C12N 2760/16033; C12N 2760/16122; C12N 2760/16123; C12N 2760/16134; C12N 2760/16152; C12P 21/02

See application file for complete search history.

(56) References Cited

U.S. PATENT DOCUMENTS

| | | | |
|---|---|---|---|
| 2013/0315955 A1 | 11/2013 | Holtz et al. | |
| 2016/0122777 A1* | 5/2016 | Couture | C12N 15/8257 800/317.3 |
| 2017/0189519 A1* | 7/2017 | Impagliazzo | A61P 31/16 |
| 2021/0162037 A1* | 6/2021 | Jasny | A61K 39/145 |

FOREIGN PATENT DOCUMENTS

| | | |
|---|---|---|
| EP | 2570484 A1 | 3/2013 |
| JP | 2016514674 A | 5/2016 |
| JP | 2021528972 A | 10/2021 |

(Continued)

OTHER PUBLICATIONS

Garten RJ, et al. Hemagglutinin [Influenza A virus (A/California/Jul. 2009(H1N1))]. GenBank: ACP44189.1; Jun. 1, 2009. (Year: 2009).*

(Continued)

*Primary Examiner* — Rachel B Gill
(74) *Attorney, Agent, or Firm* — RAPHAEL BELLUM PLLC

(57) ABSTRACT

The present invention relates to the production of modified influenza vial proteins in plants. More specifically, the present invention relates to producing and increasing influenza virus-like particle (VLP) production in plants, wherein the VLPs comprise the modified influenza viral proteins, such as modified influenza hemagglutinin (HA). The HA protein may comprising an amino acid sequence comprising at least one substitution when compared to a corresponding wildtype amino acid sequence. Further provided are nucleic acid encoding the modified HA protein. Furthermore methods of producing an influenza virus like particle (VLP) and methods of increasing yield of production of an influenza virus like particle (VLP) in a plant, portion of a plant, or a plant cell, are also provided.

16 Claims, 33 Drawing Sheets
Specification includes a Sequence Listing.

(56) References Cited

FOREIGN PATENT DOCUMENTS

| | | | |
|---|---|---|---|
| WO | WO2009009876 A1 | 1/2009 | |
| WO | WO2009076778 A1 | 6/2009 | |
| WO | WO2010003225 A1 | 1/2010 | |
| WO | WO2010003235 A1 | 1/2010 | |
| WO | WO2010006452 A1 | 1/2010 | |
| WO | WO2010148511 A1 | 12/2010 | |
| WO | WO2011035422 A1 | 3/2011 | |
| WO | 2013044390 A1 | 4/2013 | |
| WO | WO2013079473 A1 | 6/2013 | |
| WO | WO2013177444 A2 | 11/2013 | |
| WO | 2014151488 A1 | 9/2014 | |
| WO | WO2014153674 A1 | 10/2014 | |
| WO | WO2014191435 A1 | 12/2014 | |
| WO | WO2015020913 A2 | 2/2015 | |
| WO | WO-2017191258 A1 * | 11/2017 | ............. A61K 39/12 |
| WO | WO2018073340 A1 | 4/2018 | |
| WO | 2018078053 A1 | 5/2018 | |
| WO | 2020000101 A1 | 1/2020 | |

OTHER PUBLICATIONS

Zhang S, Sherwood RW, Yang Y, Fish T, Chen W, McCardle JA, Jones RM, Yusibov V, May ER, Rose JK, Thannhauser TW. Comparative characterization of the glycosylation profiles of an influenza hemagglutinin produced in plant and insect hosts. Proteomics. Apr. 2012;12(8):1269-88. (Year: 2012).*

Brooke CB. Biological activities of 'noninfectious' influenza A virus particles. Future Virol. Jan. 2014;9(1):41-51. (Year: 2014).*

Ha, Y., et al. H5 avian and H9 swine influenza virus haemagglutinin structures: possible origin of influenza subtypes. The EMBO Journal (2002) 21(5): 865-875.

Castelan-Vega et al. The hemagglutinin of the infuenza A(H1N1)pdm09 is mutating towards stability. (Adv Appl Bioinform Chem. 2014;7:37-44).

Cotter, Christopher et al. A single amino acid in the stalk region of the H1N1pdm Influenza Virus HA protein affects viral fusion, stability and infectivity. (PLoS Pathog, 2014;10(1):e1003831.

Antanasijevic et al. (J Biol Chem. 2014;289(32):22237-45).

Lu, Yuan, et al. Production and stabilization of the trimeric influenza hemagglutinin stem domain for potentially broadly protective influenza vaccines. (Proc Natl Acad Sci USA. 2014:111(1):125-30).

Holtz, Kathleen M., et al. Modifications of cystine residues in the transmembrane cytoplasmic domains of a recombinant hemagglutinin protein prevent cross-linked multimer formation and potency loss. (BMC Biotechnology. 2014;14:111.

Air, Gillian. Sequence relationships among the hemagglutinin genes of 12 subtypes of influenza A Virus. Pros. Nat'l Academy of Sciences USA. (1981) vol. 78:12, 7639-7643.

Suzuki, Yoshiyuki, and Nei, Masatoshi Origin and Evolution of Influenza Virus Hemagglutinin Genes. Mol. Biol. Evol. 2002, 19:501-509.

Fouchier, Ron A.M., et al., Characterization of a novel influenza A virus Hemagglutinin subtype (H16) obtaind from Black-headed gulls. J Virol. Mar. 2005;79(5):2814-22.

Ben-Bassat, Arie, et al. Processing of the Initiation methionine from proteins: properties of the *Escherichia coli* methionine aminopeptidase and its gene structure. (J. Bacteriol, 169:751-757, 1987).

O'Regan, Michael et al. Cloning and nucleotide sequence of the phosphoenolpyruvate carboxylase-coding gene of Corynebacterium glutamicum ATCC13032. (Gene, 77:237-251, 1989).

Sahin-Toth, Miklos et al. Cysteine scanning mutagenesis of the N-terminal 32 amino acid residues in the lactose permease of *Escherichia coli*. (Protein Scl, 3:240-247, 1994).

Hochuli, E., et al Genetic approach to facilitate purification of recombinant proteins with a novel metal chelate adsorbent. Nature Biotechnology, 6:1321-1325, 1988).

Henikoff, Steven, et al., Amino acid substitution matrices from protein blocks. Proc. Natl. Acad. Sci. USA, 89:10915-10919, 1992.

Yang et al. (Structural stability of influenza A(H1N1)pdm09 virus hemagglutinins, J. Virol.2014;88(9):4828-4838).

Clark, Amelia, et al. Antigenicity of the 2015-2016 seasonal H1N1 human influenza virus HA and HA proteins. PLOS one 2017, pp. 1-27.

GenBank accession AOZ84818.1. May 24, 2023.

Eshaghi et al., "Genetic characterization of seasonal influenza A (H3N2) viruses in Ontario during 2010-2011 influenza season: high prevalence of mutations at antigenic sites," Influenza and Other Respiratory Viruses. Dec. 6, 2013. pp. 250-257.

GenBank accession A0A1D8H6M7. May 23, 2018.

UniProt Accession AOA1P7ZM40. Apr. 12, 2017.

UniProt Accession A0A119TUY4. Feb. 15, 2017.

Thyagarajan, Bargavi, et al. The inherent mutational tolerance and antigenic evolvability of influenza hemagglutinin. eLife Jul. 8, 2014, pp. 1-26.

* cited by examiner

Figure 1

```
CLUSTAL O(1.2.4) multiple sequence alignment

HA0_A-Calif-7-09_H1N1           DTLCIGYHANNSTDTVDTVLEKNVTVTHSVNLLEDKHNGKLCKLRGVAPLHLGKCNIAGW    60
HA0_A-Hond-17734-16_H1N1        DTLCIGYHANNSTDTVDTVLEKNVTVTHSVNLLEDKHNGKLCKLRGVPPLHLGKCNIAGW    60
HA0_A-Darw-11-15_H1N1           DTLCIGYHANNSTDTVDTVLEKNVTVTHSVNLLEDKHNGKLCKLRGVAPLHLGKCNIAGW    60
HA0_A-CostaRica-0513-16_H1N1    DTLCIGYHANNSTDTVDTVLEKNVTVTHSVNLLEDKHNGKLCKLRGVAPLHLGKCNIAGW    60
HA0_A-Mich-45-15_H1N1           DTLCIGYHANNSTDTVDTVLEKNVTVTHSVNLLEDKHNGKLCKLRGVAPLHLGKCNIAGW    60
HA0_A-Mass-06-17_H1N1           DTLCIGYHANNSTDTVDTVLEKNVTVTHSVNLLEDKHNGKLCKLRGVAPLHLGKCNIAGW    60
                                *********************************************** ************

HA0_A-Calif-7-09_H1N1           ILGNPECESLSTASSWSYIVETPSSDNGTCYPGDFIDYEELREQLSSVSSFERFEIFPKT    120
HA0_A-Hond-17734-16_H1N1        ILGNPECEPLSTASSWSYIVETSSSDNGTCYPGDFINYEELREQLSSVSSFERFEIFPKT    120
HA0_A-Darw-11-15_H1N1           ILGNPECESLSTASSWSYIVETSSSDNGTCYPGDFINYEELREQLSSVSSFERFEIFPKT    120
HA0_A-CostaRica-0513-16_H1N1    ILGNPECESLSTASSWSYIVETSNSDNGTCYPGDFINYEELREQLSSVSSFERFEIFPKT    120
HA0_A-Mich-45-15_H1N1           ILGNPECESLSTASSWSYIVETSNSDNGTCYPGDFINYEELREQLSSVSSFERFEIFPKT    120
HA0_A-Mass-06-17_H1N1           ILGNPECESLSTARSWSYIVETSNSDNGTCYPGDFINYEELREQLSSVSSFERFEIFPKT    120
                                ******** **** ******** .***********:************************

HA0_A-Calif-7-09_H1N1           SSWPNHDSNKGVTAACPHAGAKSFYKNLIWLVKKGNSYPKLSKSYINDKGKEVLVLWGIH    180
HA0_A-Hond-17734-16_H1N1        SSWPNHDSNKGVTAACPHAGAKSFYKNLIWLVKKGNSYPKLSQSYINDKGKEVLVLWGIH    180
HA0_A-Darw-11-15_H1N1           SSWPNHDSNKGVTAACPHAGAKSFYKNLIWLTKKGNSYPKLSQSYINDKGKEILVLWGIH    180
HA0_A-CostaRica-0513-16_H1N1    SSWPNHDSNKGVTAACPHAGAKSFYKNLIWLVKKGNSYPKLNQSYVNDKGKEVLVLWGIH    180
HA0_A-Mich-45-15_H1N1           SSWPNHDSNKGVTAACPHAGAKSFYKNLIWLVKKGNSYPKLNQSYINDKGKEVLVLWGIH    180
HA0_A-Mass-06-17_H1N1           SSWPNHDSNKGVTAACPHAGAKSFYKNLIWLVKKGNSYPKLNQSYINDKGKEVLVLWGIH    180
                                *******************************.*********.:**:******:*******

HA0_A-Calif-7-09_H1N1           HPSTSADQQSLYQNADAYVFVGSSRYSKKFKPEIAIRPKVRDQEGRMNYYWTLVEPGDKI    240
HA0_A-Hond-17734-16_H1N1        HPSTTADQQSLYQNADAYVFVGTSRYSKKFKPEIAIRPKVRDQEGRMNYYWTLVEPGDKI    240
HA0_A-Darw-11-15_H1N1           HPSTTADQQSLYQNADAYVFVGTSRYSKKFKPEIAIRPKVRDQEGRMNYYWTLVEPGDKI    240
HA0_A-CostaRica-0513-16_H1N1    HPPTTADQQSLYQNADAYVFVGTSKYSKKFKPEIATRPKVRDQEGRMNYYWTLVEPGDKI    240
HA0_A-Mich-45-15_H1N1           HPSTTADQQSLYQNADAYVFVGTSRYSKKFKPEIATRPKVRDQEGRMNYYWTLVEPGDKI    240
HA0_A-Mass-06-17_H1N1           HPSTTADQQSLYQNADAYVFVGTSRYSKKFKPEIATRPKVRDQEGRMNYYWTLVEPGDKI    240
                                ** *:*****************:*:********** ************************

HA0_A-Calif-7-09_H1N1           TFEATGNLVVPRYAFAMERNAGSGIIISDTPVHDCNTTCQTPKGAINTSLPFQNIHPITI    300
HA0_A-Hond-17734-16_H1N1        TFEATGNLVVPRYAFTMERNAGSGIIISDTPVHDCNTTCQTPEGAINTSLPFQNIHPITI    300
HA0_A-Darw-11-15_H1N1           TFEATGNLVVPRYAFTMERNAGSGIIISDTPVHDCNTTCQTPEGAINTSLPFQNIHPITI    300
HA0_A-CostaRica-0513-16_H1N1    TFEATGNLVVPRYAFTMERNAGSGIIISDTPVHDCNTTCQTPEGAINTSLPFQNIHPITI    300
HA0_A-Mich-45-15_H1N1           TFEATGNLVVPRYAFTMERNAGSGIIISDTPVHDCNTTCQTPEGAINTSLPFQNIHPITI    300
HA0_A-Mass-06-17_H1N1           TFEATGNLVVPRYAFTMERNAGSGIIISDTPVHDCNTTCQTPEGAINTSLPFQNVHPITI    300
                                ***************:**************************:***********:*****
```

Continuation of Fig 1

```
HA0_A-Calif-7-09_H1N1             GKCPKYVKSTKLRLATGLRNIPSIQSRGLFGAIAGFIEGGWTGMVDGWYGYHHQNEQGSG   360
HA0_A-Hond-17734-16_H1N1          GKCPKYVKSTKLRLATGLRNVPSIQSRGLFGAIAGFIEGGWTGMVDGWYGYHHQNEQGSG   360
HA0_A-Darw-11-15_H1N1             GKCPKYVKSTKLRLATGLRNVPSIQSRGLFGAIAGFIEGGWTGMVDGWYGYHHQNEQGSG   360
HA0_A-CostaRica-0513-16_H1N1      GKCPKYVKSTKLRLATGLRNVPSIQSRGLFGAIAGFIEGGWTGMVDGWYGYHHQNEQGSG   360
HA0_A-Mich-45-15_H1N1             GKCPKYVKSTKLRLATGLRNVPSIQSRGLFGAIAGFIEGGWTGMVDGWYGYHHQNEQGSG   360
HA0_A-Mass-06-17_H1N1             GKCPKYVKSTKLRLATGLRNVPSIQSRGLFGAIAGFIEGGWTGMVDGWYGYHHQNEQGSG   360
                                  ********************:***************************************

HA0_A-Calif-7-09_H1N1             YAADLKSTQNAIDEITNKVNSVIEKMNTQFTAVGKEFNHLEKRIENLNKKVDDGFLDIWT   420
HA0_A-Hond-17734-16_H1N1          YAADQKSTQSAIDKITNKVNSVIEKMNTQFTAVGKEFNHLEKRIENLNKKVDDGFLDIWT   420
HA0_A-Darw-11-15_H1N1             YAADLKSTQNAIDKITNKVNSVIEKMNTQFTAVGKEFNHLEKRIENLNKKVDDGFLDIWT   420
HA0_A-CostaRica-0513-16_H1N1      YAADLKSTQNAIDKITNKVNSVIEKMNTQFTAVGKEFNHLEKRIENLNKKVDDGFLDIWT   420
HA0_A-Mich-45-15_H1N1             YAADLKSTQNAIDKITNKVNSVIEKMNTQFTAVGKEFNHLEKRIENLNKKVDDGFLDIWT   420
HA0_A-Mass-06-17_H1N1             YAADLKSTQNAIDKITNKVNSVIEKMNTQFTAVGKEFNHLEKRIENLNKKVDDGFLDIWT   420
                                  **** ****.***:**********************************************

HA0_A-Calif-7-09_H1N1             YNAELLVLLENERTLDYHDSNVKNLYEKVRSQLKNNAKEIGNGCFEFYHKCDNTCMESVK   480
HA0_A-Hond-17734-16_H1N1          YNAELLVLLENERTLDYHDSNVKNLYEKVRNQLKNNAKEIGNGCFEFYHKCDNTCMESVK   480
HA0_A-Darw-11-15_H1N1             YNAELLVLLENERTLDYHDSNVKNLYEKVRNQLKNNAKEIGNGCFEFYHKCDNTCMESVK   480
HA0_A-CostaRica-0513-16_H1N1      YNAELLVLLENERTLDYHDSNVKNLYEKVRNQLKNNAKEIGNGCFEFYHKCDNTCMESVK   480
HA0_A-Mich-45-15_H1N1             YNAELLVLLENERTLDYHDSNVKNLYEKVRNQLKNNAKEIGNGCFEFYHKCDNTCMESVK   480
HA0_A-Mass-06-17_H1N1             YNAELLVLLENERTLDYHDSNVKNLYEKVRNQLKNNAKEIGNGCFEFYHKCDNTCMESVK   480
                                  ******************************.*****************************

HA0_A-Calif-7-09_H1N1             NGTYDYPKYSEEAKLNREEIDGVKLESTRIYQILAIYSTVASSLVLVVSLGAISFWMCSN   540
HA0_A-Hond-17734-16_H1N1          NGTYDYPKYSEEAKLNREKIDGVKLESTRIYQILAIYSTVASSLVLVVSLGAISFWMCSN   540
HA0_A-Darw-11-15_H1N1             NGTYDYPKYSGEAKLNREKIEGVKLESTRIYQILAIYSTVASSLVLVVSLGAISFWMCSN   540
HA0_A-CostaRica-0513-16_H1N1      NGTYDYPKYSEEAKLNREKIDGVKLESTRIYQILAIYSTVASSLVLVVSLGAISFWMCSN   540
HA0_A-Mich-45-15_H1N1             NGTYDYPKYSEEAKLNREKIDGVKLESTRIYQILAIYSTVASSLVLVVSLGAISFWMCSN   540
HA0_A-Mass-06-17_H1N1             NGTYDYPKYSEEAKLNREKIDGVKLESTRIYQILAIYSTVASSLVLVVSLGAISFWMCSN   540
                                  ********** *******:*:***************************************

HA0_A-Calif-7-09_H1N1             GSLQCRICI 549
HA0_A-Hond-17734-16_H1N1          GSLQCRICI 549
HA0_A-Darw-11-15_H1N1             GSLQCRICI 549
HA0_A-CostaRica-0513-16_H1N1      GSLQCRICI 549
HA0_A-Mich-45-15_H1N1             GSLQCRICI 549
HA0_A-Mass-06-17_H1N1             GSLQCRICI 549
                                  *********
```

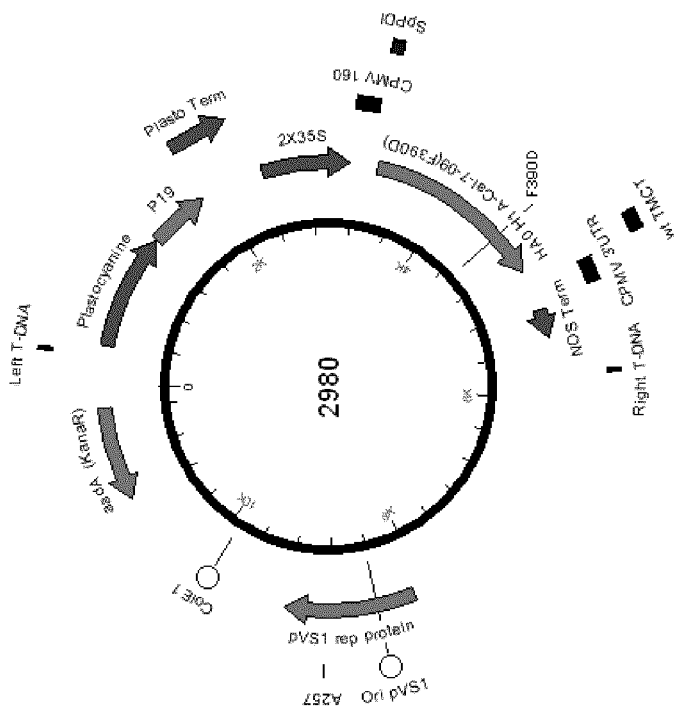
Figure 6A: Schematic representation of vector 1314
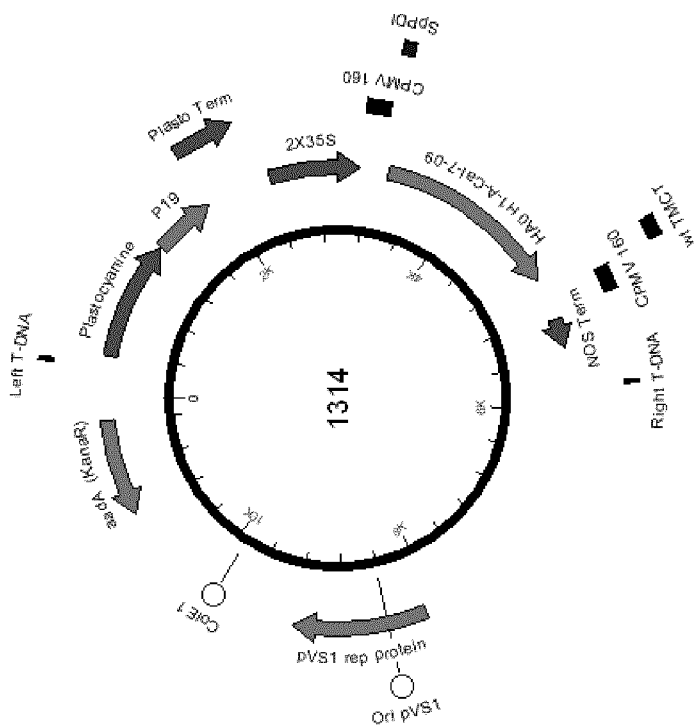
Figure 6B: Schematic representation of vector 2980

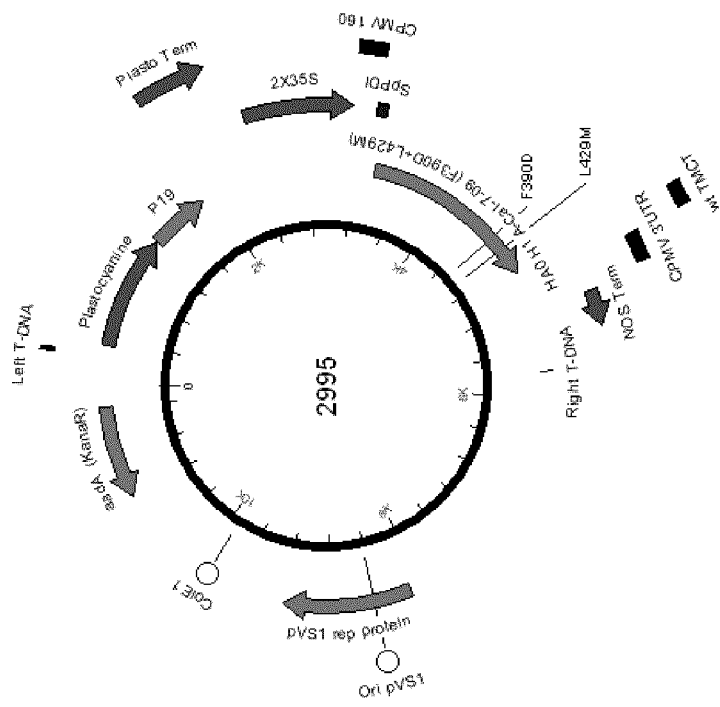
Figure 6D: Schematic representation of vector 2995
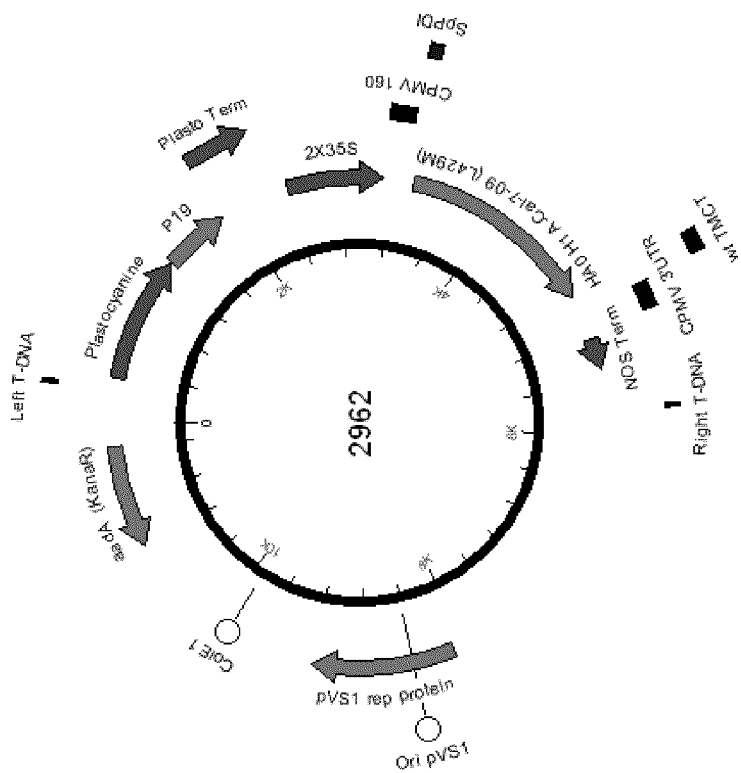
Figure 6C: Schematic representation of vector 2962

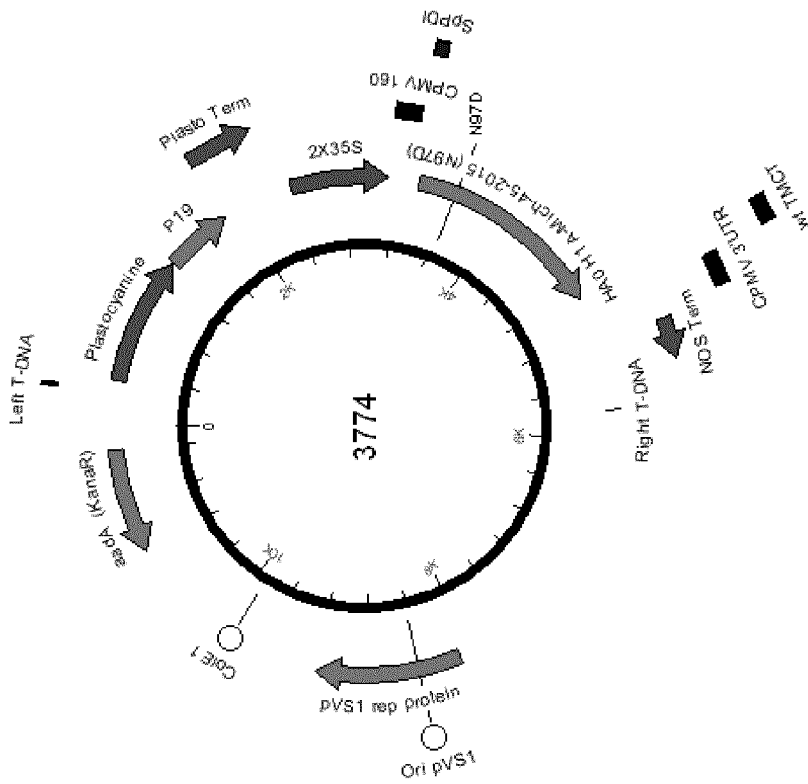
Figure 6F: Schematic representation of vector 3774
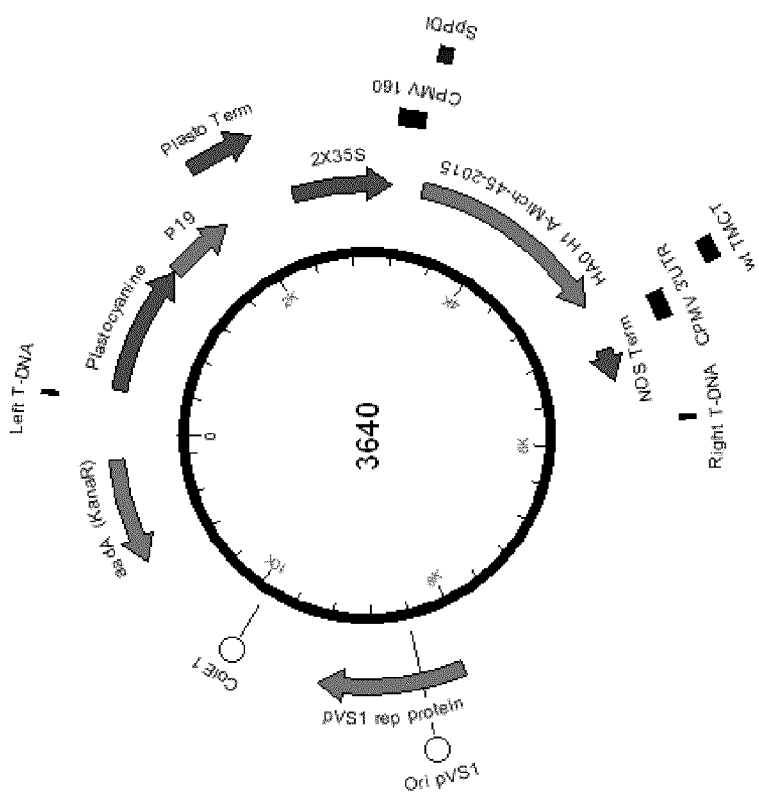
Figure 6E: Schematic representation of vector 3640

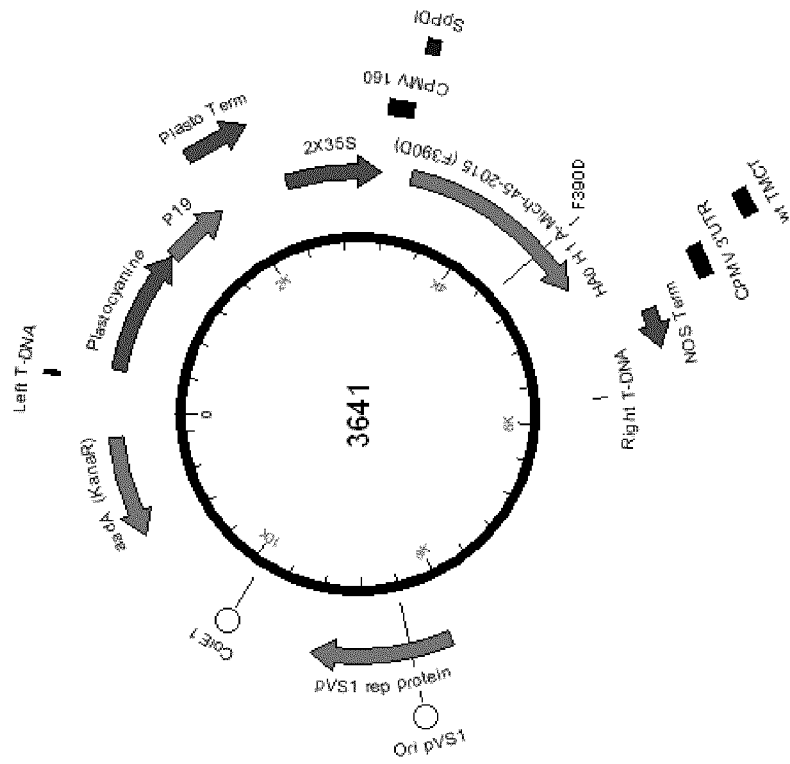
Figure 6H: Schematic representation of vector 3641
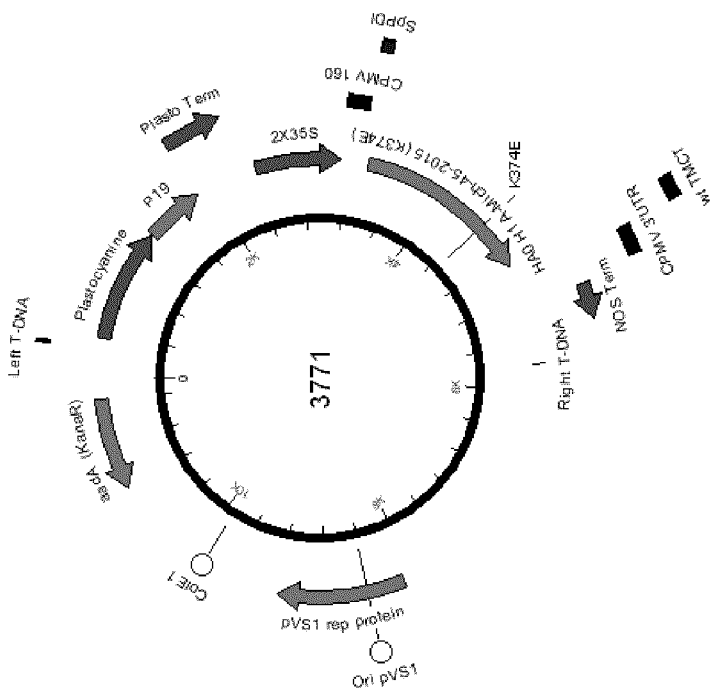
Figure 6G: Schematic representation of vector 3771

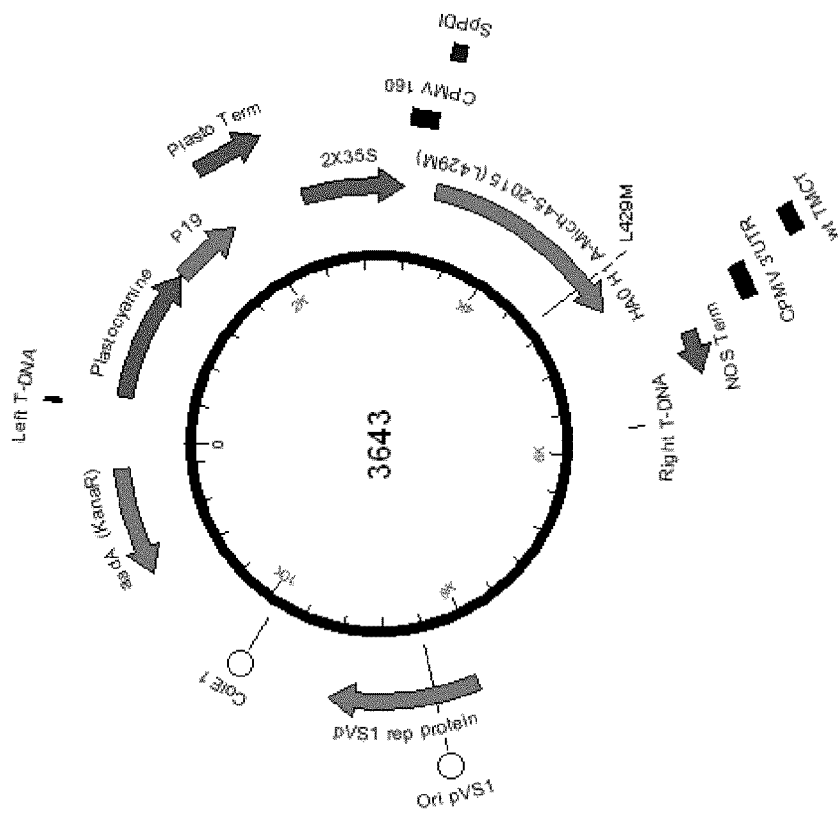
Figure 6J: Schematic representation of vector 3880
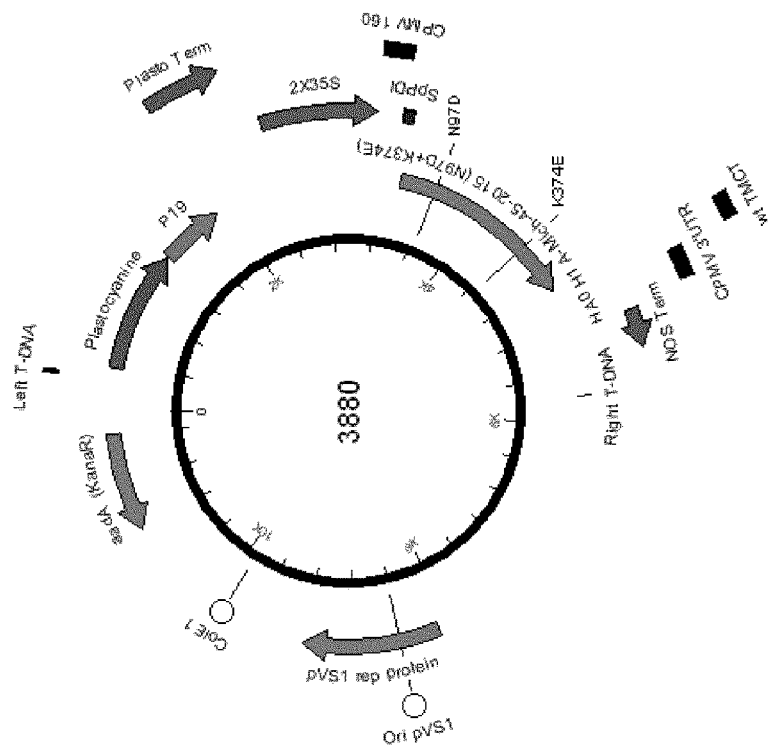
Figure 6I: Schematic representation of vector 3643

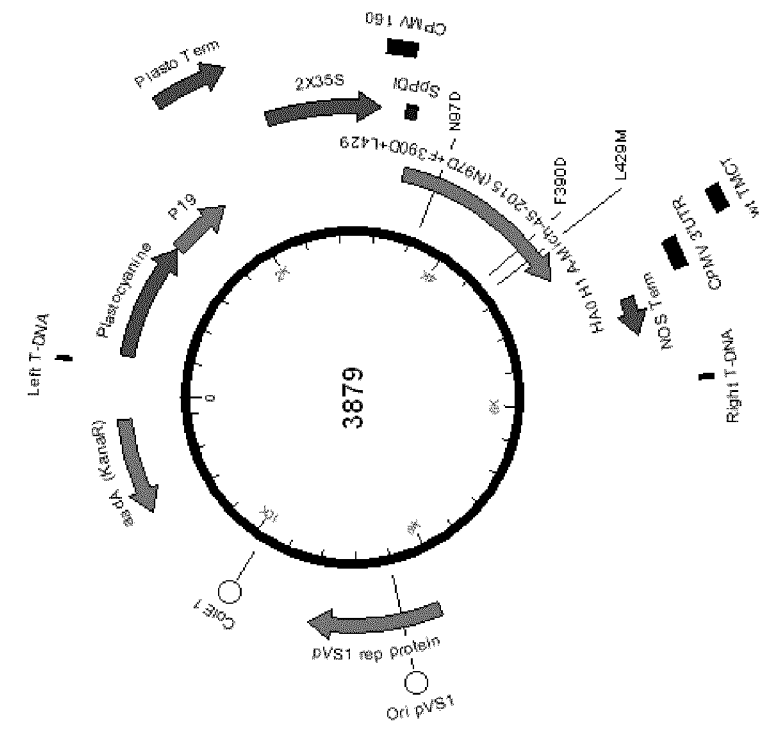
Figure 6L: Schematic representation of vector 3879
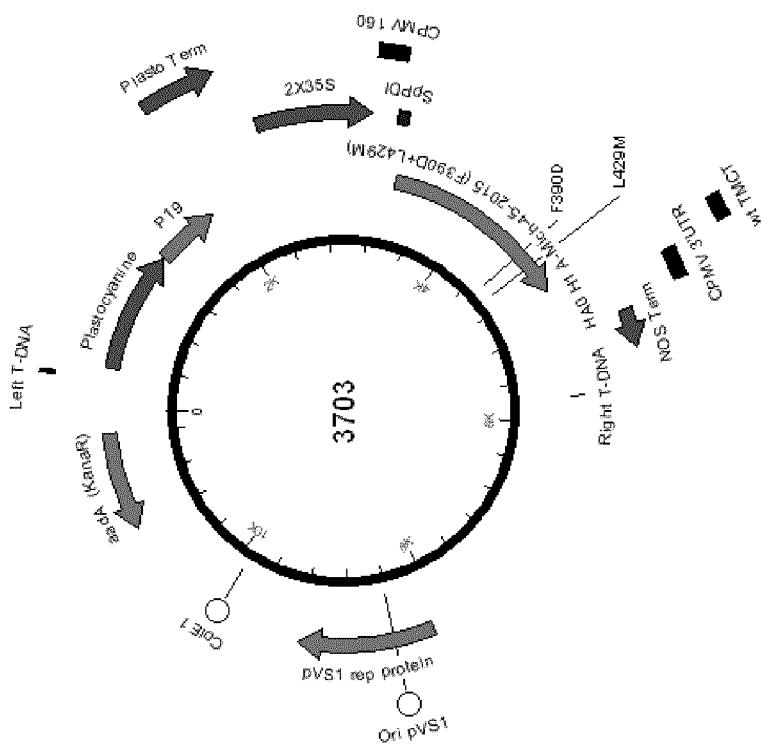
Figure 6K: Schematic representation of vector 3703

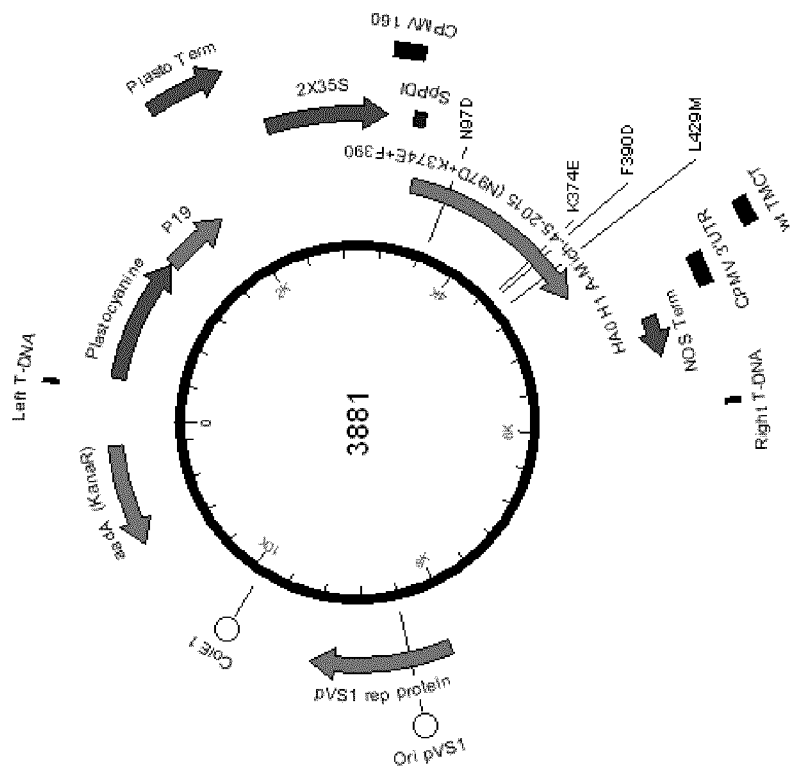
Figure 6N: Schematic representation of vector 3881
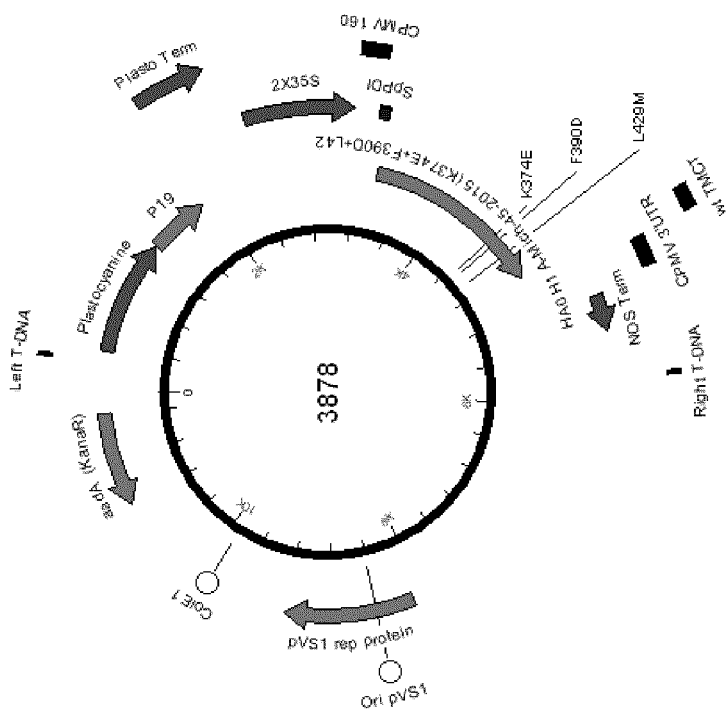
Figure 6M: Schematic representation of vector 3878

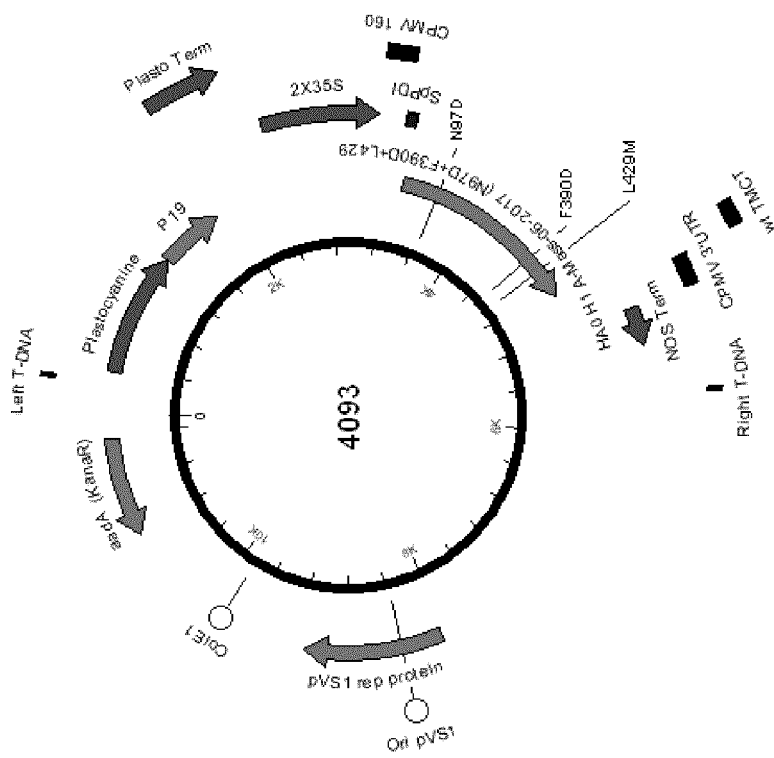
Figure 6P: Schematic representation of vector 4093
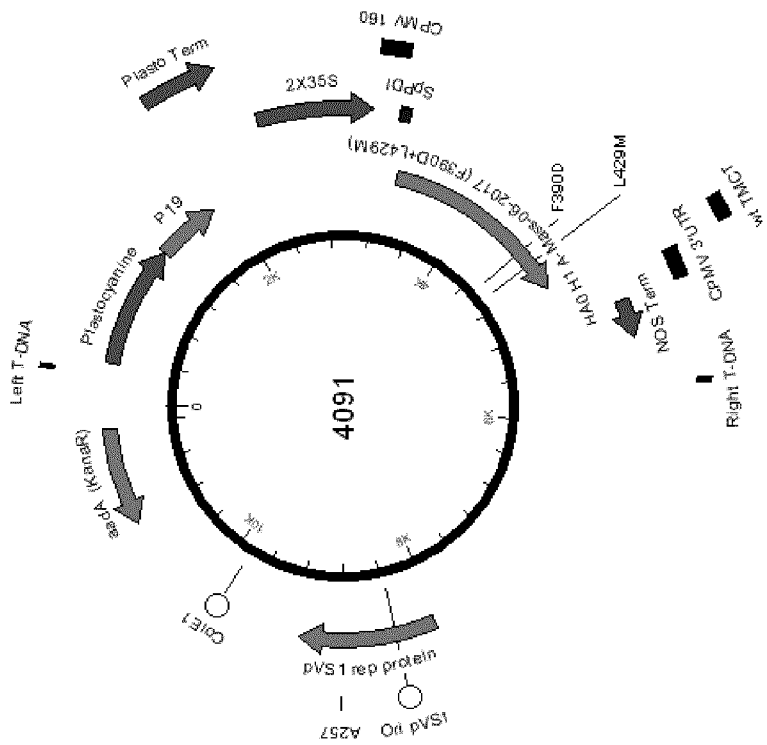
Figure 6O: Schematic representation of vector 4091

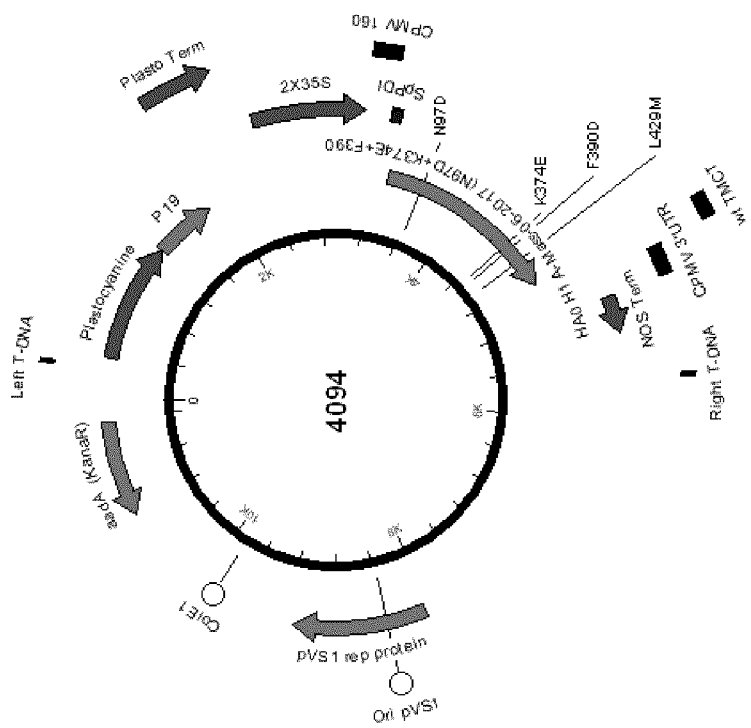
Figure 6R: Schematic representation of vector 4094
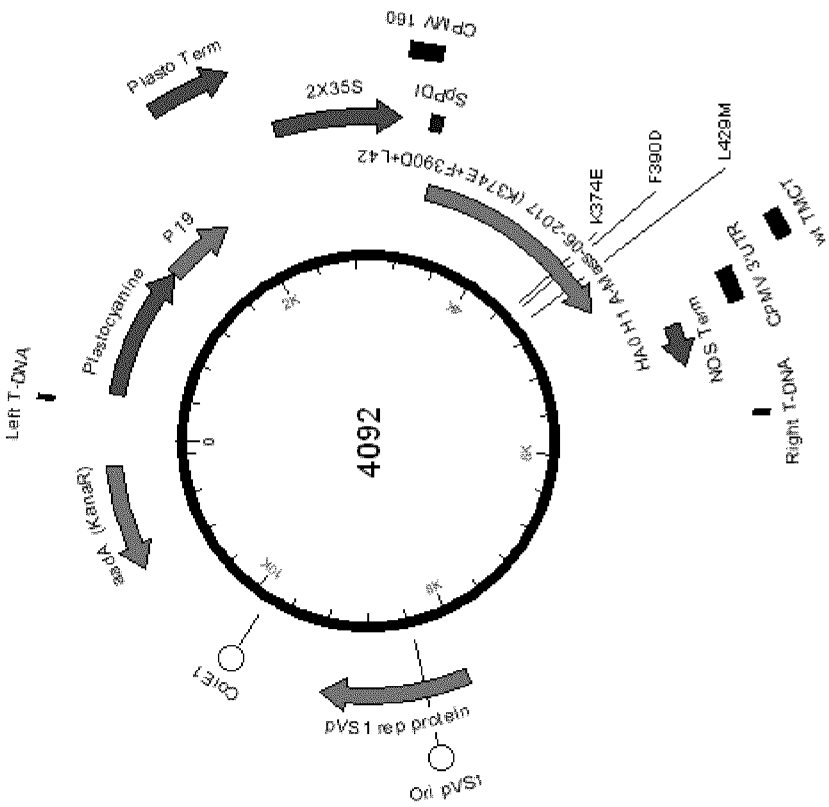
Figure 6Q: Schematic representation of vector 4092

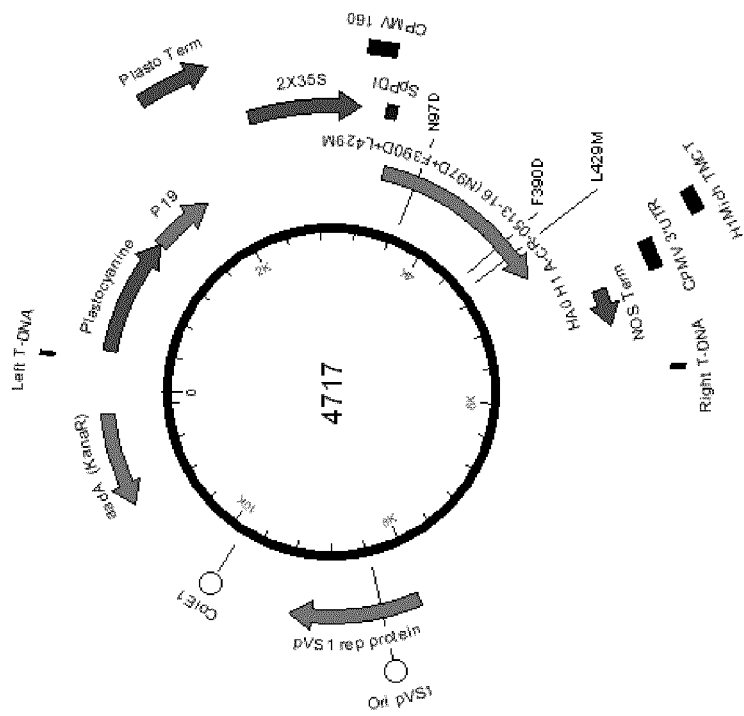
Figure 6T: Schematic representation of vector 4717
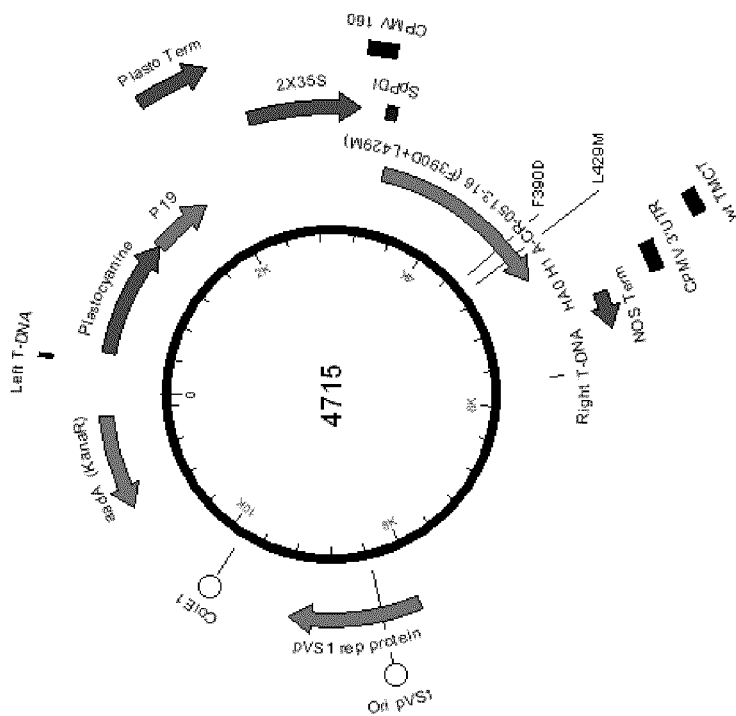
Figure 6S: Schematic representation of vector 4715

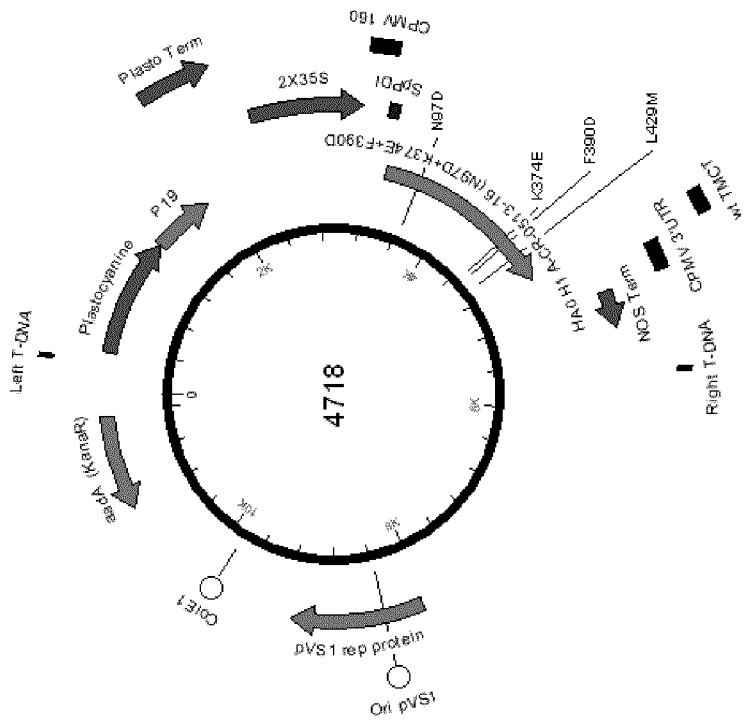
Figure 6V: Schematic representation of vector 4718
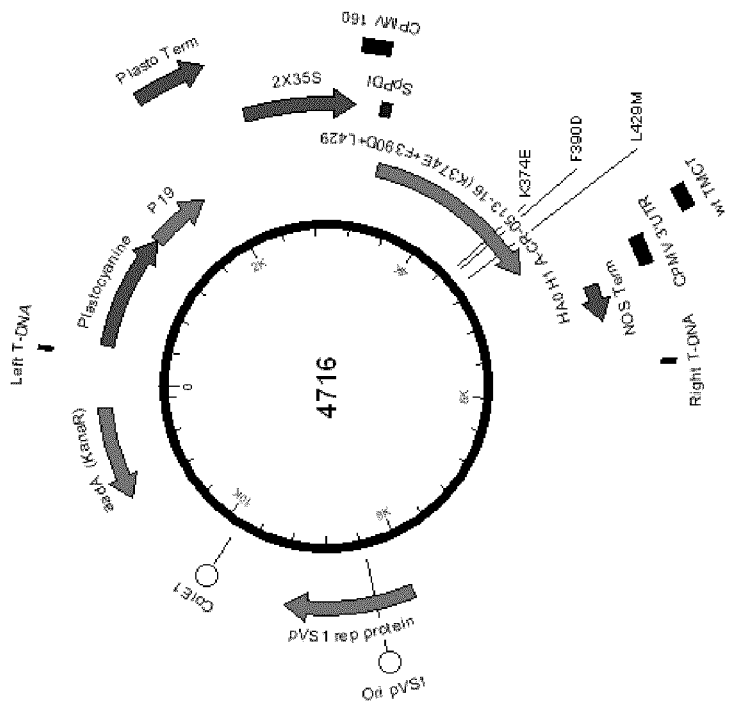
Figure 6U: Schematic representation of vector 4716

Figure 6X: Schematic representation of vector 3950
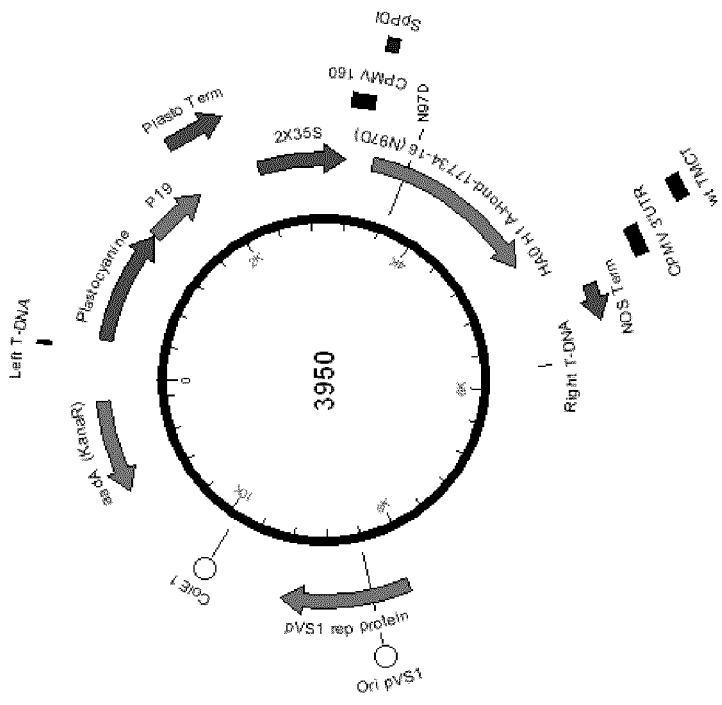
Figure 6W: Schematic representation of vector 3944
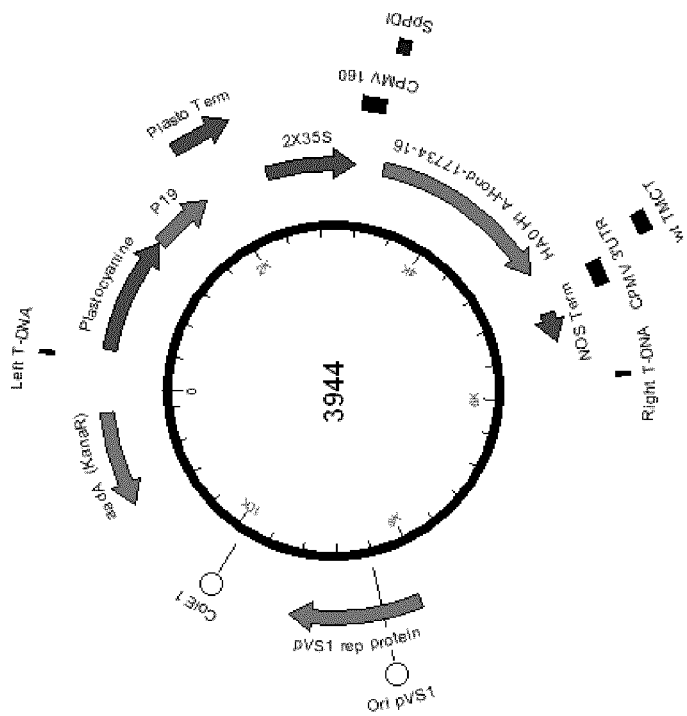

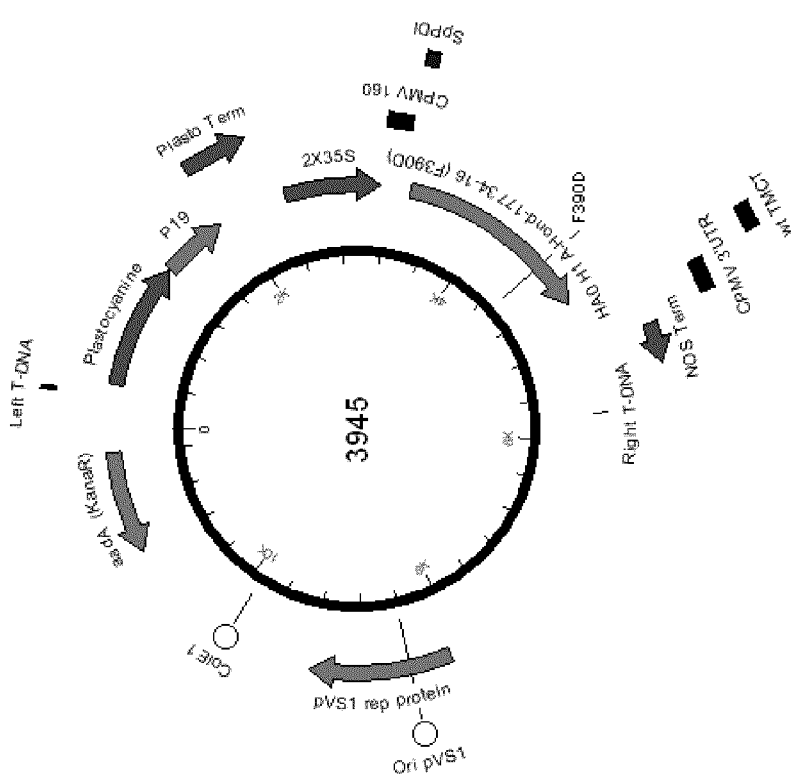
Figure 6Z: Schematic representation of vector 3945
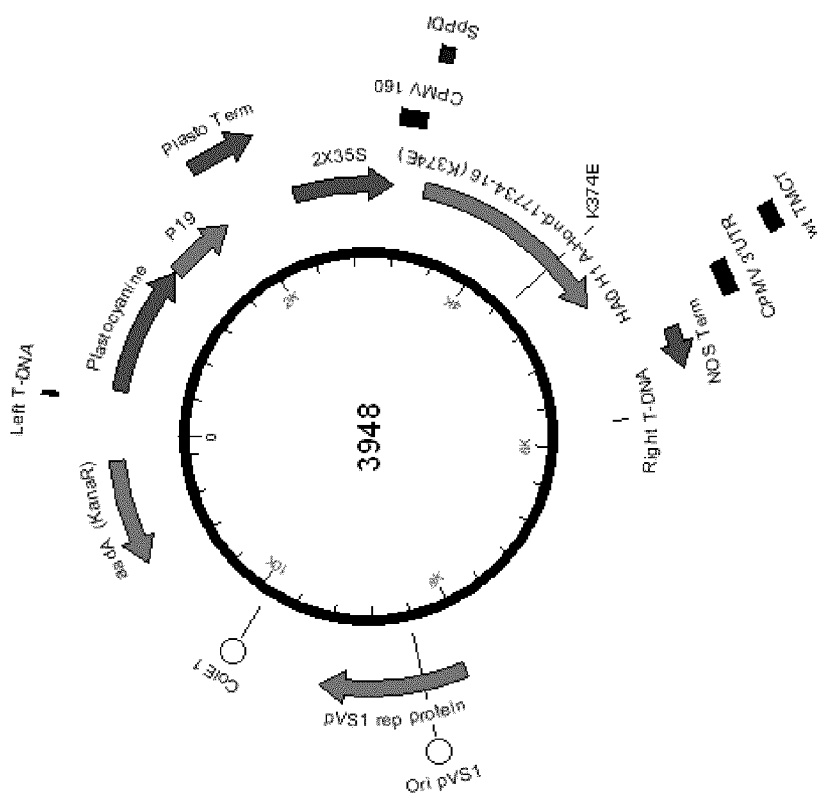
Figure 6Y: Schematic representation of vector 3948

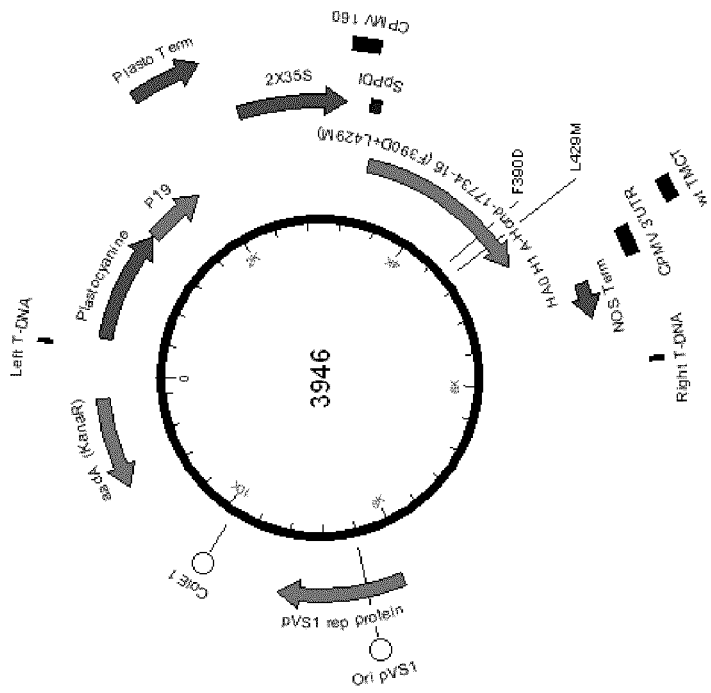
Figure 6BB: Schematic representation of vector 3946
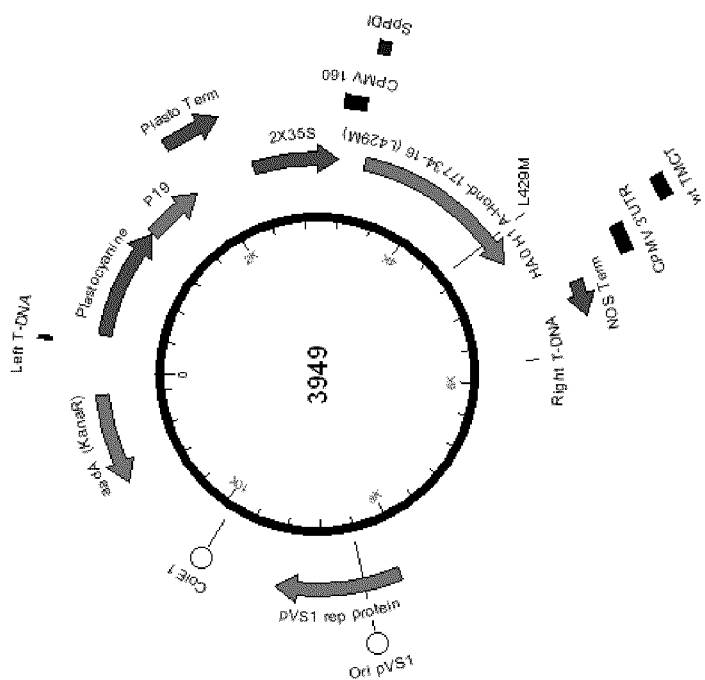
Figure 6AA: Schematic representation of vector 3949

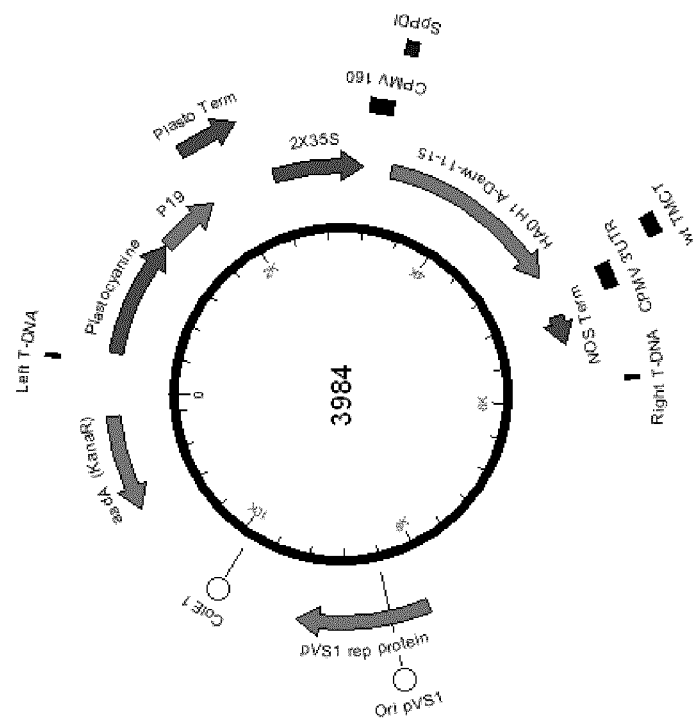
Figure 6DD: Schematic representation of vector 3984
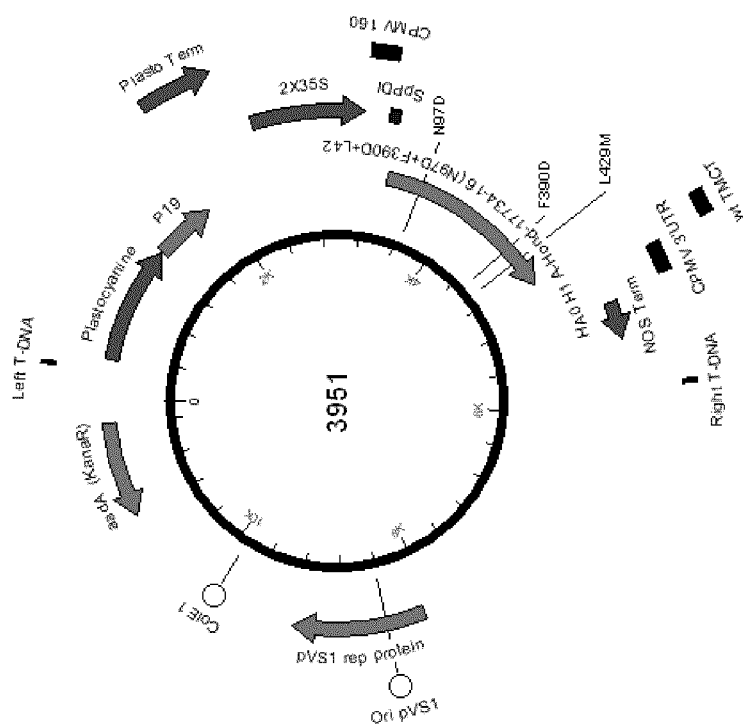
Figure 6CC: Schematic representation of vector 3951

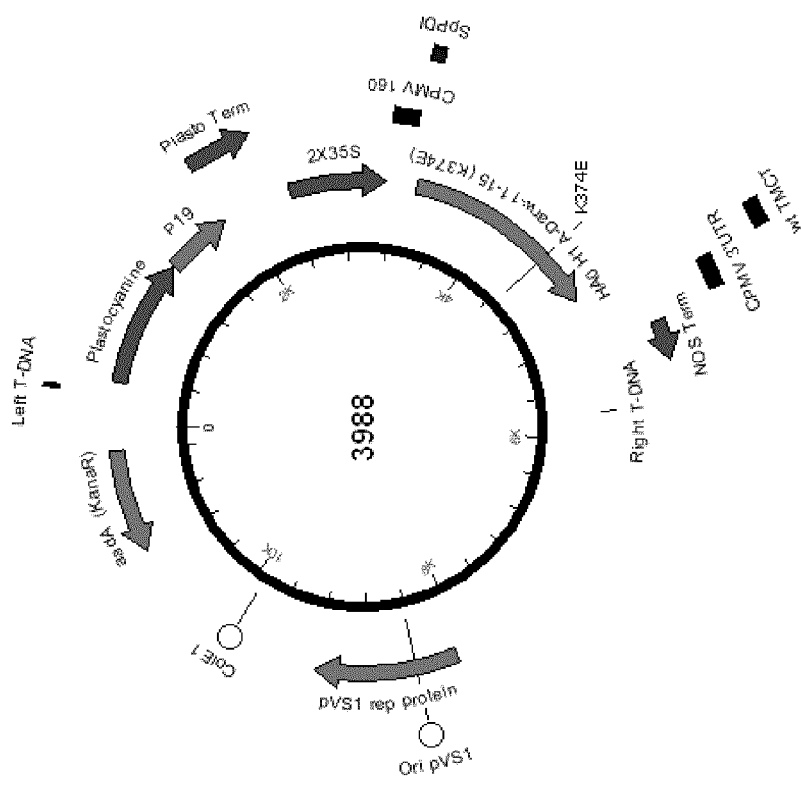
Figure 6FF: Schematic representation of vector 3988
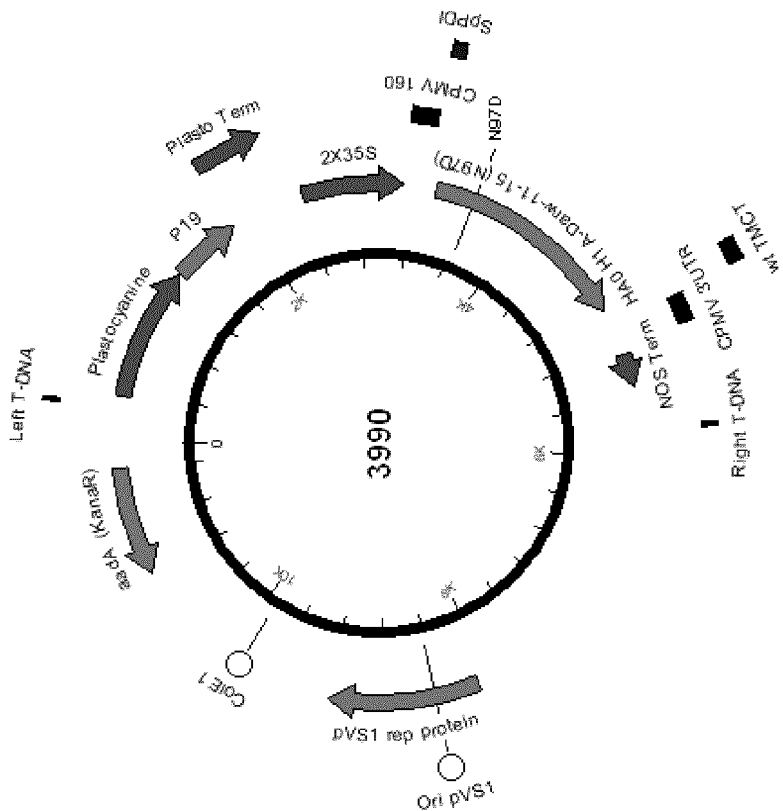
Figure 6EE: Schematic representation of vector 3990

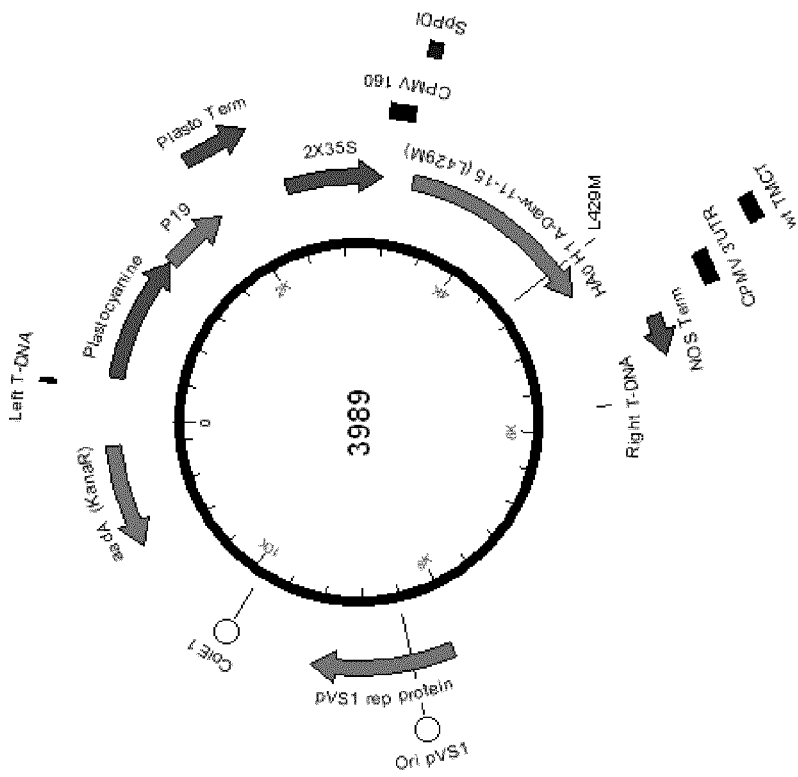
Figure 6 HH: Schematic representation of vector 3989
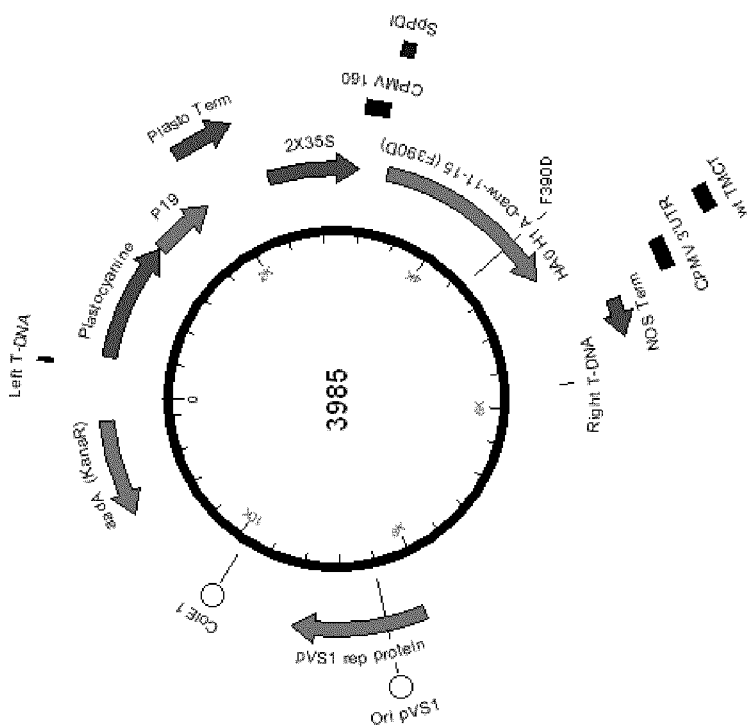
Figure 6 GG: Schematic representation of vector 3985

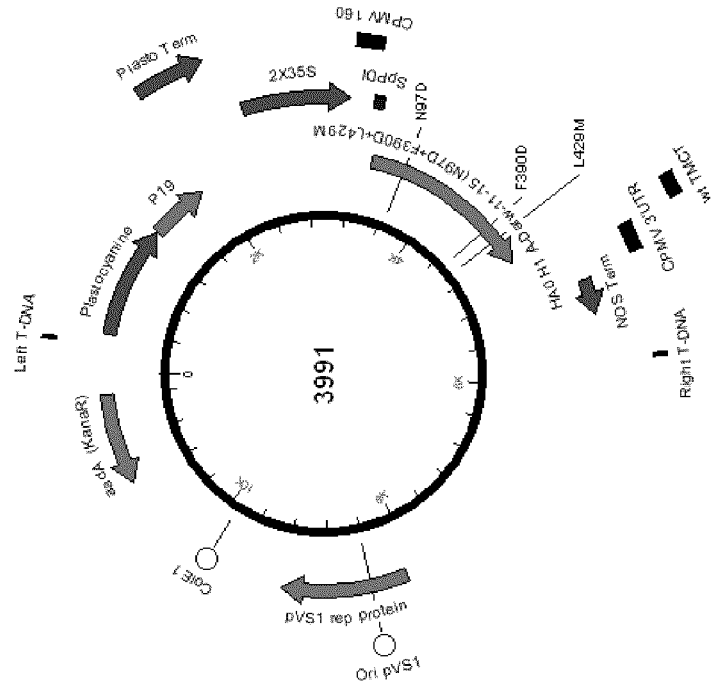
Figure 6 JJ: Schematic representation of vector 3991
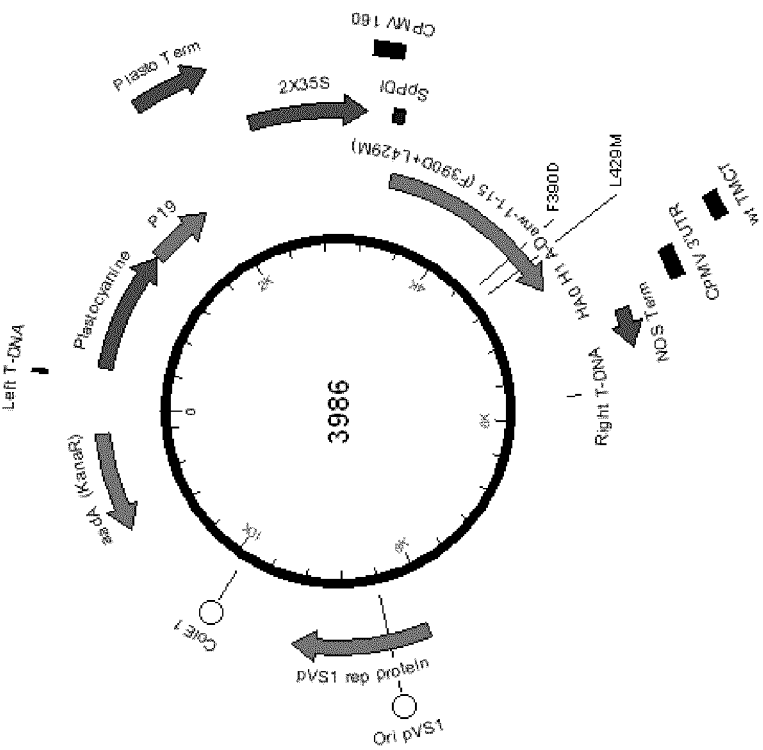
Figure 6 II: Schematic representation of vector 3986

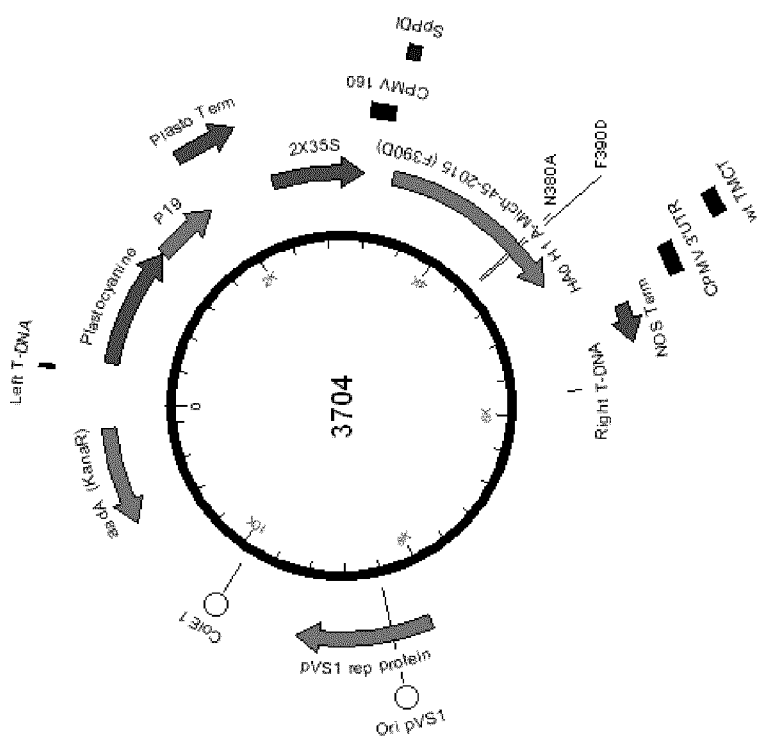
Figure 6LL: Schematic representation of vector 3704
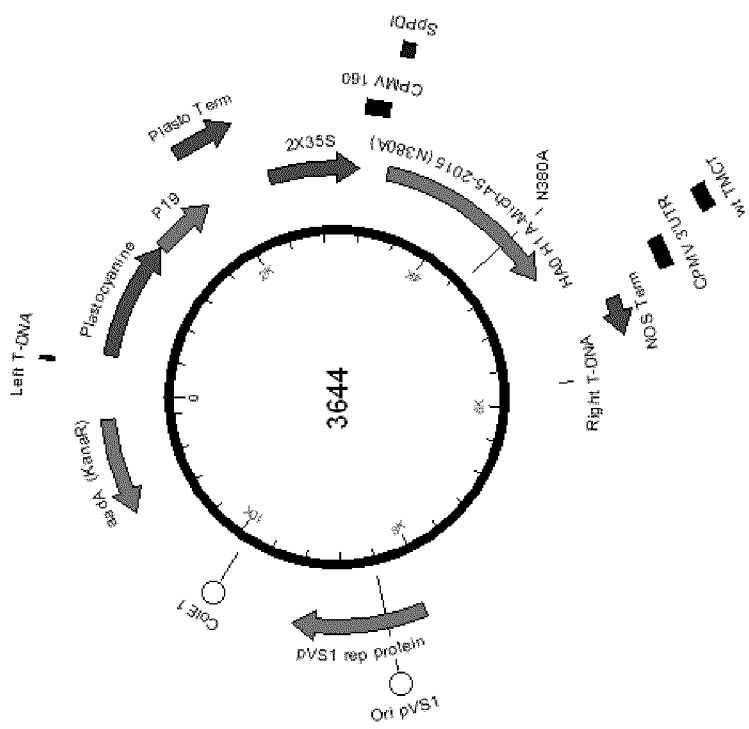
Figure 6KK: Schematic representation of vector 3644

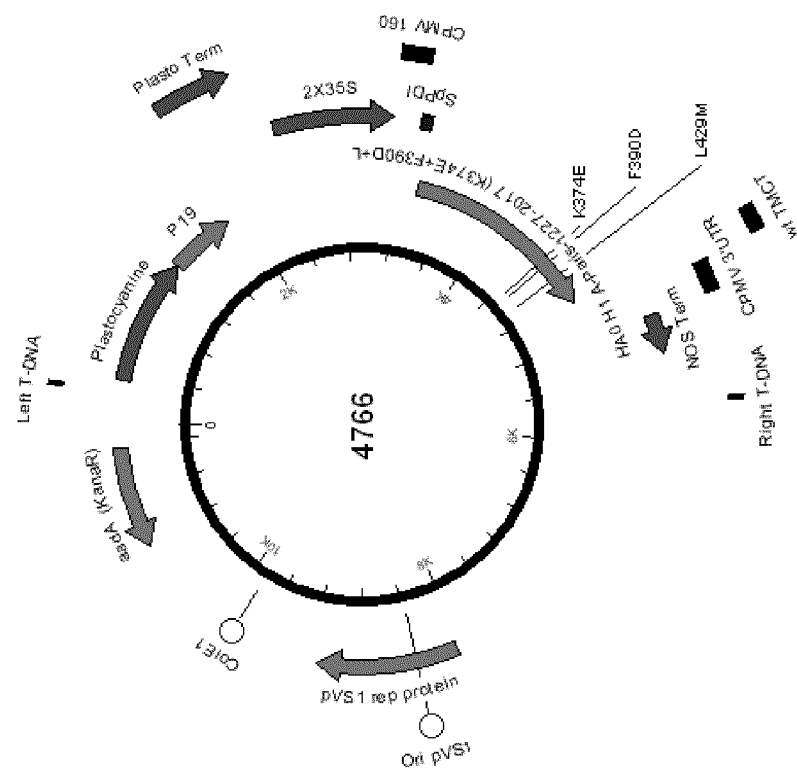
Figure 6NN: Schematic representation of vector 4766
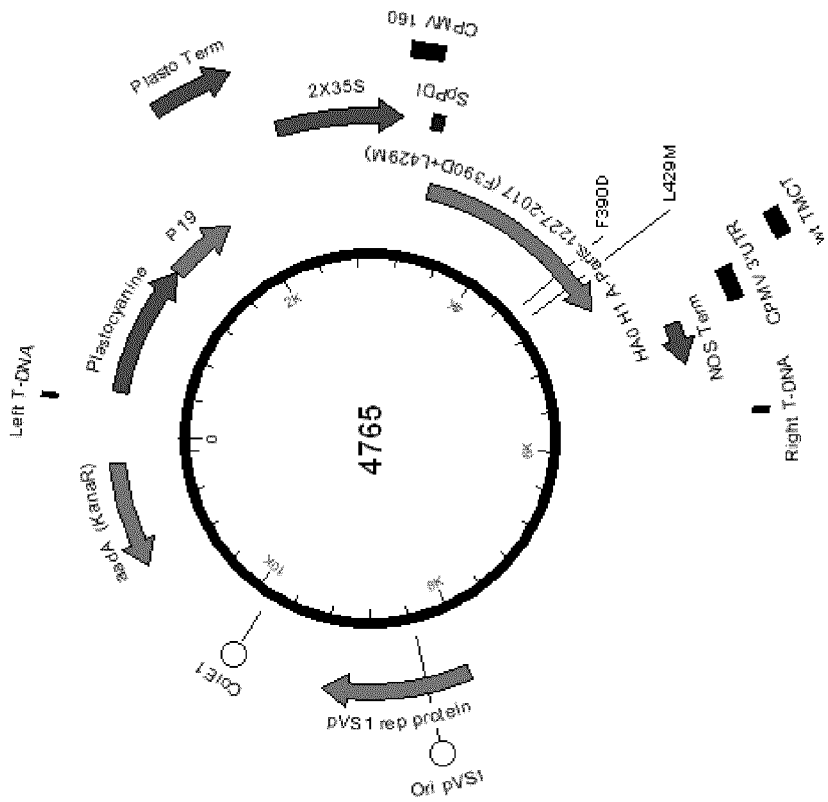
Figure 6MM: Schematic representation of vector 4765

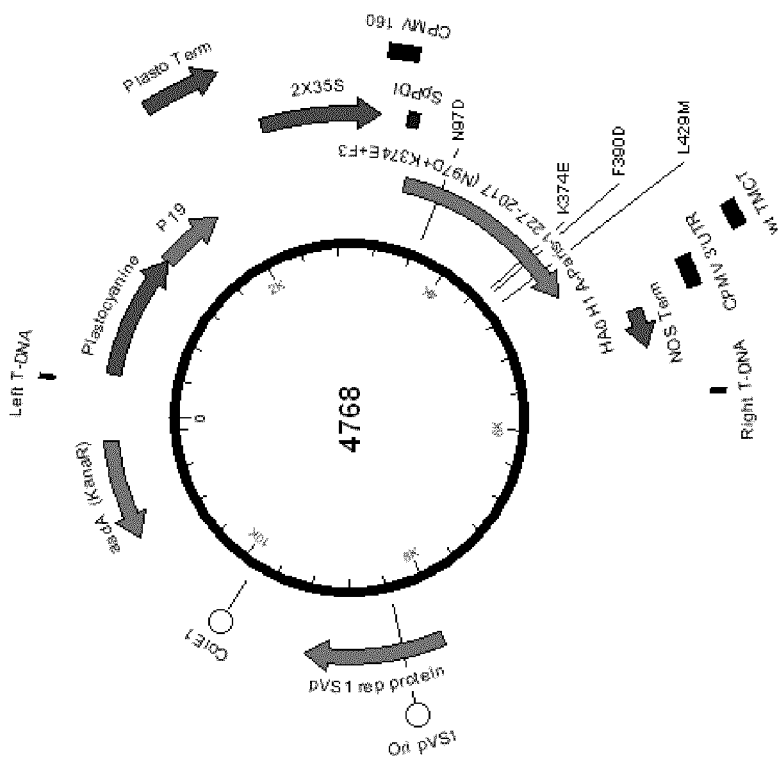
Figure 6PP: Schematic representation of vector 4768
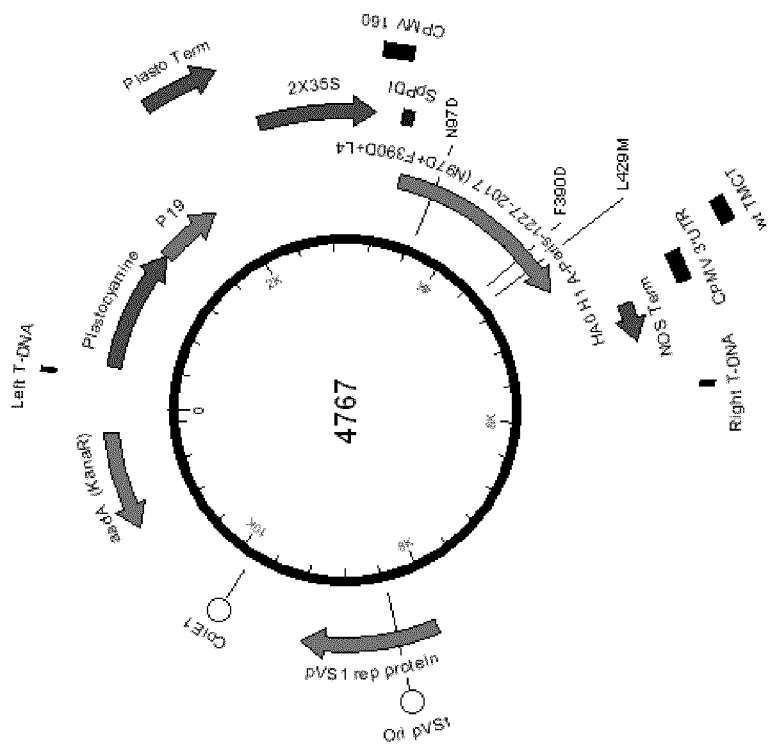
Figure 6OO: Schematic representation of vector 4767

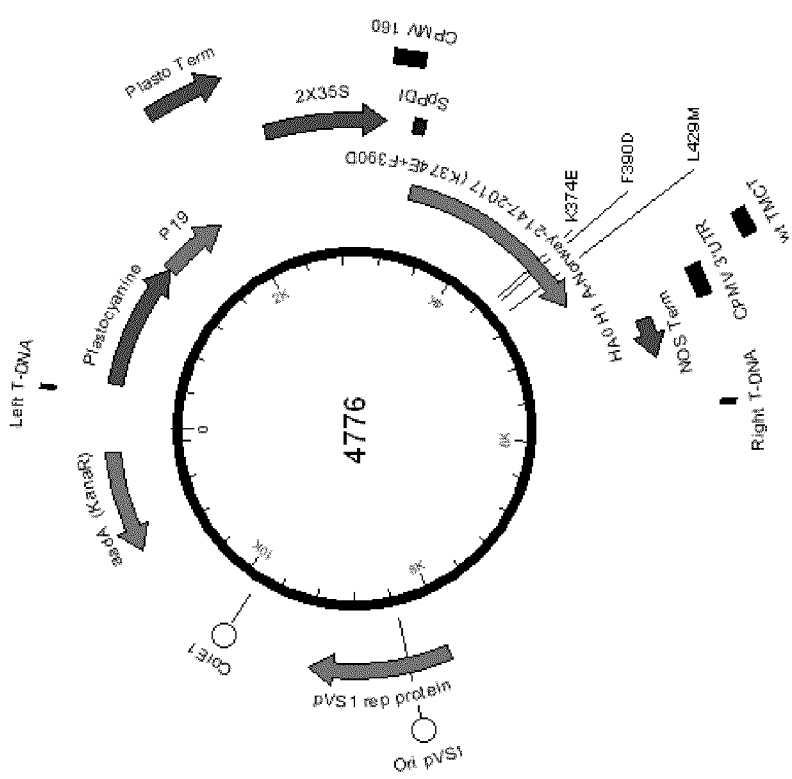
Figure 6RR: Schematic representation of vector 4776
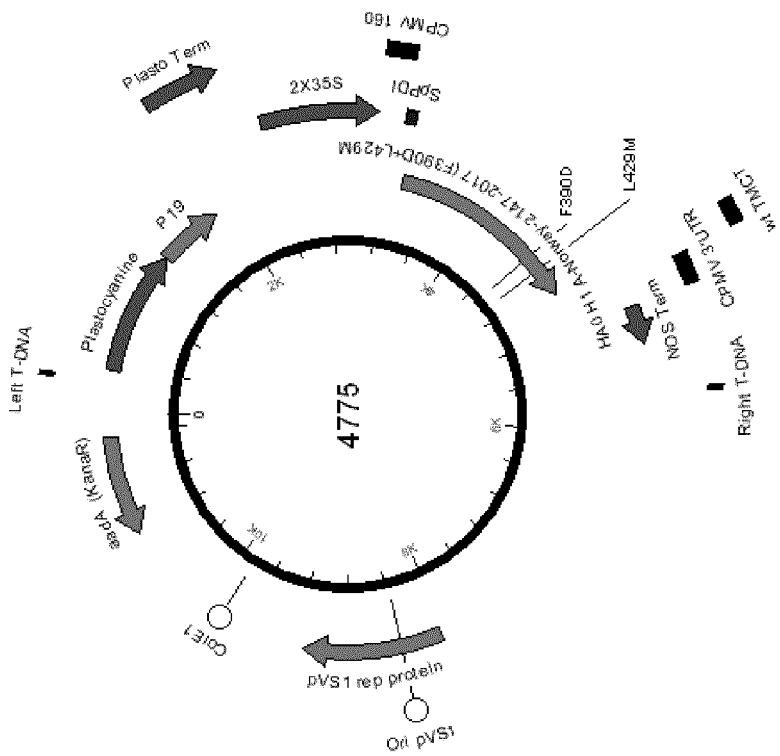
Figure 6QQ: Schematic representation of vector 4775

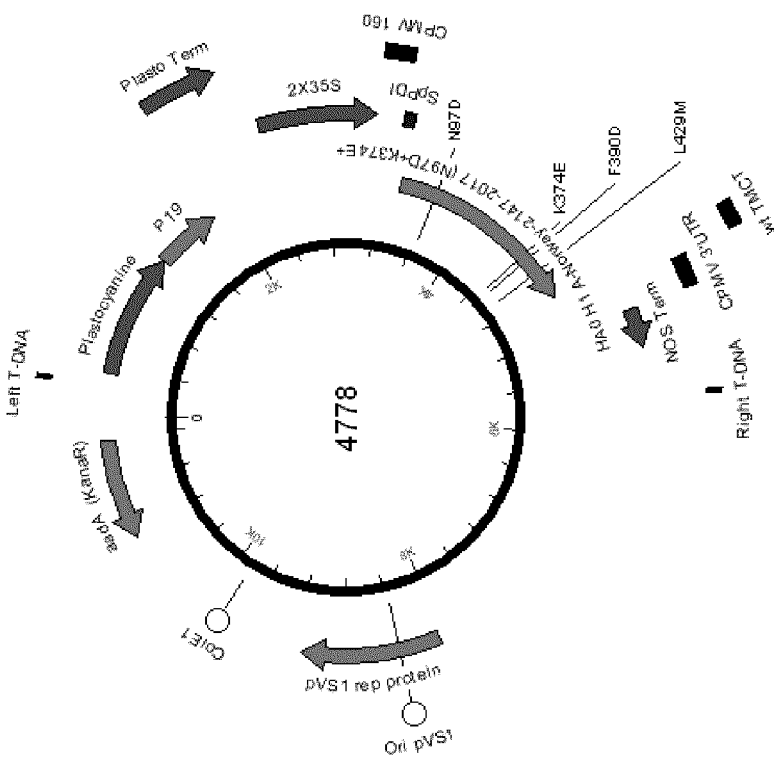
Figure 6TT: Schematic representation of vector 4778
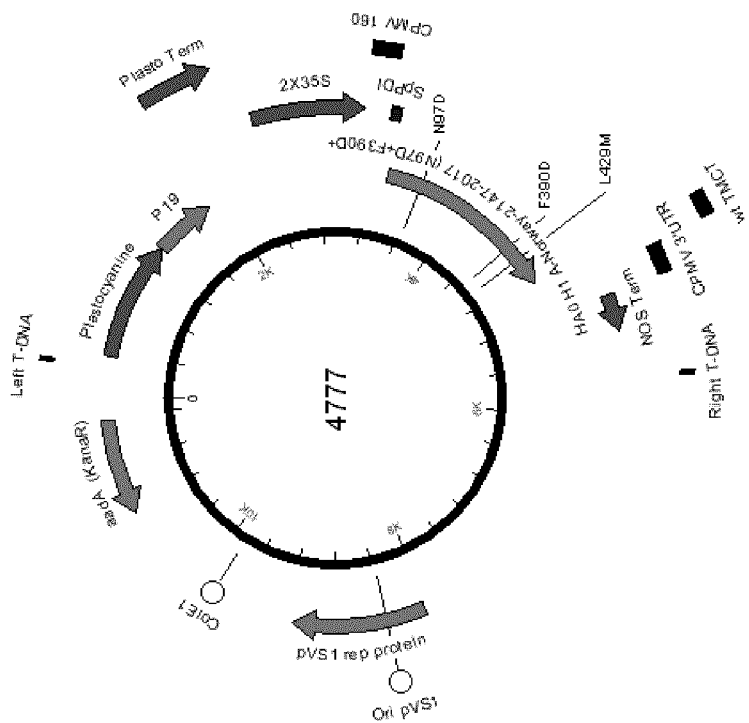
Figure 6SS: Schematic representation of vector 4777

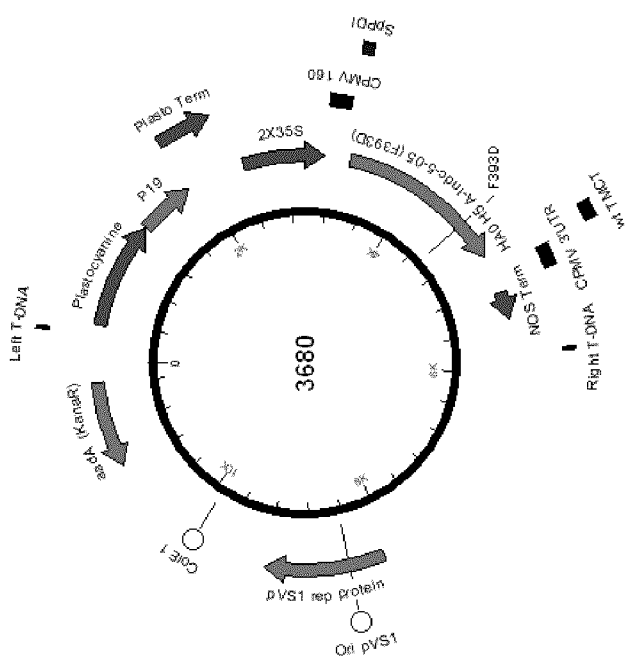
Figure 7B: Schematic representation of vector 3680
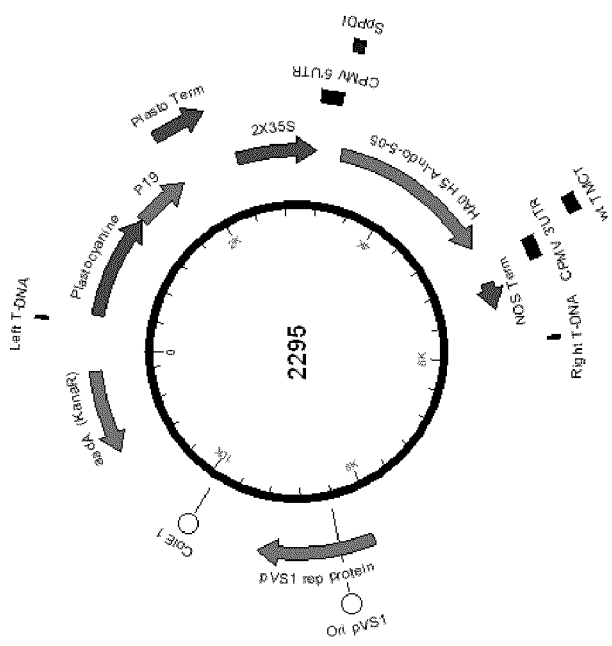
Figure 7A: Schematic representation of vector 2295

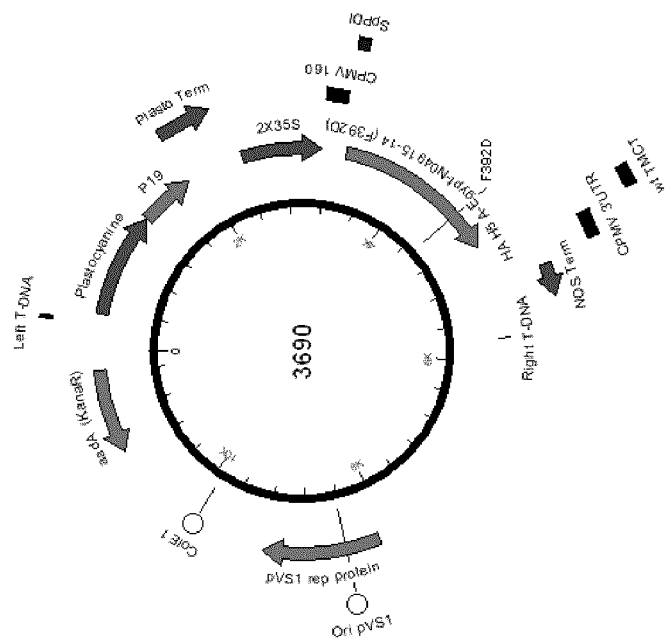
Figure 7D: Schematic representation of vector 3690
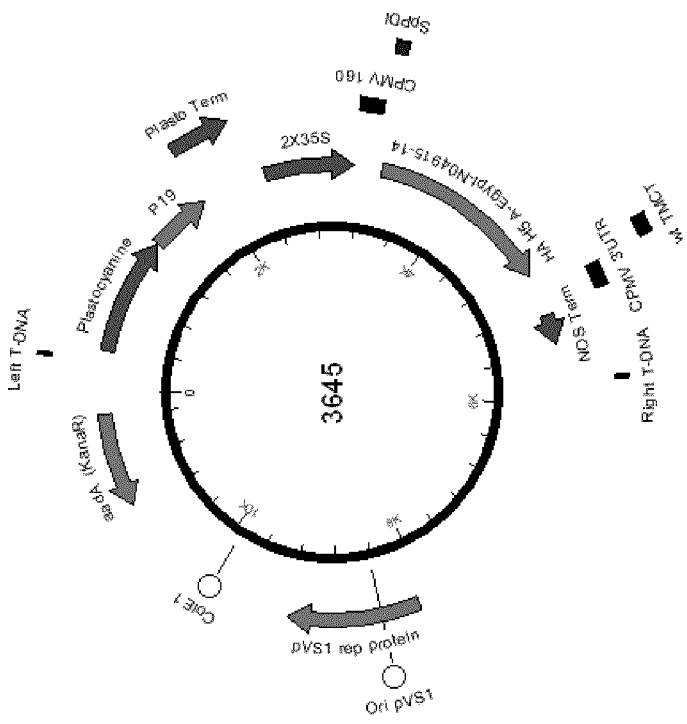
Figure 7C: Schematic representation of vector 3645

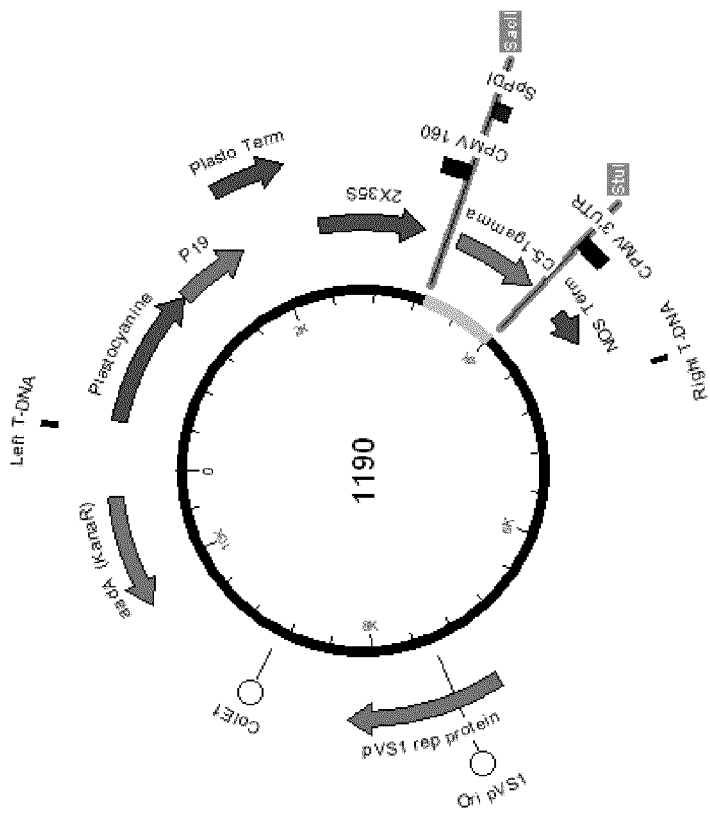
Figure 8: Schematic representation of vector 1190

INFLUENZA VIRUS HEMAGGLUTININ MUTANTS

FIELD OF INVENTION

The present invention relates to producing mutant viral proteins in plants. More specifically, the present invention relates to producing and increasing influenza virus-like particle production in plants.

BACKGROUND OF THE INVENTION

Influenza viruses are enveloped, single-stranded-RNA viruses of the Orthomyxoviridae family. Influenza viruses are highly contagious and can cause mild to serious illness across all age groups.

Vaccination remains the most effective method to prevent influenza infection. Conventionally, vaccination is accomplished using live attenuated or whole inactivated forms of the virus, which elicit an immune response when administered to a patient. To eliminate the potential risk of live attenuated and whole inactivated viruses re-acquiring the competency to replicate and become infectious, vaccines comprising recombinant viral proteins have also been used to elicit protective immunity to influenza infection.

However, the use of recombinant viral proteins as the immunogenic component of vaccines is subject to a number of limitations. Firstly, in the absence of the full complement of viral proteins and genetic components required for optimal expression and proper protein folding, the yield of recombinant viral proteins in standard in vitro expression systems may be insufficient for the purpose of vaccine production. Second, recombinant viral protein vaccines may exhibit poor immunogenicity, owing to improper folding, poor antigen presentation, and/or the generation of a primarily humoral immune response that is ineffective in conferring long-lasting, protective immunity.

There are four types of influenza virus: A, B, C and D, of which influenza A and B are the causative organism for seasonal disease epidemics in humans.

Influenza A viruses are further divided based on the expression of hemagglutinin (HA) and neuraminidase (NA) glycoprotein subtypes on the surface of the virus. There are 18 different HA subtypes (H1-H18).

HA is a trimeric lectin that facilitates binding of the influenza virus particle to sialic acid-containing proteins on the surface of target cells and mediates release of the viral genome into the target cell. HA proteins comprise two structural elements: the head, which is the primary target of seroprotective antibodies; and the stalk. A publication by Ha et al. 2002 (EMBO J. 21:865-875; which is incorporated herein by reference) illustrates the relative orientation of the various subdomains of the stem domain cluster (SDC) and head domain cluster (HDC) in several influenza subtypes, based on Xray crystallographic structures.

HA is translated as a single polypeptide, HA0 (assembled as trimers), that must be cleaved by a serine endoprotease between the HA1 (~40 kDa) and HA2 (~20 kDa) subdomains. After cleavage, the two disulfide-bonded protein domains adopt the requisite conformation necessary for viral infectivity. HA1 forms the globular head domain containing vestigial esterase domains E1' and E2 and a receptor-binding site (RBS), and the RBS the least conserved segment of influenza virus. HA2 is a single-pass integral membrane protein with fusion peptide (FP), soluble ectodomain (SE), transmembrane (TM), and cytoplasmic tail (CT) with respective lengths of approximately 25, 160, 25, and 10 residues. HA2 together with the N and C terminal HA1 residues forms a stalk domain, which includes the transmembrane region, and is relatively conserved.

Various mutations in influenza virus proteins, particularly influenza HA, have been investigated.

For example, Castelán-Vega et al. (*Adv Appl Bioinform Chem.* 2014; 7:37-44) used a stability prediction algorithm to compare 7,479 full-length amino acid sequences of HA from the influenza A (H1N1)pdm09 virus and identified that D104N, A259T, S124N, and E172K mutations resulted in a predicted enhancement of influenza HA stability. In contrast, S206T, K285E, and E47K mutations had a predicted destabilizing effect on HA.

In comparing the sequences of the original influenza A (H1N1)pdm [A/California/7/2009] and a later-emerging influenza strain [A/Brisbane/10/2010], Cotter et al. (*PLoS Pathog.* 2014; 10(1):e1003831) identified that a E47K mutation in the stalk region of A/California/7/2009 HA stabilized the trimer structure, lowered the pH for membrane fusion, and increased the thermal and acid stability of the virus. Cotter et al. additionally observed that A/California/7/2009 E47K mutant HA was more infectious in ferrets than its wildtype counterpart.

Antanasijevic et al. (*J Biol Chem.* 2014; 289(32):22237-45) investigated the structure-function properties of H5 HA stem loop region by site directed mutagenesis at 14 different positions. A/Vietnam/1203/04 (H5N1) mutants were expressed in HEK 293T cells and Antanasijevic reported that most mutations in the stem loop region did not disrupt expression, proteolytic processing, viral assembly, or receptor binding. However, Antanasijevic observed that HA1-D26K, HA1-M102L, HA2-V52A and HA2-I55A mutants (based on H3 numbering) exhibited significantly reduced levels of total HA, suggesting reduced expression and/or assembly of HA into viral particles. HA1-D26K, HA2-T49A and HA2-M102L mutants also exhibited lower hemagglutination titers as compared to wildtype virus. Antanasijevic additionally observed that all single mutants exhibited decreased entry into A549 lung cells, with the most pronounced impairment shown in HA1-D26K and HA2-I55A mutants. Antanasijivec further demonstrated that the HA2-L99A mutant was more sensitive to A549 lung cell inhibition by C179 neutralizing antibody as compared to wildtype virus, suggesting that the mutation enhances antibody binding and/or the mode of neutralizing action. In contrast, HA1-I28A, HA1-M31A, HA1-M31L, HA2-I45A, and HA2-155V mutants were rendered less sensitive to entry inhibition by C179 neutralizing antibody.

WO2013/177444 and its companion publication Lu et al. (*Proc Natl Acad Sci USA.* 2014; 111(1):125-30) reported a method for the production of properly folded HA stem domain from A/California/05/2009 (H1N1) using an *Escherichia coli*-based cell-free protein expression system and a simple refolding protocol. For inducing the trimerization of HA stem domain, either a chloramphenicol acetyl transferase (CAT) or foldon domain was fused to the C terminus of the HA. To mitigate newly exposed hydrophobicity and/or intermolecular ion pairing causing aggregation of expressed HA stem protein, five groups of mutations were evaluated: M1 (I69T+I72E+I74T+C77T); M2 (I69T+I72E+I74T+C77T+F164D); M3 (I69T+I72E+I74T+C77T+F164D+L174D); M4 (F164D); and M5 (F164D+L174D). Lu observed that the M5 (F164D+L174D) mutations appeared to be the most influential mutations for improving HA stem protein solubility. Additional deletions (H38 to C43 and C49 to N61) and a C77T mutation were made to M5 mutants to avoid the formation of undesirable disulfide bonds, reduce surface hydrophobicity and pI, and avoid regions with disordered structure.

U.S. application Ser. No. 13/838,796 and its companion publication by Holtz et al. (*BMC Biotechnology*. 2014; 14:111) teach the improved stability and maintained potency of recombinant HA by the mutation of cysteine residues in the carboxy terminal region of the HA protein including the transmembrane (TM) and cytosolic domain (CT). Specifically, Holtz et al. demonstrate C539A, C546A, C549A, C524S and C528A mutations in recombinant Perth/16/2009 HA (H3N2). Mutation of all five cysteine residues, or different subsets thereof, resulted in HA yields, purities, particle size, hemagglutination activity, and thermostability comparable to recombinant wildtype HA protein. In contrast, C64S and C76S mutations resulted in significantly reduced HA expression, indicating the critical role of these residues in proper HA folding. By using a single radial immune-diffusion assay (SRID), Holtz et al. also show that the five cysteine residue mutations improve potency of recombinant HA as compared to wildtype protein, by preventing disulfide cross-linking in the TM and CT domains. The mutant HA proteins maintain potency for at least 12 months at 25° C., whereas wildtype HA protein exhibited less than 40% potency after only 50 days post purification.

WO2015/020913 teaches the mutation of specific residues at one or more positions selected from the group of 403, 406, 411, 422, 429, 432, 433, and 435 of influenza A/Puerto Rico/8/1934 (H1N1) to tyrosine. These mutations facilitate the formation of di-tyrosine cross-links that stabilize or "lock" the stalk domain of influenza HA in its native trimeric conformation.

WO2013/079473 discloses a modified influenza HA lacking a globular head domain. The polypeptide taught in WO2013/079473 comprises an HA1 domain where amino acids 53 to 620 (with reference to A/Brisbane/59/2007 [H1N1] numbering) are deleted and replaced with covalently linked sequence of 0 to 10 amino acids, and an HA2 domain, wherein the C-terminal amino acid of the HA1 domain is an amino acid other than arginine or lysine, and wherein one or more amino acids at position 406, 409, 413 and 416 are mutated to an amino acid selected from the group consisting of serine, threonine, asparagine, glutamine, arginine, histidine, lysine, aspartic acid, glutamic acid, and glycine.

WO2014/191435 similarly teaches a modified influenza HA comprising an HA1 domain having a deleted segment replaced with a covalently linked sequence of 0 to 50 amino acids, and an HA2 domain, wherein the HA is resistant to cleavage at the junction between HA1 and HA2 and wherein one or more amino acids at positions 337, 340, 352, 353, 402, 406, 409, 413 and/or 416 have been mutated.

Virus-like particles (VLPs) are potential candidates for inclusion in immunogenic compositions. VLPs closely resemble mature virions, but they do not contain viral genomic material. Therefore, VLPs are non-replicative in nature, which make them safe for administration as a vaccine. In addition, VLPs can be engineered to express viral glycoproteins on the surface of the VLP, which is their most native physiological configuration. Moreover, since VLPs resemble intact virions and are multivalent particulate structures, VLPs may be more effective in inducing neutralizing antibodies to the glycoprotein than soluble envelope protein antigens.

VLPs have been produced in plants (see for example WO2009/076778; WO2009/009876; WO 2009/076778; WO 2010/003225; WO 2010/003235; WO2010/006452; WO2011/03522; WO 2010/148511; and WO2014153674, which are incorporated herein by reference).

WO2009/076778 teaches a method of producing influenza VLPs in plants comprising introducing a nucleic acid having a regulatory region active in the plant operatively linked to a nucleotide sequence encoding an influenza HA from a type A or type B influenza.

WO2009/009876 teaches a method of producing influenza HA VLPs in plants, wherein influenza HA self-assembles into VLPs in plant cells and bud from plant cell membranes.

WO2010/003225 discloses a method of producing influenza HA VLPs in plants comprising introducing a nucleic acid having a regulatory region active in the plant, operatively linked to a nucleotide sequence encoding an influenza HA from A/California/04/09 (H1N1).

WO2010/006452 teaches the production of VLPs comprising modified influenza HA proteins, wherein glycosylation sites at positions 154, 165, 286, or combinations thereof (with reference to A/Vietnam/1194/04 [H5N1] numbering), have been abolished by mutating the residues at said positions to amino acids other than asparagine. WO2010/006452 further teaches that amino acids at positions 156, 167, 288, or combinations thereof, may be mutated to residues other than serine or threonine to similarly abolish the N-linked glycosylation signal triad "N-X-S/T". By selectively deleting glycosylation sites located in the globular head of the HA protein, WO2010/006452 demonstrates that the resulting HA protein has increased antigenicity and broader cross-reactivity.

WO2011/035422 teaches a method of preparing plant-derived VLPs comprising: obtaining a plant or plant matter comprising apoplast-localized VLPs; producing a protoplast/spheroplast fraction and an apoplast fraction; and recovering the apoplast fraction comprising the plant-derived VLPs.

WO2010/148511 discloses a method for producing influenza VLPs in plants, wherein the VLPs comprise chimeric HA proteins. The chimeric HA proteins comprise a stem domain cluster having an F'1, F'2 and F subdomain; a head domain cluster having an RB, E1 and E2 subdomain; and a transmembrane domain cluster having a transmembrane domain and a C-terminal tail domain, wherein at least one subdomain is derived from a first influenza strain and the other subdomains are derived from one or more second influenza strain.

WO2014/153674 teaches a method of producing influenza VLPs in a plant, wherein the VLPs comprise modified influenza HA having a modified proteolytic loop. The modified proteolytic loop comprises the removal of the proteolytic cleavage site between HA1 and HA2 domains of the HA0 precursor. The HA protein is thus stabilized and increased protein yields are achieved as compared to native HA protein.

SUMMARY OF THE INVENTION

The present invention relates to the production of modified influenza viral proteins in plants. More specifically, the present invention relates to producing and increasing influenza virus-like particle (VLP) production in plants, wherein the VLPs comprise the modified influenza viral proteins for example a modified hemagglutinin (HA) protein.

It is an object of the invention to provide an improved method to increase influenza VLP production in plants.

According to the present invention, there is provided:

A nucleic acid comprising a nucleotide sequence encoding a modified influenza H1 hemagglutinin (HA) protein, the HA protein comprising an amino acid sequence comprising at least one substitution when compared to a corresponding wildtype amino acid sequence, said at least one substitution being at one or more than one amino acid corresponding to amino acids at position 97, 374, 390 or 429 of H1 A/Michigan/45/15 HA.

The HA protein may comprise an amino acid sequence with a substitution to a non-asparagine at the amino acid corresponding to the amino acid at position 97 of H1 A/Michigan/45/15 HA. The HA protein may comprise an amino acid sequence with a substitution to an aspartic acid or a conserved substitution of aspartic acid at the amino acid corresponding to the amino acid at position 97 of H1 A/Michigan/45/15 HA.

The HA protein may comprise an amino acid sequence with a substitution to a non-lysine at the amino acid corresponding to the amino acid at position 374 of H1 A/Michigan/45/15 HA. The HA protein may comprise an amino acid sequence with a substitution to a glutamic acid or a conserved substitution of glutamic acid at the amino acid corresponding to the amino acid at position 374 of H1 A/Michigan/45/15 HA.

The HA protein may comprise an amino acid sequence with a substitution to a non-phenylalanine at the amino acid corresponding to the amino acid at position 390 of H1 A/Michigan/45/15 HA. The HA protein may comprise an amino acid sequence with a substitution to an aspartic acid or a conserved substitution of aspartic acid at the amino acid corresponding to the amino acid at position 390 of H1 A/Michigan/45/15 HA.

The HA protein may comprise an amino acid sequence with a substitution to a non-leucine at the amino acid corresponding to the amino acid at position 429 of H1 A/Michigan/45/15 HA. The HA protein may comprise an amino acid sequence with a substitution to a methionine or a conserved substitution of methionine at the amino acid corresponding to the amino acid at position 429 of H1 A/Michigan/45/15 HA.

The HA protein may further comprise an amino acid sequence with a substitution to a non-asparagine at the amino acid corresponding to the amino acid at position 380 of H1 A/Michigan/45/15 HA. The HA protein may comprise an amino acid sequence with a substitution to a alanine or a conserved substitution of alanine at the amino acid corresponding to the amino acid at position 380 of H1 A/Michigan/45/15 HA.

The HA protein may further comprise an amino acid sequence with a first substitution to a non-phenylalanine at the amino acid corresponding to amino acid at position 390 of H1 A/Michigan/45/15 HA and a second substitution to a non-leucine at the amino acid corresponding to amino acid at position 429 of H1 A/Michigan/45/15 HA. The HA protein may further comprise an amino acid sequence with a first substitution to an aspartic acid or a conserved substitution of aspartic acid at the amino acid corresponding to amino acid at position 390 of H1 A/Michigan/45/15 HA and a second substitution to a methionine or a conserved substitution of methionine at the amino acid corresponding to amino acid at position 429 of H1 A/Michigan/45/15 HA.

The HA protein may further comprise an amino acid sequence with a first substitution to a non-asparagine at the amino acid corresponding to amino acid at position 97 of H1 A/Michigan/45/15 HA and a second substitution to a non-lysine at the amino acid corresponding to amino acid at position 374 of H1 A/Michigan/45/15 HA. The HA protein may further comprise an amino acid sequence with a first substitution to an aspartic acid or a conserved substitution of aspartic acid at the amino acid corresponding to amino acid at position 97 of H1 A/Michigan/45/15 HA and a second substitution to glutamic acid or a conserved substitution of glutamic acid at the amino acid corresponding to amino acid at position 374 of H1 A/Michigan/45/15 HA.

The HA protein may further comprise an amino acid sequence with a first substitution to a non-asparagine at the amino acid corresponding to amino acid at position 97 of H1 A/Michigan/45/15 HA, a second substitution to a non-phenylalanine at the amino acid corresponding to amino acid at position 390 of H1 A/Michigan/45/15 HA and a third substitution to a non-leucine at the amino acid corresponding to amino acid at position 429 of H1 A/Michigan/45/15 HA. The HA protein may further comprise an amino acid sequence with a first substitution to an aspartic acid or a conserved substitution of aspartic acid at the amino acid corresponding to amino acid at position 97 of H1 A/Michigan/45/15 HA, a second substitution to an aspartic acid or a conserved substitution of aspartic acid at the amino acid corresponding to amino acid at position 390 of H1 A/Michigan/45/15 HA and a third substitution to a methionine or a conserved substitution of methionine at the amino acid corresponding to amino acid at position 429 of H1 A/Michigan/45/15 HA.

The HA protein may further comprise an amino acid sequence with a first substitution to a non-lysine at the amino acid corresponding to amino acid at position 374 of H1 A/Michigan/45/15 HA, a second substitution to a non-phenylalanine at the amino acid corresponding to amino acid at position 390 of H1 A/Michigan/45/15 HA and a third substitution to a non-leucine at the amino acid corresponding to amino acid at position 429 of H1 A/Michigan/45/15 HA. The HA protein may further comprise an amino acid sequence with a first substitution to a glutamic acid or a conserved substitution of glutamic acid at the amino acid corresponding to amino acid at position 374 of H1 A/Michigan/45/15 HA, a second substitution to an aspartic acid or a conserved substitution of aspartic acid at the amino acid corresponding to amino acid at position 390 of H1 A/Michigan/45/15 HA and a third substitution to a methionine or a conserved substitution of methionine at the amino acid corresponding to amino acid at position 429 of H1 A/Michigan/45/15 HA.

The HA protein may further comprise an amino acid sequence with a first substitution a non-asparagine at the amino acid corresponding to amino acid at position 97 of H1 A/Michigan/45/15 HA, a second substitution to a non-lysine at the amino acid corresponding to amino acid at position 374 of H1 A/Michigan/45/15 HA, a third substitution to a non-phenylalanine at the amino acid corresponding to amino acid at position 390 of H1 A/Michigan/45/15 HA and a fourth substitution to a non-leucine at the amino acid corresponding to amino acid at position 429 of H1 A/Michigan/45/15 HA. The HA protein may further comprise an amino acid sequence with a first substitution to an aspartic acid or a conserved substitution of aspartic acid at the amino acid corresponding to amino acid at position 97 of H1 A/Michigan/45/15 HA, a second substitution to a glutamic acid or a conserved substitution of glutamic acid at the amino acid corresponding to amino acid at position 374 of H1 A/Michigan/45/15 HA, a third substitution to an aspartic acid or a conserved substitution of aspartic acid at the amino acid corresponding to amino acid at position 390 of H1 A/Michigan/45/15 HA and a fourth substitution to a methionine or a conserved substitution of methionine at the amino acid corresponding to amino acid at position 429 of H1 A/Michigan/45/15 HA.

Further provided are HA protein encoded by the recombinant nucleic acids as described above and virus-like particle (VLP) comprising the HA protein encoded by the recombinant nucleic acids as described above.

It is therefore provided a modified influenza H1 hemagglutinin (HA) protein, the HA protein comprising an amino acid sequence comprising at least one substitution when compared to a corresponding wildtype amino acid sequence, said at least one substitution being at one or more than one amino acid corresponding to amino acid at position 97, 374, 390 or 429 of H1 A/Michigan/45/15 HA.

Furthermore a method of producing an influenza virus like particle (VLP) in a plant, portion of a plant, or a plant cell, is provided, the method comprising:
 a) introducing the recombinant nucleic acid as described above into the plant, portion of the plant, or plant cell; and
 b) incubating the plant, portion of the plant, or plant cell under conditions that permit expression of the HA protein encoded by the recombinant nucleic acid, thereby producing the VLP. The method may further comprises a step c) of harvesting the plant, portion of the plant, or plant cell, and purifying the VLP.

It is further provided a method of producing an influenza virus like particle (VLP) in a plant, portion of a plant, or a plant cell, comprising:
 a) providing a plant, portion of a plant, or plant cell comprising the recombinant nucleic acid as described above; and
 b) incubating the plant, portion of the plant, or plant cell under conditions that permit expression of the HA protein encoded by the recombinant nucleic acid, thereby producing the VLP. The method may further comprises a step c) of harvesting the plant, portion of the plant, or plant cell, and purifying the VLP.

Furthermore, it is provided a method of increasing yield of production of an influenza virus like particle (VLP) in a plant, portion of a plant, or a plant cell, comprising: a) introducing the recombinant nucleic acid into the plant, portion of the plant, or plant cell; or providing a plant, portion of a plant, or plant cell comprising the recombinant nucleic acid; and b) incubating the plant, portion of the plant, or plant cell under conditions that permit expression of the HA protein encoded by the recombinant nucleic acid, thereby producing the VLP at a higher yield compared to plant, portion of the plant, or plant cell expressing an unmodified influenza HA protein. The method may further comprises a step c) of harvesting the plant, portion of the plant, or plant cell, and purifying the VLP.

The methods may further comprise introducing a second nucleic acid encoding a proton channel protein; wherein the plant, portion of the plant, or plant cell is incubated under conditions that permit expression of the proton channel protein encoded by the second nucleic acid. The proton channel protein may be an influenza A subtype M2 protein.

It is further provided a VLP produced by the method as described herewith.

The VLP may comprise one or more than one lipid derived from the plant, portion of the plant, or plant cell, plant-specific N-glycans, modified N-glycans or a combination thereof.

In addition a method of producing an antibody or antibody fragment is provided, the method comprising administering the VLP as described to a subject, or a host animal, thereby producing the antibody or the antibody fragment. Antibodies or the antibody fragments produced by the method are also provided.

Furthermore it is provided a plant, portion of the plant, or plant cell comprising the recombinant nucleic acid or HA protein encoded by the recombinant nucleic acid. The HA protein may form VLP. Accordingly, a plant, portion of the plant, or plant cell comprising VLP comprising HA protein encoded by the recombinant nucleic acid are also provided.

In addition, it is provided a composition for inducing an immune response comprising, an effective dose of the VLP as described herewith, and a pharmaceutically acceptable carrier, adjuvant, vehicle or excipient. A method for inducing immunity to an influenza infection in a subject, the method comprising administering the VLP as described is also provided. The VLP may be administered to the subject orally, intranasally, intramuscularly, intraperitoneally, intravenously or subcutaneously.

Furthermore, it is provided a modified influenza hemagglutinin (HA) protein comprising an amino acid sequence having from about 30% to about 100%, sequence identity or sequence similarity with a sequence of the sequences of SEQ ID NO: 18, SEQ ID NO: 22, SEQ ID NO: 24, SEQ ID NO: 4, SEQ ID NO: 28, SEQ ID NO: 32, SEQ ID NO: 36, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 72, SEQ ID NO: 77, SEQ ID NO: 80, SEQ ID NO: 82, SEQ ID NO: 84, SEQ ID NO: 86, SEQ ID NO: 89, SEQ ID NO: 91, SEQ ID NO: 93, SEQ ID NO: 95, SEQ ID NO: 97, SEQ ID NO: 105, SEQ ID NO: 108, SEQ ID NO: 124, SEQ ID NO: 126, SEQ ID NO: 128, SEQ ID NO: 140, SEQ ID NO: 143, SEQ ID NO: 145, SEQ ID NO: 147, SEQ ID NO: 149, provided that the influenza HA protein comprises at least on substitution as described herewith and is able to form VLPs, induces an immune response when administered to a subject, induces hemagglutination or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a sequence alignment of the amino acid sequences of hemagglutinin (HA) of A/California/7/09 (H1N1) (SEQ ID NO: 130); A/Honduras/17734/16 (H1N1) (SEQ ID NO:131); A/Darwin/11/15 (H1N1) (SEQ ID NO: 132); A/Costa Rica/0513/16 (H1N1) (SEQ ID NO: 133); A/Michigan/45/15 (H1N1) (SEQ ID NO: 134); A/Massachusetts/06/17 (H1N1) (SEQ ID NO: 135). Outlined residues align with amino acids D97, E374, F390, and L429 of HA from influenza H1 strains (H1N1) for example A/California/7/09 (H1N1).

09 mutant H1, L429M A/California/07/09 mutant H1, and F390D A/California/07/09 mutant H1.

Figure 3B:
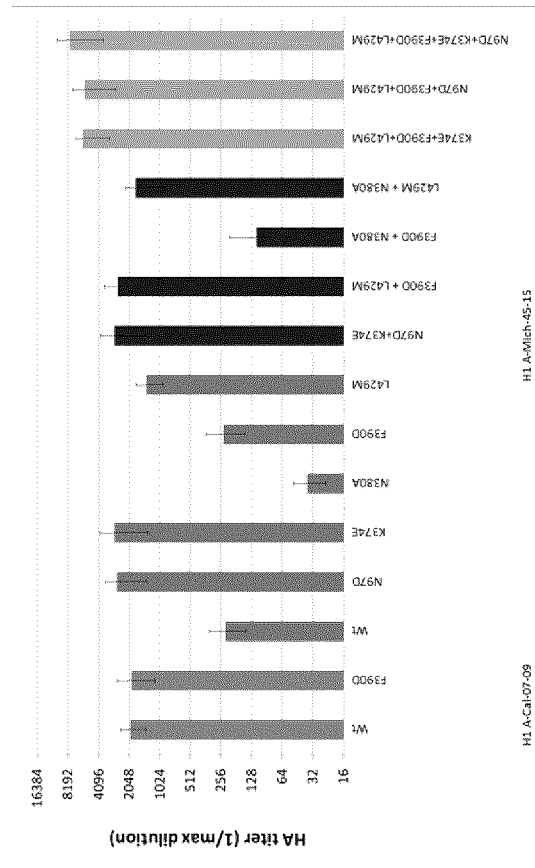
Figure 3A:
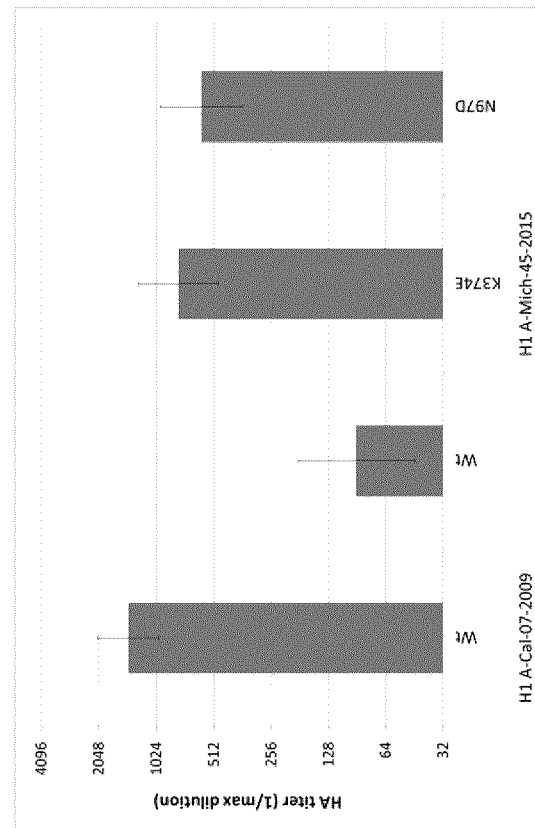

FIG. 3A shows the hemagglutination titers of wildtype A/California/07/09 H1, wildtype A/Michigan/45/15 H1, K374E A/Michigan/45/15 mutant H1 and N97D A/Michigan/45/15 mutant H1. FIG. 3B shows the hemagglutination titers of wildtype A/California/07/09 H1, F390D A/California/07/09 mutant H1, wildtype A/Michigan/45/15 H1, N97D A/Michigan/45/15 mutant H1, K374E A/Michigan/45/15 mutant H1, N380A A/Michigan/45/15 mutant H1, F390D A/Michigan/45/15 mutant H1, L429M A/Michigan/45/15 mutant H1, N97D+K374E A/Michigan/45/15 mutant H1, F390D+L429M A/Michigan/45/15 mutant H1, F390D+N380A A/Michigan/45/15 mutant H1, L429M+N380A A/Michigan/45/15 mutant H1, K374E+F390D+L429M A/Michigan/45/15 mutant H1, N97D+F390D+L429M A/Michigan/45/15 mutant H1 and N97D+K374E+F390D+L429M A/Michigan/45/15 mutant H1.

FIG. 4A shows the hemagglutination titers of wildtype A/Michigan/45/15 H1, N97D A/Michigan/45/15 mutant H1, K374E A/Michigan/45/15 mutant H1, F390D A/Michigan/45/15 mutant H1, L429M A/Michigan/45/15 mutant H1, F390D+L429M A/Michigan/45/15 mutant H1 and N97+F390D+L429M A/Michigan/45/15 mutant H1; hemagglutination titers of wildtype A/Honduras/17734/16 H1, N97D A/Honduras/17734/16 mutant H1, K374E A/Honduras/17734/16 mutant H1, F390D A/Honduras/17734/16 mutant H1, L429M A/Honduras/17734/16 mutant H1, F390D+L429M A/Honduras/17734/16 mutant H1, and N97D+F390D+L429M A/Honduras/17734/16 mutant H1; and hemagglutination titers of wildtype A/Darwin/11/15 H1, N97D A/Darwin/11/15 mutant H1, K374E A/Darwin/11/15 mutant H1, F390D A/Darwin/11/15 mutant H1, L429M A/Darwin/11/15 mutant H1 F390D+L429M A/Darwin/11/15 mutant H1 and N97D+F390D+L429M A/Darwin/11/15 mutant H1. FIG. 4B shows the hemagglutination titers of F390D+L429M A/Michigan/45/15, F390D+L429M A/Massachusetts/06/17 mutant H1, K374E+F390D+L429M A/Massachusetts/06/17 mutant H1, N97D+F390D+L429M A/Massachusetts/06/17 mutant H1, and N97D+K374E+F390D+L429M A/Massachusetts/06/17 mutant H1; hemagglutination titers of F390D+L429M A/Costa Rica/0513/16 mutant H1, K374E+F390D+L429M A/Costa Rica/0513/16 mutant H1, N97D+F390D+L429M A/Costa Rica/0513/16 mutant H1, and N97D+K374E+F390D+L429M A/Costa Rica/0513/16 mutant H1. FIG. 4C shows the hemagglutination titers of F390D+L429M A/Michigan/45/15, F390D+L429M A/Paris/1227/2017 mutant H1, K374E+F390D+L429M A/Paris/1227/2017 mutant H1, N97D+F390D+L429M A/Paris/1227/2017mutant H1, and N97D+K374E+F390D+L429M A/Paris/1227/2017 mutant H1; hemagglutination titers of F390D+L429M A/Norway/2147/2017 mutant H1, K374E+F390D+L429M A/Norway/2147/2017 mutant H1, N97D+F390D+L429M A/Norway/2147/2017 mutant H1, and N97D+K374E+F390D+L429M A/Norway/2147/2017 mutant H1.

FIG. 5 shows the hemagglutination titers of wildtype A/Indonesia/5/2005 H5, wildtype A/Egypt/N04915/2014 H5, F393D A/Indonesia/5/2005 mutant H5, F393D A/Egypt/N04915/2014 mutant H5, N383A A/Indonesia/5/2005 mutant H5, and N383A A/Egypt/N04915/2014 mutant H5. The numbering is in accordance with A/Indonesia/5/2005.

FIG. 6A shows a schematic representation of vector 1314 (H1 A-Cal-7-2009). FIG. 6B shows a schematic representation of vector 2980 (H1 A-Cal-7-09 (F390D)). FIG. 6C shows a schematic representation of vector 2962 (H1 A-Cal-7-09 (L429M)). FIG. 6D shows a schematic representation of vector 2995 (H1 A-Cal-7-09 (F390D+L429M)). FIG. 6E shows a schematic representation of vector 3640 (H1 A-Mich-45-2015). FIG. 6F shows a schematic representation of vector 3774 (H1 A-Mich-45-2015 (N97D). FIG. 6G shows a schematic representation of vector 3771 (H1 A-Mich-45-2015 (K374E). FIG. 6H shows a schematic representation of vector 3641 (H1 A-Mich-45-2015 (F390D). FIG. 6I shows a schematic representation of vector 3643 (H1 A-Mich-45-2015 (L429M)). FIG. 6J shows a schematic representation of vector 3880 (H1 A-Mich-45-2015 (N97D+K374E)). FIG. 6K shows a schematic representation of vector 3703 (H1 A-Mich-45-2015 (F390D+L429M)). FIG. 6L shows a schematic representation of vector 3879 (H1 A-Mich-45-2015 (N97D+F390D+L429M)). FIG. 6M shows a schematic representation of vector 3878 (H1 A-Mich-45-2015 (K374E+F390D+L429M)). FIG. 6N shows a schematic representation of vector 3881 (H1 A-Mich-45-2015 (N97D+K374E+F390D+L429M)). FIG. 6O shows a schematic representation of vector 4091 (H1 A-Mass-06-2017 (F390D+L429M). FIG. 6P shows a schematic representation of vector 4093 (H1 A-Mass-06-2017 (N97D+F390D+L429M)). FIG. 6Q shows a schematic representation of vector 4092 (H1 A-Mass-06-2017 (K374E+F390D+L429M)). FIG. 6R shows a schematic representation of vector 4094 (H1 A-Mass-06-2017 (N97D+K374E+F390D+L429M)). FIG. 6S shows a schematic representation of vector 4715 (H1 A-CostaRica-0513-2016 (F390D+L429M)). FIG. 6T shows a schematic representation of vector 4717 (H1 A-CostaRica-0513-2016 (N97D+F390D+L429M)). FIG. 6U shows a schematic representation of vector 4716 (H1 A-CostaRica-0513-2016 (K374E+F390D+L429M)). FIG. 6V shows a schematic representation of vector 4718 (H1 A-CostaRica-0513-2016 (N97D+K374E+F390D+L429M)). FIG. 6W shows a schematic representation of vector 3944 (H1 A-Hond-17734-16). FIG. 6X shows a schematic representation of vector 3950 (H1 A-Hond-17734-16 (N97D)). FIG. 6Y shows a schematic representation of vector 3948 (H1 A-Hond-17734-16 (K374E)). FIG. 6Z shows a schematic representation of vector 3945 (H1 A-Hond-17734-16 (F390D)). FIG. 6AA shows a schematic representation of vector 3949 (H1 A-Hond-17734-16 (L429M)). FIG. 6BB shows a schematic representation of vector 3946 (H1 A-Hond-17734-16 (F390D+L429M)). FIG. 6CC shows a schematic representation of vector 3951 (H1 A-Hond-17734-16 (N97D+F390D+L429M)). FIG. 6DD shows a schematic representation of vector 3984 (H1 A-Darw-11-15). FIG. 6EE shows a schematic representation of vector 3990 (H1 A-Darw-11-15 (N97D)). FIG. 6FF shows a schematic representation of vector 3988 (H1 A-Darw-11-15 (K374E)). FIG. 6GG shows a schematic representation of vector 3985 (H1 A-Darw-11-15 (F390D)). FIG. 6HH shows a schematic representation of vector 3989 (H1 A-Darw-11-15 (L429M)). FIG. 6II shows a schematic representation of vector 3986 (H1 A-Darw-11-15 (F390D+L429M)). FIG. 6JJ shows a schematic representation of vector 3991 (H1 A-Darw-11-15 (N97D+F390D+L429M)). FIG. 6KK shows a schematic representation of vector 3644 (H1 A-Mich-45-2015 (N380A)). FIG. 6LL shows a schematic representation of vector 3704 (H1 A-Mich-45-2015 (F390D+N380A)). FIG. 6MM shows a schematic representation of vector 4765 (A/Paris/1227/17 (F390D+L429M)). FIG. 6NN shows a schematic representation of vector 4766 (A/Paris/1227/17 (K374E+F390D+L429M)). FIG. 6OO shows a schematic representation of vector 4767 (A/Paris/1227/17 (N97D+F390D+L429M)). FIG. 6PP shows a schematic representation of vector 4768 (A/Paris/1227/17 (N97D+K374E+

F390D+L429M)). FIG. 6QQ shows a schematic representation of vector 4775 (A/Norway/2147/17 (F390D+L429M)). FIG. 6RR shows a schematic representation of vector 4776 (A/Norway/2147/17 (K374E+F390D+L429M)). FIG. 6SS shows a schematic representation of vector 4777 (A/Norway/2147/17 (N97D+F390D+L429M)). FIG. 6TT shows a schematic representation of vector 4778 (A/Norway/2147/17 (N97D+K374E+F390D+L429M)).

FIG. 7A shows a schematic representation of vector 2295 (H5 A-Indo-5-05). FIG. 7B shows a schematic representation of vector 3680 (H5 A-Indo-5-05 (F393D)). FIG. 7C shows a schematic representation of vector 3645 (H5 A-Egypt-N04915-14). FIG. 7D shows a schematic representation of vector 3690 (H5 A-Egypt-N04915-14 (F392D)).

FIG. 8 shows a schematic representation of vector 1190 (Vector for In-Fusion cloning into CPMV 160-based expression cassette).

DETAILED DESCRIPTION

The following description is of a preferred embodiment.

As used herein, the terms "comprising", "having", "including", "containing", and grammatical variations thereof, are inclusive or open-ended and do not exclude additional, un-recited elements and/or method steps. The term "consisting essentially of" when used herein in connection with a product, use or method, denotes that additional elements and/or method steps may be present, but that these additions do not materially affect the manner in which the recited method or use functions. The term "consisting of" when used herein in connection with a product, use or method, excludes the presence of additional elements and/or method steps. A product, use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion', "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, herbaceous plants. Furthermore plants may include, but are not limited to, agricultural crops including for example canola, Brassica spp., maize, Nicotiana spp., (tobacco) for example, Nicotiana benthamiana, Nicotiana rustica, Nicotiana tabacum, Nicotiana alata, Arabidopsis thaliana, alfalfa, potato, sweet potato (Ipomoea batatus), ginseng, pea, oat, rice, soybean, wheat, barley, sunflower, cotton, corn, rye (Secale cereale), Sorghum (Sorghum bicolor, Sorghum vulgare), safflower (Carthamus tinctorius).

The term "plant portion", as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term "construct", "vector" or "expression vector", as used herein, refers to a recombinant nucleic acid for transferring exogenous nucleic acid sequences into host cells (e.g. plant cells) and directing expression of the exogenous nucleic acid sequences in the host cells. "Expression cassette" refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the Arabidopsis ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004), the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC contact (when compared to the wild type nucleotide sequence) exhibits increased expression within a plant, portion of a plant, or a plant cell, when compared to expression of the non-human optimized (or lower GC content) nucleotide sequence.

Modified influenza hemagglutinin (HA) proteins (also termed modified HA protein, modified influenza HA protein, modified HA, modified influenza HA, mutant HA, influenza mutant HA, influenza HA variants or HA variants) and methods of producing modified influenza HA proteins in plants are described herein. The modified influenza HA proteins disclosed herewith comprise modifications or mutations that have been found to result in improved HA characteristics as compared to the wildtype HA or unmodified HA proteins. For example, the modified influenza HA protein may have an amino acid sequence with at least one substitution of an amino acid when compared to a corresponding wildtype amino acid sequence.

Examples of improved characteristics of the modified HA protein include, increased HA protein yield when expressed in plant cells as compared to the wildtype or unmodified HA of the same strain or subtype of influenza that does not comprise the modification(s) or mutation(s); improved hemagglutination titer of the modified HA protein when compared to the wildtype or unmodified HA protein; improved integrity, stability, or both integrity and stability, of virus like particles (VLPs) that are comprised of the modified HA proteins as compared to the integrity, stability or both of VLPs comprising wildtype HA that does not comprise the modification(s) or mutation(s); increased VLP yield when expressed in plant cells as compared to the wildtype level of VLP production that does not comprise the modification(s) or mutation(s); and a combination thereof.

Influenza Subtypes and Strain

The term "influenza virus subtype" as used herein refers to influenza A virus variants that are characterized by various combinations of the hemagglutinin (H or HA) and neuramidase (N) viral surface proteins. According to the present specification, influenza virus subtypes and hemagglutinin (HA) from such virus subtypes may be referred to by their H number, such as, for example, "HA of the H1 subtype", "H1 HA", or "H1 influenza". The term "subtype" specifically includes all individual "strains" within each subtype, which usually result from mutations and may show different pathogenic profiles. Such strains may also be referred to as various "isolates" of a viral subtype. Accordingly, as used herein, the terms "strains" and "isolates" may be used interchangeably.

Traditionally, different strains of influenza have been categorized based upon, e.g., the ability of influenza to agglutinate red blood cells (RBCs or erythrocytes). Antibodies specific for particular influenza strains may bind to the virus and, thus, prevent such agglutination. Assays determining strain types based on such inhibition are typically known as hemagglutinin inhibition assays (HI assays or HAI assays) and are standard and well known methods in the art to characterize influenza strains.

However, HA proteins from different virus strains also show significant sequence similarity at both the nucleic acid and amino acid levels. This level of similarity varies when strains of different subtypes are compared, with some strains clearly displaying higher levels of similarity than others (Air, Proc. Natl. Acad. Sci. USA, 1981, 78:7643). The levels of amino acid similarity vary between virus strains of one subtype and virus strains of other subtypes (Air, Proc. Natl. Acad. Sci. USA, 1981, 78:7643). This variation is sufficient to establish discrete subtypes and the evolutionary lineage of the different strains, but the DNA and amino acid sequences of different strains are still readily aligned using conventional bioinformatics techniques (Air, Proc. Natl. Acad. Sci. USA, 1981, 78:7643; Suzuki and Nei, Mol. Biol. Evol. 2002, 19:501).

Multiple nucleotide sequences, or corresponding polypeptide sequences of hemagglutinin (HA), may be aligned to determine a "consensus" or "consensus sequence" of a subtype (see FIG. 1).

Based on sequence similarities, influenza virus subtypes can further be classified by reference to their phylogenetic group. Phylogenetic analysis (Fouchier et al., J Virol. 2005 March; 79(5):2814-22) has demonstrated a subdivision of HAs that falls into two main groups (Air, Proc. Natl. Acad. Sci. USA, 1981, 78:7643): inter alia the H1, H2, H5 and H9 subtypes in phylogenetic group 1 and inter alia the H3, H4 and H7 subtypes in phylogenetic group 2.

New influenza HA proteins, HA modifications, HA protein variants and mutants are created by introducing changes to the amino acid sequence of HA protein that results in an improved characteristic of the HA as described above. Isolation of nucleic acids encoding such HA molecules is routine, as is modification of the nucleic acid to introduce changes in the amino acid sequence, e.g., by site-directed mutagenesis.

Modified influenza HA proteins and methods of producing modified influenza HA proteins in plants are described herein. It has been observed that the modification for example by substitution of specific amino acids in HA proteins for example HA from subtype H1 results in improved characteristics of the modified HA protein when compared to the wildtype HA protein or unmodified HA protein.

The one or more than one modification, mutation or substitution of the HA protein as described herein are not located in known epitopic regions of the HA protein nor do these modifications, mutations or substitutions add or remove glycosylation sites within the HA protein.

The HA protein, mutant HA protein or modified HA protein as described herein is modified and comprises one or more than one mutation, modification, or substitution in its amino acid sequence at any one or more amino acid that correspond with amino acids at positions 97, 374, 380, 390 or 429 of A/Michigan/45/15 HA (SEQ ID NO: 134; see FIG. 1) or A/California/07/09 HA (SEQ ID NO: 130; see FIG. 1).

By "correspond to an amino acid" or "corresponding to an amino acid", it is meant that an amino acid corresponds to an amino acids in a sequence alignment with an influenza reference strain as described below.

The amino acid residue number or residue position of HA is in accordance with the numbering of the HA of an influenza reference strain. For example in the case of influenza H1 the reference strain may be A/Michigan/45/15 HA (SEQ ID NO: 134; see FIG. 1) or A/California/07/09 HA (SEQ ID NO: 130 see FIG. 1). The corresponding amino acid positions may be determined by aligning the sequences of the HA (for example H1 HA) with the sequence of HA of their respective reference strain. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)). An amino acid sequence alignment of several influenza A HA domains, which are not to be considered limiting, is shown in FIG. 1.

When referring to modifications, mutants or variants, the wild type amino acid residue (also referred to as simply 'amino acid') is followed by the residue number and the new or substituted amino acid. For example, substitution of Aspartic Acid (D, Asp) for Asparagine (N, Asn) in residue or amino acid at position 97 is denominated N97D (see Table 1).

The modified HA, HA mutants or variants for example modified H1 HA are designated in the same manner by using the single letter amino acid code for the wild-type residue followed by its position and the single letter amino acid code of the replacement residue. Multiple mutants are indicated by component single mutants separated by slashes (/) or pluses (+). Thus for example the H1 HA mutant N380A/L429M is a di-substituted mutant in which Alanine (A, Ala) replaces Asparagine (N, Asp) at residue position 380 and Methionine (M, Met) replaces Leucine (L, Leu) at residue position 429 and the H1 HA mutant protein N380A/F390D is a di-substituted variant in which Alanine (A, Ala) replaces Asparagine (N, Asn) at position 380 and Aspartic Acid (D, Asp) replaces Phenylalanine (F, Phe) at position in the H1 HA protein.

TABLE 1

Positions of modification in HA and the corresponding amino acid/residue position in reference strains of influenza H1 and H5. The exemplified modification is shown in brackets.

| Position of Modification in HA (exemplification) | H1 HA[1] | H5 HA[2] |
|---|---|---|
| 97 (N97D) | D97 | D97 |
| 374 (K374E) | E374 | G377 |
| 382 (N382A) | N380 | N383 |
| 390 (F390D) | F390 | F393 |
| 429 (L429M) | L429 | M432 |

[1]A/Michigan/45/15 or A/California/07/09
[2]A/Indonesia/05/05

The modified influenza hemagglutinin (HA) protein may comprise an amino acid sequence having at least one amino acid substitution when compared to a corresponding wild-type amino acid sequence.

By "amino acid substitution" or "substitution" it is meant the replacement of an amino acid in the amino acid sequence of a protein with a different amino acid. The terms amino acid, amino acid residue or residue are used interchangeably in the disclosure. One or more amino acids may be replaced with one or more amino acids that are different than the original or wildtype amino acid at this position, without changing the overall length of the amino acid sequence of the protein. The substitution or replacement may be experimentally induced by altering the codon sequence in a nucleotide sequence encoding the protein to the codon sequence of a different amino acid compared to the original or wildtype amino acid. The resulting protein is a modified protein, for example a modified influenza HA protein. The modified influenza HA protein does not occur naturally.

The modified HA includes non-naturally occurring HA protein, having at least one modification to naturally occurring HA and having improved characteristics compared to naturally occurring HA protein from which the amino acid sequence of the modified HA is derived. Modified HA proteins have an amino acid sequence, not found in nature, which is derived by replacement of one or more amino acid residues of an HA protein with one or more different amino acids.

Accordingly, modified HA, mutant HA or recombinant HA refers to an HA in which the DNA sequence encoding the naturally-occurring HA is modified to produce a modified or mutant DNA sequence which encodes the modification, mutation or substitution of one or more amino acids in the HA amino acid sequence.

Some of the residues identified for modification, mutation or substitution correspond to conserved residues whereas others are not. In the case of residues which are not conserved, the replacement of one or more amino acids is limited to substitutions which produce a modified HA which has an amino acid sequence that does not correspond to one found in nature. In the case of conserved residues, such modification, substitution or replacements should also not result in a naturally-occurring HA sequences.

Conservative Substitutions

As described herein, residues in HA proteins may be identified and modified, substituted or mutated to produce modified HA protein or HA protein variants. The substitutions or mutations at specific positions are not limited to the amino acid substitutions described herewith or as given in the examples. For example, the HA variants may contain conserved or conservative substitutions of describes amino acid substitutions.

As used herein, the term "conserved substitution" or "conservative substitution" and grammatical variations thereof, refers to the presence of an amino acid residue in the sequence of the HA protein that is different from, but is in the same class of amino acid as the described substitution or described residue (i.e., a nonpolar residue replacing a nonpolar residue, an aromatic residue replacing an aromatic residue, a polar-uncharged residue replacing a polar-uncharged residue, a charged residue replacing a charged residue). In addition, conservative substitutions can encompass a residue having an interfacial hydropathy value of the same sign and generally of similar magnitude as the residue that is replacing the wildtype residue.

As used herein, the term "nonpolar residue" refers to glycine (G, Gly), alanine (A, Ala), valine (V, Val), leucine (L, Leu), isoleucine (I, Ile), and proline (P, Pro); the term "aromatic residue" refers to phenylalanine (F, Phe), tyrosine (Y, Tyr), and tryptophan (W, Trp); the term "polar uncharged residue" refers to serine (S, Ser), threonine (T, Thr), cysteine (C, Cys), methionine (M, Met), asparagine (N, Asn) and glutamine (Q, Gln); the term "charged residue" refers to the negatively charged amino acids aspartic acid (D, Asp) and glutamic acid (E, Glu), as well as the positively charged amino acids lysine (K, Lys), arginine (R, Arg), and histidine (H, His). Other classification of amino acids may be as follows:

amino acids with hydrophobic side chain (aliphatic): Alanine (A, Ala), Isoleucine (I, Ile), Leucine (L, Leu), Methionine (M, Met) and Valine (V, Val);
amino acids with hydrophobic side chain (aromatic): Phenylalanine (F, Phe), Tryptophan (W, Trp), Tyrosine (Y, Tyr);
amino acids with polar neutral side chain: Asparagine (N, Asn), Cysteine (C, Cys), Glutamine (Q, Gln), Serine (S, Ser) and Threonine (T, Thr);
amino acids with electrically charged side chains (acidic): Aspartic acid (D, Asp), Glutamic acid (E, Glu);
amino acids with electrically charged side chains (basic): Arginine (R, Arg); Histidine (H, His), Lysine (K, Lys), Glycine G, Gly) and Proline (P, Pro).

Conservative amino acid substitutions are likely to have a similar effect on the activity of the resultant HA protein variant or modified HA protein, as the original substitution or modification. Further information about conservative substitutions can be found, for instance, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988) and in widely used textbooks of genetics and molecular biology.

The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions: Table 2.

TABLE 2

Exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | He, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

The nucleotide sequence encoding the modified HA protein may be optimized for human codon usage, for increased GC content, or a combination thereof. The modified HA protein may be expressed in a plant, portion of a plant, or plant cell.

H1 HA Modifications

Modified influenza H1 HA proteins and methods of producing modified influenza H1 HA proteins in plants are described herein. It has been observed that the modification of specific amino acids in HA proteins from subtype H1 results in improved characteristics of the modified H1 HA protein when compared to the wildtype H1 HA protein or unmodified H1 HA protein.

A total of 42 single, double, and/or triple modifications were tested to improve the characteristics of the H1 HA protein. As described herewith and as shown in the Examples, only modifications or combinations of modifications at specific positions improved the characteristics of the H1 HA protein. Modifications at 32 positions or combinations of positions had negative effects on the characteristics of the H1 HA protein (data not shown).

Examples of improved characteristics of the H1 HA mutant protein include, increased HA protein yield or accumulation when expressed in plant cells as compared to the wildtype or unmodified H1 HA of the same strain or subtype of influenza that does not comprise the modification(s) or mutation(s); improved hemagglutination titer of the modified or mutated HA protein when compared to the wildtype or unmodified H1 HA protein; improved integrity, stability, or both integrity and stability, of VLPs that are comprised of the modified H1 HA proteins as compared to the integrity, stability or both of VLPs comprising wildtype HA that does not comprise the mutation(s); increased VLP yield when expressed in plant cells as compared to the wildtype level of VLP production that does not comprise the modification(s) or mutation(s); and a combination thereof.

The modified H1 HA protein or mutant H1 HA protein as described herein is modified and comprises one or more than one mutation, or modification, at any one or more residues in sequence alignment with positions 97, 374, 380, 390 and/or 429 of A/California/07/09 HA (SEQ ID NO: 130; see FIG. 1). It is therefore provided influenza H1 HA polypeptides, proteins, and/or protein complexes such as for example virus-like particle (VLP) that comprise modifications or mutations at one or more of amino acid positions 97, 374, 380, 390 and/or 429, where such amino acid numbering is based upon the sequence of H1 A/California/07/09 HA as shown in FIG. 1 (SEQ ID NO: 130), or at amino acid positions that correspond to such amino acid positions, for example as determined by alignment of an H1 HA amino acid sequence to SEQ ID NO: 130. Non-limiting examples of influenza H1 HA amino acid sequences that comprise one or more of such mutations include SEQ ID NOs: 131, 132, 133, 134, 135, 138 and 139.

The modified H1 HA protein described herewith includes H1 HA protein with amino acid sequences that have about 70, 75, 80, 85, 87, 90, 91, 92, 93 94, 95, 96, 97, 98, 99, 100% or any amount therebetween, sequence identity, or sequence similarity, with the amino acid sequence encoding HA from H1 (SEQ ID NO: 130, 131, 132, 133, 134, 135, 138 or 139), wherein the amino acid sequence has one or more than one mutation, or modification, at any one or more residues in sequence alignment with positions 97, 374, 380, 390 and 429 of A/California/07/09 HA (SEQ ID NO: 130) and wherein the HA proteins when expressed form VLP.

Furthermore, the H1 HA protein may be encoded by a nucleotide sequence that has about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 (SEQ ID NO: 130, 131, 132, 133, 134, 135, 138 or 139), wherein the H1 HA protein has one or more than one mutation, or modification, at any one or more residues in sequence alignment with positions 97, 374, 380, 390 and 429 of A/California/07/09 HA and wherein the nucleotide sequence encodes HA proteins that when expressed form VLP.

Non-limiting examples of strains from which the H1 HA might be derived are A/California/07/09 (H1N1, SEQ ID NO: 130), A/Michigan/45/15 (H1N1, SEQ ID NO: 134), A/Massachusetts/06/17 (H1N1, SEQ ID NO: 135), A/Costa Rica/0513/16 (H1N1, SEQ ID NO: 133), A/Honduras/17734/16 (H1N1, SEQ ID NO: 131), A/Darwin/11/15 (H1N1, SEQ ID NO: 132), A/Paris/1227/2017 (SEQ ID NO: 138), or A/Norway/2147/2017 (SEQ ID NO: 139)

The modified or mutant H1 HA may be mono-substituted, di-substituted, tri-substituted or quadruple-substituted at residues at position 97, 374, 380, 390 or 429. In the mono-substituted H1 HA, one residue may be mutated at position 97, 374, 380, 390 or 429. In the di-substituted H1 HA, two residues may be substituted, for example residues at position 380 and 429, 97 and 374 or 390 and 429 may be substituted. In the tri-substituted H1 HA mutant, three residues may be substituted. For example residues at position 97, 390 and 429 or residues at position 97, 374 and 429 may be substituted. In the quadruple-substituted H1 HA mutant, four residues may be substituted. For example residues at position 97, 374, 390 and 429 may be substituted. (All H1 HA numbering is accordance with sequence alignment to reference strain A/California/07/09 HA).

Non limiting examples of modified H1 HA proteins include the following modifications or mutations in the HA sequence when compared with the H1 HA wildtype sequence (numbering is in accordance with A/California/07/09 HA):

mono-substituted H1 HA mutants: N97D, K374E, F390D or L429M;
di-substituted H1 HA mutant: N390A/L429M, N97D/K374E or N380/L429M;
tri-substituted H1 HA mutant: N97D/F390D/L429M or K374E/F390D/L429M;
quadruple-substituted H1 HA mutant: N97D/K374E/F390D/L429M.

The one or more than one mutations described herein specifically increase influenza HA protein production and VLP yield in plants. It was observed that mutations at other positions significantly reduced, or had no significant effect, on influenza HA protein accumulation or VLP production in plant cells.

Mono-Substituted H1 HA
Modification at Position 97

In one aspect of the disclosure, the modified H1 HA may have at least residue at position 97 modified. This residue is not involved in receptor binding of the HA and it has been shown that the residue is located in one of the vestigial esterase (VE) subdomains in the globular head of the HA. Xray crystallography showed that the residue is buried inside the HA trimer. Therefore, the residue is not part of the antigenic sites and is not involved in antigenic change, nor is it recognized by broadly neutralizing antibodies.

In influenza A (H1N1)pdm09 this residue has been predicted to be involved in the stability of HA (see Castelán-Vega et al. 2014). However, Castelán-Vega et al points out that single point mutations seem to have little impact on HA stability and cites Yang et al. (Structural stability of influenza A(H1N1)pdm09 virus hemagglutinins, J. Virol. 2014; 88(9):4828-4838). Yang et al. used size exclusion chromatography analysis of recombinant HA ectodomain to compare the differences among recombinant trimeric HA proteins from early 2009 pandemic H1N1 viruses, which dissociate to monomers, with those of more recent virus HAs that can be expressed as trimers. Yang et al. found that A/Texas/1/2011 (Tex 11) has a unique Asp97Asn (D97N) substitution in HA compared to the four other A(H1N1) pdm09 virus strains that were examined for sequences differences. However, influenza H1 HA strains having evolved since then have an Asparagine (N, Asn) at position 97 (see FIG. 1, sequence alignment of H1), suggesting an evolutionary advantage for H1 HA strains having Asparagine (N, Asn) at this position. Accordingly, it was unexpected that the modification from an Asparagine (N, Asn) at position 97 to a non-Asparagine lead to improved characteristics of the H1 HA protein as described herein.

Figures 4A, 4B:
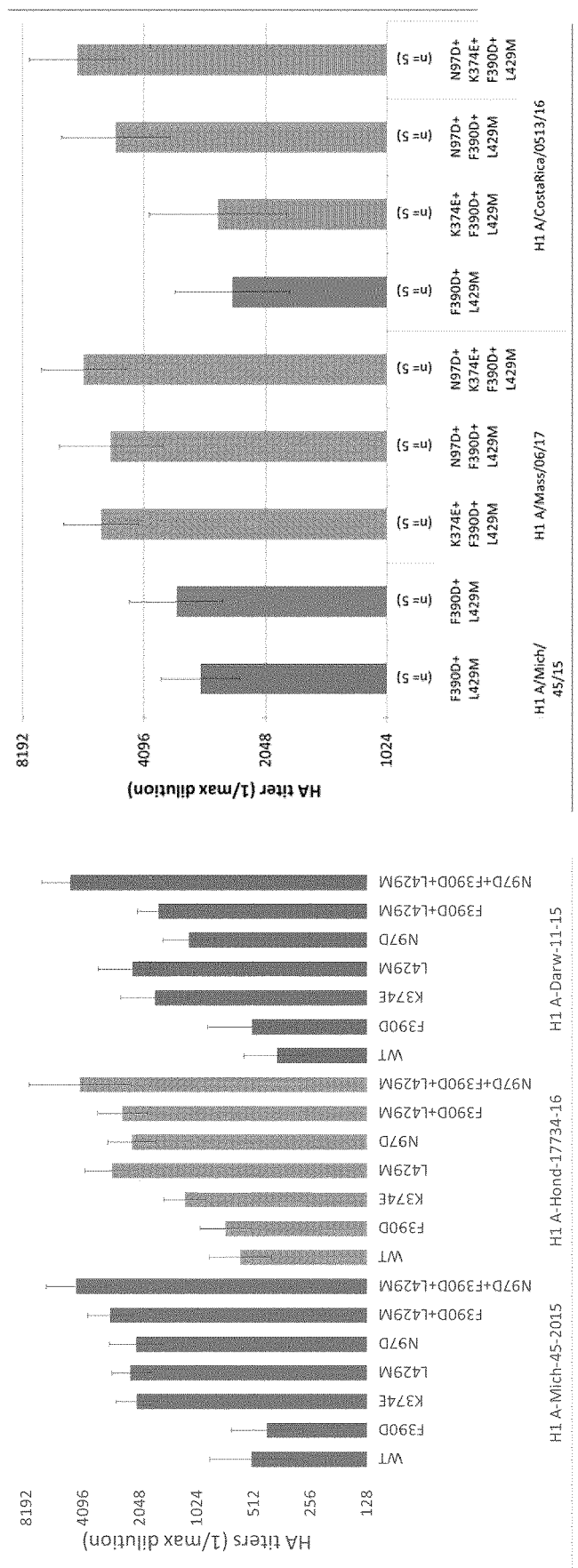
Figure 4C:
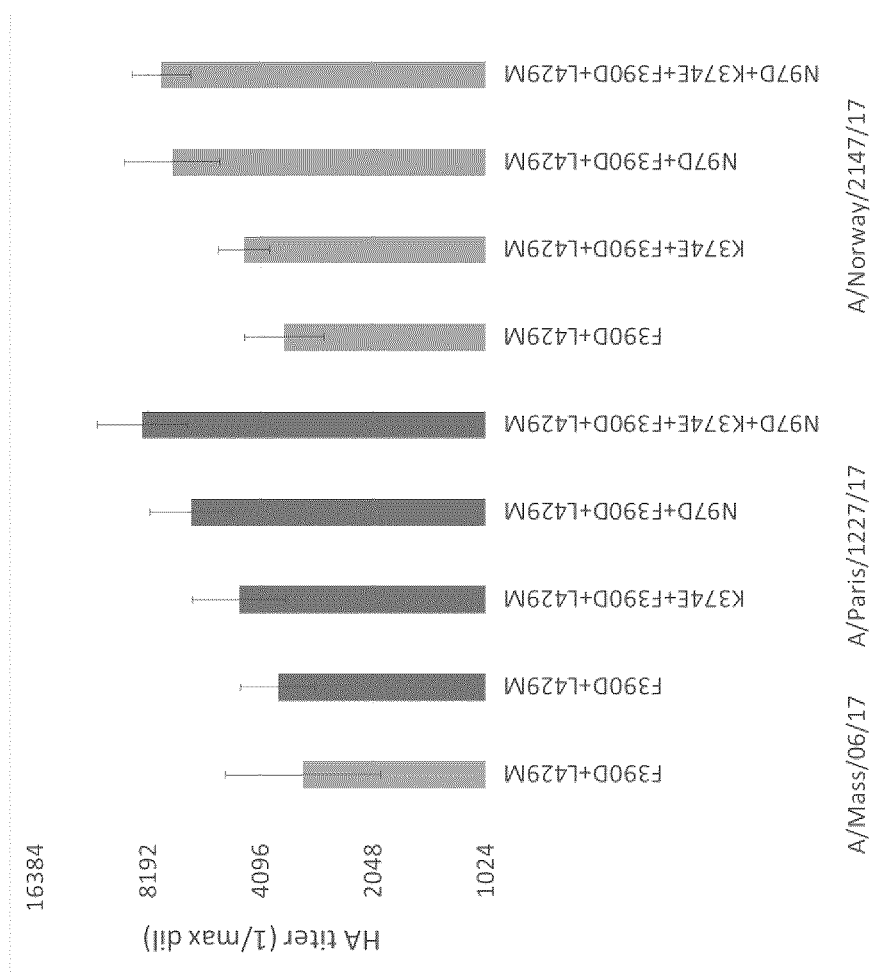

As shown in FIGS. 3A, 3B, 4A and 4B, H1 HA having the residue at position 97 changed from for example Asparagine (N, Asn) to Aspartic Acid (Asp; D), hereinafter referred to as N97D, showed an increase of up to 1200% in hemagglutination titer as compared to an H1 HA that has Asparagine (N, Asn) at this position (see also Table 5A). FIG. 3A shows that HA from A/Michigan/45/15 with the N97D substitution exhibited an approximate 1100% increase in hemagglutination titer when compared to A/Michigan/45/15 HA wildtype (also referred to as H1 Michigan). HA from A/Honduras/17734/16 with the N97D substitution showed an approximate 375% increase in hemagglutination titer as compared to wildtype A/Honduras/17734/16 HA (see FIGS. 4A and 4B). Furthermore, as shown in FIGS. 4A and 4B, HA from A/Darwin/11/15 with a N97D substitution exhibited an approximate 300% increase in hemagglutination titer when compared wildtype A/Darwin/11/15 HA.

In one aspect it is therefore provided that the residue at position 97 (numbering in accordance with A/California/07/09 HA numbering) of an H1 HA may be modified to replace a charged amino acid at position 97 with a polar amino acid at position 97 to produce a modified H1 HA with a non-naturally occurring sequence. For example the H1 HA protein may be modified to contain an Aspartic Acid (D, Asp) or any other polar amino acid for example Glutamine (Q, Gln), Histidine (H, His), Serine (S, Ser), Threonine (T, Thr), Tyrosine (Y, Tyr), Cystein (C, Cys), or Tryptophane (W, Trp) at position 97.

The H1 HA may be modified to replace an Asparagine (N, Asn) at position 97 with a non-Asparagine at position 97. For example the HA protein may be mutated to contain an Aspartic Acid (D, Asp) or a conserved substitution of Aspartic Acid (D, Asp) that is not Asparagine (N, Asn) at position 97. The conserved substitution may for example be Glutamic Acid (E, Glu), Glutamine (Q, Gln) or Serine (S, Ser). Furthermore, the H1 HA may be modified to replace an non-Aspartic Acid (D, Asp) with an Aspartic Acid (D, Asp) or a conserved substitution of Aspartic Acid (D, Asp) that is not Asparagine (N, Asn) at position 97. The conserved substitution of Aspartic Acid may for example be Glutamic Acid (E, Glu), Glutamine (Q, Gln) or Serine (S, Ser).

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 (SEQ ID NO: 134), wherein the amino acid sequence has Aspartic Acid (D, Asp), or a conserved substitution of Aspartic Acid (D, Asp) that is not Asparagine (N, Asn) for example Glutamic Acid (E, Glu), Glutamine (Q, Gln) or Serine (S, Ser) at position 97, wherein the modified H1 HA sequence does not occur naturally and wherein the HA proteins when expressed form VLP.

The present specification also provides a nucleic acid comprising a nucleotide sequence encoding a modified H1 HA with a substitution at position 97 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 (SEQ ID NO: 134), wherein the nucleotide sequence encodes a modified H1 HA protein that has Aspartic Acid (D, Asp), or a conserved substitution of Aspartic Acid (D, Asp) that is not Asparagine (N, Asn) for example Glutamic Acid (E, Glu), Glutamine (Q, Gln) or Serine (S, Ser) at position 97, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 97 of the modified H1 HA, encodes Aspartic Acid (D, Asp), or a conserved substitution of Aspartic Acid (D, Asp) that is not Asparagine (N, Asn) for example Glutamic Acid (E, Glu), Glutamine (Q, Gln) or Serine (S, Ser) at position 97 and wherein the modified H1 HA sequence does not occur naturally.

For example the modified H1 HA may have one or more modification; wherein at least residue 97 of H1 HA is modified as described herewith. For example the modified H1 HA may be a mono-substituted, di-substituted, tri-substituted or quadruple-substituted H1 HA wherein at least the residue at position 97 is modified. In non-limiting examples the modified H1 HA may have a substituted residue at position 97 and one or more substitutions at positions 374, 390, 429 or a combination thereof, wherein the modified H1 HA sequence does not occur naturally.

Furthermore, it is provided a method of producing VLPs that comprise a modified H1 HA with a substitution at position 97 as described above in a plant. The method involves introducing a nucleic acid encoding a modified H1 HA with a substitution at position 97 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 97 as described above in a plant. The method involves introducing a nucleic acid encoding a modified H1 HA with a substitution at position 97 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 97. The VLP may be produced by the method as provided by the present disclosure. The VLP comprising the modified H1 HA show improved characteristics when compared to VLPs that comprise the unmodified H1 HA protein.

Modification at Position 374

In one aspect of the disclosure, the residue at position 374 in H1 HA (numbering in accordance with A/California/07/09 HA numbering) may be substituted. This residue is located in the stem portion of HA of H1.

Cotter et al. (*PLoS Pathog.* 2014; 10(1):e1003831) identified that a E47K (HA2 numbering) mutation in the stalk region of A/California/7/2009 HA stabilized the trimer structure, lowered the pH for membrane fusion, and increased the thermal and acid stability of the virus. Position 47 of the HA2 stalk region of H1N1 in Cotter is equivalent to position 374 (HA0 numbering of A/California/7/2009) in the present disclosure. Cotter et al. additionally observed that A/California/7/2009 E47K mutant HA was more infectious in ferrets than its wildtype counterpart. Similar results were obtained by Yang et al. 2014 (J. Virol. May 2014 vol. 88 no. 94828-4838), who showed that the introduction of a basic side change at position 374 by changing Glutamic Acid to Lysine at this position, potentially forms a new salt bridge across monomer interface to Glu 21 on the adjacent chain and thus improving stability at a lower pH. Yang et al. found that the presence of Lysine at position 374 enhances the ability of the mutant Tex09 ectodomain trimer to withstand changes in both heat and acidity to levels equivalent to those of Washi 1 recHA.

However, it was unexpectedly found that the replacement of for example Lysine (K, Lys) with a Glutamic Acid (E, Glu) at position 374 (K374E) of HA of influenza H1 Michigan (A/Michigan/45/15 (H1N1)) leads to an approximate 1200% increase in hemagglutination titer as compared to extracts from plants expressing the H1 HA wildtype (see FIGS. 3A, 3B, 4A, 4B and Table 5A).

In one aspect it is therefore provided that the residue at position 374 (numbering in accordance with A/California/07/09 HA numbering) of an H1 HA may be modified to replace a non-Glutamic Acid with Glutamic acid (E, Glu) at position 374 to produce a modified H1 HA with a non-naturally occurring sequence. The H1 HA may be modified to replace a non-Glutamic Acid with Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser). Furthermore, a Lysine (K, Lys) at position 374 may be substituted with a non-Lysine at position 374 to produce a modified H1 HA with a non-naturally occurring sequence. For example, Lysine (K, Lys) at position 374 may be substituted with Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser).

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 Michigan (A/Michigan/45/15, SEQ ID NO: 134), wherein the amino acid sequence has Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374, wherein the modified H1 HA sequence does not occur naturally and wherein the HA proteins when expressed form VLP.

The present specification also provides a nucleic acid comprising a nucleotide sequence encoding a H1 HA with a substitution at position 374 operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 Michigan (A/Michigan/45/15, SEQ ID NO: 136), wherein the nucleotide sequence encodes a hemagglutinin protein that has Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 374, encodes Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), wherein the modified H1 HA sequence does not occur naturally and wherein the HA proteins when expressed form VLP.

For example the modified H1 HA may have one or more modification; wherein at least residue 374 of H1 HA is modified as described herewith. For example the modified H1 HA may be a mono-substituted, di-substituted, ti-substituted or quadruple-substituted H1 HA wherein at least the residue at position 374 is modified. In non-limiting examples the modified H1 HA may have a substituted residue at position 374 and one or more substitutions at positions 97, 390, 429 or a combination thereof wherein the modified H1 HA sequence does not occur naturally.

Furthermore, the present specification provides a method of producing VLPs that comprise a modified H1 HA with a substitution at position 374 in a plant. The method involves introducing a nucleic acid encoding a modified H1 HA with a substitution at position 374 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 374 as described above in a plant. The method involves introducing a nucleic acid encoding a modified H1 HA with a substitution at position 374 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 374. The VLP may be produced by the method as provided by the present specification. The VLP comprising the modified H1 HA show improved characteristics when compared to VLPs that comprise the unmodified H1 HA protein.

Modification at Position 390

In one aspect of the disclosure, the residue at position 390 in H1 HA (numbering in accordance with A/California/07/09 HA numbering) may be substituted.

WO2013/177444 and its companion publication Lu et al. (Proc Natl Acad Sci USA. 2014; 111(1):125-30) reported a method for the production of properly folded HA stem domain from A/California/05/2009 (H1N1) using an *Escherichia coli*-based cell-free protein expression system and a simple refolding protocol. For inducing the trimerization of HA stem domain, either a chloramphenicol acetyl transferase (CAT) or foldon domain was fused to the C terminus of the HA. To mitigate newly exposed hydrophobicity and/or intermolecular ion pairing causing aggregation of expressed HA stem protein, five groups of mutations were evaluated: M1 (I69T+I72E+I74T+C77T); M2 (I69T+I72E+I74T+C77T+F164D); M3 (I69T+I72E+I74T+C77T+F164D+L174D); M4 (F164D); and M5 (F164D+L174D). Lu notes that the soluble yield of the mutants was low and that insoluble inclusion bodies were formed. Lu further notes that mutants M3 and M5 produced much fewer aggregates than the wild-type of other variants and therefore developed mutant M5 (F164D+L174D) further. Lu observed that the M5 (F164D+L174D) mutations appeared to be the most influential mutations for improving HA stem protein solubility. Position 164 of Lu is equivalent to position 390 in the present disclosure. Lu's M4 (F164D) mutation showed no advantage over the other mutation tested and in fact was inferior to mutations M3 (I69T+I72E+I74T+C77T+F164D+L174D) and M5 (F164D+L174D).

When Phenylalanine (F, Phe) at position 390 and Leucine (L, Leu) at position 400 (H1 HA numbering) which corresponds to Phenylalanine at position 164 and Leucine at position 174 of M5 (F164D+L174D) of Lu, were altered in the H1 HA of the current disclosure no increases VLP yield was observed and the H1 F390D+L400D mutant showed a complete loss of hemagglutination activity (data not shown). Therefore the equivalent mutation of the M5 mutant in Lu did not lead to an improvement of characteristics in H1 HA that was expressed in plants.

Unexpectedly it was found that when a hydrophobic amino acid at position 390 in H1 HA was substituted with a charged amino acid, an approximate 60% increase in VLP yield following iodixanol gradient purification was observed from plants expressing the H1 HA with the substitution at position 390 when compared to plants that had been infiltrated with wildtype construct (see FIGS. 3B, 4A, 4B, Tables 5A, 5B). In addition, as shown in Table 5C, the full process yield increased to 226%. However, the equivalent modification in HA from H5 (F393D) lead to a decrease in hemagglutination titer (see FIG. 5, Table 6).

In one aspect it is therefore provided that the residue at position 390 (numbering in accordance with A/California/07/09 HA numbering) of an H1 HA may be modified to replace a hydrophobic amino acid at position 390 with a charged amino acid at position 390 to produce a modified H1 HA with a non-naturally occurring sequence. For example the H1 HA protein may be modified to contain an Aspartic Acid (D, Asp) or a conserved substitution of Aspartic Acid (D, Asp) at position 390. The conserved substitution of Aspartic Acid may for example be Asparagine (N, Asn), Glutamic Acid (E, Glu), Glutamine (Q, Gln) or Serine (S, Ser).

The H1 HA may be modified to replace a non-Aspartic Acid with an Aspartic Acid (D, Asp) or a conserved substitution of Aspartic Acid (D, Asp) at position 390. The conserved substitution of Aspartic Acid may for example be Asparagine (N, Asn), Glutamic Acid (E, Glu), Glutamine (Q, Gln) or Serine (S, Ser). Furthermore, the H1 HA may be modified to replace a Phenylalanine (F, Phe) at position 390 with a non-Phenylalanine at position 390. For example the HA protein may be modified to contain an Aspartic Acid (D, Asp) or a conserved substitution of Aspartic Acid (D, Asp) at position 390. The conserved substitution of Aspartic Acid may for example be Asparagine (N, Asn), Glutamic Acid (E, Glu), Glutamine (Q, Gln) or Serine (S, Ser).

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (SEQ ID NO: 134), wherein the amino acid sequence has Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390, wherein the modified H1 HA sequence does not occur naturally and wherein the HA proteins when expressed form VLP.

The present disclosure also provides a nucleic acid comprising a nucleotide sequence encoding a modified H1 HA with a substitution at position 390 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (SEQ ID NO: 136), wherein the nucleotide sequence encodes a modified H1 HA protein that has Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 390 of the modified H1 HA, encodes Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390, wherein the modified H1 HA sequence does not occur naturally and wherein the HA proteins when expressed form VLP.

For example the modified H1 HA may have one or more modification; wherein at least residue 390 of H1 HA is modified as described herewith. For example the modified H1 HA may be a mono-substituted, di-substituted, tri-substituted or quadruple-substituted H1 HA wherein at least the residue at position 390 is modified. In non-limiting examples the modified H1 HA may have a substituted residue at position 390 and one or more substitutions at positions 97, 374, 380, 429 or a combination thereof.

Furthermore, it is provided a method of producing VLPs that comprise a modified H1 HA with a substitution at position 390 as described above in a plant. The method involves introducing a nucleic acid encoding a modified H1 HA with a substitution at position 390 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 390 as described above in a plant. The method involves introducing a nucleic acid encoding a modified H1 HA with a substitution at position 390 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 390. The VLP may be produced by the method as provided by the present specification. The VLP comprising the modified H1 HA show improved characteristics when compared to VLPs that comprise the unmodified H1 HA protein.

Modification at Position 429

In one aspect of the disclosure, the residue at position 429 in H1 HA (numbering in accordance with H1 A/Michigan/45/15 (SEQ ID NO: 134)) may be modified.

Antanasijevic et al. (*J Biol Chem.* 2014; 289(32):22237-45) investigated the structure-function properties of H5 HA stem loop region by site directed mutagenesis at 14 different positions. Antanasijevic observed that HAT-D26K, HAT-M102L, HA2-V52A and HA2-155A mutants (based on H3 numbering) exhibited significantly reduced levels of total HA, suggesting reduced expression and/or assembly of HA into viral particles. HA1-D26K, HA2-T49A and HA2-M102L mutants also exhibited lower hemagglutination titers as compared to wildtype virus. Position 102 in the HA of H5 of Antanasijevic corresponds to position 429 in H1 HA of the current specification.

When HA of H1 was modified to introduce alterations at V19I (HAT-128V), L20M (HAT-M31L), T368A (HA2-T41A), N380A (HA2-N53A) or L429M (HA2-M102L), it was found that the T368A resulted in complete loss of activity, V19I and L20M were found to have lower activity while N380A and L429M displayed higher activity than H1 A/California wildtype HA.

It appears therefore that the majority of residues identified by Antanasijevic as being of importance to the expression and/or assembly or hemagglutination titer of HA from H5 do not translate to a similar importance in HA from H1.

Figure 2C:
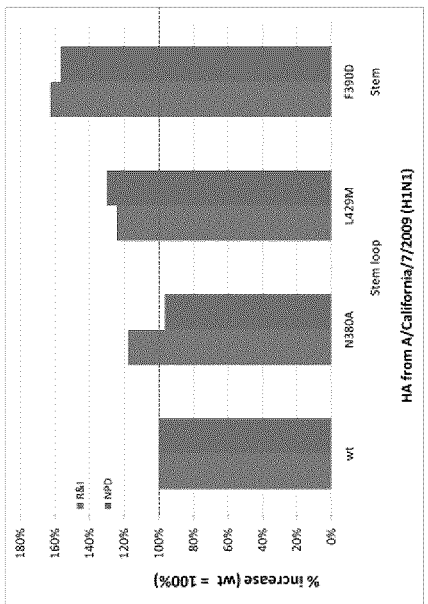
FIG. 2C shows the post-density gradient VLP yields of wildtype A/California/07/09 H1, N380A A/California/07/

However, as shown in FIGS. 2A, 2B, 2C, 3B, 4A and 4B, when residue 429 in H1 HA was mutated from a Leucine (L, Leu) to a Methionine (M, Met), the modified H1 HA exhibited increase in hemagglutination titer (100-160%) as compared to wildtype H1 HA (also see Table 5A). Furthermore, as seen in FIG. 2C, plants expressing H1 HA with a substitution at position 429 show an approximate 30% increase in VLP yield following sucrose gradient purification, in comparison to plants infiltrated with wildtype construct (also see Table 5B). In addition, as shown in Table 5C, the full process yield increased to 260%.

Figure 2A:
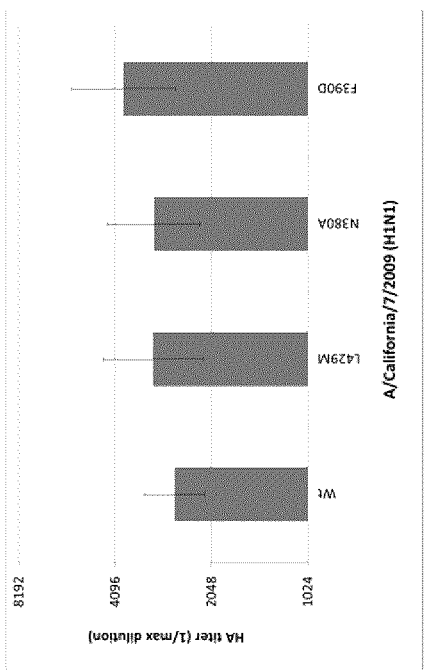
FIG. 2A shows the hemagglutination titers of wildtype A/California/07/09 H1, L429M A/California/07/09 mutant H1, N380A A/California/7/09 mutant H1 and F390D A/California/7/09 mutant H1.
Figure 2B:
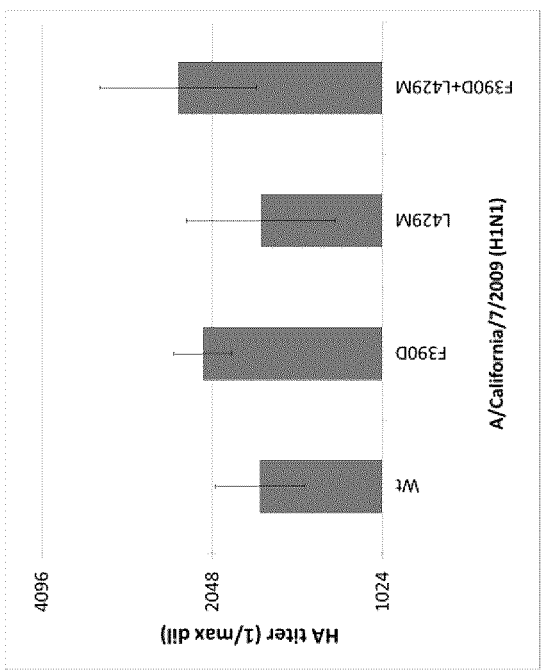
FIG. 2B shows the hemagglutination titers of wildtype A/California/07/09 H1, F390D A/California/07/09 mutant H1, L429M A/California/07/09 mutant H1, and F390D+L429M A/California/07/09 mutant H1, expressed as percentages relative to wildtype A/California/07/09.

In addition, di-substituted H1 HA, wherein phenylalanine at position 390 was modified to an aspartic acid and leucine at position 429 was modified to a methionine exhibited an approximate 60% increase in hemagglutination titer when compared to the unmodified H1 HA (see FIG. 2B).

In one aspect it is therefore provided that the residue at position 429 (numbering in accordance with H1 A/Michigan/45/15 amino acid sequence (SEQ ID NO: 134)) of an H1 HA may be modified to replace a Leucine (L, Leu) at position 429 with another hydrophobic amino acid that is not Leucine to produce a modified H1 HA with a non-naturally occurring sequence. For example the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

Furthermore, the H1 HA may be modified to replace a Leucine (L, Leu) at position 429 with a non-Leucine at position 429. For example the HA protein may be mutated to contain a Methionine (M, Met) or a conserved substitution of Methionine (M, Met) that is not Leucine (L, Leu) at position 429. The conserved substitution of Methionine may for example be Isoleucine (I, Ile), Glutamine (Q, Gln), Valine (V, Val) or Phenylalanine (F, Phe). Furthermore, the H1 HA may be modified to replace a non-Methionine at position 429 with Methionine (M, Met) or a conserved substitution of Methionine (M, Met) that is not Leucine (L, Leu) at position 429. The conserved substitution of Methionine may for example be Isoleucine (I, Ile), Glutamine (Q, Gln), Valine (V, Val) or Phenylalanine (F, Phe).

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 Michigan (A/Michigan/45/15 (H1N1), SEQ ID NO: 134), wherein the amino acid sequence has a Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The present disclosure also provides a nucleic acid comprising a nucleotide sequence encoding a modified H1 HA with a substitution at position 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (SEQ ID NO: 136), wherein the nucleotide sequence encodes a modified H1 HA protein that has a Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 429 of the modified H1 HA, encodes a Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

For example the modified H1 HA may have one or more modification; wherein at least residue 429 of H1 HA is modified as described herewith. For example the modified H1 HA may be a mono-substituted, di-substituted, tri-substituted or quadruple-substituted H1 HA wherein at least the residue at position 429 is modified. In non-limiting examples the modified H1 HA may have a substituted residue at position 429 and one or more substitutions at positions 97, 374, 380, 390 or a combination thereof.

Furthermore, it is provided a method of producing VLPs that comprise a modified H1 HA with a substitution at position 429 as described above in a plant. The method involves introducing a nucleic acid encoding a modified H1 HA with a substitution at position 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 429 as described above in a plant. The method involves introducing a nucleic acid encoding a modified H1 HA with a substitution at position 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 429. The VLP may be produced by the method as provided by the present specification. The VLP comprising the modified H1 HA show improved characteristics when compared to VLPs that comprise the unmodified H1 HA protein.

Di-Substituted H1 HA

It is further provided H1 HA proteins that comprise at least a di-substitution or di-modification. Accordingly, the H1 HA protein has at least two modifications from the wildtype H1 HA protein. For example the H1 HA may have any two combinations of the following residues modified: 97, 374, 380, 390 and 429 (numbering in accordance with H1 A/Michigan/45/15 (SEQ ID NO: 134)).

Modification of Position 380 and 429

In one aspect of the specification, the modified H1 HA may have at least residues at position 380 and 429 modified.

As shown in FIG. 3B H1 HA having the residue at position 380 modified from an Asparagine to Alanine, and the residue at position 429 modified from leucine to a methionine exhibited an approximate 800% increase in hemagglutination titer as compared to wildtype H1 HA (also see Table 5A).

It is therefore provided in one aspect that the residues at position 380 and 429 (numbering in accordance with H1 A/Michigan/45/15 (SEQ ID NO: 134)) of an H1 HA may be modified to replace an Asparagine (N, Asn) at position 380 with a non-Asparagine at position 380 and to replace Leucine (L, Leu) at position 429 with a non-Leucine at position 429 to produce a modified H1 HA with a non-naturally occurring sequence. For example H1 HA may be modified to replace a polar amino acid at position 380 with a hydrophobic amino acid at position 380 and to replace Leucine (L, Leu) at position 429 with another hydrophobic amino acid that is not Leucine to produce a modified H1 HA with a non-naturally occurring sequence.

For example the H1 HA protein may be modified to contain an Alanine (A, Ala) or a conserved substitution of Alanine at position 380. The conserved substitution of Alanine may for example be Serine (S, Ser), Glycine (G, Gly), Threonine (T, Thr), Cystein (C, Cys) or Valine (V, Val). Furthermore the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1) (SEQ ID NO:134), wherein the amino acid sequence has Alanine, or a conserved substitution of Alanine for example Serine (S, Ser), Glycine (G, Gly), Threonine (T, Thr), Cystein (C, Cys) or Valine (V, Val) at position 380 and the amino acid sequence has Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The present specification also provides a nucleic acid comprising a nucleotide sequence encoding a modified H1 HA with a substitution at position 380 and 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1) (SEQ ID NO: 136), wherein the nucleotide sequence encodes a modified H1 HA protein that has Alanine, or a conserved substitution of Alanine for example Serine (S, Ser), Glycine (G, Gly), Threonine (T, Thr), Cystein (C, Cys) or Valine (V, Val) at position 380 and Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encodes amino acid residue 380 of the modified H1 HA encodes Alanine, or a conserved substitution of Alanine, for example Serine (S, Ser), Glycine (G, Gly), Threonine (T, Thr), Cystein (C, Cys) or Valine (V, Val) and the nucleotide codon that encodes amino acid residue 429 of the modified H1 HA, encodes an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

Furthermore, it is provided a method of producing VLPs that comprise a modified H1 HA with a substitution at positions 380 and 429 as described above in a plant. The method involves introducing a nucleic acid encoding a modified H1 HA with a substitution at position 380 and 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 380 and 429 as described above in a plant. The method involves introducing a nucleic acid encoding a modified H1 HA with a substitution at position 380 and 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 380 and 429. The VLP may be produced by the method as provided by the present specification. The VLP comprising the modified H1 HA show improved characteristics when compared to VLPs that comprise the unmodified H1 HA protein.

Modification of Position 390 and 429

In one aspect of the disclosure, the modified H1 HA may have at least residues at position 390 and 429 modified.

As shown in FIGS. 2B, 3B, 4A, 4B and Table 5A, H1 HA having the residue at position 390 modified from a phenylalanine to aspartic acid, and the residue at position 429 modified from leucine to a methionine exhibited an approximate 400-1200% increase in hemagglutination titer as compared to wildtype H1 HA. In addition, as shown in Table 5C, the full process yield increased to 633%.

It is therefore provided in one aspect that the residues at position 390 and 429 (numbering in accordance with H1 A/Michigan/45/15 (SEQ ID NO: 134)) of an H1 HA may be modified to replace a Phenylalanine (F, Phe) at position 390 with a non-Phenylalanine at position 390 and to replace Leucine (L, Leu) at position 429 with a non-Leucine at position 429 to produce a modified H1 HA with a non-naturally occurring sequence. For example H1 HA may be modified to replace a hydrophobic amino acid at position 390 with a charged amino acid at position 390 and to replace Leucine (L, Leu) at position 429 with another hydrophobic amino acid that is not Leucine to produce a modified H1 HA with a non-naturally occurring sequence.

For example the H1 HA protein may be modified to contain an Aspartic Acid (D, Asp) or a conserved substitution of Aspartic Acid (D, Asp) at position 390. The conserved substitution may for example be Asparagine (N, Asn), Glutamic Acid (E, Glu), Glutamine (Q, Gln) or Serine (S, Ser). Furthermore the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1)(SEQ ID NO: 134), wherein the amino acid sequence has Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390 and the amino acid sequence has Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The present specification also provides a nucleic acid comprising a nucleotide sequence encoding a modified H1 HA with a substitution at position 390 and 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1)(SEQ ID NO: 136), wherein the nucleotide sequence encodes a modified H1 HA protein that has Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390 and Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encodes amino acid residue 390 of the modified H1 HA encodes Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the nucleotide codon that encodes amino acid residue 429 of the modified H1 HA, encodes an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

For example the modified H1 HA may have one or more modification; wherein at least residues 390 and 429 of H1 HA is modified as described herewith. For example the modified H1 HA may be a di-substituted, tri-substituted or quadruple-substituted H1 HA wherein at least the residue at position 390 and 429 are modified. In non-limiting examples the modified H1 HA may have a substituted residue at positions 390 and 429 and one or more substitutions at positions 97, 374, 380 or a combination thereof.

Furthermore, it is provided a method of producing VLPs that comprise a modified H1 HA with a substitution at positions 390 and 429 as described above in a plant. The method involves introducing a nucleic acid encoding a modified H1 HA with a substitution at position 390 and 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 390 and 429 as described above in a plant. The method involves introducing a nucleic acid encoding a modified H1 HA with a substitution at position 390 and 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 390 and 429. The VLP may be produced by the method as provided by the present specification. The VLP comprising the modified H1 HA show improved characteristics when compared to VLPs that comprise the unmodified H1 HA protein.

Modification of Position 97 and 374

In one aspect of the disclosure, the modified H1 HA may have at least residues at position 97 and 374 modified.

As shown in FIG. 3B and Table 5A, H1 HA having residue at position 97 modified from asparagine to an aspartic acid and residue at position 374 modified from a lysine to a glutamic acid exhibit an approximate 1200% increase in hemagglutination titer as compared to wildtype H1 HA.

In one aspect it is therefore provided that the residues at position 97 and 374 (numbering in accordance with H1 A/Michigan/45/15 (SEQ ID NO: 134)) of an H1 HA may be modified to replace a Asparagine (N, Asn) at position 97 with a non-Asparagine at position 97 and to replace Lysine (K, Lys) at position 374 with a non-Lysine at position 374 to produce a modified H1 HA with a non-naturally occurring sequence. For example H1 HA may be modified to replace a charged amino acid at position 97 with a polar amino acid at position 97 and to replace a charged amino acid at position 374 with another charged amino acid that is not Lysine (K, Lys) to produce a modified H1 HA with a non-naturally occurring sequence.

For example the H1 HA protein may be modified to contain an Aspartic Acid (D, Asp) or a conserved substitution of Aspartic Acid (D, Asp) that is not at Asparagine (N, Asn) position 97. The conserved substitution may for example be Glutamic Acid (E, Glu), Glutamine (Q, Gln) or Serine (S, Ser). Furthermore the H1 HA protein may be modified to contain Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1) (SEQ ID NO: 134), wherein the amino acid sequence at position 97 has Aspartic Acid (D, Asp), or a conserved substitution of Aspartic Acid (D, Asp) that is not Asparagine (N, Asn); for example, Glutamic Acid (E, Glu), Glutamine (Q, Gln) or Serine (S, Ser) at position 97 and the amino acid sequence has at position 374 Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), wherein the modified H1 HA sequence does not occur naturally and wherein the HA proteins when expressed form VLP.

The present specification also provides a nucleic acid comprising a nucleotide sequence encoding a modified H1 HA with a substitution at position 97 and 374 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1) (SEQ ID NO: 136), wherein the nucleotide sequence encodes a modified H1 HA protein that has at position 97 Aspartic Acid (D, Asp), or a conserved substitution of Aspartic Acid (D, Asp) that is not Asparagine (N, Asn); for example, Glutamic Acid (E, Glu), Glutamine (Q, Gln) or Serine (S, Ser) and the amino acid sequence has at position 374 Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 97 of the modified H1 HA encodes Aspartic Acid (D, Asp), or a conserved substitution of Aspartic Acid (D, Asp) that is not Asparagine (N, Asn); for example, Glutamic Acid (E, Glu), Glutamine (Q, Gln) or Serine (S, Ser) and the nucleotide codon that encode amino acid residue 374 of the modified H1 HA, encodes Glutamic acid (E, Glu), or a conserved substitution of Glutamic acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), wherein the modified H1 HA sequence does not occur naturally and wherein the HA proteins when expressed form VLP.

For example the modified H1 HA may have one or more modification; wherein at least residues 97 and 374 of H1 HA are modified as described herewith. For example the modified H1 HA may be a di-substituted, tri-substituted or quadruple-substituted H1 HA wherein at least the residue at position 97 and 374 are modified. In non-limiting examples the modified H1 HA may have a substituted residue at positions 97 and 374 and one or more substitutions at positions 380, 390 and 429 or a combination thereof.

Furthermore, it is provided a method of producing VLPs that comprise a modified H1 HA with a substitution at positions 97 and 374 as described above in a plant. The method involves introducing a nucleic acid encoding a modified H1 HA with a substitution at position 97 and 374 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with a substitution at position 97 and 374 as described above in a plant. The method involves introducing a nucleic acid encoding a modified H1 HA with a substitution at position 97 and 374 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with a substitution at position 97 and 374. The VLP may be produced by the method as provided by the present specification. The VLP comprising the modified H1 HA show improved characteristics when compared to VLPs that comprise the unmodified H1 HA protein.

Tri-Substituted H1 HA

Modification at Position 97, 390 and 429

It is further provided H1 HA proteins that comprise at least a tri-substitution or tri-modification. Accordingly, the H1 HA protein has at least three modifications from the wildtype H1 HA protein. For example the H1 HA may have any three combinations of the following residues modified: 97, 374, 390 and 429 (numbering in accordance H1 A/Michigan/45/15 (SEQ ID NO: 134)).

In one aspect of the specification, the modified H1 HA may have residues at least at position 97, 390 and 429 modified.

As shown for example in FIGS. 3B, 4A and 4B, H1 HA having the residue at position 97 modified from Asparagine to Aspartic Acid, residue at position 390 modified from phenylalanine to aspartic acid and residue 429 modified from leucine to a methionine exhibited an approximate 2600% increase in hemagglutination titer as compared to wildtype H1 HA. In addition, as shown in Table 5C, the full process yield increased to 647%.

It is therefore provided in one aspect that the residues at position 97, 390 and 429 (numbering in accordance with H1 A/Michigan/45/15 (SEQ ID NO: 134)) of an H1 HA may be modified to replace Asparagine (N, Asn) at position 97 with a non-Asparagine, Phenylalanine (F, Phe) at position 390 with a non-Phenylalanine and to replace Leucine at position 429 with a non-Leucine (L, Leu) to produce a modified H1 HA with a non-naturally occurring sequence. For example H1 HA may be modified to replace a polar amino acid with a charged amino acid at position 97, a hydrophobic amino acid at position 390 with a charged amino acid and to replace leucine at position 429 with another hydrophobic amino acid that is not Leucine to produce a modified H1 HA with a non-naturally occurring sequence.

For example the H1 HA protein may be modified to contain an Aspartic Acid (D, Asp) or a conserved substitution of Aspartic Acid (D, Asp) that is not Asparagine (N, Asn) at position 97. The conserved substitution of Aspartic Acid may for example be Glutamic Acid (E, Glu), Glutamine (Q, Gln) or Serine (S, Ser). The modified H1 HA may further contain an Aspartic Acid (D, Asp) or a conserved substitution of Aspartic Acid (D, Asp) at position 390. The conserved substitution of Aspartic Acid may for example be Asparagine (N, Asn), Glutamic Acid (E, Glu), Glutamine (Q, Gln) or Serine (S, Ser). Furthermore the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1) (SEQ ID NO: 134), wherein the amino acid sequence has at position 97 Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser), the amino acid sequence has at position 390 Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the amino acid sequence has at position 429 Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

The present disclosure also provides a nucleic acid comprising a nucleotide sequence encoding a modified H1 HA with a substitution at position 97, 390 and 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1) (SEQ ID NO: 136), wherein the nucleotide sequence encodes a modified H1 HA protein that has Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser) at position 97, Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390 and Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 97 of the modified H1 HA encodes Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser), the nucleotide codon that encode amino acid residue 390 of the modified H1 HA encodes Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the nucleotide codon that encode amino acid residue 429 of the modified H1 HA, encodes an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

For example the modified H1 HA may have one or more modification; wherein at least residues 97, 390 and 429 of H1 HA is modified as described herewith. For example the modified H1 HA may be a tri-substituted or quadruple-substituted H1 HA wherein the residue at least at position 97, 390 and 429 are modified. In non-limiting examples the modified H1 HA may have substituted residues at positions 97, 390, 429 and 374.

Furthermore, it is provided a method of producing VLPs that comprise a modified H1 HA with a substitution at positions 97, 390 and 429 as described above in a plant. The method involves introducing a nucleic acid encoding a modified H1 HA with substitutions at position 97, 390 and 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with substitution at position 97, 390 and 429 as described above in a plant. The method involves introducing a nucleic acid encoding a modified H1 HA with substitution at position 97, 390 and 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with substitution at position 97, 390 and 429. The VLP may be produced by the method as provided by the present specification. The VLP comprising the modified H1 HA show improved characteristics when compared to VLPs that comprise the unmodified H1 HA protein.

Modification of Positions 374, 390 and 429

In one aspect of the disclosure, the modified H1 HA may have residues at least at position 374, 390 and 429 modified.

As shown for example in FIG. 3B, H1 HA having the residue at position 374 modified from Lysine to glutamic acid, residue at position 390 modified from phenylalanine to aspartic acid and residue 429 modified from leucine to a methionine exhibited an approximate 2500% increase in hemagglutination titer as compared to wildtype H1 HA. In addition, as shown in Table 5C, the full process yield increased to 689%.

It is therefore provided in one aspect that the residues at position 374, 390 and 429 (numbering in accordance with H1 A/Michigan/45/15 (SEQ ID NO: 134)) of an H1 HA may be modified to replace Lysine (K, Lys) at position 374 with a non-Lysine, Phenylalanine (F, Phe) at position 390 with a non-Phenylalanine and to replace Leucine at position 429 with a non-Leucine to produce a modified H1 HA with a non-naturally occurring sequence. For example H1 HA may be modified to replace Lysine with a charged amino acid that is not-Lysine at position 374, a hydrophobic amino acid at position 390 with a charged amino acid and to replace Leucine (L, Leu) at position 429 with another hydrophobic amino acid that is not Leucine to produce a modified H1 HA with a non-naturally occurring sequence.

For example the H1 HA protein may be modified to contain Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374. The modified H1 HA may further contain an Aspartic Acid (D, Asp) or a conserved substitution of Aspartic Acid (D, Asp) at position 390. The conserved substitution may for example be Asparagine (N, Asn), Glutamic Acid (E, Glu), Glutamine (Q, Gln) or Serine (S, Ser). Furthermore the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1) (SEQ ID NO: 134), wherein the amino acid sequence has at position 374 Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), the amino acid sequence has at position 390 Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the amino acid sequence has at position 429 Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

The present specification also provides a nucleic acid comprising a nucleotide sequence encoding a modified H1 HA with a substitution at position 374, 390 and 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1)(SEQ ID NO: 136), wherein the nucleotide sequence encodes a modified H1 HA protein that has Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374, Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390 and Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429, wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 374 of the modified H1 HA encodes Glutamic Acid (E, Glu) or a conserved substitution of Glutamic Acid (E, Glu) that is not Lysine (K, Lys) for example Aspartic acid (D, Asp), Gluta- mine (Q, Gln), Arginine (R, Arg), Asparagine (N, Asn), Histidine (H, His) or Serine (S, Ser), the nucleotide codon that encode amino acid residue 390 of the modified H1 HA encodes Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the nucleotide codon that encode amino acid residue 429 of the modified H1 HA, encodes an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

For example the modified H1 HA may have one or more modification; wherein at least residues 374, 390 and 429 of H1 HA is modified as described herewith. For example the modified H1 HA may be a tri-substituted or quadruple-substituted H1 HA wherein at least the residue at position 374, 390 and 429 are modified. In non-limiting examples the modified H1 HA may have substituted residues at positions 374, 390, 429 and 97.

Furthermore, it is provided a method of producing VLPs that comprise a modified H1 HA with a substitution at positions 374, 390 and 429 as described above in a plant. The method involves introducing a nucleic acid encoding a modified H1 HA with substitutions at position 374, 390 and 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with substitution at position 374, 390 and 429 as described above in a plant. The method involves introducing a nucleic acid encoding a modified H1 HA with substitution at position 374, 390 and 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with substitution at position 374, 390 and 429. The VLP may be produced by the method as provided by the present specification. The VLP comprising the modified H1 HA show improved characteristics when compared to VLPs that comprise the unmodified H1 HA protein.

Quadruple-Substituted H1 HA

Modification at Positions 97, 374, 390 and 429

It is further provided H1 HA proteins that comprise at least a quadruple-substitution or quadruple-modification. Accordingly, the H1 HA protein has at least four modifications from the wildtype H1 HA protein. For example the H1 HA may have modifications at positions 97, 374, 390 and 429 (numbering in accordance with H1 A/Michigan/45/15 (SEQ ID NO: 134)).

Accordingly, in one aspect of the specification, the modified H1 HA may have residues at least at position 97, 374, 390 and 429 modified.

As shown for example in FIG. 3B, H1 HA having residue at position 97 modified from Asparagine to Aspartic Acid, residue at position 374 modified from lysine to glutamic acid, residue at position 390 modified from phenylalanine to aspartic acid and residue at position 429 modified from leucine to a methionine exhibited an approximate 3300% increase in hemagglutination titer as compared to wildtype H1 HA.

In one aspect it is therefore provided that the residues at position 97, 374, 390 and 429 (numbering in accordance with A/California/07/09 HA) of an H1 HA may be modified to replace Asparagine (N, Asn) at position 97 with a non-Asparagine, Lysine at position 374 with a non-Lysine, Phenylalanine (F, Phe) at position 390 with a non-Phenylalanine and to replace Leucine at position 429 with a non-Leucine to produce a modified H1 HA with a non-naturally occurring sequence. For example H1 HA may be modified to replace a polar amino acid with a charged amino acid at position 97, replace Lysine with a charged amino acid that is not-Lysine at position 374, replace a hydrophobic amino acid at position 390 with a charged amino acid and to replace Leucine (L, Leu) at position 429 with another hydrophobic amino acid that is not Leucine to produce a modified H1 HA with a non-naturally occurring sequence.

For example the H1 HA protein may be modified to contain an Aspartic Acid (D, Asp) or a conserved substitution of Aspartic Acid (D, Asp) that is not Asparagine (N, Asn) at position 97. The conserved substitution of Aspartic Acid may for example be Glutamic Acid (E, Glu), Glutamine (Q, Gln) or Serine (S, Ser). Furthermore, the H1 HA protein may be modified to contain Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374. The modified H1 HA may further contain an Aspartic Acid (D, Asp) or a conserved substitution of Aspartic Acid (D, Asp) at position 390. The conserved substitution of Aspartic Acid may for example be Asparagine (N, Asn), Glutamic Acid (E, Glu), Glutamine (Q, Gln) or Serine (S, Ser). Furthermore the H1 HA protein may be modified to contain an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe) at position 429.

For example the modified H1 HA protein may have an amino acid sequence that has about 70, 75, 80, 85, 87, 90, 91, 92, 93 94, 95, 96, 97, 98, 99, 100% or any amount therebetween, sequence identity, or sequence similarity, with the amino acid sequence of HA from H1 A/Michigan/45/15 (H1N1) (SEQ ID NO: 134), wherein the amino acid sequence has at position 97 Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser), the amino acid sequence has at position 374 Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser), the amino acid sequence has at position 390 Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the amino acid sequence has at position 429 Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

The present specification also provides a nucleic acid comprising a nucleotide sequence encoding a modified H1 HA with a substitution at position 97, 374, 390 and 429 as described above operatively linked to a regulatory region active in a plant.

For example the nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 A/Michigan/45/15 (H1N1) (SEQ ID NO: 136), wherein the nucleotide sequence encodes a modified H1 HA protein that has Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser) at position 97, Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374, Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) at position 390 and Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

The nucleotide sequences may have about 70, 75, 80, 85, 87, 90, 91, 92, 93 94, 95, 96, 97, 98, 99, 100% or any amount therebetween, sequence identity, or sequence similarity, with the nucleotide sequence of SEQ ID NO: 136, wherein the nucleotide codon that encode amino acid residue 97 of the modified H1 HA encodes Aspartic Acid (D, Asp) or a conserved substitution of Aspartic Acid (D, Asp) that is not Asparagine (N, Asn) for example Glutamic Acid (E, Glu), Glutamine (Q, Gln) or Serine (S, Ser), the nucleotide codon that encode amino acid residue 374 of the modified H1 HA encodes Glutamic Acid (E, Glu) or a conserved substitution of Glutamic Acid (E, Glu) that is not Lysine (K, Lys) for example Aspartic acid (D, Asp), Glutamine (Q, Gln), Arginine (R, Arg), Asparagine (N, Asn), Histidine (H, His) or Serine (S, Ser) at position 374, the nucleotide codon that encode amino acid residue 390 of the modified H1 HA encodes Aspartic Acid (D, Asp), or a conserved substitution of Aspartic Acid (D, Asp) for example Asparagine (N, Asn), Glutamic Acid (E, Glu), Glutamine (Q, Gln) or Serine (S, Ser) and the nucleotide codon that encode amino acid residue 429 of the modified H1 HA, encodes an Methionine (M, Met) or a conserved substitution of Methionine (M, Met) that is not Leucine (L, Leu) for example Isoleucine (I, Ile), Glutamine (Q, Gln), Valine (V, Val) or Phenylalanine (F, Phe), wherein the modified H1 HA sequence does not occur naturally and wherein the HA proteins when expressed form VLP.

For example the modified H1 HA may have one or more modification; wherein at least residues 97, 374, 390 and 429 of H1 HA is modified as described herewith. For example the modified H1 HA may be a quadruple-substituted H1 HA wherein the residue at position 97, 374, 390 and 429 are modified.

Furthermore, it is provided a method of producing VLPs that comprise a modified H1 HA with a substitution at positions 97, 374, 390 and 429 as described above in a plant. The method involves introducing a nucleic acid encoding a modified H1 HA with substitutions at position 97, 374, 390 and 429 operatively linked to a regulatory region active in the plant, into the plant, or portion of the plant, and incubating the plant or portion of the plant under conditions that permit the expression of the nucleic acid, thereby producing the VLPs.

In addition, it is provided a method of increasing yield of VLPs that comprise a modified H1 HA with substitution at position 97, 374, 390 and 429 as described above in a plant. The method involves introducing a nucleic acid encoding a modified H1 HA with substitution at position 97, 374, 390 and 429 operatively linked to a regulatory region active in the plant, into the plant, or portion of the plant, and incubating the plant or portion of the plant under conditions that permit the expression of the nucleic acid, thereby producing the VLPs.

The present specification further provides for a VLP comprising a H1 HA with substitution at position 97, 374, 390 and 429. The VLP may be produced by the method as provided by the present specification. The VLP comprising the modified H1 HA show improved characteristics when compared to VLPs that comprise the unmodified H1 HA protein.

Also provided herein are methods of increasing production or yield of VLPs comprising mutant influenza HAs in plants. For example, a method may involve introducing a nucleic acid encoding a mutant influenza HA, as described herein, into the plant, portion of the plant, or plant cell. The nucleic acid encoding the mutant influenza HA may be optimized for human codon usage, increased GC content, or a combination thereof. One or more than one mutant influenza HA protein may be expressed in a plant, portion of the plant, or plant cell, in order to produce a VLP comprising one or more than one mutant influenza HA protein. Alternatively, the method may comprise providing a plant, portion of the plant, or plant cell that comprises the nucleic acid encoding the mutant influenza HA protein in order to produce a VLP comprising the one or more than one mutant influenza HA protein.

The methods of producing a VLP comprising a mutant influenza HA may further comprise a step of introducing a second nucleic acid sequence into the plant, portion of the plant, or plant cell, wherein the second nucleic acid encodes a proton channel protein that is co-expressed with the mutant influenza HA. For example, the proton channel protein may be an influenza A subtype M2 protein, such as A/New Caledonia/20/99 M2. The co-expression of the proton channel protein may lead to an increased accumulation of mutant influenza HA protein and/or VLP comprising the mutant influenza HA protein as for example described in WO 2013/044390 which is incorporated herein by reference.

Furthermore, the mutant influenza HA might further comprise a modified proteolytic loop or cleavage site as described in WO 2013/044390 and WO 2014/153674 and which are incorporated herein by reference.

By "co-expression", it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *Agrobacterium tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *A. tumefaciens* suspensions permits co-expression of multiple transgenes.

The nucleic acid encoding a mutant influenza HA as described herein may further comprise sequences that enhance expression of the mutant influenza HA in a plant, portion of the plant, or plant cell. Sequences that enhance expression may include, a cowpea mosaic virus (CPMV) enhancer element in operative association with the nucleic acid encoding the mutant influenza HA protein.

The nucleic acid comprising a nucleotide sequence encoding a modified influenza hemagglutinin (HA) protein, as described herein may further comprise sequences that enhance expression of the HA protein in the plant, portion of the plant, or plant cell. Sequences that enhance expression may include, a CPMV enhancer element, or a plant-derived expression enhancer, in operative association with the nucleic acid encoding the modified influenza hemagglutinin (HA) protein. The sequence encoding the modified influenza hemagglutinin (HA) may also be optimized for human codon usage, increased GC content, or a combination thereof.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX (where X=160, 155, 150, 114), for example CPMV 160, CPMVX+(where X=160, 155, 150, 114), for example CPMV 160+, CPMV-HT+, CPMV HT+ [WT115], or CPMV HT+[511](WO2015/143567; WO2015/103704 which are incorporated herein by reference). The CPMV expression enhancer may be used within a plant expression system comprising a regulatory region that is operatively linked with the CPMV expression enhancer sequence and a nucleotide sequence of interest.

The term "CPMV enhancer element", as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX, CPMVX+, CPMV-HT+, CPMV HT+ [WT115], or CPMV HT+[511] (WO2015/14367; WO2015/103704 which are incorporated herein by reference). The CPMV expression enhancer may be used within a plant expression system comprising a regulatory region that is operatively linked with the CPMV expression enhancer sequence and a nucleotide sequence of interest.

The term "5'UTR" or "5' untranslated region" or "5' leader sequence" refers to regions of an mRNA that are not translated. The 5'UTR typically begins at the transcription start site and ends just before the translation initiation site or start codon of the coding region. The 5' UTR may modulate the stability and/or translation of an mRNA transcript.

The term "plant-derived expression enhancer", as used herein, refers to a nucleotide sequence obtained from a plant, the nucleotide sequence encoding a 5'UTR. Examples of a plant derived expression enhancer are described in U.S. Provisional Patent Application No. 62/643,053 (Filed Mar. 14, 2018; which is incorporated herein by reference) or in Diamos A. G. et al. (2016, Front Plt Sci. 7:1-15; which is incorporated herein by reference). The plant-derived expression enhancer may be selected from nbMT78, nbATL75, nbDJ46, nbCHP79, nbEN42, atHSP69, atGRP62, atPK65, atRP46, nb30S72, nbGT61, nbPV55, nbPPI43, nbPM64 and nbH2A86 as described in U.S. 62/643,053). The plant derived expression enhancer may be used within a plant expression system comprising a regulatory region that is operatively linked with the plant-derived expression enhancer sequence and a nucleotide sequence of interest.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one mutant influenza HA protein is expressed in a plant, portion of the plant, or plant cell, the one or more than one mutant influenza HA proteins self-assemble into VLPs. The plant, portion of the plant, or plant cell, may be harvested under suitable extraction and purification conditions to maintain the integrity of the VLP, and the VLP comprising the one or more than one mutant influenza HA may be purified.

The present invention also provides the use of a mutant influenza HA, or VLP comprising the mutant influenza HA, as described herein, for inducing immunity to an influenza infection in a subject. Also disclosed herein is an antibody or antibody fragment, prepared by administering the mutant influenza HA or VLP comprising the mutant influenza HA, to a subject or a host animal. Further provided is a composition comprising an effective dose of a mutant influenza HA or VLP comprising the mutant influenza HA, as described herein, and a pharmaceutically acceptable carrier, adjuvant, vehicle, or excipient, for inducing an immune response in a subject. Also provided is a vaccine for inducing an immune response in a subject, wherein the vaccine comprises an effective dose of the mutant influenza HA.

Also provided herein are methods for inducing immunity to an influenza infection in a subject comprising of administering the mutant influenza HA or VLP comprising the mutant influenza HA, to a subject orally, intranasally, intramuscularly, intraperitoneally, intravenously, or subcutaneously.

The term "influenza virus", as used herein, refers to an enveloped viral strain of the family Orthomyxoviridae that is characterized as having a negative sense single-stranded RNA genome. The influenza virus genome comprises eight gene segments coding for 12-14 proteins depending on the strain.

There are four types of influenza virus: A, B, C and D, of which influenza A and B are the causative organism for seasonal disease epidemics in humans. Influenza A is further classified based on the expression of HA and neuraminidase (NA) glycoprotein subtypes.

The term "hemagglutinin" or "HA", as used herein, refers to a trimeric lectin that facilitates binding of the influenza virus particle to sialic acid-containing proteins on the surface of target cells and mediates release of the viral genome into the target cell. There are 18 different HA subtypes (H1-H18). HA proteins comprise two structural elements: the head, which is the primary target of seroprotective antibodies; and the stalk. HA is translated as a single polypeptide, HA0 (assembled as trimers), that must be cleaved by a serine endoprotease between the HA1 (~40 kDa) and HA2 (~20 kDa) subdomains. After cleavage, the two disulfide-bonded protein domains adopt the requisite conformation necessary for viral infectivity.

Influenza A HA proteins or modified influenza A HA proteins as disclosed herein, include any known HA proteins derived from any known influenza A strain, but also modifications to known influenza A strains that develop over time. For example, influenza HA may be derived from A/California/07/09 (H1N1), A/Michigan/45/15 (H1N1), A/Massachusetts/06/17 (H1N1), A/Costa Rica/0513/16 (H1N1), A/Honduras/17734/16 (H1N1), or A/Darwin/11/15 (H1N1). Influenza A HA may include HA derived from strains, wherein the HA has about 30-100%, or any amount therebetween, amino acid sequence identity to any HA derived from the influenza A strains listed above, provided that the influenza HA protein comprises at least one substitution as described herewith and is able to form VLPs, induces an immune response when administered to a subject, induces hemagglutination or a combination thereof.

For example, influenza HA proteins may have 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity, percent identity, percent similarity) to any HA derived from the influenza A strains listed above and comprises at least one substitution as described herewith and is able to form VLPs, induces an immune response when administered to a subject, induces hemagglutination or a combination thereof. An amino acid sequence alignment of several influenza A HA domains, which are not to be considered limiting, is shown in FIG. 1.

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

The term "virus-like particle", VLP, "virus like particles", or "VLPs", as used herein, refers to influenza particles that comprise one or more than one influenza HA protein, and that self-assemble into non-replicating, non-infectious viral capsid structures lacking all parts of the influenza genome.

Influenza HA Protein Production in Plants

Influenza A HA protein includes any HA protein comprising an amino acid sequence having from about 30 to about 100%, from about 40 to about 100%, from about 50 to about 100%, from about 60 to about 100%, from about 70 to about 100%, from about 80 to about 100%, from about 85 to about 100%, from about 90 to about 100%, from 95 to about 100%, or from about 97 to about 100% from about 98 to about 100%, or any amount therebetween, sequence identity or sequence similarity with influenza A HA sequence from a A/California/07/09 (H1N1, SEQ ID NO: 130), A/Michigan/45/15 (H1N1, SEQ ID NO: 134), A/Massachusetts/06/17 (H1N1, SEQ ID NO: 135), A/Costa Rica/0513/16 (H1N1, SEQ ID NO: 133), A/Honduras/17734/16 (H1N1, SEQ ID NO: 131), A/Darwin/11/15 (H1N1, SEQ ID NO: 132), A/Paris/1227/2017 (SEQ ID NO: 138), and A/Norway/2147/2017 (SEQ ID NO: 139), provided that the influenza HA protein comprises at least one substitution as described herewith and is able to form VLPs, induces an immune response when administered to a subject, induces hemagglutination or a combination thereof.

Furthermore the modified influenza HA protein includes any HA protein comprising an amino acid sequence having from about 30% to about 100%, from about 40% to about 100%, from about 50% to about 100%, from about 60% to about 100%, from about 70% to about 100%, from about 80% to about 100%, from about 85% to about 100%, from about 90% to about 100%, from 95% to about 100%, or from about 97% to about 100% from about 98% to about 100%, or any amount therebetween, sequence identity or sequence similarity with a sequence of the sequences of SEQ ID NO: 18, SEQ ID NO: 22, SEQ ID NO: 24, SEQ ID NO: 4, SEQ ID NO: 28, SEQ ID NO: 32, SEQ ID NO: 36, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 68, SEQ ID NO: 72, SEQ ID NO: 76, SEQ ID NO: 80, SEQ ID NO: 82, SEQ ID NO: 84, SEQ ID NO: 86, SEQ ID NO: 89, SEQ ID NO: 91, SEQ ID NO: 93, SEQ ID NO: 95, SEQ ID NO: 97, SEQ ID NO: 105, SEQ ID NO: 108, SEQ ID NO: 124, SEQ ID NO: 126, SEQ ID NO: 128, SEQ ID NO: 140, SEQ ID NO: 142, SEQ ID NO: 144, SEQ ID NO: 146, SEQ ID NO: 148, provided that the influenza HA protein comprises at least one substitution as described herewith and is able to form VLPs, induces an immune response when administered to a subject, induces hemagglutination or a combination thereof.

As described herein, one or more than one specific mutation or modification in influenza HA results in increased accumulation of HA protein and increased VLP production in plants, as compared to wildtype influenza HA.

Examples of mutant influenza A HA proteins having enhanced influenza HA and/or VLP production in plants include, but are not limited to the following:
F390D A/California/07/09 Mutant H1 (Construct #2980, SEQ ID NO: 18); L429M A/California/07/09 Mutant H1 (Construct #2962, SEQ ID NO: 22); F390D+L429M A/California/07/09 Mutant H1 (Construct #2995, SEQ ID NO: 24); N380A A/Michigan/45/15 Mutant H1 (Construct #3644, SEQ ID NO: 105); F390D+N380A A/Michigan/45/15 Mutant H1 (Construct #3704, SEQ ID NO: 108); N97D A/Michigan/45/15 Mutant H1 (Construct #3774, SEQ ID NO: 28); K374E A/Michigan/45/15 Mutant H1 (Construct #3771, SEQ ID NO: 32); F390D A/Michigan/45/15 Mutant H1 (Construct #3641, SEQ ID NO: 36); L429M A/Michigan/45/15 Mutant H1 (Construct #3643, SEQ ID NO: 39); N97D+K374E A/Michigan/45/15 Mutant H1 (Construct #3880, SEQ ID NO: 41); F390D+L429M A/Michigan/45/15 Mutant H1 (Construct #3703, SEQ ID NO: 43); N97D+F390D+L429M A/Michigan/45/15 Mutant H1 (Construct #3879, SEQ ID NO: 45); K374E+F390D+L429M A/Michigan/45/15 Mutant H1 (Construct #3878, SEQ ID NO:47); N97D+K374E+F390D+L429M A/Michigan/45/15 Mutant H1 (Construct #3881, SEQ ID NO:49); F390D+L429M A/Massachusetts/06/17 Mutant H1 (Construct #4091, SEQ ID NO:51); N97D+F390D+L429M A/Massachusetts/06/17 Mutant H1 (Construct #4093, SEQ ID NO:53); K374E+F390D+L429M A/Massachusetts/06/17 Mutant H1 (Construct #4092, SEQ ID NO: 55); N97D+K374E+F390D+L429M A/Massachusetts/06/17 Mutant H1 (Construct #4094, SEQ ID NO: 57); F390D+L429M A/Costa Rica/0513/16 Mutant H1 (Construct #4715, SEQ ID NO:59); N97D+F390D+L429M A/Costa Rica/0513/16 Mutant H1 (Construct #4717, SEQ ID NO:61); K374E+F390D+L429M A/Costa Rica/0513/16 Mutant H1 (Construct #4716, SEQ ID NO:63); N97D+K374E+F390D+L429M A/Costa Rica/0513/16 Mutant H1 (Construct #4718, SEQ ID NO:65); N97D A/Honduras/17734/16 Mutant H1 (Construct #3950, SEQ ID NO: 68); K374E A/Honduras/17734/16 Mutant H1 (Construct #3948, SEQ ID NO: 72); F390D A/Honduras/17734/16 Mutant H1 (Construct #3945, SEQ ID NO: 75); L429M A/Honduras/17734/16 Mutant H1 (Construct #3949, SEQ ID NO: 80); F390D+L429M A/Honduras/17734/16 Mutant H1 (Construct #3946, SEQ ID NO:82); N97D+F390D+L429M A/Honduras/17734/16 Mutant H1 (Construct #3951, SEQ ID NO:84); N97D A/Darwin/11/15 Mutant H1 (Construct #3990, SEQ ID NO: 86); K374E A/Darwin/11/15 Mutant H1 (Construct #3988, SEQ ID NO:89); F390D A/Darwin/11/15 Mutant H1 (Construct #3985, SEQ ID NO: 91); L429M A/Darwin/11/15 Mutant H1 (Construct #3989, SEQ ID NO:93); F390D+L429M A/Darwin/11/15 Mutant H1 (Construct #3986, SEQ ID NO:95); N97D+F390D+L429M A/Darwin/11/15 Mutant H1 (Construct #3991, SEQ ID NO: 97); F390D+L429M A/Paris/1227/2017 Mutant H1 (Construct #4765, SEQ ID NO: 124), K374E+F390D+L429M A/Paris/1227/2017 Mutant H1 (Construct #4766, SEQ ID NO: 126), N97D+F390D+L429M A/Paris/1227/2017 Mutant H1 (Construct #4767, SEQ ID NO: 128), N97D+K374E+F390D+L429M A/Paris/1227/2017 Mutant H1 (Construct #4768, SEQ ID NO: 140); F390D+L429M A/Norway/2147/2017 mutant H1 (Construct #4775, SEQ ID NO:142), K374E+F390D+L429M A/Norway/2147/2017 mutant H1 (Construct #4776, SEQ ID NO: 144), N97D+F390D+L429M A/Norway/2147/

2017 mutant H1 (Construct #4777, SEQ ID NO: 146), and N97D+K374E+F390D+L429M A/Norway/2147/2017 mutant H1 (Construct #4778, SEQ ID NO: 148).

Induction of Immunity Against Influenza Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza HA antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of influenza virus.

The term "epitope" or "epitopes", as used herein, refers to a structural part of an antigen to which an antibody specifically binds.

Immune responses elicited in response to administration of plant-produced wildtype influenza HA proteins or VLPs, or mutant influenza HA proteins or VLPs may for example be observed in Balb/C mice. Serum samples from blood collected from animals may be analyzed by ELISA for H1-specific total IgG and IgA antibodies. Mice immunized with either plant-produced wildtype influenza HA or mutant influenza HA proteins may exhibit HA-specific IgG antibody titers in sera for each treatment group.

Plant Expression

The constructs of the present invention may be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrvre, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100: 247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al. (2987, *Nature* 327: 70-73); Freeman et al. (1984, *Plant Cell Physiol.* 29: 1353), Howell et al. (1985, *Science* 227: 1229-1231), DeBlock et al. (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth*, 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages 41-50; Liu and Lomonossoff, 2002, *Journal of Virological Methods*, 105:343-348; which is incorporated herein by reference). Alternatively, a vacuum-based transient expression method, as described by Kapila et al. (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy R R D ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, portion of the plant or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

TABLE 3

SEQ ID NOs and Description of Sequences

| SEQ ID NO: | Description of Sequence |
|---|---|
| SEQ ID NO: 1 | PDI-H1 Cal DNA |
| SEQ ID NO: 2 | PDI-H1 Cal AA |
| SEQ ID NO: 3 | PDI-H1 Mich DNA |
| SEQ ID NO: 4 | PDI-H1 Mich AA |
| SEQ ID NO: 5 | PDI-H1 Mass DNA |
| SEQ ID NO: 6 | PDI-H1 Mass AA |
| SEQ ID NO: 7 | PDI-H1 CostaR DNA |
| SEQ ID NO: 8 | PDI-H1 CostaR AA |
| SEQ ID NO: 9 | PDI-H1 Hond DNA |
| SEQ ID NO: 10 | PDI-H1 Hond AA |
| SEQ ID NO: 11 | PDI-H1 Darw DNA |

TABLE 3-continued

SEQ ID NOs and Description of Sequences

| SEQ ID NO: | Description of Sequence |
|---|---|
| SEQ ID NO: 12 | PDI-H1 Darw AA |
| SEQ ID NO: 13 | IF-CPMV(fl5'UTR)_SpPDI.c |
| SEQ ID NO: 14 | IF-H1cTMCT.S1-4r |
| SEQ ID NO: 15 | H1Cal(F390D).r |
| SEQ ID NO: 16 | H1Cal(F390D).c |
| SEQ ID NO: 17 | PDI-H1 Cal-F390D DNA |
| SEQ ID NO: 18 | PDI-H1 Cal-F390D AA |
| SEQ ID NO: 19 | H1Cal(L429M).r |
| SEQ ID NO: 20 | H1Cal(L429M).c |
| SEQ ID NO: 21 | PDI-H1 Cal-L429M DNA |
| SEQ ID NO: 22 | PDI-H1 Cal-L429M AA |
| SEQ ID NO: 23 | PDI-H1 Cal-F390D + L429MDNA |
| SEQ ID NO: 24 | PDI-H1 Cal-F390D + L429MAA |
| SEQ ID NO: 25 | H1 Michi(N97D).r |
| SEQ ID NO: 26 | H1 Michi(N97D).c |
| SEQ ID NO: 27 | PDI-H1 Mich-N97D DNA |
| SEQ ID NO: 28 | PDI-H1 Mich-N97D AA |
| SEQ ID NO: 29 | H1Mich(K374E).r |
| SEQ ID NO: 30 | H1Mich(K374E).c |
| SEQ ID NO: 31 | PDI-H1 Mich-K374E DNA |
| SEQ ID NO: 32 | PDI-H1 Mich-K374E AA |
| SEQ ID NO: 33 | H1Mich(F390D).r |
| SEQ ID NO: 34 | H1Mich(F390D).c |
| SEQ ID NO: 35 | PDI-H1 Mich-F390D DNA |
| SEQ ID NO: 36 | PDI-H1 Mich-F390D AA |
| SEQ ID NO: 37 | H1Mich(L429M).c |
| SEQ ID NO: 38 | PDI-H1 Mich-L429M DNA |
| SEQ ID NO: 39 | PDI-H1 Mich-L429M AA |
| SEQ ID NO: 40 | PDI-H1 Mich-N97D + K374E DNA |
| SEQ ID NO: 41 | PDI-H1 Mich-N97D + K374E AA |
| SEQ ID NO: 42 | PDI-H1 Mich-F390D + L429M DNA |
| SEQ ID NO: 43 | PDI-H1 Mich-F390D + L429M AA |
| SEQ ID NO: 44 | PDI-H1 Mich-N97D + F390D + L429M DNA |
| SEQ ID NO: 45 | PDI-H1 Mich-N97D + F390D + L429M AA |
| SEQ ID NO: 46 | PDI-H1 Mich-K374E + F390D + L429M DNA |
| SEQ ID NO: 47 | PDI-H1 Mich-K374E + F390D + L429M AA |
| SEQ ID NO: 48 | PDI-H1 Mich-N97D + K374E + F390D + L429M DNA |
| SEQ ID NO: 49 | PDI-H1 Mich-N97D + K374E + F390D + L429M AA |
| SEQ ID NO: 50 | PDI-H1 Mass-F390D + L429M DNA |
| SEQ ID NO: 51 | PDI-H1 Mass-F390D + L429M AA |
| SEQ ID NO: 52 | PDI-H1 Mass-N97D + F390D + L429M DNA |
| SEQ ID NO: 53 | PDI-H1 Mass-N97D + F390D + L429M AA |
| SEQ ID NO: 54 | PDI-H1 Mass-K374E + F390D + L429M DNA |
| SEQ ID NO: 55 | PDI-H1 Mass-K374E + F390D + L429M AA |
| SEQ ID NO: 56 | PDI-H1 Mass-N97D + K374E + F390D + L429M DNA |
| SEQ ID NO: 57 | PDI-H1 Mass-N97D + K374E + F390D + L429M AA |
| SEQ ID NO: 58 | PDI-H1 CR-F390D + L429M DNA |
| SEQ ID NO: 59 | PDI-H1 CR-F390D + L429M AA |
| SEQ ID NO: 60 | PDI-H1 CR-N97D + F390D + L429M DNA |
| SEQ ID NO: 61 | PDI-H1 CR-N97D + F390D + L429M AA |
| SEQ ID NO: 62 | PDI-H1 CR-K374E + F390D + L429M DNA |
| SEQ ID NO: 63 | PDI-H1 CR-K374E + F390D + L429M AA |
| SEQ ID NO: 64 | PDI-H1 CR-N97D + K374E + F390D + L429M DNA |
| SEQ ID NO: 65 | PDI-H1 CR-N97D + K374E + F390D + L429M AA |
| SEQ ID NO: 66 | H1Hond(N97D).c |
| SEQ ID NO: 67 | PDI-H1 Hond-N97D DNA |
| SEQ ID NO: 68 | PDI-H1 Hond-N97D AA |
| SEQ ID NO: 69 | H1Hond(K374E).r |
| SEQ ID NO: 70 | H1Hond(K374E).c |
| SEQ ID NO: 71 | PDI-H1 Hond-K374E DNA |
| SEQ ID NO: 72 | PDI-H1 Hond-K374E AA |
| SEQ ID NO: 73 | H1Hond(F390D).r |
| SEQ ID NO: 74 | H1Hond(F390D).c |
| SEQ ID NO: 75 | PDI-H1 Hond-F390D DNA |
| SEQ ID NO: 76 | PDI-H1 Hond-F390D AA |
| SEQ ID NO: 77 | H1Hond(L429M).r |
| SEQ ID NO: 78 | H1Hond(L429M).c |
| SEQ ID NO: 79 | PDI-H1 Hond-L429M DNA |
| SEQ ID NO: 80 | PDI-H1 Hond-L429M AA |
| SEQ ID NO: 81 | PDI-H1 Hond-F390D + L429M DNA |
| SEQ ID NO: 82 | PDI-H1 Hond-F390D + L429M AA |
| SEQ ID NO: 83 | PDI-H1 Hond-N97D + F390D + L429M DNA |
| SEQ ID NO: 84 | PDI-H1 Hond-N97D + F390D + L429M AA |

TABLE 3-continued

SEQ ID NOs and Description of Sequences

| SEQ ID NO: | Description of Sequence |
|---|---|
| SEQ ID NO: 85 | PDI-H1 Darw-N97D DNA |
| SEQ ID NO: 86 | PDI-H1 Darw-N97D AA |
| SEQ ID NO: 87 | H1Darw(K374E).r |
| SEQ ID NO: 88 | PDI-H1 Darw-K374E DNA |
| SEQ ID NO: 89 | PDI-H1 Darw-K374E AA |
| SEQ ID NO: 90 | PDI-H1 Darw-F390D DNA |
| SEQ ID NO: 91 | PDI-H1 Darw-F390D AA |
| SEQ ID NO: 92 | PDI-H1 Darw-L429M DNA |
| SEQ ID NO: 93 | PDI-H1 Darw-L429M AA |
| SEQ ID NO: 94 | PDI-H1 Darw-F390D + L429M DNA |
| SEQ ID NO: 95 | PDI-H1 Darw-F390D + L429M AA |
| SEQ ID NO: 96 | PDI-H1 Darw-N97D + F390D + L429M DNA |
| SEQ ID NO: 97 | PDI-H1 Darw-N97D + F390D + L429M AA |
| SEQ ID NO: 98 | Cloning vector 1190 from left to right T-DNA |
| SEQ ID NO: 99 | Construct 1314 from 2X35S prom to NOS term |
| SEQ ID NO: 100 | Construct 2980 from 2X35S prom to NOS term |
| SEQ ID NO: 101 | Construct 2995 from 2X35S prom to NOS term |
| SEQ ID NO: 102 | H1Mich(N380A).r |
| SEQ ID NO: 103 | H1Cal(N380A).c |
| SEQ ID NO: 104 | PDI-H1 Mich-N380A DNA |
| SEQ ID NO: 105 | PDI-H1 Mich-N380A AA |
| SEQ ID NO: 106 | H1Mich(N380A + F390D).r |
| SEQ ID NO: 107 | PDI-H1 Mich-F390D + N380A DNA |
| SEQ ID NO: 108 | PDI-H1 Mich-F390D + N380A AA |
| SEQ ID NO: 109 | IF-H5ITMCT.sl-4r |
| SEQ ID NO: 110 | PDI-H5 Indo DNA |
| SEQ ID NO: 111 | PDI-H5 Indo AA |
| SEQ ID NO: 112 | H5Ind(F393D).r |
| SEQ ID NO: 113 | H5Ind(F393D).c |
| SEQ ID NO: 114 | PDI-H5 Indo-F393D DNA |
| SEQ ID NO: 115 | PDI-H5 Indo-F393D AA |
| SEQ ID NO: 116 | IF-H5_Egy.r |
| SEQ ID NO: 117 | PDI-H5 Egypt DNA |
| SEQ ID NO: 118 | PDI-H5 Egypt AA |
| SEQ ID NO: 119 | H5Egy(F392D).r |
| SEQ ID NO: 120 | H5Egy(F392D).c |
| SEQ ID NO: 121 | PDI-H5 Egypt-F392D DNA |
| SEQ ID NO: 122 | PDI-H5 Egypt-F392D AA |
| SEQ ID NO: 123 | PDI-H1 Par-F390D + L429M DNA |
| SEQ ID NO: 124 | PDI-H1 Par-F390D + L429M AA |
| SEQ ID NO: 125 | PDI-H1 Par-K374E + F390D + L429M DNA |
| SEQ ID NO: 126 | PDI-H1 Par-K374E + F390D + L429M AA |
| SEQ ID NO: 127 | PDI-H1 Par-N97D + F390D + L429M DNA |
| SEQ ID NO: 128 | PDI-H1 Par-N97D + F390D + L429M AA |
| SEQ ID NO: 129 | PDI-H1 Par-N97D + K374E + F390D + L429M DNA |
| SEQ ID NO: 130 | A/California/7/09 (H1N1) (aa) |
| SEQ ID NO: 131 | A/Honduras/17734/16 (H1N1) (aa) |
| SEQ ID NO: 132 | A/Darwin/11/15 (H1N1) (aa) |
| SEQ ID NO: 133 | A/Costa Rica/0513/16 (H1N1) (aa) |
| SEQ ID NO: 134 | A/Michigan/45/15 (H1N1) (aa) |
| SEQ ID NO: 135 | A/Massachusetts/06/17 (H1N1) (aa) |
| SEQ ID NO: 136 | A/Michigan/45/15 (nt) |
| SEQ ID NO: 137 | A/California/7/09 (H1N1) (nt) |
| SEQ ID NO: 138 | A/Paris/1227/2017 (aa) |
| SEQ ID NO: 139 | A/Norway/2147/2017 |
| SEQ ID NO: 140 | PDI-H1 Par-N97D + K374E + F390D + L429M AA |
| SEQ ID NO: 141 | PDI-H1 Nor-F390D + L429M DNA |
| SEQ ID NO: 142 | PDI-H1 Nor-F390D + L429M AA |
| SEQ ID NO: 143 | PDI-H1 Nor-K374E + F390D + L429M DNA |
| SEQ ID NO: 144 | PDI-H1 Nor-K374E + F390D + L429M AA |
| SEQ ID NO: 145 | PDI-H1 Nor-N97D + F390D + L429M DNA |
| SEQ ID NO: 146 | PDI-H1 Nor-N97D + F390D + L429M AA |
| SEQ ID NO: 147 | PDI-H1 Nor-N97D + K374E + F390D + L429M DNA |
| SEQ ID NO: 148 | PDI-H1 Nor-N97D + K374E + F390D + L429M AA |

The present invention will be further illustrated in the following examples.

Example 1: Influenza HA Constructs

The influenza HA constructs were produced using techniques well known within the art. For example wildtype A-California-07-09 HA, F390D A-California-07-09 HA and F390D+L429M A-California-07-09 HA were cloned as described below. Other H1 mutants were obtained using similar techniques and the HA sequences primers, templates and products are described in Example 3 (Influenza HA and VLP Production in Plants) and Table 4.

A summary of the wildtype and mutated HA proteins, primers, templates and products is provided in Table 4 below.

A. Modification of H1 HA

2X35S/CPMV 160/PDISP-HA0 H1 A-California-07-09/ NOS (Construct Number 1314)

A sequence encoding mature HA0 from influenza HA from A/California/07/09 fused to alfalfa PDI secretion signal peptide (PDISP) was cloned into 2X35S/CPMV 160/NOS expression system using the following PCR-based method. A fragment containing the PDISP-A/California/07/09 coding sequence was amplified using primers IF-CPMV (fl5'UTR)_SpPDI.c (SEQ ID NO: 13) and IF-H1cTMCT.S1-4r (SEQ ID NO: 14), using PDISP-H1 A/California/7/09 gene sequence (SEQ ID NO: 1) as template. The PCR product was cloned in 2X35S/CPMV 160/NOS expression system using In-Fusion cloning system (Clontech, Mountain View, CA). Construct number 1190 (FIG. 8) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 98. The resulting construct was given number 1314 (SEQ ID NO: 99). The amino acid sequence of mature HA0 from influenza HA from A/California/07/09 fused to alfalfa PDI secretion signal peptide (PDISP) is presented in SEQ ID NO: 2. A representation of plasmid 1314 is presented in FIG. 6A.

2X35S/CPMV 160/PDISP-HA0 H1 A-California-07-09 (F390D)/NOS (Construct Number 2980)

A sequence encoding mature HA0 from influenza HA from A/California/07/09 (F390D) fused to alfalfa PDI secretion signal peptide (PDISP) was cloned into 2X35S/CPMV 160/NOS expression system using the following PCR-based method. In a first round of PCR, a fragment containing the PDISP-H1 A/California/07/09 with the mutated F390D amino acid was amplified using primers IF-CPMV (fl5'UTR)_SpPDI.c (SEQ ID NO: 13) and H1Cal(F390D).r (SEQ ID NO: 15), using PDISP-H1 A/California/7/09 gene sequence (SEQ ID NO: 1) as template. A second fragment containing the F390D mutation with the remaining of the H1 A/California/07/09 was amplified using H1Cal(F390D).c (SEQ ID NO: 16) and IF-H1cTMCT.S1-4r (SEQ ID NO: 14), using PDISP-H1 A/California/07/09 gene sequence (SEQ ID NO: 1) as template. The PCR products from both amplifications were then mixed and used as template for a second round of amplification using IF-CPMV(fl5'UTR)_SpPDI.c (SEQ ID NO: 13) and IF-H1cTMCT.S1-4r (SEQ ID NO: 14) as primers. The final PCR product was cloned in 2X35S/CPMV 160/NOS expression system using In-Fusion cloning system (Clontech, Mountain View, CA). Construct number 1190 (FIG. 8) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 98. The resulting construct was given number 2980 (SEQ ID NO: 100). The amino acid sequence of mutated PDISP-HA from A/California/07/09 (F390D) is presented in SEQ ID NO: 18. A representation of plasmid 2980 is presented in FIG. 6B.

2X35S/CPMV 160/PDISP-HA0 H1 A-California-07-09 (F390D+L429M)/NOS (Construct Number 2995)

A sequence encoding mature HA0 from influenza HA from A/California/07/09 (F390D+L429M) fused to alfalfa PDI secretion signal peptide (PDISP) was cloned into 2X35S/CPMV 160/NOS expression system using the following PCR-based method. In a first round of PCR, a fragment containing the PDISP-H1 A/California/07/09 with the mutated F390D and L429M amino acids was amplified using primers IF-CPMV(fl5'UTR)_SpPDI.c (SEQ ID NO: 13) and H1Cal(L429M).r (SEQ ID NO: 19), using PDISP-H1 A/California/7/09 (F390D) gene sequence (SEQ ID NO: 17) as template. A second fragment containing the L429M mutation with the remaining of the H1 A/California/07/09 was amplified using H1Cal(L429M).c (SEQ ID NO: 20) and IF-H1cTMCT.S1-4r (SEQ ID NO: 14), PDISP-H1 A/California/7/09 (F390D) gene sequence (SEQ ID NO: 17) as template. The PCR products from both amplifications were then mixed and used as template for a second round of amplification using IF-CPMV(fl5'UTR)_SpPDI.c (SEQ ID NO: 13) and IF-H1cTMCT.S1-4r (SEQ ID NO: 14) as primers. The final PCR product was cloned in 2X35S/CPMV 160/NOS expression system using In-Fusion cloning system (Clontech, Mountain View, CA). Construct number 1190 (FIG. 8) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 98. The resulting construct was given number 2995 (SEQ ID NO: 101). The amino acid sequence of mutated PDISP-HA from A/California/07/09 (F390D+L429M) is presented in SEQ ID NO: 24. A representation of plasmid 2995 is presented in FIG. 6D.

Example 2: Methods

*Agrobacterium tumefaciens* Transfection

*Agrobacterium tumefaciens* strain AGL1 was transfected by electroporation with the wildtype influenza HA or mutant influenza HA expression vectors using the methods described by D'Aoust et al., 2008 (*Plant Biotech. J.* 6:930-40). Transfected *Agrobacterium* were grown in YEB medium supplemented with 10 mM 2-(N-morpholino)ethanesulfonic acid (MES), 20 µM acetosyringone, 50 µg/ml kanamycin and 25 µg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

Agrobacteria transfected with each wildtype influenza HA or mutant influenza HA expression vector were grown in a YEB medium supplemented with 10 mM 2-(N-morpholino)ethanesulfonic acid (MES), 20 µM acetosyringone, 50 µg/ml kanamycin and 25 µg/ml of carbenicillin pH 5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Proteins were extracted from fresh biomass cut into ~1 $cm^2$ pieces by an overnight enzymatic extraction at room temperature using an orbital shaker. The slurry was then filtered through a large pore nylon filter to remove coarse undigested vegetal tissue.

To obtain the "Full Process yields", the slurry was centrifuged to remove protoplasts and intracellular contaminants. The supernatant was clarified by depth-filtration. The clarified fraction was then loaded over a cation exchange column with a step-elution step with increasing concentrations of NaCl. The purified VLPs were concentrated by TFF, diafiltered against a formulation buffer and passed through a filter. Protein content of purified VLP was analysed by BCA assay and activity was analysed by a hemagglutination assay. Relative yields were obtained by comparing the protein yields from the new construct to the native construct used as control.

To obtain the "Post-Density Gradient Yields", the slurry was centrifuged to remove protoplasts and intracellular contaminants. The supernatant was centrifuged further to remove additional debris. The supernatant was the clarified by depth-filtration using glass fiber filter. The clarified fraction was then loaded on a discontinuous iodixanol density gradient. Separation density gradient centrifugation was performed as follows: 38 ml tubes containing discontinuous iodixanol density gradient in Tris buffer (successive layers of 35%, 30%, 25%, 20%, 15, 10% and 5%) were prepared and overlaid with clarified extract. The gradients were centrifuged at 120 000 g for 2 hours (4° C.). After centrifugation, the first 5 mL collected from the bottom to the top were discarded while the next 5 mL were collected for protein content analysis (BCA), activity measurement (hemagglutination assay) and intensity measurement of the HA0 band on a reduced SDS-PAGE (densitometry). Relative yields were obtained by comparing the HA0 band intensity from the new construct to the native construct used as control.

Hemagglutination Assay

Hemagglutination assay was based on a method described by Nayak and Reichl (2004). Briefly, serial double dilutions of the test samples (100 µL) were made in V-bottomed 96-well microtiter plates containing 100 µL PBS, leaving 100 µL of diluted sample per well. One hundred microliters of a 0.25% turkey (for H1) red blood cells suspension (Bio Link Inc., Syracuse, NY) were added to each well, and plates were incubated for 2h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, CT) was diluted in PBS and run as a control on each plate.

Protein Analysis and Immunoblotting

Immunoblotting was performed with a first incubation with a primary mAb, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Example 3: Influenza HA and VLP Production in Plants

A. Modification of H1 HA

The influenza HA constructs were produced using techniques well known within the art (see Example 1). A summary of the wildtype and mutated HA proteins, primers, templates and products is provided in Table 4 below. The sequences used are provided in Example 4 and in the sequence listing.

F390D A California 07 09 Mutant H1

F390D A/California/07/09 Mutant H1 was constructed by mutating the phenylalanine residue at position 390 of wildtype A/California/07/09 H1 to aspartic acid (Construct #2980). As shown in FIGS. 2A and 2B, purified extracts from N. benthamiana plants agroinfiltrated with Construct #2980 exhibited an approximate 60% increase in hemagglutination titer as compared to extracts from N. benthamiana plants agroinfiltrated with wildtype A/California/07/09 H1 (Construct #1314). Furthermore, as seen in FIG. 2C, N. benthamiana plants agroinfiltrated with Construct #2980 exhibited an approximate 60% increase in VLP yield following iodixanol gradient purification, in comparison to plants infiltrated with wildtype construct.

L429M A/California/07/09 Mutant H1

L429M A/California/07/09 Mutant H1 was constructed by mutating the leucine residue at position 429 of wildtype A/California/07/09 H1 to methionine (Construct #2962). As shown in FIGS. 2A and 2B, purified extracts from N. benthamiana plants agroinfiltrated with Construct #2962 exhibited an approximate 20% increase in hemagglutination titer as compared to extracts from N. benthamiana plants agroinfiltrated with wildtype A/California/07/09 H1 (Construct #1314). Furthermore, as seen in FIG. 2C, N. benthamiana plants agroinfiltrated with Construct #2962 exhibited an approximate 30% increase in VLP yield following iodixanol gradient purification, in comparison to plants infiltrated with wildtype construct.

F390D+L429M A/California/07/09 Mutant H1

F390D+L429M A/California/07/09 Mutant H1 was constructed by introducing a double mutation to the wildtype sequence of A/California/07/09 H1, wherein the phenylalanine at position 390 was mutated to an aspartic acid and the leucine at position 429 was mutated to a methionine residue (Construct #2995). As shown in FIG. 2B, purified extracts from N. benthamiana plants agroinfiltrated with Construct #2995 exhibited an approximate 60% increase in hemagglutination titer as compared to extracts from N. benthamiana plants agroinfiltrated with wildtype A/California/07/09 H1 (Construct #1314).

N97D A/Michigan/45/15 Mutant H1

N97D A/Michigan/45/15 Mutant H1 was constructed by mutating the asparagine residue at position 97 of wildtype A/Michigan/45/15 H1 to aspartic acid (Construct #3774). As shown in FIGS. 3A and 3B, purified extracts from N. benthamiana plants agroinfiltrated with Construct #3774 exhibited an approximate 1100% increase in hemagglutination titer as compared to extracts from N. benthamiana plants agroinfiltrated with wildtype A/Michigan/45/15 H1 (Construct #3640).

K374EA/Michigan/45/15 Mutant H1

K374E A/Michigan/45/15 Mutant H1 was constructed by mutating the lysine residue at position 374 of wildtype A/Michigan/45/15 H1 to glutamic acid (Construct #3771). As shown in FIGS. 3A and 3B, purified extracts from N. benthamiana plants agroinfiltrated with Construct #3771 exhibited an approximate 1100% increase in hemagglutination titer as compared to extracts from N. benthamiana plants agroinfiltrated with wildtype A/Michigan/45/15 H1 (Construct #3640).

F390D A/Michigan/45/15 Mutant H1

F390D A/Michigan/45/15 Mutant H1 was constructed by mutating the phenylalanine residue at position 390 of wildtype A/Michigan/45/15 H1 to aspartic acid (Construct #3641). As shown in FIG. 3B, purified extracts from N. benthamiana plants agroinfiltrated with Construct #3641 exhibited a similar activity in hemagglutination titer as compared to extracts from N. benthamiana plants agroinfiltrated with wildtype A/Michigan/45/15 H1 (Construct #3640). However, when full process yield for the purified VLPs with H1 was measured and increase to 172% compared to the wildtype was observed (see Table 5C).

L429M A/Michigan/45/15 Mutant H1

L429M A/Michigan/45/15 Mutant H1 was constructed by mutating the leucine residue at position 429 of wildtype A/Michigan/45/15 H1 to aspartic acid (Construct #3643). As shown in FIG. 3 B, purified extracts from N. benthamiana plants agroinfiltrated with Construct #3643 exhibited an approximate 500% increase in hemagglutination titer as compared to extracts from N. benthamiana plants agroinfiltrated with wildtype A/Michigan/45/15 H1 (Construct #3640).

N97D+K374E A/Michigan/45/15 Mutant H1

N97D+K374E A/Michigan/45/15 Mutant H1 was constructed by introducing a double mutation to the wildtype sequence of wildtype A/Michigan/45/15, wherein the asparagine at position 97 was replaced with an aspartic acid residue, and the lysine at position 374 was replaced with a glutamic acid residue (Construct #3880). As shown in FIG. 3B, purified extracts from N. benthamiana plants agroinfiltrated with Construct #3880 exhibited an approximate 1100% increase in hemagglutination titer as compared to extracts from N. benthamiana plants agroinfiltrated with wildtype A/Michigan/45/15 H1 (Construct #3640).

F390D+L429M A/Michigan/45/15 Mutant H1

F390D+L429M A/Michigan/45/15 Mutant H1 was constructed by introducing a double mutation to the wildtype sequence of wildtype A/Michigan/45/15, wherein the phenylalanine at position 390 was mutated to an aspartic acid residue, and the leucine at position 429 was replaced with a methionine residue (Construct #3703). As shown in FIG. 3B, purified extracts from N. benthamiana plants agroinfiltrated with Construct #3703 exhibited an approximate 1100% increase in hemagglutination titer as compared to extracts from *N. benthamiana* plants agroinfiltrated with wildtype A/Michigan/45/15 H1 (Construct #3640).

N97D+F390D+L429M A/Michigan/45/15 Mutant H1

N97D+F390D+L429M A/Michigan/45/15 Mutant H1 was constructed by introducing a triple mutation to the wildtype sequence of wildtype A/Michigan/45/15, wherein the asparagine at position 97 was mutated to an aspartic acid residue, the phenylalanine at position 390 was mutated to an aspartic acid residue, and the leucine at position 429 was replaced with a methionine residue (Construct #3879). As shown in FIG. 3B, purified extracts from *N. benthamiana* plants agroinfiltrated with Construct #3879 exhibited an approximate 2300% increase in hemagglutination titer as compared to extracts from *N. benthamiana* plants agroinfiltrated with wildtype A/Michigan/45/15 H1 (Construct #3640).

K374E+F390D+L429M A/Michigan/4515 Mutant H1

K374E+F390D+L429M A/Michigan/45/15 Mutant H1 was constructed by introducing a triple mutation to the wildtype sequence of wildtype A/Michigan/45/15, wherein the lysine at position 374 was mutated to a glutamic acid residue, the phenylalanine at position 390 was mutated to an aspartic acid residue, and the leucine at position 429 was replaced with a methionine residue (Construct #3878). As shown in FIG. 3B, purified extracts from *N. benthamiana* plants agroinfiltrated with Construct #3878 exhibited an approximate 2500% increase in hemagglutination titer as compared to extracts from *N. benthamiana* plants agroinfiltrated with wildtype A/Michigan/45/15 H1 (Construct #3640).

N97D+K374E+F390D+L429M A/Michigan/45/15 Mutant H1

N97D+K374E+F390D+L429M A/Michigan/45/15 Mutant H1 was constructed by introducing a quadruple mutation to the wildtype sequence of wildtype A/Michigan/45/15, wherein the asparagine at position 97 was mutated to an aspartic acid residue, the lysine at position 374 was mutated to a glutamic acid residue, the phenylalanine at position 390 was mutated to an aspartic acid residue, and the leucine at position 429 was replaced with a methionine residue (Construct #3881). As shown in FIG. 3B, purified extracts from *N. benthamiana* plants agroinfiltrated with Construct #3881 exhibited an approximate 3300% increase in hemagglutination titer as compared to extracts from *N. benthamiana* plants agroinfiltrated with wildtype A/Michigan/45/15 H1 (Construct #3640).

N97D+F390D+L429M A/Massachusetts/06/17Mutant H1

N97D+F390D+L429M A/Massachusetts/06/17 Mutant H1 was constructed by introducing a triple mutation to the wildtype sequence of wildtype A/Massachusetts/06/17, wherein the asparagine at position 97 was mutated to an aspartic acid residue, the phenylalanine at position 390 was mutated to an aspartic acid residue, and the leucine at position 429 was replaced with a methionine residue (Construct #4093). As shown in FIG. 4B, purified extracts from *N. benthamiana* plants agroinfiltrated with Construct #4093 exhibited an approximate 40% increase in hemagglutination titer as compared to extracts from *N. benthamiana* plants agroinfiltrated with the double mutant construct, F390D+L429M A/Massachusetts/06/17 Mutant H1 (Construct #4091).

K374E+F390D+L429M A/Massachusetts/06/17 Mutant H1

K374E+F390D+L429M A/Massachusetts/06/17 Mutant H1 was constructed by introducing a triple mutation to the wildtype sequence of wildtype A/Massachusetts/06/17, wherein the lysine at position 374 was mutated to an glutamic acid residue, the phenylalanine at position 390 was mutated to an aspartic acid residue, and the leucine at position 429 was replaced with a methionine residue (Construct #4092). As shown in FIG. 4B, purified extracts from *N. benthamiana* plants agroinfiltrated with Construct #4092 exhibited an approximate 50% increase in hemagglutination titer as compared to extracts from *N. benthamiana* plants agroinfiltrated with the double mutant construct, F390D+L429M A/Massachusetts/06/17 Mutant H1 (Construct #4091).

N97D+K374E+F390D+L429M A/Massachusetts/06/17Mutant H1

N97D+K374E+F390D+L429M A/Massachusetts/06/17 Mutant H1 was constructed by introducing a quadruple mutation to the wildtype sequence of wildtype A/Massachusetts/06/17, wherein the asparagine at position 97 was mutated to an aspartic acid residue, the lysine at position 374 was mutated to an glutamic acid residue, the phenylalanine at position 390 was mutated to an aspartic acid residue, and the leucine at position 429 was replaced with a methionine residue (Construct #4094). As shown in FIG. 4B, purified extracts from *N. benthamiana* plants agroinfiltrated with Construct #4094 exhibited an approximate 70% increase in hemagglutination titer as compared to extracts from *N. benthamiana* plants agroinfiltrated with the double mutant construct, F390D+L429M A/Massachusetts/06/17 Mutant H1 (Construct #4091).

N97D+F390D+L429M A/Costa Rica/0513/16 Mutant H1

N97D+F390D+L429M A/Costa Rica/0513/16 Mutant H1 was constructed by introducing a triple mutation to the wildtype sequence of wildtype A/Costa Rica/0513/16, wherein the asparagine at position 97 was mutated to an aspartic acid residue, the phenylalanine at position 390 was mutated to an aspartic acid residue, and the leucine at position 429 was replaced with a methionine residue (Construct #4717). As shown in FIG. 4B, purified extracts from *N. benthamiana* plants agroinfiltrated with Construct #4717 exhibited an approximate 100% increase in hemagglutination titer as compared to extracts from *N. benthamiana* plants agroinfiltrated with the double mutant construct, F390D+L429M A/Costa Rica/0513/16 Mutant H1 (Construct #4715).

K374E+F390D+L429M A/Costa Rica/0513/16 Mutant H1

K374E+F390D+L429M A/Costa Rica/0513/16 Mutant H1 was constructed by introducing a triple mutation to the wildtype sequence of wildtype A/Costa Rica/0513/16, wherein the lysine at position 374 was mutated to a glutamic acid residue, the phenylalanine at position 390 was mutated to an aspartic acid residue, and the leucine at position 429 was replaced with a methionine residue (Construct #4716). As shown in FIG. 4B, purified extracts from *N. benthamiana* plants agroinfiltrated with Construct #4716 exhibited an approximate 10% increase in hemagglutination titer as compared to extracts from *N. benthamiana* plants agroinfiltrated with the double mutant construct, F390D+L429M A/Costa Rica/0513/16 Mutant H1 (Construct #4715).

N97D+K374E+F390D+L429M A/Costa Rica/0513/16 Mutant H1

N97D+K374E+F390D+L429M A/Costa Rica/0513/16 Mutant H1 was constructed by introducing a quadruple mutation to the wildtype sequence of wildtype A/Costa Rica/0513/16, wherein the asparagine at position 97 was mutated to an aspartic acid residue, the lysine at position 374 was mutated to a glutamic acid residue, the phenylalanine at position 390 was mutated to an aspartic acid residue, and the leucine at position 429 was replaced with a methionine residue (Construct #4718). As shown in FIG. 4B, purified extracts from *N. benthamiana* plants agroinfiltrated with Construct #4718 exhibited an approximate 140% increase in hemagglutination titer as compared to extracts from *N. benthamiana* plants agroinfiltrated with the double mutant construct, F390D+L429M A/Costa Rica/0513/16 Mutant H1 (Construct #4715).

N97D A/Honduras/17734/16 Mutant H1

N97D A/Honduras/17734/16 Mutant H1 was constructed by mutating the asparagine residue at position 97 of wildtype A/Honduras/17734/16 H1 to aspartic acid (Construct #3950). As shown in FIG. 4A, purified extracts from *N. benthamiana* plants agroinfiltrated with Construct #3950 exhibited an approximate 300% increase in hemagglutination titer as compared to extracts from *N. benthamiana* plants agroinfiltrated with wildtype A/Honduras/17734/16 H1 (Construct #3944).

K374E A/Honduras/17734/16 Mutant H1

K374E A/Honduras/17734/16 Mutant H1 was constructed by mutating the lysine residue at position 374 of wildtype A/Honduras/17734/16 H1 to glutamic acid (Construct #3948). As shown in FIG. 4A, purified extracts from *N. benthamiana* plants agroinfiltrated with Construct #3948 exhibited an approximate 100% increase in hemagglutination titer as compared to extracts from *N. benthamiana* plants agroinfiltrated with wildtype A/Honduras/17734/16 H1 (Construct #3944).

F390D A/Honduras/17734/16 Mutant H1

F390D A/Honduras/17734/16 Mutant H1 was constructed by mutating the phenylalanine residue at position 390 of wildtype A/Honduras/17734/16 H1 to aspartic acid (Construct #3945). As shown in FIG. 4A, purified extracts from *N. benthamiana* plants agroinfiltrated with Construct #3945 exhibited an approximate 30% increase in hemagglutination titer as compared to extracts from *N. benthamiana* plants agroinfiltrated with wildtype A/Honduras/17734/16 H1 (Construct #3944).

L429M A/Honduras/17734/16 Mutant H1

L429M A/Honduras/17734/16 Mutant H1 was constructed by mutating the leucine residue at position 429 of wildtype A/Honduras/17734/16 H1 to methionine (Construct #3949). As shown in FIG. 4A, purified extracts from *N. benthamiana* plants agroinfiltrated with Construct #3949 exhibited an approximate 400% increase in hemagglutination titer as compared to extracts from *N. benthamiana* plants agroinfiltrated with wildtype A/Honduras/17734/16 H1 (Construct #3944).

F390D+L429M A/Honduras/17734/16 Mutant H1

F390D+L429M A/Honduras/17734/16 Mutant H1 was constructed by introducing a double mutation to the wildtype sequence of wildtype A/Honduras/17734/16, wherein the phenylalanine at position 390 was mutated to an aspartic acid residue, and the leucine at position 429 was replaced with a methionine residue (Construct #3946). As shown in FIG. 4A, purified extracts from *N. benthamiana* plants agroinfiltrated with Construct #3946 exhibited an approximate 300% increase in hemagglutination titer as compared to extracts from *N. benthamiana* plants agroinfiltrated with wildtype A/Honduras/17734/16 H1 (Construct #3944).

N97D+F390D+L429M A/Honduras/17734/16 Mutant H1

N97D+F390D+L429M A/Honduras/17734/16 Mutant H1 was constructed by introducing a triple mutation to the wildtype sequence of wildtype A/Honduras/17734/16, wherein the asparagine at position 97 was mutated to an aspartic acid residue, the phenylalanine at position 390 was mutated to an aspartic acid residue, and the leucine at position 429 was replaced with a methionine residue (Construct #3951). As shown in FIG. 4A, purified extracts from *N. benthamiana* plants agroinfiltrated with Construct #3951 exhibited an approximate 600% increase in hemagglutination titer as compared to extracts from *N. benthamiana* plants agroinfiltrated with wildtype A/Honduras/17734/16 H1 (Construct #3944).

N97D A/Darwin/11/15 Mutant H1

N97D A/Darwin/11/15 Mutant H1 was constructed by mutating the asparagine residue at position 97 of wildtype A/Darwin/11/15 H1 to aspartic acid (Construct #3990). As shown in FIG. 4A, purified extracts from *N. benthamiana* plants agroinfiltrated with Construct #3990 exhibited an approximate 200% increase in hemagglutination titer as compared to extracts from *N. benthamiana* plants agroinfiltrated with wildtype A/Darwin/11/15 H1 (Construct #3984).

K374E A/Darwin/11/15 Mutant H1

K374E A/Darwin/11/15 Mutant H1 was constructed by mutating the lysine residue at position 374 of wildtype A/Darwin/11/15 H1 to glutamic acid (Construct #3988). As shown in FIG. 4A, purified extracts from *N. benthamiana* plants agroinfiltrated with Construct #3988 exhibited an approximate 300% increase in hemagglutination titer as compared to extracts from *N. benthamiana* plants agroinfiltrated with wildtype A/Darwin/11/15 H1 (Construct #3984).

F390D A/Darwin/11/15 Mutant H1

F390D A/Darwin/11/15 Mutant H1 was constructed by mutating the phenylalanine residue at position 390 of wildtype A/Darwin/11/15 H1 to aspartic acid (Construct #3985). As shown in FIG. 4A, purified extracts from *N. benthamiana* plants agroinfiltrated with Construct #3985 exhibited an approximate 50% increase in hemagglutination titer as compared to extracts from *N. benthamiana* plants agroinfiltrated with wildtype A/Darwin/11/15 H1 (Construct #3984).

L429M A/Darwin/11/15 Mutant H1

L429M A/Darwin/11/15 Mutant H1 was constructed by mutating the leucine residue at position 429 of wildtype A/Darwin/11/15 H1 to methionine (Construct #3989). As shown in FIG. 4A, purified extracts from *N. benthamiana* plants agroinfiltrated with Construct #3989 exhibited an approximate 500% increase in hemagglutination titer as compared to extracts from *N. benthamiana* plants agroinfiltrated with wildtype A/Darwin/11/15 H1 (Construct #3984).

F390D+L429M A/Darwin/11/15 Mutant H1

F390D+L429M A/Darwin/11/15 Mutant H1 was constructed by introducing a double mutation to the wildtype sequence of wildtype A/Darwin/11/15, wherein the phenylalanine at position 390 was mutated to an aspartic acid residue, and the leucine at position 429 was replaced with a methionine residue (Construct #3986). As shown in FIG. 4A, purified extracts from *N. benthamiana* plants agroinfiltrated with Construct #3986 exhibited an approximate 300% increase in hemagglutination titer as compared to extracts from *N. benthamiana* plants agroinfiltrated with wildtype A/Darwin/11/15 H1 (Construct #3984).

N97D+F390D+L429M A/Darwin/11/15 Mutant H1

N97D+F390D+L429M A/Darwin/11/15 Mutant H1 was constructed by introducing a triple mutation to the wildtype sequence of wildtype A/Darwin/11/15, wherein the asparagine at position 97 was mutated to an aspartic acid residue, the phenylalanine at position 390 was mutated to an aspartic acid residue, and the leucine at position 429 was replaced with a methionine residue (Construct #3991). As shown in FIG. 4A, purified extracts from *N. benthamiana* plants agroinfiltrated with Construct #3991 exhibited an approximate 1100% increase in hemagglutination titer as compared to extracts from *N. benthamiana* plants agroinfiltrated with wildtype A/Darwin/11/15 H1 (Construct #3984).

F390D+L429M A/Paris/1227/2017 Mutant H1

F390D+L429M A/Paris/1227/2017 Mutant H1 was constructed by introducing a double mutation to the wildtype sequence of wildtype A/Paris/1227/2017, wherein the phenylalanine at position 390 was mutated to an aspartic acid residue, and the leucine at position 429 was replaced with a methionine residue (Construct #4765). As shown in FIG. 4C, purified extracts from *N. benthamiana* plants agroinfiltrated with Construct #4765 exhibited an approximate 117% increase in hemagglutination titer as compared to extracts from *N. benthamiana* plants agroinfiltrated with F390D+L429M A/Massachusetts/06/17 Mutant H1 (Construct #4091).

K374+F390D+L429M A/Paris/1227/2017

K374E+F390D+L429M A/Paris/1227/2017 Mutant H1 was constructed by introducing a triple mutation to the wildtype sequence of wildtype A/Paris/1227/2017, wherein the lysine at position 374 was mutated to a glutamic acid residue, the phenylalanine at position 390 was mutated to an aspartic acid residue, and the leucine at position 429 was replaced with a methionine residue (Construct #4766). As shown in FIG. 4C, purified extracts from *N. benthamiana* plants agroinfiltrated with Construct #4766 exhibited an approximate 127% increase in hemagglutination titer as compared to extracts from *N. benthamiana* plants agroinfiltrated with F390D+L429M A/Paris/1227/2017 Mutant H1 (Construct #4765).

N97D+F390D+L429M A/Paris/1227/2017

N97D+F390D+L429M A/Paris/1227/2017 Mutant H1 was constructed by introducing a triple mutation to the wildtype sequence of wildtype A/Paris/1227/2017, wherein the asparagine at position 97 was mutated to an aspartic acid residue, the phenylalanine at position 390 was mutated to an aspartic acid residue, and the leucine at position 429 was replaced with a methionine residue (Construct #4767). As shown in FIG. 4C, purified extracts from *N. benthamiana* plants agroinfiltrated with Construct #4767 exhibited an approximate 171% increase in hemagglutination titer as compared to extracts from *N. benthamiana* plants agroinfiltrated with F390D+L429M A/Paris/1227/2017 Mutant H1 (Construct #4765).

N97D+K374E+F390D+L429M A/Paris/1227/2017

N97D+K374E+F390D+L429M A/Paris/1227/2017 Mutant H1 was constructed by introducing a quadruple mutation to the wildtype sequence of wildtype A/Paris/1227/2017, wherein the asparagine at position 97 was mutated to an aspartic acid residue, the lysine at position 374 was mutated to a glutamic acid residue, the phenylalanine at position 390 was mutated to an aspartic acid residue, and the leucine at position 429 was replaced with a methionine residue (Construct #4768). As shown in FIG. 4C, purified extracts from *N. benthamiana* plants agroinfiltrated with Construct #4768 exhibited an approximate 230% increase in hemagglutination titer as compared to extracts from *N. benthamiana* plants agroinfiltrated with F390D+L429M A/Paris/1227/2017 Mutant H1 (Construct #4765).

F390D+L429M A/Norway/2147/2017 Mutant H1

F390D+L429M A/Norway/2147/2017 Mutant H1 was constructed by introducing a double mutation to the wildtype sequence of wildtype A/Norway/2147/2017, wherein the phenylalanine at position 390 was mutated to an aspartic acid residue, and the leucine at position 429 was replaced with a methionine residue (Construct #4775). As shown in FIG. 4C, purified extracts from *N. benthamiana* plants agroinfiltrated with Construct #4775 exhibited an approximate 112% increase in hemagglutination titer as compared to extracts from *N. benthamiana* plants agroinfiltrated with F390D+L429M A/Massachusetts/06/17 Mutant H1 (Construct #4091).

K374+F390D+L429M A/Norway/2147/2017

K374E+F390D+L429M A/Norway/2147/2017 Mutant H1 was constructed by introducing a triple mutation to the wildtype sequence of wildtype A/Norway/2147/2017, wherein the lysine at position 374 was mutated to a glutamic acid residue, the phenylalanine at position 390 was mutated to an aspartic acid residue, and the leucine at position 429 was replaced with a methionine residue (Construct #4776). As shown in FIG. 4C, purified extracts from *N. benthamiana* plants agroinfiltrated with Construct #4776 exhibited an approximate 128% increase in hemagglutination titer as compared to extracts from *N. benthamiana* plants agroinfiltrated with F390D+L429M A/Norway/2147/2017 Mutant H1 (Construct #4775).

N97D+F390D+L429M A/Norway/2147/2017

N97D+F390D+L429M A/Norway/2147/2017 Mutant H1 was constructed by introducing a triple mutation to the wildtype sequence of wildtype A/Norway/2147/2017, wherein the asparagine at position 97 was mutated to an aspartic acid residue, the phenylalanine at position 390 was mutated to an aspartic acid residue, and the leucine at position 429 was replaced with a methionine residue (Construct #4777). As shown in FIG. 4C, purified extracts from *N. benthamiana* plants agroinfiltrated with Construct #4777 exhibited an approximate 200% increase in hemagglutination titer as compared to extracts from *N. benthamiana* plants agroinfiltrated with F390D+L429M A/Norway/2147/2017 Mutant H1 (Construct #4775).

N97D+K374E+F390D+L429M A/Norway/2147/2017

N97D+K374E+F390D+L429M A/Norway/2147/2017 Mutant H1 was constructed by introducing a quadruple mutation to the wildtype sequence of wildtype A/Norway/2147/2017, wherein the asparagine at position 97 was mutated to an aspartic acid residue, the lysine at position 374 was mutated to a glutamic acid residue, the phenylalanine at position 390 was mutated to an aspartic acid residue, and the leucine at position 429 was replaced with a methionine residue (Construct #4778). As shown in FIG. 4C, purified extracts from *N. benthamiana* plants agroinfiltrated with Construct #4778 exhibited an approximate 213% increase in hemagglutination titer as compared to extracts from *N. benthamiana* plants agroinfiltrated with F390D+L429M A/Norway/2147/2017 Mutant H1 (Construct #4775).

N380A A/Michigan/45/15

N380A A/Michigan/45/15 Mutant H1 was constructed by mutating the asparagine at position 380 of wildtype A/Michigan/45/15 H1 to an alanine residue (Construct #3644). As seen in FIGS. 3B and 3C, purified extracts from *N. benthamiana* plants agroinfiltrated with Construct #3644 exhibited an approximate 80% decrease in hemagglutination titer as compared to extracts from *N. benthamiana* plants agroinfiltrated with wildtype A/Michigan/45/15 H1 (Construct #3640).

N380A+F390D A/Michigan/45/15

A N380A+F390D A/Michigan/45/15 Mutant H1 was also constructed, wherein a double mutation was introduced into wildtype A/Michigan/45/15 H1 by replacing the asparagine at position 380 with an alanine residue, and replacing the phenylalanine at position 390 with an aspartic acid residue (Construct #3704). As seen in FIG. 3B, purified extracts from *N. benthamiana* plants agroinfiltrated with Construct #3704 exhibited an approximate 50% decrease in hemagglutination titer as compared to extracts from *N. benthamiana* plants agroinfiltrated with wildtype A/Michigan/45/15

H1 (Construct #3640). In view of the reduced hemagglutination titer observed with the N380A A/Michigan/45/15 Mutant H1, these results suggest that mutation of the asparagine residue at position 380 negatively affects the expression of influenza HA protein and/or the stability of influenza HA protein in plants.

The one or more than one mutations described herein specifically increase influenza HA protein production and VLP yield in plants. It was observed that mutations at other positions significantly reduced, or had no significant effect, on influenza HA protein accumulation or VLP production in plant cells.

The increased hemagglutination titers achieved with the influenza HA proteins comprising the one or more than one mutation described herein was also observed to be specific to influenza H1 HAs. Similar enhancements were not observed in plants agroinfiltrated with constructs encoding mutant influenza HAs derived from non-H1 strains.

Figure 5:
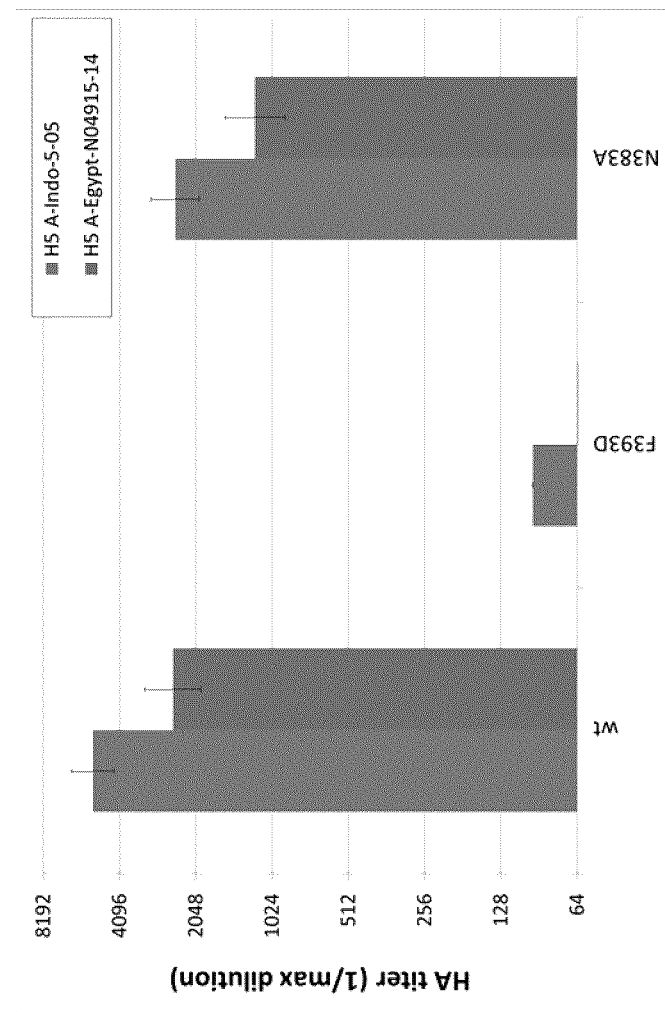

For example, F393D A/Indonesia/5/2005 Mutant H5 was constructed by mutating the phenylalanine at position 393 of wildtype A/Indonesia/5/2005 H5 to aspartic acid (Construct #3680). As shown in FIG. 5, purified extracts from *N. benthamiana* plants agroinfiltrated with Construct #3680 exhibited an approximate 98% reduction in hemagglutination titer as compared to extracts from *N. benthamiana* plants agroinfiltrated with wildtype A/Indonesia/5/2005 H5 (Construct #2295).

Similarly, purified extracts from *N. benthamiana* plants agroinfiltrated with F392D A/Egypt/N04915/2014 Mutant H5 (Construct #3690), exhibited an approximate 99% reduction in hemagglutination titer as compared to extracts from *N. benthamiana* plants agroinfiltrated with wildtype A/Egypt/N04915/2014 H5 (Construct #3645) (see FIG. 5, Table 6).

The one or more than one mutations described herein specifically increase influenza HA protein production and VLP yield in plants. It was observed that mutations at other positions significantly reduced, or had no significant effect, on influenza HA protein accumulation or VLP production in plant cells.

TABLE 4

Examples of constructs that have been prepared as described herein. Sequences are provided in Example 4 and the sequence listing.

| Construct Name | TMCT | Construct # | FIG. | Primer 1 | Primer 2 | Primer 3 |
| --- | --- | --- | --- | --- | --- | --- |
| H1 A-Cal-7-2009 | Wt | 1314 | 6A | SEQ ID NO: 13 | SEQ ID NO: 14 | — |
| H1 A-Cal-7-09 (F390D) | Wt | 2980 | 6B | SEQ ID NO: 13 | SEQ ID NO: 15 | SEQ ID NO: 16 |
| H1 A-Cal-7-09 (L429M) | Wt | 2962 | 6C | SEQ ID NO: 13 | SEQ ID NO: 19 | SEQ ID NO: 20 |
| H1 A-Cal-7-09 (F390D + L429M) | Wt | 2995 | 6D | SEQ ID NO: 13 | SEQ ID NO: 19 | SEQ ID NO: 20 |
| H1 A-Mich-45-2015 | Wt | 3640 | 6E | SEQ ID NO: 13 | SEQ ID NO: 14 | — |
| H1 A-Mich-45-2015 (N97D) | Wt | 3774 | 6F | SEQ ID NO: 13 | SEQ ID NO: 25 | SEQ ID NO: 26 |
| H1 A-Mich-45-2015 (K374E) | Wt | 3771 | 6G | SEQ ID NO: 13 | SEQ ID NO: 29 | SEQ ID NO: 30 |
| H1 A-Mich-45-2015 (F390D) | Wt | 3641 | 6H | SEQ ID NO: 13 | SEQ ID NO: 33 | SEQ ID NO: 34 |
| H1 A-Mich-45-2015 (L429M) | Wt | 3643 | 6I | SEQ ID NO: 13 | SEQ ID NO: 19 | SEQ ID NO: 37 |
| H1 A-Mich-45-2015 (N97D + K374E) | Wt | 3880 | 6J | SEQ ID NO: 13 | SEQ ID NO: 29 | SEQ ID NO: 30 |
| H1 A-Mich-45-2015 (F390D + L429M) | Wt | 3703 | 6K | SEQ ID NO: 13 | SEQ ID NO: 33 | SEQ ID NO: 34 |
| H1 A-Mich-45-2015 (N97D + F390D + L429M) | Wt | 3879 | 6L | SEQ ID NO: 13 | SEQ ID NO: 25 | SEQ ID NO: 26 |
| H1 A-Mich-45-2015 (K374E + F390D + L429M) | Wt | 3878 | 6M | SEQ ID NO: 13 | SEQ ID NO: 29 | SEQ ID NO: 30 |
| H1 A-Mich-45-2015 (N97D + K374E + F390D + L429M) | Wt | 3881 | 6N | SEQ ID NO: 13 | SEQ ID NO: 25 | SEQ ID NO: 26 |
| H1 A-Mass-06-2017 (F390D + L429M) | Wt | 4091 | 6O | SEQ ID NO: 13 | SEQ ID NO: 14 | — |
| H1 A-Mass-06-2017 (N97D + F390D + L429M) | Wt | 4093 | 6P | SEQ ID NO: 13 | SEQ ID NO: 25 | SEQ ID NO: 26 |
| H1 A-Mass-06-2017 (K374E + F390D + L429M) | Wt | 4092 | 6Q | SEQ ID NO: 13 | SEQ ID NO: 29 | SEQ ID NO: 30 |
| H1 A-Mass-06-2017 (N97D + K374E + F390D + L429M) | Wt | 4094 | 6R | SEQ ID NO: 13 | SEQ ID NO: 25 | SEQ ID NO: 26 |
| H1 A-CostaRica-0513-2016 (F390D + L429M) | Wt | 4715 | 6S | SEQ ID NO: 13 | SEQ ID NO: 14 | — |
| H1 A-CostaRica-0513-2016 (N97D + F390D + L429M) | Wt | 4717 | 6T | SEQ ID NO: 13 | SEQ ID NO: 25 | SEQ ID NO: 26 |
| H1 A-CostaRica-0513-2016 (K374E + F390D + L429M) | Wt | 4716 | 6U | SEQ ID NO: 13 | SEQ ID NO: 29 | SEQ ID NO: 30 |
| H1 A-CostaRica-0513-2016 (N97D + K374E + F390D + L429M) | Wt | 4718 | 6V | SEQ ID NO: 13 | SEQ ID NO: 25 | SEQ ID NO: 26 |
| H1 A-Hond-17734-16 | Wt | 3944 | 6W | SEQ ID NO: 13 | SEQ ID NO: 14 | — |
| H1 A-Hond-17734-16 (N97D) | Wt | 3950 | 6X | SEQ ID NO: 13 | SEQ ID NO: 25 | SEQ ID NO: 66 |
| H1 A-Hond-17734-16 (K374E) | Wt | 3948 | 6Y | SEQ ID NO: 13 | SEQ ID NO: 69 | SEQ ID NO: 70 |
| H1 A-Hond-17734-16 (F390D) | Wt | 3945 | 6Z | SEQ ID NO: 13 | SEQ ID NO: 74 | SEQ ID NO: 75 |
| H1 A-Hond-17734-16 (L429M) | Wt | 3949 | 6AA | SEQ ID NO: 13 | SEQ ID NO: 77 | SEQ ID NO: 78 |
| H1 A-Hond-17734-16 (F390D + L429M) | Wt | 3946 | 6BB | SEQ ID NO: 13 | SEQ ID NO: 74 | SEQ ID NO: 75 |
| H1 A-Hond-17734-16 (N97D + F390D + L429M) | Wt | 3951 | 6CC | SEQ ID NO: 13 | SEQ ID NO: 25 | SEQ ID NO: 66 |
| H1 A-Darw-11-15 | Wt | 3984 | 6DD | SEQ ID NO: 13 | SEQ ID NO: 14 | — |
| H1 A-Darw-11-15 (N97D) | Wt | 3990 | 6EE | SEQ ID NO: 13 | SEQ ID NO: 25 | SEQ ID NO: 26 |
| H1 A-Darw-11-15 (K374E) | Wt | 3988 | 6FF | SEQ ID NO: 13 | SEQ ID NO: 29 | SEQ ID NO: 87 |
| H1 A-Darw-11-15 (F390D) | Wt | 3985 | 6GG | SEQ ID NO: 13 | SEQ ID NO: 74 | SEQ ID NO: 75 |
| H1 A-Darw-11-15 (L429M) | Wt | 3989 | 6HH | SEQ ID NO: 13 | SEQ ID NO: 77 | SEQ ID NO: 78 |
| H1 A-Darw-11-15 (F390D + L429M) | Wt | 3986 | 6II | SEQ ID NO: 13 | SEQ ID NO: 77 | SEQ ID NO: 78 |
| H1 A-Darw-11-15 (N97D + F390D + L429M) | Wt | 3991 | 6JJ | SEQ ID NO: 13 | SEQ ID NO: 25 | SEQ ID NO: 26 |
| H1 A-Mich-45-2015 (N380A) | Wt | 3644 | 6KK | SEQ ID NO: 13 | SEQ ID NO: 102 | SEQ ID NO: 103 |
| H1 A-Mich-45-2015 (F390D + N380A) | Wt | 3704 | 6LL | SEQ ID NO: 13 | SEQ ID NO: 106 | SEQ ID NO: 103 |
| H5 A-Indo-5-05 | Wt | 2295 | 7A | SEQ ID NO: 13 | SEQ ID NO: 109 | — |
| H5 A-Indo-5-05 (F393D) | Wt | 3680 | 7B | SEQ ID NO: 13 | SEQ ID NO: 112 | SEQ ID NO: 113 |
| H5 A-Egypt-N04915-14 | Wt | 3645 | 7C | SEQ ID NO: 13 | SEQ ID NO: 116 | — |
| H5 A-Egypt-N04915-14 (F392D) | Wt | 3690 | 7D | SEQ ID NO: 13 | SEQ ID NO: 119 | SEQ ID NO: 120 |
| A/Paris/1227/17 (F390D + L429M) | Wt | 4765 | 6MM | SEQ ID NO: 13 | SEQ ID NO: 14 | — |

TABLE 4-continued

Examples of constructs that have been prepared as described herein. Sequences are provided in Example 4 and the sequence listing.

| | | | | | | |
|---|---|---|---|---|---|---|
| A/Paris/1227/17 (K374E + F390D + L429M) | Wt | 4766 | 6NN | SEQ ID NO: 13 | SEQ ID NO: 29 | SEQ ID NO: 30 |
| A/Paris/1227/17 (N97D + F390D + L429M) | Wt | 4767 | 6OO | SEQ ID NO: 13 | SEQ ID NO: 25 | SEQ ID NO: 26 |
| A/Paris/1227/17 (N97D + K374E + F390D + L429M) | Wt | 4768 | 6PP | SEQ ID NO: 13 | SEQ ID NO: 29 | SEQ ID NO: 30 |
| A/Norway/2147/17 (F390D + L429M) | Wt | 4775 | 6QQ | SEQ ID NO: 13 | SEQ ID NO: 14 | — |
| A/Norway/2147/17 (K374E + F390D + L429M) | Wt | 4776 | 6RR | SEQ ID NO: 13 | SEQ ID NO: 29 | SEQ ID NO: 30 |
| A/Norway/2147/17 (N97D + F390D + L429M) | Wt | 4777 | 6SS | SEQ ID NO: 13 | SEQ ID NO: 25 | SEQ ID NO: 26 |
| A/Norway/2147/17 (N97D + K374E + F390D + L429M) | Wt | 4778 | 6TT | SEQ ID NO: 13 | SEQ ID NO: 29 | SEQ ID NO: 30 |

| Construct Name | Primer 4 | Template for PCR | Resulting Gene | Resulting Protein |
|---|---|---|---|---|
| H1 A-Cal-7-2009 | — | SEQ ID NO: 1 | SEQ ID NO: 1 | SEQ ID NO: 2 |
| H1 A-Cal-7-09 (F390D) | SEQ ID NO: 14 | SEQ ID NO: 1 | SEQ ID NO: 17 | SEQ ID NO: 18 |
| H1 A-Cal-7-09 (L429M) | SEQ ID NO: 14 | SEQ ID NO: 1 | SEQ ID NO: 21 | SEQ ID NO: 22 |
| H1 A-Cal-7-09 (F390D + L429M) | SEQ ID NO: 14 | SEQ ID NO: 17 | SEQ ID NO: 23 | SEQ ID NO: 24 |
| H1 A-Mich-45-2015 | — | SEQ ID NO: 3 | SEQ ID NO: 3 | SEQ ID NO: 4 |
| H1 A-Mich-45-2015 (N97D) | SEQ ID NO: 14 | SEQ ID NO: 3 | SEQ ID NO: 27 | SEQ ID NO: 28 |
| H1 A-Mich-45-2015 (K374E) | SEQ ID NO: 14 | SEQ ID NO: 3 | SEQ ID NO: 31 | SEQ ID NO: 32 |
| H1 A-Mich-45-2015 (F390D) | SEQ ID NO: 14 | SEQ ID NO: 3 | SEQ ID NO: 35 | SEQ ID NO: 36 |
| H1 A-Mich-45-2015 (L429M) | SEQ ID NO: 14 | SEQ ID NO: 3 | SEQ ID NO: 38 | SEQ ID NO: 39 |
| H1 A-Mich-45-2015 (N97D + K374E) | SEQ ID NO: 14 | SEQ ID NO: 27 | SEQ ID NO: 40 | SEQ ID NO: 41 |
| H1 A-Mich-45-2015 (F390D + L429M) | SEQ ID NO: 14 | SEQ ID NO: 38 | SEQ ID NO: 42 | SEQ ID NO: 43 |
| H1 A-Mich-45-2015 (N97D + F390D + L429M) | SEQ ID NO: 14 | SEQ ID NO: 42 | SEQ ID NO: 44 | SEQ ID NO: 45 |
| H1 A-Mich-45-2015 (K374E + F390D + L429M) | SEQ ID NO: 14 | SEQ ID NO: 42 | SEQ ID NO: 46 | SEQ ID NO: 47 |
| H1 A-Mich-45-2015 (N97D + K374E + F390D + L429M) | SEQ ID NO: 14 | SEQ ID NO: 46 | SEQ ID NO: 48 | SEQ ID NO: 49 |
| H1 A-Mass-06-2017 (F390D + L429M) | — | SEQ ID NO: 50 | SEQ ID NO: 50 | SEQ ID NO: 51 |
| H1 A-Mass-06-2017 (N97D + F390D + L429M) | SEQ ID NO: 14 | SEQ ID NO: 50 | SEQ ID NO: 52 | SEQ ID NO: 53 |
| H1 A-Mass-06-2017 (K374E + F390D + L429M) | SEQ ID NO: 14 | SEQ ID NO: 50 | SEQ ID NO: 54 | SEQ ID NO: 55 |
| H1 A-Mass-06-2017 (N97D + K374E + F390D + L429M) | SEQ ID NO: 14 | SEQ ID NO: 54 | SEQ ID NO: 56 | SEQ ID NO: 57 |
| H1 A-CostaRica-0513-2016 (F390D + L429M) | — | SEQ ID NO: 58 | SEQ ID NO: 58 | SEQ ID NO: 59 |
| H1 A-CostaRica-0513-2016 (N97D + F390D + L429M) | SEQ ID NO: 14 | SEQ ID NO: 58 | SEQ ID NO: 60 | SEQ ID NO: 61 |
| H1 A-CostaRica-0513-2016 (K374E + F390D + L429M) | SEQ ID NO: 14 | SEQ ID NO: 58 | SEQ ID NO: 62 | SEQ ID NO: 62 |
| H1 A-CostaRica-0513-2016 (N97D + K374E + F390D + L429M) | SEQ ID NO: 14 | SEQ ID NO: 62 | SEQ ID NO: 64 | SEQ ID NO: 65 |
| H1 A-Hond-17734-16 | — | SEQ ID NO: 9 | SEQ ID NO: 10 | SEQ ID NO: 10 |
| H1 A-Hond-17734-16 (N97D) | SEQ ID NO: 14 | SEQ ID NO: 9 | SEQ ID NO: 67 | SEQ ID NO: 68 |
| H1 A-Hond-17734-16 (K374E) | SEQ ID NO: 14 | SEQ ID NO: 9 | SEQ ID NO: 71 | SEQ ID NO: 72 |
| H1 A-Hond-17734-16 (F390D) | SEQ ID NO: 14 | SEQ ID NO: 9 | SEQ ID NO: 76 | SEQ ID NO: 77 |
| H1 A-Hond-17734-16 (L429M) | SEQ ID NO: 14 | SEQ ID NO: 9 | SEQ ID NO: 79 | SEQ ID NO: 80 |
| H1 A-Hond-17734-16 (F390D + L429M) | SEQ ID NO: 14 | SEQ ID NO: 79 | SEQ ID NO: 81 | SEQ ID NO: 82 |
| H1 A-Hond-17734-16 (N97D + F390D + L429M) | SEQ ID NO: 14 | SEQ ID NO: 81 | SEQ ID NO: 83 | SEQ ID NO: 84 |
| H1 A-Darw-11-15 | — | SEQ ID NO: 11 | SEQ ID NO: 11 | SEQ ID NO: 12 |
| H1 A-Darw-11-15 (N97D) | SEQ ID NO: 14 | SEQ ID NO: 11 | SEQ ID NO: 85 | SEQ ID NO: 86 |
| H1 A-Darw-11-15 (K374E) | SEQ ID NO: 14 | SEQ ID NO: 11 | SEQ ID NO: 88 | SEQ ID NO: 89 |
| H1 A-Darw-11-15 (F390D) | SEQ ID NO: 14 | SEQ ID NO: 11 | SEQ ID NO: 90 | SEQ ID NO: 91 |
| H1 A-Darw-11-15 (L429M) | SEQ ID NO: 14 | SEQ ID NO: 11 | SEQ ID NO: 92 | SEQ ID NO: 93 |
| H1 A-Darw-11-15 (F390D + L429M) | SEQ ID NO: 14 | SEQ ID NO: 90 | SEQ ID NO: 94 | SEQ ID NO: 95 |
| H1 A-Darw-11-15 (N97D + F390D + L429M) | SEQ ID NO: 14 | SEQ ID NO: 94 | SEQ ID NO: 96 | SEQ ID NO: 97 |
| H1 A-Mich-45-2015 (N380A) | SEQ ID NO: 14 | SEQ ID NO: 104 | SEQ ID NO: 3 | SEQ ID NO: 105 |
| H1 A-Mich-45-2015 (F390D + N380A) | SEQ ID NO: 14 | SEQ ID NO: 35 | SEQ ID NO: 107 | SEQ ID NO: 108 |
| H5 A-lndo-5-05 | — | SEQ ID NO: 110 | SEQ ID NO: 110 | SEQ ID NO: 111 |
| H5 A-lndo-5-05 (F393D) | SEQ ID NO: 109 | SEQ ID NO: 110 | SEQ ID NO: 114 | SEQ ID NO: 115 |
| H5 A-Egypt-N04915-14 | — | SEQ ID NO: 117 | SEQ ID NO: 117 | SEQ ID NO: 118 |
| H5 A-Egypt-N04915-14 (F392D) | SEQ ID NO: 116 | SEQ ID NO: 117 | SEQ ID NO: 121 | SEQ ID NO: 122 |
| A/Paris/1227/17 (F390D + L429M) | — | SEQ ID NO: 123 | SEQ ID NO: 127 | SEQ ID NO: 124 |
| A/Paris/1227/17 (K374E + F390D + L429M) | SEQ ID NO: 14 | SEQ ID NO: 123 | SEQ ID NO: 127 | SEQ ID NO: 126 |
| A/Paris/1227/17 (N97D + F390D + L429M) | SEQ ID NO: 14 | SEQ ID NO: 123 | SEQ ID NO: 127 | SEQ ID NO: 128 |
| A/Paris/1227/17 (N97D + K374E + F390D + L429M) | SEQ ID NO: 14 | SEQ ID NO: 127 | SEQ ID NO: 127 | SEQ ID NO: 140 |
| A/Norway/2147/17 (F390D + L429M) | — | SEQ ID NO: 141 | SEQ ID NO: 141 | SEQ ID NO: 142 |
| A/Norway/2147/17 (K374E + F390D + L429M) | SEQ ID NO: 14 | SEQ ID NO: 141 | SEQ ID NO: 143 | SEQ ID NO: 144 |
| A/Norway/2147/17 (N97D + F390D + L429M) | SEQ ID NO: 14 | SEQ ID NO: 141 | SEQ ID NO: 145 | SEQ ID NO: 146 |
| A/Norway/2147/17 (N97D + K374E + F390D + L429M) | SEQ ID NO: 14 | SEQ ID NO: 145 | SEQ ID NO: 147 | SEQ ID NO: 148 |

Example 3: Hemagglutination Titer, Post-density Gradient Yields and Full Process Yields A Summary of the measured Hemagglutination Titer is given in Table 5A. Hemagglutination Titer were measured as described in Example 2. The relative hemagglutination titer were obtained by comparing the hemagglutination titer of the mutated or modified HA protein to wildtype HA (Tables 5A).

A Summary of the measured Post-Density Gradient Yields is given in Table 5B. Post-Density Gradient Yields were measured as described in Example 2. Relative yields were obtained by comparing the HA0 band intensity from the mutated or modified HA protein to the HA0 band intensity of wildtype HA (Table 5B).

A Summary of the measured Full Process Yield is given in Table 5C. Full Process Yield were obtained as described above in Example 2. Relative yields were obtained by comparing the protein yield from the mutated or modified HA protein to the protein yield of wildtype HA (Table 5C).

TABLE 5A

Summary of relative Hemagglutination Titer for H1. Numbering is in accordance with A/Michigan/45/15 HA.

|  | WT | N97D | K374E | N380A | F390D | L429M | N380A + L429M |
|---|---|---|---|---|---|---|---|
| H1 A/California/07/09 | 100% |  |  | 120% | 100-160% | 100-120% |  |
| H1 A/Michigan/45/15 | 100% | 400-1200% | 400-1200% | 20% | 80-100% | 400-600% | 800% |
| H1 A/Massachusetts/06/17 |  |  |  |  |  |  |  |
| H1 A/CostaRica/0513/16 |  |  |  |  |  |  |  |
| H1 A/Honduras/17734/16 | 100% | 400% | 200% |  | 120-130% | 500% |  |
| H1 A/Darwin/11/15 | 100% | 300% | 400% |  | 140-150% | 600% |  |
| H1 A/Paris/1227/2017 |  |  |  |  |  |  | 117% |
| A/Norway/2147/2017 |  |  |  |  |  |  | 112% |

|  | N97D + K374E | F390D + L429M | N97D + F390D + L429M | K374E + F390D + L429M | N97D + K374E + F390D + L429M |
|---|---|---|---|---|---|
| H1 A/California/07/09 |  | 140-160% |  |  |  |
| H1 A/Michigan/45/15 | 1200% | 400-1200% | 800-2400% | 2400-2600% | 3200-3400% |
| H1 A/Massachusetts/06/17 |  | 100% | 140% | 150% | 170% |
| H1 A/CostaRica/0513/16 |  | 100% | 200% | 110% | 240% |
| H1 A/Honduras/17734/16 |  | 400% | 500-700% |  |  |
| H1 A/Darwin/11/15 |  | 400% | 1200% |  |  |
| H1 A/Paris/1227/2017 |  |  | 171% | 127% | 230% |
| A/Norway/2147/2017 |  |  | 200% | 128% | 213% |

TABLE 5B

Summary of relative Post-Density Gradient Yields for H1. Numbering is in accordance with A/Michigan/45/15 HA.

|  | WT | N380A | F390D | L429M |
|---|---|---|---|---|
| H1 A/California/07/09 | 100% | 100% | 157% | 130% |

TABLE 5C

Summary of relative Full Process Yield for H1. Numbering is in accordance with A/Michigan/45/15 HA.

|  | WT | F390D | L429M | F390D + L429M | N97D + F390D + L429M | K374E + F390D + L429M |
|---|---|---|---|---|---|---|
| H1 A/California/07/09 | 100% | 226% |  |  |  |  |
| H1 A/Michigan/45/15 | 100% | 172% | 260% | 633% | 647% | 689% |

TABLE 6

Summary of relative Hemagglutination Titer for H5. Numbering in accordance with H5 A/Indonesia/5/2005

|  | WT | N383A | F393D |
|---|---|---|---|
| H5 A/Indonesia/5/2005 | 100% | 50% | 2% |
| H5 A/Egypt/N04915/2014 | 100% | 50% | 1% |

Example 4: Sequences

The following sequences were used (also see Table 4):

```
PDI-H1 Cal DNA (SEQ ID NO: 1)
ATGGCGAAAAACGTTGCGATTTTCGGCTTATTGTTTTCTCTTCTTGTGTTGGTTCCTTCTCAGATCTTC
GCTGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGCTCATGGTCCTACATTGTGGAAACACCTAGTTCAGACAATGGAACGTGTTAC
```

-continued

```
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CATGCTGGAGCAAAAGCTTCTACAAAAATTTAATATGGCTAGTTAAAAAAGGAAATTCATACCCAAAG
CTCAGCAAATCCTACATTAATGATAAAGGGAAAGAAGTCCTCGTGCTATGGGCATTCACCATCCATCT
ACTAGTGCTGACCAACAAAGTCTCTATCAGAATGCAGATGCATATGTTTTTGTGGGGTCATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCGCAATGGAAAGAAATGCTGGATCTGGTATTATCATTTCAGATACACCAGTCCACGATTGC
AATACAACTTGTCAAACACCCAAGGGTGCTATAAACACCAGCCTCCCATTTCAGAATATACATCCGATC
ACAATTGGAAAATGTCCAAATATGTAAAAAGCACAAAATTGAGACTGGCCACAGGATTGAGGAATATC
CCGTCTATTCAATCTAGAGGACTATTTGGGGCCATTGCCGGTTTCATTGAAGGGGGTGGACAGGGATG
GTAGATGGATGGTACGGTTATCACCATCAAAATGAGCAGGGGTCAGGATATGCAGCCGACCTGAAGAGC
ACACAGAATGCCATTGACGAGATTACTAACAAAGTAAATTCTGTTATTGAAAAGATGAATACACAGTTC
ACAGCAGTAGGTAAAGAGTTCAACCACCTGGAAAAAAGAATAGAGAATTTAAATAAAAAAGTTGATGAT
GGTTTCCTGGACATTTGGACTTACAATGCCGAACTGTTGGTTCTATTGGAAAATGAAAGAACTTTGGAC
TACCACGATTCAAATGTGAAGAACTTATATGAAAAGGTAAGAAGCCAGCTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAGAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGTTTCTGGATGTGCTCTAATGGGTCTCTACAGTGTAGAATATGTATTTAA

PD1-H1 Cal AA (SEQ ID NO: 2)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETPSSDNGTCYPGDFIDYEELREQLSSVSSFERF
EIFPKTSSWPNHDSNKGVTAACPHAGAKSFYKNLIWLVKKGNSYPKLSKSYINDKGKEVLVLWGIHHPS
TSADQQSLYQNADAYVFVGSSRYSKKFKPETATRPKVRDQEGRMNYYWTLVEPGDKITFEATGNLVVPR
YAFAMERNAGSGIIISDTPVHDCNTTCQTPKGAINTSLPFQNTHPITIGKCPKYVKSTKLRLATGLRNI
PSIQSRGLFGAIAGFIEGGWTGMVDGWYGYHHQNEQGSGYAADLKSTQNAIDEITNKVNSVIEKMNTQF
TAVGKEFNHLEKRIENLNKKVDDGELDIWTYNAELLVLLENERTLDYHDSNVKNLYEKVRSQLKNNAKE
IGNGCFEFYHKCDNTCMESVKNGTYDYPKYSEEAKLNREEIDGVKLESTRIYQILAIYSTVASSLVLVV
SLGAISFWMCSNGSLQCRICI

PDI-H1 Mich DNA (SEQ ID NO: 3)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich AA (SEQ ID NO: 4)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERE
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNIHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGFLDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI PDI-H1 Mass DNA (SEQ ID NO: 5)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAGCTTCTACAAAAACTTGATATGGCTAGTTAAAAAAGGAAATTCATACCCAAAG
```

CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGTTC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Mass AA (SEQ ID NO: 6)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERE
EIFPKTSSWPNHDSNKGVTAACPHAGAKSFYKNLVLVKKGNSYPINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGFLDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI PDI-H1 CostaR DNA (SEQ ID NO: 7)
ATGGCGAAAAACGTTGCGATTTTCGGCTTATTGTTTTCTCTTCTTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACGTGAATGATAAAGGGAAAGAAGTCCTCGTGCTGTGGGGCATTCACCATCCACCC
ACTACTGCTGACCAACAAAGTCTCTATCAGAATGCAGATGCATATGTTTTTGTGGGGACATCAAAGTAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGTTC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 CostaR AA (SEQ ID NO: 8)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYVNDKGKEVLVLWGIHHPP
TTADQQSLYQNADAYVFVGTSKYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI PDI-H1 Hond DNA (SEQ ID NO: 9)
ATGGCGAAAAACGTTGCGATTTTCGGCTTATTGTTTTCTCTTCTTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCAATTATGAGGAGCTAAGGGAGCAATTGAGCTCAGTGTCATCATTTGAGAGATTT
GAGATATTCCCCAAGACAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT -continued

```
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGTTC
ACAGCAGTGGGTAAAGAGTTCAACCACTTGGAAAAAGAATAGAGAATTTAAATAAAAAAGTTGATGAT
GGTTTCCTGGACATTTGGACTTACAATGCCGAACTGCTGGTTCTATTGGAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTAATGGGTCTCTACAGTGTAGAATATGTATTTAA

PDI-H1 Hond AA (SEQ ID NO: 10)
MAKNVAIFGLLFSLLVLVPSQIFADTLCIGYHANNSTDTVDTVLEKNVTVTHSVNLLEDKHNGKLCKLR
GVPPLHLGKCNIAGWILGNPECEPLSTASSWSYIVETSSSDNGTCYPGDFINYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI PDI-H1 Darw DNA (SEQ ID NO: 11)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACATCTAGTTCAGACAATGGAACGTGTTAC
CCAGGAGATTTCATCAATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAGGGAAATTCATACCCAAAG
CTCAGCCAATCCTACATTAATGATAAAGGGAAAGAAATCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGTTC
ACAGCAGTGGGTAAAGAGTTCAACCACTTGGAAAAAGAATAGAGAATTTAAATAAAAAAGTTGATGAT
GGTTTCCTGGACATTTGGACTTACAATGCCGAACTGCTGGTTCTATTGGAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGGATTTACCAAATTTTGGCGATCTATTCAACTGTCGCCAGTTCATTGGTACTGGTAGTC
TCCCTGGGGGCAATCAGCTTCTGGATGTGCTAATGGGTCTCTACAGTGTAGAATATGTATTTAA PDI-H1 Darw AA (SEQ ID NO: 12)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFINYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGELDIWTYNAELLVLLENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI IF-CPMV(f15'UTR)_SpPDI.c (SEQ ID NO: 13)
TCGTGCTTCGGCACCAGTACAATGGCGAAAAACGTTGCGATTTTCGGCT IF-H1cTMCT.S1-4r (SEQ ID NO: 14)
ACTAAAGAAAATAGGCCTTTAAATACATATTCTACACTGTAGAGAC H1Cal(F390D).r (SEQ ID NO: 15)
CTCTTTACCTACTGCTGTGTCCTGTGTATTCATCTTTTCAATAACAGAATTTA H1Cal(F390D).c (SEQ ID NO: 16)
TTATTGAAAAGATGAATACACAGGACACAGCAGTAGGTAAAGAGTTCAAC PDI-H1 Cal-F390D DNA sequence (SEQ ID NO: 17)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
```

-continued

AATGTAACAGTAACACACTCTGTTAACCTTCTAGAAGACAAGCATAACGGGAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGCTCATGGTCCTACATTGTGGAAACACCTAGTTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CATGCTGGAGCAAAAAGCTTCTACAAAAATTTAATATGGCTAGTTAAAAAAGGAAATTCATACCCAAAG
CTCAGCAAATCCTACATTAATGATAAAGGGAAAGAAGTCCTCGTGCTATGGGGCATTCACCATCCATCT
ACTAGTGCTGACCAACAAAGTCTCTATCAGAATGCAGATGCATATGTTTTTGTGGGGTCATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCGCAATGGAAAGAAATGCTGGATCTGGTATTATCATTTCAGATACACCAGTCCACGATTGC
AATACAACTTGTCAAACACCCAAGGGTGCTATAAACACCAGCCTCCCATTTCAGAATATACATCCGATC
ACAATTGGAAAATGTCCAAAATATGTAAAAAGCACAAAATTGAGACTGGCCACAGGATTGAGGAATATC
CCGTCTATTCAATCTAGAGGACTATTTGGGGCCATTGCCGGTTTCATTGAAGGGGGGTGGACAGGGATG
GTAGATGGATGGTACGGTTATCACCATCAAAATGAGCAGGGGTCAGGATATGCAGCCGACCTGAAGAGC
ACACAGAATGCCATTGACGAGATTACTAACAAAGTAAATTCTGTTATTGAAAAGATGAATACACAGGAC
ACAGCAGTAGGTAAAGAGTTCAACCACCTGGAAAAAAGAATAGAGAATTTAAATAAAAAAGTTGATGAT
GGTTTCCTGGACATTTGGACTTACAATGCCGAACTGTTGGTTCTATTGGAAAATGAAAGAACTTTGGAC
TACCACGATTCAAATGTGAAGAACTTATATGAAAAGGTAAGAAGCCAGCTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAGAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGTTTCTGGATGTGCTCTAATGGGTCTCTACAGTGTAGAATATGTATTTAA

PDI-H1 Cal-F390D AA sequence (SEQ ID NO: 18)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETPSSDNGTCYPGDFIDYEELREQLSSVSSFERF
EIFPKTSSWPNHDSNKGVTAACPHAGAKSFYKNLIWLVKKGNSYPKLSKSYINDKGKEVLVLWGIHHPS
TSADQQSLYQNADAYVFVGSSRYSKKFKPETATRPKVRDQEGRMNYYWTLVEPGDKITFEATGNLVVPR
YAFAMERNAGSGIIISDTPVHDCNTTCQTPKGAINTSLPFQNTHPITIGKCPKYVKSTKLRLATGLRNI
PSIQSRGLFGAIAGFIEGGWTGMVDGWYGYHHQNEQGSGYAADLKSTQNAIDEITNKVNSVIEKMNTQD
TAVGKEENHLEKRIENLNKKVDDGELDIWTYNAELLVLLENERTLDYHDSNVKNLYEKVRSQLKNNAKE
IGNGCFEFYHKCDNTCMESVKNGTYDYPKYSEEAKLNREEIDGVKLESTRIYQILAIYSTVASSLVLVV
SLGAISFWMCSNGSLQCRICI H1Cal(L429M).r (SEQ ID NO: 19)
GTTCTTTCATTTTCCATTAGAACCAACAGTTCGGCATTGTAAGTCCAA H1Cal(L429M).c (SEQ ID NO: 20)
CGAACTGTTGGTTCTAATGGAAAATGAAAGAACTTTGGACTACCACGA PDI-H1 Cal-L429M DNA sequence (SEQ ID NO: 21)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGCTCATGGTCCTACATTGTGGAAACACCTAGTTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CATGCTGGAGCAAAAAGCTTCTACAAAAATTTAATATGGCTAGTTAAAAAAGGAAATTCATACCCAAAG
CTCAGCAAATCCTACATTAATGATAAAGGGAAAGAAGTCCTCGTGCTATGGGGCATTCACCATCCATCT
ACTAGTGCTGACCAACAAAGTCTCTATCAGAATGCAGATGCATATGTTTTTGTGGGGTCATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCGCAATGGAAAGAAATGCTGGATCTGGTATTATCATTTCAGATACACCAGTCCACGATTGC
AATACAACTTGTCAAACACCCAAGGGTGCTATAAACACCAGCCTCCCATTTCAGAATATACATCCGATC
ACAATTGGAAAATGTCCAAAATATGTAAAAAGCACAAAATTGAGACTGGCCACAGGATTGAGGAATATC
CCGTCTATTCAATCTAGAGGACTATTTGGGGCCATTGCCGGTTTCATTGAAGGGGGGTGGACAGGGATG
GTAGATGGATGGTACGGTTATCACCATCAAAATGAGCAGGGGTCAGGATATGCAGCCGACCTGAAGAGC
ACACAGAATGCCATTGACGAGATTACTAACAAAGTAAATTCTGTTATTGAAAAGATGAATACACAGTTC
ACAGCAGTAGGTAAAGAGTTCAACCACCTGGAAAAAAGAATAGAGAATTTAAATAAAAAAGTTGATGAT
GGTTTCCTGGACATTTGGACTTACAATGCCGAACTGTTGGTTCTAATGGAAAATGAAAGAACTTTGGAC
TACCACGATTCAAATGTGAAGAACTTATATGAAAAGGTAAGAAGCCAGCTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAGAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGTTTCTGGATGTGCTCTAATGGGTCTCTACAGTGTAGAATATGTATTTAA PDI-H1 Cal-L429M AA sequence (SEQ ID NO: 22)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETPSSDNGTCYPGDFIDYEELREQLSSVSSFERF
EIFPKTSSWPNHDSNKGVTAACPHAGAKSFYKNLIWLVKKGNSYPKLSKSYINDKGKEVLVLWGIHHPS
TSADQQSLYQNADAYVFVGSSRYSKKFKPETATRPKVRDQEGRMNYYWTLVEPGDKITFEATGNLVVPR
YAFAMERNAGSGIIISDTPVHDCNTTCQTPKGAINTSLPFQNTHPITIGKCPKYVKSTKLRLATGLRNI
PSIQSRGLFGAIAGFIEGGWTGMVDGWYGYHHQNEQGSGYAADLKSTQNAIDEITNKVNSVIEKMNTQF
TAVGKEENHLEKRIENLNKKVDDGELDIWTYNAELLVLMENERTLDYHDSNVKNLYEKVRSQLKNNAKE
IGNGCFEFYHKCDNTCMESVKNGTYDYPKYSEEAKLNREEIDGVKLESTRIYQILAIYSTVASSLVLVV
SLGAISFWMCSNGSLQCRICI*

PDI-H1 Cal-F390D + L429M DNA sequence (SEQ ID NO: 23)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGCTCATGGTCCTACATTGTGGAAACACCTAGTTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CATGCTGGAGCAAAAAGCTTCTACAAAAATTTAATATGGCTAGTTAAAAAAGGAAATTCATACCCAAAG
CTCAGCAAATCCTACATTAATGATAAAGGGAAAGAAGTCCTCGTGCTATGGGGCATTCACCATCCATCT
ACTAGTGCTGACCAACAAAGTCTCTATCAGAATGCAGATGCATATGTTTTTGTGGGGTCATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCGCAATGGAAAGAAATGCTGGATCTGGTATTATCATTTCAGATACACCAGTCCACGATTGC
AATACAACTTGTCAAACACCCAAGGGTGCTATAAACACCAGCCTCCCATTTCAGAATATACATCCGATC
ACAATTGGAAAATGTCCAAAATATGTAAAAAGCACAAAATTGAGACTGGCCACAGGATTGAGGAATATC
CCGTCTATTCAATCTAGAGGACTATTTGGGGCCATTGCCGGTTTCATTGAAGGGGGTGGACAGGGATG
GTAGATGGATGGTACGGTTATCACCATCAAAATGAGCAGGGTCAGGATATGCAGCCGACCTGAAGAGC
ACACAGAATGCCATTGACGAGATTACTAACAAAGTAAATTCTGTTATTGAAAAGATGAATACACAGGAC
ACAGCAGTAGGTAAAGAGTTCAACCACCTGGAAAAAGAATAGAGAATTTAAATAAAAAAGTTGATGAT
GGTTTCCTGGACATTTGGACTTACAATGCCGAACTGTTGGTTCTAATGGAAAATGAAAGAACTTTGGAC
TACCACGATTCAAATGTGAAGAACTTATATGAAAAGGTAAGAAGCCAGCTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAGAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGTTTCTGGATGTGCTCTAATGGGTCTCTACAGTGTAGAATATGTATTTAA PDI-H1 Cal-F390D + L429M AA sequence (SEQ ID NO: 24)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETPSSDNGTCYPGDFIDYEELREQLSSVSSFERE
EIFPKTSSWPNHDSNKGVTAACPHAGAKSFYKNLIWLVKKGNSYPKLSKSYINDKGKEVLVLWGIHHPS
TSADQQSLYQNADAYVFVGSSRYSKKFKPEIAIRPKVRDQEGRMNYYWTLVEPGDKITFEATGNLVVPR
YAFAMERNAGSGIIISDTPVHDCNTTCQTPKGAINTSLPFQNIHPITIGKCPKYVKSTKLRLATGLRNI
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRSQLKNNAKE
IGNGCFEFYHKCDNTCMESVKNGTYDYPKYSEEAKLNREEIDGVKLESTRIYQILAIYSTVASSLVLVV
SLGAISFWMCSNGSLQCRICI*

H1Mich(N97D).r (SEQ ID NO: 25)
TAGCTCCTCATAATCGATGAAATCTCCTGGGTAACACGTTCCATTGTCTGAA H1Mich(N97D).c (SEQ ID NO: 26)
CCCAGGAGATTTCATCGATTATGAGGAGCTAAGAGAGCAATTGAGCTCAG PDI-H1 Mich-N97D DNA (SEQ ID NO: 27)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-N97D AA (SEQ ID NO: 28)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERE
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNIHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGFLDIWTYNAELLVLLENERTLDYHDSNVKNLYEKVRNQLKNNAKE -continued IGNGCFEFYHKCDNTCMESVKNGTYDYPKYSEEAKLNREKIDGVKLESTRIYQILAIYSTVASSLVLVV
SLGAISFWMCSNGSLQCRICI*

H1Mich(K374E).r (SEQ ID NO: 29)
TTTGTTAGTAATCTCGTCAATGGCATTTTGTGTGCTCTTCAGGTCGGCTGCATATCC H1Mich(K374E).c (SEQ ID NO: 30)
ACAAAATGCCATTGACGAGATTACTAACAAAGTAAATTCTGTTATTGAAA PDI-H1 Mich-K374E DNA (SEQ ID NO: 31)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-K374E AA (SEQ ID NO: 32)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSNDGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQF
TAVGKEFNHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Mich(F390D).r (SEQ ID NO: 33)
CCCACTGCTGTGTCCTGTGTATTCATCTTTTCAATAACAGAATTTACTT H1Mich(F390D).c (SEQ ID NO: 34)
AAAGATGAATACACAGGACACAGCAGTGGGTAAAGAGTTCAACCACCTG PDI-H1 Mich-F390D DNA (SEQ ID NO: 35)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-F390D AA (SEQ ID NO: 36)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Mich(L429M).c (SEQ ID NO: 37)
CGAACTGTTGGTTCTAATGGAAAATGAAAGAACTTTGGACTATCACGATTCAAA PDI-H1 Mich-L429M DNA (SEQ ID NO: 38)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-L429M AA (SEQ ID NO: 39)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mich-N97D + K374E DNA (SEQ ID NO: 40)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-N97D + K374E AA (SEQ ID NO: 41)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mich-F390D + L429M DNA (SEQ ID NO: 42)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAAGGATCAAGAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-F390D + L429M AA (SEQ ID NO: 43)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mich-N97D + F390D + L429M DNA (SEQ ID NO: 44)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-N97D + F390D + L429M AA (SEQ ID NO: 45)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mich-K374E + F390D + L429M DNA (SEQ ID NO: 46)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAAGGATCAAGAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-K374E + F390D + L429M AA (SEQ ID NO: 47)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mich-N97D + K374E + F390D + L429M DNA (SEQ ID NO: 48)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-N97D + K374E + F390D + L429M AA (SEQ ID NO: 49)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mass-F390D + L429M DNA (SEQ ID NO: 50)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAAGGATCAAGAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mass-F390D + L429M AA (SEQ ID NO: 51)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mass-N97D + F390D + L429M DNA (SEQ ID NO: 52)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mass-N97D + F390D + L429M AA (SEQ ID NO: 53)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mass-K374E + F390D + L429M DNA (SEQ ID NO: 54)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAAGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mass-K374E + F390D + L429M AA (SEQ ID NO: 55)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Mass-N97D + K374E + F390D + L429M DNA (SEQ ID NO: 56)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mass-N97D + K374E + F390D + L429M AA (SEQ ID NO: 57)
MAKNVAIFGLLFSLLVLVPSQIFADTLCIGYHANNSTDTVDTVLEKNVTVHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 CR-F390D + L429M DNA (SEQ ID ON: 58)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGCAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACGTGAATGATAAAGGGAAAGAAGTCCTCGTGCTGTGGGCATTCACCATCCACCC
ACTACTGCTGACCAACAAAGTCTCTATCAGAATGCAGATGCATATGTTTTTGTGGGGACATCAAAGTAC
AGCAAGAAGTTCAAGCCGGAAATAGCAACAAGACCCAAAGTGAAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 CR-F390D + L429M AA (SEQ ID NO: 59)
MAKNVAIFGLLFSLLVLVPSQIFADTLCIGYHANNSTDTVDTVLEKNVTVHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYVNDKGKEVLVLWGIHHPP
TTADQQSLYQNADAYVFVGTSKYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 CR-N97D + F390D + L429M DNA (SEQ ID NO: 60)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACGTGAATGATAAAGGGAAAGAAGTCCTCGTGCTGTGGGCATTCACCATCCACCC
ACTACTGCTGACCAACAAAGTCTCTATCAGAATGCAGATGCATATGTTTTTGTGGGGACATCAAAGTAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 CR-N97D + F390D + L429M AA (SEQ ID NO: 61)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERF
EIFPKTSSWPNHDSNKGVTAACPHAGAKSFYKNLIWLVKKGNSYPKLNQSYVNDKGKEVLVLWGIHHPP
TTADQQSLYQNADAYVFVGTSKYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 CR-K374E + F390D + L429M DNA (SEQ ID NO: 62)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGCAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACGTGAATGATAAAGGGAAAGAAGTCCTCGTGCTGTGGGCATTCACCATCCACCC
ACTACTGCTGACCAACAAAGTCTCTATCAGAATGCAGATGCATATGTTTTTGTGGGGACATCAAAGTAC
AGCAAGAAGTTCAAGCCGGAAATAGCAACAAGACCCAAAGTGAAGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 CR-K374E + F390D + L429M AA (SEQ ID NO: 63)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYVNDKGKEVLVLWGIHHPP
TTADQQSLYQNADAYVFVGTSKYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGELDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 CR-N97D + K374E + F390D + L429M DNA (SEQ ID NO: 64)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACGTGAATGATAAAGGGAAAGAAGTCCTCGTGCTGTGGGCATTCACCATCCACCC
ACTACTGCTGACCAACAAAGTCTCTATCAGAATGCAGATGCATATGTTTTTGTGGGGACATCAAAGTAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 CR-N97D + K374E + F390D + L429M AA (SEQ ID NO: 65)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFIDYEELREQLSSVSSFERF
EIFPKTSSWPNHDSNKGVTAACPHAGAKSFYKNLIWLVKKGNSYPKLNQSYVNDKGKEVLVLWGIHHPS
TTADQQSLYQNADAYVFVGTSKYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Hond(N97D).c (SEQ ID NO: 66)
CCCAGGAGATTTCATCGATTATGAGGAGCTAAGGGAGCAATTGAGCTCAG PDI-H1 Hond-N97D DNA (SEQ ID NO: 67)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCGATTATGAGGAGCTAAGGGAGCAATTGAGCTCATCATTTGAGAGATTT
GAGATATTCCCCAAGACAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGTGGACAGGGATG
GTAGATGGATGGTACGGTTATCACCATCAAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGTTC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTATTGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Hond-N97D AA (SEQ ID NO: 68)
MAKNVAIFGLLFSLLVLVPSQIFADTLCIGYHANNSTDTVDTVLEKNVTVTHSVNLLEDKHNGKLCKLR
GVPPLHLGKCNIAGWILGNPECEPLSTASSWSYIVETSSSDNGTCYPGDFIDYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Hond(K374E).r (SEQ ID NO: 69)
TTTGTTAGTAATCTCGTCAATGGCACTTTGTGTGCTCTTCTGGTCGGCTGCATATCC H1Hond(K374E).c (SEQ ID NO: 70)
ACAAAGTGCCATTGACGAGATTACTAACAAAGTAAATTCTGTTATTGAAA PDI-H1 Hond-K374E DNA (SEQ ID NO: 71)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCAATTATGAGGAGCTAAGGGAGCAATTGAGCTCAGTGTCATCATTTGAGAGATTT
GAGATATTCCCCAAGACAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAAATGAGCAGGGGTCAGGATATGCAGCCGACCAGAAGAGC
ACACAAAGTGCCATTGACGAGATTACTAACAAAGTAAATTCTGTTATTGAAAAGATGAATACACAGTTC
ACAGCAGTGGGTAAAGAGTTCAACCACTTGGAAAAAAGAATAGAGAATTTAAATAAAAAAGTTGATGAT -continued GGTTTCCTGGACATTTGGACTTACAATGCCGAACTGCTGGTTCTATTGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Hond-K374E AA (SEQ ID NO: 72)
MAKNVAIFGLLFSLLVLVPSQIFADTLCIGYHANNSTDTVDTVLEKNVTVTHSVNLLEDKHNGKLCKLR
GVPPLHLGKCNIAGWILGNPECEPLSTASSWSYIVETSSSDNGTCYPGDFINYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDEITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Hond(F390D).r (SEQ ID NO: 73)
ACCCACTGCTGTGTCCTGTGTATTCATCTTTTCAATAACAGAATTTACTT H1Hond(F390D).c (SEQ ID NO: 74)
AAAGATGAATACACAGGACACAGCAGTGGGTAAAGAGTTCAACCACTTGG PDI-H1 Hond-F390D DNA (SEQ ID NO: 75)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCAATTATGAGGAGCTAAGGGAGCAATTGAGCTCAGTGTCATCATTTGAGAGATTT
GAGATATTCCCCAAGACAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGGAC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTATTGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Hond-F390D AA (SEQ ID NO: 76)
MAKNVAIFGLLFSLLVLVPSQIFADTLCIGYHANNSTDTVDTVLEKNVTVTHSVNLLEDKHNGKLCKLR
GVPPLHLGKCNIAGWILGNPECEPLSTASSWSYIVETSSSDNGTCYPGDFINYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQD
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Hond(L429M).r (SEQ ID NO: 77)
TCTTTCATTTTCCATTAGAACCAGCAGTTCGGCATTGTAAGTCCAAATGTCCAGG H1Hond(L429M).c (SEQ ID NO: 78)
CGAACTGCTGGTTCTAATGGAAAATGAAAGAACTTTGGACTACCACGA PDI-H1 Hond-L429M DNA (SEQ ID NO: 79)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCAATTATGAGGAGCTAAGGGAGCAATTGAGCTCAGTGTCATCATTTGAGAGATTT
GAGATATTCCCCAAGACAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC

```
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGTTC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTAATGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Hond-L429M AA (SEQ ID NO: 80)
MAKNVAIFGLLFSLLVLVPSQIFADTLCIGYHANNSTDVDTVLEKNVTVTHSVNLLEDKHNGKLCKLR
GVPPLHLGKCNIAGWILGNPECEPLSTASSWSYIVETSSSDNGTCYPGDFINYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQF
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Hond-F390D + L429M DNA (SEQ ID NO: 81)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCAATTATGAGGAGCTAAGGGAGCAATTGAGCTCAGTGTCATCATTTGAGAGATTT
GAGATATTCCCCAAGCAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGGAC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTAATGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Hond-F390D + L429M AA (SEQ ID NO: 82)
MAKNVAIFGLLFSLLVLVPSQIFADTLCIGYHANNSTDVDTVLEKNVTVTHSVNLLEDKHNGKLCKLR
GVPPLHLGKCNIAGWILGNPECEPLSTASSWSYIVETSSSDNGTCYPGDFINYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Hond-N97D + F390D + L429M DNA (SEQ ID NO: 83)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCATAACGGGAAACTATGCAAACTAAGA
GGGGTACCCCCATTGCATTTGGGTAAATGTAACATTGCTGGCTGGATCCTGGGAAATCCAGAGTGTGAA
CCACTCTCCACAGCAAGTTCATGGTCCTACATTGTGGAAACATCTAGTTCAGACAATGGAACGTGTTAC
CCAGGAGATTTCATCGATTATGAGGAGCTAAGGGAGCAATTGAGCTCAGTGTCATCATTTGAGAGATTT
GAGATATTCCCCAAGCAAGTTCATGGCCCAATCATGACTCGAACAAAGGTGTAACAGCAGCATGTCCT
CACGCTGGGGCAAAAAGCTTCTACAAAAATTTAATATGGCTAGTTAAAAAAGGAAATTCATACCCAAAG
CTCAGCCAATCCTACATTAATGATAAAGGAAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
```

-continued

AATACAACTTGTCAGACACCCGAGGGTGCTATAAACACCAGCCTCCCATTTCAGAATATACATCCGATC
ACAATTGGGAAATGTCCAAAGTATGTAAAAAGCACAAAATTGAGACTGGCCACAGGATTGAGGAATGTC
CCATCTATTCAATCTAGAGGCCTATTCGGGGCGATTGCCGGCTTCATTGAAGGGGGGTGGACAGGGATG
GTAGATGGATGGTACGGTTATCACCATCAAAATGAGCAGGGGTCAGGATATGCAGCCGACCAGAAGAGC
ACACAAAGTGCCATTGACAAAATTACTAACAAAGTAAATTCTGTTATTGAAAAGATGAATACACAGGAC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTAATGGAAAATGAAAGAACTTTGGAC
TACCACGACTCAAATGTGAAGAACTTGTATGAAAAGGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Hond-N97D + F390D + L429M AA (SEQ ID NO: 84)
MAKNVAIFGLLFSLLVLVPSQIFADTLCIGYHANNSTDTVDTVLEKNVTVTHSVNLLEDKHNGKLCKLR
GVPPLHLGKCNIAGWILGNPECEPLSTASSWSYIVETSSSDNGTCYPGDFIDYEELREQLSSVSSFERF
EIFPKTSSWPNHDSNKGVTAACPHAGAKSFYKNLIWLVKKGNSYPKLSQSYINDKGKEVLVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADQKSTQSAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Darw-N97D DNA (SEQ ID NO: 85)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACATCTAGTTCAGACAATGGAACGTGTTAC
CCAGGAGATTTCATCGATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGTTC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTATTGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Darw-N97D AA (SEQ ID NO: 86)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFIDYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI*

H1Darw(K374E).r (SEQ ID NO: 87)
TTTGTTAGTAATCTCGTCAATGGCATTTTGTGTGCTCTTCAGGTCGGCTGCATACC PDI-H1 Darw-K374E DNA (SEQ ID NO: 88)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACATCTAGTTCAGACAATGGAACGTGTTAC
CCAGGAGATTTCATCAATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC

```
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGGTATGCAGCCGACCTGAAGAGC
ACACAAAATGCCATTGACGAGATTACTAACAAAGTAAATTCTGTTATTGAAAAGATGAATACACAGTTC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTATTGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Darw-K374E AA (SEQ ID NO: 89)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFINYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI*

PDI-H1 Darw-F390D DNA (SEQ ID NO: 90)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACTCTAGTTCAGACAATGGAACGTGTTAC
CCAGGAGATTTCATCAATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGGAC
ACAGCAGTGGGTAAAGAGTTCAACCACTTGGAAAAAAGAATAGAGAATTTAAATAAAAAAGTTGATGAT
GGTTTCCTGGACATTTGGACTTACAATGCCGAACTGCTGGTTCTATTGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Darw-F390D AA (SEQ ID NO: 91)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFINYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI*

PDI-H1 Darw-L429M DNA (SEQ ID NO: 92)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACTCTAGTTCAGACAATGGAACGTGTTAC
CCAGGAGATTTCATCAATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
```

-continued

```
GTAGATGGATGGTACGGTTATCACCATCAAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGTTC
ACAGCAGTGGGTAAAGAGTTCAACCACTTGGAAAAAGAATAGAGAATTTAAATAAAAAAGTTGATGAT
GGTTTCCTGGACATTTGGACTTACAATGCCGAACTGCTGGTTCTAATGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Darw-L429M AA (SEQ ID NO: 93)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFINYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQF
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI*

PDI-H1 Darw-F390D + L429M DNA (SEQ ID NO: 94)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACATCTAGTTCAGACAATGGAACGTGTTAC
CCAGGAGATTTCATCAATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGGAC
ACAGCAGTGGGTAAAGAGTTCAACCACTTGGAAAAAGAATAGAGAATTTAAATAAAAAAGTTGATGAT
GGTTTCCTGGACATTTGGACTTACAATGCCGAACTGCTGGTTCTAATGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Darw-F390D + L429M AA (SEQ ID NO: 95)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSSSDNGTCYPGDFINYEELREQLSSVSSFERF
EIFPKTSSWPNHDSNKGVTAACPHAGAKSFYKNLIWLTKKGNSYPKLSQSYINDKGKEILVLWGIHHPS
TTADQQSLYQNADAYVFVGTSRYSKKFKPETATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSGEAKLNREKIEGVKLESTRIYQILAIYSTVASSLVLVV
SLGAISFWMCSNGSLQCRICI*

PDI-H1 Darw-N97D + F390D + L429M DNA (SEQ ID NO: 96)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTAGAAGACAAGCACAACGGGAAACTATGCAAACTAAGA
GGGGTAGCCCCATTGCATTTGGGTAAATGTAACATTGCTGGCTGGATCCTGGGAAACCCAGAGTGTGAA
TCACTCTCCACAGCAAGTTCATGGTCCTACATTGTGGAAACATCTAGTTCAGACAATGGAACGTGTTAC
CCAGGAGATTTCATCGATTATGAGGAGCTAAGAGAGCAATTGAGCTCAGTGTCATCATTTGAAAGATTT
GAGATATTCCCCAAGACAAGTTCATGGCCCAATCATGACTCGAACAAAGGTGTAACGGCAGCATGTCCT
CACGCTGGAGCAAAAAGCTTCTACAAAAATTTAATATGGCTAACTAAAAAAAGGAAATTCATACCCAAAG
CTCAGCCAATCCTACATTAATGATAAAGGGAAAGAAATCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAATAAGACCCAAAGTGAGGGATCAAGAAGGGAGAATGAACTAT
TACTGGACACTAGTAGAGCCAGGTGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTGAAAAGCACAAAATTGAGACTGGCCACAGGATTGAGGAATGTC
CCATCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGGTATGCAGCCGACCTGAAGAGC
ACACAAAATGCCATTGACAAAATTACTAACAAAGTAAATTCTGTTATTGAAAAGATGAATACACAGGAC
ACAGCAGTGGGTAAAGAGTTCAACCACTTGGAAAAAGAATAGAGAATTTAAATAAAAAAGTTGATGAT
```

```
GGTTTCCTGGACATTTGGACTTACAATGCCGAACTGCTGGTTCTAATGGAAAATGAAAGAACTTTGGAC
TACCACGATTCAAATGTGAAGAACTTGTATGAAAAGGTAAGAAACCAGTTAAAAAACAATGCCAAGGAA
ATTGGAAATGGTTGCTTTGAATTTTACCACAAATGCGATAACACGTGCATGGAAAGTGTCAAAAATGGG
ACTTATGACTACCCAAAATACTCAGGGGAAGCAAAATTAAACAGAGAAAAATAGAAGGGGTAAAGCTG
GAATCAACAAGAATTTACCAAATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Darw-N97D + F390D + L429M AA (SEQ ID NO: 97)
MAKNVAIFGLLFSLLVLVPSQIFADT

```
TCCCGCAATTATACATTTAATACGCGATAGAAAACAAAATATAGCGCGCAAACTAGGATAAATTATCGC
GCGCGGTGTCATCTATGTTACTAGATCTCTAGAGTCTCAAGCTTGGCGCGCCCACGTGACTAGTGGCAC
TGGCCGTCGTTTTACAACGTCGTGACTGGGAAAACCCTGGCGTTACCCAACTTAATCGCCTTGCAGCAC
ATCCCCCTTTCGCCAGCTGGCGTAATAGCGAAGAGGCCCGCACCGATCGCCCTTCCCAACAGTTGCGCA
GCCTGAATGGCGAATGCTAGAGCAGCTTGAGCTTGGATCAGATTGTCGTTTCCCGCCTTCAGTTTAAAC
TATCAGTGTTTGACAGGATATATTGGCGGGTAAACCTAAGAGAAAAGAGCGTTTA

Construct 1314 from 2X35S prom to NOS term (SEQ ID NO: 99)
GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATC
TGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATAACATGGTGGAGCAC
GACACACTTGTCTACTCCAAAAATATCAAAGATACAGTCTCAGAAGACCAAAGGGCAATTGAGACTTTT
CAACAAAGGGTAATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAGACGTT
CCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTT
AATAGGTTTTGATAAAAGCGAACGTGGGGAAACCCGAACCAAACCTTCTTCTAAACTCTCTCTCATCTC
TCTTAAAGCAAACTTCTCTCTTGTCTTTCTTGCGTGAGCGATCTTCAACGTTGTCAGATCGTGCTTCGG
CACCAGTACAATGGCGAAAAACGTTGCGATTTTCGGCTTATTGTTTTCTCTTCTTGTGTTGGTTCCTTC
TCAGATCTTCGCTGACACATTATGTATAGGTTATCATGCGAACAATTCAACAGACACTGTAGACACAGT
ACTAGAAAAGAATGTAACAGTAACACACTCTGTTAACCTTCTAGAAGACAAGCATAACGGGAAACTATG
CAAACTAAGAGGGGTAGCCCCATTGCATTTGGGTAAATGTAACATTGCTGGCTGGATCCTGGGAAATCC
AGAGTGTGAATCACTCTCCACAGCAAGCTCATGGTCCTACATTGTGGTATTATCATTTCAGATACACCAGT
CCACGATTGCAATACAACTTGTCAAACACCCAAGGGTGCTATAAACACCAGCCTCCCATTTCAGAATAT
ACATCCGATCACAATTGGAAAATGTCCAAAATATGTAAAAAGCACAAAATTGAGACTGGCCACAGGATT
GAGGAATATCCCGTCTATTCAATCTAGAGGACTATTTGGGGCCATTGCCGGTTTCATTGAAGGGGGGTG
GACAGGGATGGTAGATGGATGGTACGGTTATCACCATCAAAATGAGCAGGGGTCAGGATATGCAGCCGA
CCTGAAGAGCACACAGAATGCCATTGACGAGATTACTAACAAAGTAAATTCTGTTATTGAAAAGATGAA
TACACAGTTCACAGCAGTAGGTAAAGAGTTCAACCACCTGGAAAAAGAATAGAGAATTTAAATAAAAA
AGTTGATGATGGTTTCCTGGACATTTGGACTTACAATGCCGAACTGTTGGTTCTATTGGAAAATGAAAG
AACTTTGGACTACCACGATTCAAATGTGAAGAACTTATATGAAAAGGTAAGAAGCCAGCTAAAAAACAA
TGCCAAGGAAATTGGAAACGGCTGCTTTGAATTTTACCACAAATGCGATAACACGTGCATGGAAAGTGT
CAAAAATGGGACTTATGACTACCCAAAATACTCAGAGGAAGCAAAATTAAACAGAGAAGAAATAGATGG
GGTAAAGCTGGAATCAACAAGGATTACCAGATTTTGGCGATCTATTCAACTGTCGCCAGTTCATTGGT
ACTGGTAGTCTCCCTGGGGCAATCAGTTTCTGGATGTGCTCTAATGGGTCTCTACAGTGTAGAATATG
TATTTAAAGGCCTATTTTCTTTAGTTTGAATTTACTGTTATTCGGTTGTGCATTTCTATGTTTGGTGAC
GGTTTTCTGTGCTCAGAGTGTGTTTATTTTATGTAATTTAATTTCTTTGTGAGCTCCTGTTTAGCAGGT
CGTCCCTTCAGCAAGGACACAAAAAGATTTTAATTTTATTAAAAAAAAAAAAAAAAAAGACCGGGAATT
CGATATCAAGCTTATCGACCTGCAGATCGTTCAAACATTTGGCAATAAAGTTTCTTAAGATTGAATCCT
GTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGCGGTGTCATCTATGTTACTAGAT Construct 2980 from 2X35S prom to NOS term (SEQ ID NO: 100)
GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATC
TGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATAACATGGTGGAGCAC
GACACACTTGTCTACTCCAAAAATATCAAAGATACAGTCTCAGAAGACCAAAGGGCAATTGAGACTTTT
CAACAAAGGGTAATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAGACGTT
CCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTT
AATAGGTTTTGATAAAAGCGAACGTGGGGAAACCCGAACCAAACCTTCTTCTAAACTCTCTCTCATCTC
TCTTAAAGCAAACTTCTCTCTTGTCTTTCTTGCGTGAGCGATCTTCAACGTTGTCAGATCGTGCTTCGG
CACCAGTACAATGGCGAAAAACGTTGCGATTTTCGGCTTATTGTTTTCTCTTCTTGTGTTGGTTCCTTC
TCAGATCTTCGCGGACACATTATGTATAGGTTATCATGCGAACAATTCAACAGACACTGTAGACACAGT
ACTAGAAAAGAATGTAACAGTAACACACTCTGTTAACCTTCTAGAAGACAAGCATAACGGGAAACTATG
CAAACTAAGAGGGGTAGCCCCATTGCATTTGGGTAAATGTAACATTGCTGGCTGGATCCTGGGAAATCC
AGAGTGTGAATCACTCTCCACAGCAAGCTCATGGTCCTACATTGTGGTATTATCATTTCAGATACACCAGT
AACGTGTTACCCAGGAGATTTCATCGATTATGAGGAGCTAAGAGAGCAATTGAGCTCAGTGTCATCATT
TGAAAGGTTTGAGATATTCCCCAAGACAAGTTCATGGCCCAATCATGACTCGAACAAAGGTGTAACGGC
AGCATGTCCTCATGCTGGAGCAAAAAGCTTCTACAAAAATTTAATATGGCTAGTTAAAAAAGGAAATTC
ATACCCAAAGCTCAGCAAATCCTACATTAATGATAAAGGGAAAGAAGTCCTCGTGCTATGGGGCATTCA
CCATCCATCTACTAGTGCTGACCAACAAAGTCTCTATCAGAATGCAGATGCATATGTTTTTGTGGGGTC
ATCAAGATACAGCAAGAAGTTCAAGCCGGAAATAGCAATAAGACCCAAAGTGAGGGATCAAGAAGGGAG
```

```
AATGAACTATTACTGGACACTAGTAGAGCCGGGAGACAAAATAACATTCGAAGCAACTGGAAATCTAGT
GGTACCGAGATATGCATTCGCAATGGAAAGAAATGCTGGATCTGGTATTATCATTTCAGATACACCAGT
CCACGATTGCAATACAACTTGTCAAACACCCAAGGGTGCTATAAACACCAGCCTCCCATTTCAGAATAT
ACATCCGATCACAATTGGAAAATGTCCAAAATATGTAAAAAGCACAAAATTGAGACTGGCCACAGGATT
GAGGAATATCCCGTCTATTCAATCTAGAGGACTATTTGGGGCCATTGCCGGTTTCATTGAAGGGGGGTG
GACAGGGATGGTAGATGGATGGTACGGTTATCACCATCAAAATGAGCAGGGGTCAGGATATGCAGCCGA
CCTGAAGAGCACACAGAATGCCATTGACGAGATTACTAACAAAGTAAATTCTGTTATTGAAAGATGAA
TACACAGGACACAGCAGTAGGTAAAGAGTTCAACCACCTGGAAAAAGAATAGAGAATTTAAATAAAAA
AGTTGATGATGGTTTCCTGGACATTTGGACTTACAATGCCGAACTGTTGGTTCTATTGGAAAATGAAAG
AACTTTGGACTACCACGATTCAAATGTGAAGAACTTATATGAAAAGGTAAGAAGCCAGCTAAAAAACAA
TGCCAAGGAAATTGGAAACGGCTGCTTTGAATTTTACCACAAATGCGATAACACGTGCATGGAAAGTGT
CAAAAATGGGACTTATGACTACCCAAAATACTCAGAGGAAGCAAAATTAAACAGAGAAGAAATAGATGG
GGTAAAGCTGGAATCAACAAGGATTTACCAGATTTTGGCGATCTATTCAACTGTCGCCAGTTCATTGGT
ACTGGTAGTCTCCCTGGGGGCAATCAGTTTCTGGATGTGCTCTAATGGGTCTCTACAGTGTAGAATATG
TATTTAAAGGCCTATTTTCTTTAGTTTGAATTTACTGTTATTCGGTGTGCATTTCTATGTTTGGTGAGC
GGTTTTCTGTGCTCAGAGTGTGTTTATTTTATGTAATTTAATTTCTTTGTGAGCTCCTGTTTAGCAGGT
CGTCCCTTCAGCAAGGACACAAAAAGATTTTAATTTTATTAAAAAAAAAAAAAAAAAAAGACCGGGAATT
CGATATCAAGCTTATCGACCTGCAGATCGTTCAAACATTTGGCAATAAAGTTTCTTAAGATTGAATCCT
GTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGGTGTCATCTATGTTACTAGAT

Construct 2995 from 2X35S prom to NOS term (SEQ ID NO: 101)
GTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATC
TGTCACTTTATTGTGAAGATAGTGGAAAAGGAAGGTGGCTCCTACAAATGCCATCATTGCGATAAAGGA
AAGGCCATCGTTGAAGATGCCTCTGCCGACAGTGGTCCCAAAGATGGACCCCCACCCACGAGGAGCATC
GTGGAAAAAGAAGACGTTCCAACCACGTCTTCAAAGCAAGTGGATTGATGTGATAACATGGTGGAGCAC
GACACACTTGTCTACTCCAAAAATATCAAAGATACAGTCTCAGAAGACCAAAGGGCAATTGAGACTTTT
CAACAAAGGGTAATATCCGGAAACCTCCTCGGATTCCATTGCCCAGCTATCTGTCACTTTATTGTGAAG
ATAGTGGAAAAGGAAGGTGGCTCCTACAAATGCCATCATTGCGATAAAGGAAAGGCCATCGTTGAAGAT
GCCTCTGCCGACAGTGGTCCCAAAGATGGACCCCCACCCACGAGGAGCATCGTGGAAAAAGAAGACGTT
CCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAAGAGGTATTAAAATCTT
AATAGGTTTTGATAAAAGCGAACGTGGGGAAACCCGAACCAAACCTTCTTCTAAACTCTCTCTCATCTC
TCTTAAAGCAAACTTCTCTCTTGTCTTTCTTGCGTGAGCGATCTTCAACGTTGTCAGATCGTGCTTCGG
CACCAGTACAATGGCGAAAAACGTTGCGATTTTCGGCTTATTGTTTTCTCTTCTTGTGTTGGTTCCTTC
TCAGATCTTCGCGGACACATTATGTATAGGTTATCATGCGAACAATTCAACAGACACTGTAGACACAGT
ACTAGAAAAGAATGTAACAGTAACACACTCTGTTAACCTTCTAGAAGACAAGCATAACGGGAAACTATG
CAAACTAAGAGGGGTAGCCCCATTGCATTTGGGTAAATGTAACATTGCTGGCTGGATCCTGGGAAATCC
AGAGTGTGAATCACTCTCCACAGCAAGCTCATGGTCCTACATTGTGGAAACACCTAGTTCAGACAATGG
AACGTGTTACCCAGGAGATTTCATCGATTATGAGGAGCTAAGAGAGCAATTGAGCTCAGTGTCATCATT
TGAAAGGTTTGAGATATTCCCCAAGACAAGTTCATGGCCCAATCATGACTCGAACAAAGGTGTAACGGC
AGCATGTCCTCATGCTGGAGCAAAAAGCTTCTACAAAAATTTAATATGGCTAGTTAAAAAAGGAAATTC
ATACCCAAAGCTCAGCAAATCCTACATTAATGATAAAGGGAAAGAAGTCCTCGTGCTATGGGCATTCA
CCATCCATCTACTAGTGCTGACCAACAAAGTCTCTATCAGAATGCAGATGCATATGTTTTTGTGGGGTC
ATCAAGATACAGCAAGAAGTTCAAGCCGGAAATAGCAATAAGACCCAAAGTGAAGACCTCAAGAAGGGAG
AATGAACTATTACTGGACACTAGTAGAGCCGGGAGACAAAATAACATTCGAAGCAACTGGAAATCTAGT
GGTACCGAGATATGCATTCGCAATGGAAAGAAATGCTGGATCTGGTATTATCATTTCAGATACACCAGT
CCACGATTGCAATACAACTTGTCAAACACCCAAGGGTGCTATAAACACCAGCCTCCCATTTCAGAATAT
ACATCCGATCACAATTGGAAAATGTCCAAAATATGTAAAAAGCACAAAATTGAGACTGGCCACAGGATT
GAGGAATATCCCGTCTATTCAATCTAGAGGACTATTTGGGGCCATTGCCGGTTTCATTGAAGGGGGGTG
GACAGGGATGGTAGATGGATGGTACGGTTATCACCATCAAAATGAGCAGGGGTCAGGATATGCAGCCGA
CCTGAAGAGCACACAGAATGCCATTGACGAGATTACTAACAAAGTAAATTCTGTTATTGAAAGATGAA
TACACAGGACACAGCAGTAGGTAAAGAGTTCAACCACCTGGAAAAAGAATAGAGAATTTAAATAAAAA
AGTTGATGATGGTTTCCTGGACATTTGGACTTACAATGCCGAACTGTTGGTTCTAATGGAAAATGAAAG
AACTTTGGACTACCACGATTCAAATGTGAAGAACTTATATGAAAAGGTAAGAAGCCAGCTAAAAAACAA
TGCCAAGGAAATTGGAAACGGCTGCTTTGAATTTTACCACAAATGCGATAACACGTGCATGGAAAGTGT
CAAAAATGGGACTTATGACTACCCAAAATACTCAGAGGAAGCAAAATTAAACAGAGAAGAAATAGATGG
GGTAAAGCTGGAATCAACAAGGATTTACCAGATTTTGGCGATCTATTCAACTGTCGCCAGTTCATTGGT
ACTGGTAGTCTCCCTGGGGGCAATCAGTTTCTGGATGTGCTCTAATGGGTCTCTACAGTGTAGAATATG
TATTTAAAGGCCTATTTTCTTTAGTTTGAATTTACTGTTATTCGGTGTGCATTTCTATGTTTGGTGAGC
GGTTTTCTGTGCTCAGAGTGTGTTTATTTTATGTAATTTAATTTCTTTGTGAGCTCCTGTTTAGCAGGT
CGTCCCTTCAGCAAGGACACAAAAAGATTTTAATTTTATTAAAAAAAAAAAAAAAAAAAGACCGGGAATT
CGATATCAAGCTTATCGACCTGCAGATCGTTCAAACATTTGGCAATAAAGTTTCTTAAGATTGAATCCT
GTTGCCGGTCTTGCGATGATTATCATATAATTTCTGTTGAATTACGTTAAGCATGTAATAATTAACATG
TAATGCATGACGTTATTTATGAGATGGGTTTTTATGATTAGAGTCCCGCAATTATACATTTAATACGCG
ATAGAAAACAAAATATAGCGCGCAAACTAGGATAAATTATCGCGCGGTGTCATCTATGTTACTAGAT H1Mich(N380A).r (SEQ ID NO: 102)
TTCAATAACAGAAGCTACTTTGTTAGTAATCTTGTCAATGGCATTTTGT H1Cal(N380A).c (SEQ ID NO: 103)
GATTACTAACAAAGTAGCTTCTGTTATTGAAAAGATGAATACACAGTT PDI-H1 Mich-N380A D -continued GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAGCTTCTGTTATTGAAAAGATGAATACACAGTTC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-N380A AA (SEQ ID NO: 105)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVASVIEKMNTQF
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

H1Mich(N380A + F390D).r (SEQ ID NO: 106)
CCCACTGCTGTGTCCTGTGTATTCATCTTTTCAATAACAGAAGCTACTT PDI-H1 Mich-F390D + N380A DNA (SEQ ID NO: 107)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGTTCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATATACATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAGCTTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTATTGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA PDI-H1 Mich-F390D + N380A AA (SEQ ID NO: 108)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTASSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNTHPITIGKCPKYVKSTKLRLATGLRNV
PSIQSRGLFGAIAGFIEGGWTGMVDGWYGYHHQNEQGSGYAADLKSTQNAIDKITNKVASVIEKMNTQD
TAVGKEENHLEKRIENLNKKVDDGELDIWTYNAELLVLLENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

IF-H5ITMCT.s1-4r (SEQ ID NO: 109)
ACTAAAGAAAATAGGCCTTTAAATGCAAATTCTGCATTGTAACGATCCAT

PDI-H5 Indo DNA (SEQ ID NO: 110)
ATGGCGAAAAACGTTGCGATTTTCGGCTTATTGTTTTCTCTTCTTGTGTTGGTTCCTTCTCAGATCTTC
GCCGATCAGATTTGCATTGGTTACCATGCAAACAATTCAACAGAGCAGGTTGACACAATCATGGAAAAG
AACGTTACTGTTACACATGCCCAAGACATACTGGAAAAGACACACAACGGGAAGCTCTGCGATCTAGAT
GGAGTGAAGCCTCTAATTTTAAGAGATTGTAGTGTAGCTGGATGGCTCCTCGGGAACCCAATGTGTGAC
GAATTCATCAATGTACCGGAATGGTCTTACATAGTGGAGAAGGCCAATCCAACCAATGACCTCTGTTAC
CCAGGGAGTTTCAACGACTATGAAGAACTGAAACACCTATTGAGCAGAATAAACCATTTTGAGAAAATT
CAAATCATCCCCAAAAGTTCTTGGTCCGATCATGAAGCCTCATCAGGAGTTAGCTCAGCATGTCCATAC
CTGGGAAGTCCCTCCTTTTTTAGAAATGTGGTATGGCTTATCAAAAAGAACAGTACATACCCAACAATA
AAGAAAAGCTACAATAATACCAACCAAGAGGATCTTTTGGTACTGTGGGAATTCACCATCCTAATGAT
GCGGCAGAGCAGACAAGGCTATATCAAAACCCAACCACCTATATTTCCATTGGGACATCAACACTAAAC
CAGAGATTGGTACCAAAATAGCTACTAGATCCAAAGTAAACGGGCAAAGTGGAAGGATGGAGTTCTTC
TGGACAATTTTAAAACCTAATGATGCAATCAACTTCGAGAGTAATGGAAATTTCATTGCTCCAGAATAT
GCATACAAAATTGTCAAGAAAGGGGACTCAGCAATTATGAAAAGTGAATTGGAATATGGTAACTGCAAC
ACCAAGTGTCAAACTCCAATGGGGGCGATAAACTCTAGTATGCCATTCCACAACATACACCCTCTCACC
ATCGGGGAATGCCCCAAATATGTGAAATCAAACAGATTAGTCCTTGCAACAGGGCTCAGAAATAGCCCT
CAAAGAGAGAGCAGAAGAAAAAGAGAGGACTATTTGGAGCTATAGCAGGTTTTATAGAGGGAGGATGG
CAGGGAATGGTAGATGGTTGGTATGGGTACCACCATAGCAATGAGCAGGGGAGTGGGTACGCTGCAGAC
AAAGAATCCACTCAAAAGGCAATAGATGGAGTCACCAATAAGGTCAACTCAATCATTGACAAAATGAAC
ACTCAGTTTGAGGCCGTTGGAAGGGAATTTAATAACTTAGAAAGGAGAATAGAGAATTTAAACAAGAAG
ATGGAAGACGGGTTTCTAGATGTCTGGACTTATAATGCCGAACTTCTGGTTCTCATGGAAAATGAGAGA
ACTCTAGACTTTCATGACTCAAATGTTAAGAACCTCTACGACAAGGTCCGACTACAGCTTAGGGATAAT
GCAAAGGAGCTGGGTAACGGTTGTTTCGAGTTCTATCACAAATGTGATAATGAATGTATGGAAAGTATA
AGAAACGGAACGTACAACTATCCGCAGTATTCAGAAGAAGCAAGATTAAAAAGAGAGGAAATAAGTGGG
GTAAAATTGGAATCAATAGGAACTTACCAAATACTGTCAATTTATTCAACAGTGGCGAGTTCCCTAGCA
CTGGCAATCATGATGGCTGGTCTATCTTTATGGATGTGCTCCAATGGATCGTTACAATGCAGAATTTGC
ATTTAA PDI-H5 Indo AA (SEQ ID NO: 111)
MAKNVAIFGLLFSLLVLVPSQIFADQICIGYHANNSTEQVDTIMEKNVTVTHAQDILEKTHNGKLCDLD
GVKPLILRDCSVAGWLLGNPMCDEFINVPEWSYIVEKANPTNDLCYPGSFNDYEELKHLLSRINHFEKI
QIIPKSSWSDHEASSGVSSACPYLGSPSFFRNVVWLIKKNSTYPTIKKSYNNTNQEDLLVLWGIHHPND
AAEQTRLYQNPTTYISIGTSTLNQRLVPKIATRSKVNGQSGRMEFFWTILKPNDAINFESNGNFTAPEY
AYKIVKKGDSAIMKSELEYGNCNTKCQTPMGAINSSMPFHNIHPLTIGECPKYVKSNRLVLATGLRNSP
QRESRRKKRGLFGAIAGFIEGGWQGMVDGWYGYHHSNEQGSGYAADKESTQKAIDGVTNKVNSIIDKMN
TQFEAVGREENNLERRIENLNKKMEDGELDVWTYNAELLVLMENERTLDFHDSNVKNLYDKVRLQLRDN
AKELGNGCFEFYHKCDNECMESIRNGTYNYPQYSEEARLKREEISGVKLESIGTYQILSIYSTVASSLA
LAIMMAGLSLWMCSNGSLQCRICI*

H5Ind(F393D).r (SEQ ID NO: 112)
CTTCCAACGGCCTCGTCCTGAGTGTTCATTTTGTCAATGATTGAGTTGA

H5Ind(F393D).c (SEQ ID NO: 113)
CAAAATGAACACTCAGGACGAGGCCGTTGGAAGGGAATTTAATAACTTA

PDI-H5 Indo-F393D DNA (SEQ ID NO: 114)
ATGGCGAAAAACGTTGCGATTTTCGGCTTATTGTTTTCTCTTCTTGTGTTGGTTCCTTCTCAGATCTTC
GCGGATCAGATTTGCATTGGTTACCATGCAAACAATTCAACAGAGCAGGTTGACACAATCATGGAAAAG
AACGTTACTGTTACACATGCCCAAGACATACTGGAAAAGACACACAACGGGAAGCTCTGCGATCTAGAT
GGAGTGAAGCCTCTAATTTTAAGAGATTGTAGTGTAGCTGGATGGCTCCTCGGGAACCCAATGTGTGAC
GAATTCATCAATGTACCGGAATGGTCTTACATAGTGGAGAAGGCCAATCCAACCAATGACCTCTGTTAC
CCAGGGAGTTTCAACGACTATGAAGAACTGAAACACCTATTGAGCAGAATAAACCATTTTGAGAAAATT
CAAATCATCCCCAAAAGTTCTTGGTCCGATCATGAAGCCTCATCAGGAGTTAGCTCAGCATGTCCATAC
CTGGGAAGTCCCTCCTTTTTTAGAAATGTGGTATGGCTTATCAAAAAGAACAGTACATACCCAACAATA
AAGAAAAGCTACAATAATACCAACCAAGAGGATCTTTTGGTACTGTGGGGAATTCACCATCCTAATGAT
GCGGCAGAGCAGACAAGGCTATATCAAAACCCAACCACCTATATTTCCATTGGGACATCAACACTAAAC
CAGAGATTGGTACCAAAAATAGCTACTAGATCCAAAGTAAACGGGCAAAGTGGAAGGATGGAGTTCTTC
TGGACAATTTTAAAACCTAATGATGCAATCAACTTCGAGAGTAATGGAAATTTCATTGCTCCAGAATAT
GCATACAAAATTGTCAAGAAAGGGGACTCAGCAATTATGAAAAGTGAATTGGAATATGGTAACTGCAAC
ACCAAGTGTCAAACTCCAATGGGGGCGATAAACTCTAGTATGCCATTCCACAACATACACCCTCTCACC
ATCGGGGAATGCCCCAAATATGTGAAATCAAACAGATTAGTCCTTGCAACAGGGCTCAGAAATAGCCCT
CAAAGAGAGAGCAGAAGAAAAAAGAGAGGACTATTTGGAGCTATAGCAGGTTTTATAGAGGGAGGATGG
CAGGGAATGGTAGATGGTTGGTATGGGTACCACCATAGCAATGAGCAGGGGAGTGGGTACGCTGCAGAC
AAAGAATCCACTCAAAAGGCAATAGATGGAGTCACCAATAAGGTCAACTCAATCATTGACAAAATGAAC
ACTCAGGACGAGGCCGTTGGAAGGGAATTTAATAACTTAGAAAGGAGAATAGAGAATTTAAACAAGAAG
ATGGAAGACGGGTTTCTAGATGTCTGGACTTATAATGCCGAACTTCTGGTTCTCATGGAAAATGAGAGA
ACTCTAGACTTTCATGACTCAAATGTTAAGAACCTCTACGACAAGGTCCGACTACAGCTTAGGGATAAT
GCAAAGGAGCTGGGTAACGGTTGTTTCGAGTTCTATCACAAATGTGATAATGAATGTATGGAAAGTATA
AGAAACGGAACGTACAACTATCCGCAGTATTCAGAAGAAGCAAGATTAAAAAGAGAGGAAATAAGTGGG
GTAAAATTGGAATCAATAGGAACTTACCAAATACTGTCAATTTATTCAACAGTGGCGAGTTCCCTAGCA
CTGGCAATCATGATGGCTGGTCTATCTTTATGGATGTGCTCCAATGGATCGTTACAATGCAGAATTTGC
ATTTAA PDI-H5 Indo-F393D AA (SEQ ID NO: 115)
MAKNVAIFGLLFSLLVLVPSQIFADQICIGYHANNSTEQVDTIMEKNVTVTHAQDILEKTHNGKLCDLD
GVKPLILRDCSVAGWLLGNPMCDEFINVPEWSYIVEKANPTNDLCYPGSFNDYEELKHLLSRINHFEKI
QIIPKSSWSDHEASSGVSSACPYLGSPSFFRNVVWLIKKNSTYPTIKKSYNNTNQEDLLVLWGIHHPND
AAEQTRLYQNPTTYISIGTSTLNQRLVPKIATRSKVNGQSGRMEFFWTILKPNDAINFESNGNFTAPEY
AYKIVKKGDSAIMKSELEYGNCNTKCQTPMGAINSSMPFHNIHPLTIGECPKYVKSNRLVLATGLRNSP
QRESRRKKRGLFGAIAGFIEGGWQGMVDGWYGYHHSNEQGSGYAADKESTQKAIDGVTNKVNSIIDKMN
TQDEAVGREENNLERRIENLNKKMEDGELDVWTYNAELLVLMENERTLDFHDSNVKNLYDKVRLQLRDN
AKELGNGCFEFYHKCDNECMESIRNGTYNYPQYSEEARLKREEISGVKLESIGTYQILSIYSTVASSLA
LAIMMAGLSLWMCSNGSLQCRICI*

IF-H5 Egy.r (SEQ ID NO: 116)
ACTAAAGAAAATAGGCCTTTAAATGCAAATTCTGCATTGTAGCGATCCATT

PDI-H5 Egypt DNA (SEQ ID NO: 117)
ATGGCGAAAAACGTTGCGATTTTCGGCTTATTGTTTTCTCTTCTTGTGTTGGTTCCTTCTCAGATCTTC
GCGGATCAGATTTGCATTGGTTACCATGCAAACAACTCGACAGAGCAGGTTGACACAATAATGGAAAAG
AATGTCACTGTTACACACGCCCAAGACATACTGGAAAAGACACACAACGGGAAACTCTGCAATCTAGAT
GGAGTGAAGCCTCTCATTTTGAGAGATTGTAGTGTAGCTGGATGGCTCCTCGGGAACCCAATGTGCGAT
GAATTCCTCAATGTGCCGGAATGGTCTTACATAGTGGAGAAAATCAATCCAGCCAATGACCTCTGTTAT
CCAGGGAATTTCAACGACTATGAAGAACTGAAACACCTATTGAGCAGAATAAACCATTTTGAGAAAATT
CAGATCATTCCCAAAGATTCTTGGTCAGATCATGAAGCCTCGGGAGTGAGCTCAGCATGCCCATACCAA
GGAAGATCCTCCTTTTTTAGAAATGTTGTATGGCTTACCAAAAGAACGATGCATACCCAACAATAAAG
AAAAGTTACAATAATACTAACCAAGAAGATCTTTTGGTACTATGGGGGATTCACCATCCAAATGATGCT
GCAGAGCAGACAAGGCTTTATCAAACCCAACTACCTATATCTCCGTTGGGACATCAACACTAAACCAG
AGATTGGTACCCAAAATAGCTACTAGATCTAAGGTAAACGGGCAAAGTGGAAGGATGGAGTTCTTTTGG
ACAATTTTAAAATCGAATGATGCAATAAACTTTGAGAGCAATGGAAACTTCATTGCTCCAGAAAATGCA
TACAAAATTGTCAAGAAAGGAGATTCAACAATTATGAAAAGTGAGTTGGAATATAGTAACTGCAACACC
AAGTGTCAGACTCCAATAGGGGCGATAAACTCCAGTATGCCATTCCACAACATCCACCCTCTCACCATC
GGGGAATGCCCCAAATATGTGAAATCAAACAGATTAGTCCTTGCTACTGGGCTCAGGAATAGCCCTCAA
GGAGAGAAAAGAAGAAAAAAGAGAGGACTATTCGGAGCCATAGCAGGCTTTATAGAGGGAGGATGGCAG
GGAATGGTAGATGGTTGGTATGGGTACCACCATAGCAACGAGCAGGGGAGTGGGTACGCTGCAGACAAA
GAATCCACTCAAAGGGCTATAGATGGAGTCACCAATAAGGTCAATTCGATCATTGACAAAATGAACACT
CAGTTTGAGGCTGTTGGAAGGGAATTTAATAACTTAGAAAGGAGAATAGAAAATTTAAACAAGAAGATG
GAAGACGGATTCCTAGATGTCTGGACTTATAATGCTGAACTTCTGGTTCTCATGGAAAATGAGAGAACT
CTAGACTTTCATGACTCAAATGTCAAGAATCTTTATGACAAGGTCCGACTACAGCTTAGGGATAATGCA
AAGGAGCTTGGTAACGGTTGTTTCGAGTTCTATCACAGATGTGATAATGAATGTATGGAAAGTGTAAGA
AACGGAACGTATGACTACCCTCAATATTCAGAAGAAGCAAGATTAAAAAGAGAGGAAATAAGTGGAGTA
AAATTGGAGTCAATAGGAACTTACCAAATACTGTCAATTTATTCAACAGTGGCGAGCTCCCTAGCACTG
GCAATCATGGTGGCTGGTCTATCTTTATGGATGTGCTCCAATGGATCGCTACAATGCAGAATTTGCATT
TAA PDI-H5 Egypt AA (SEQ ID NO: 118)
MAKNVAIFGLLFSLLVLVPSQIFADQICIGYHANNSTEQVDTIMEKNVTVTHAQDILEKTHNGKLCNLD
GVKPLILRDCSVAGWLLGNPMCDEFLNVPEWSYIVEKINPANDLCYPGNENDYEELKHLLSRINHFEKI
QIIPKDSWSDHEASGVSSACPYQGRSSFFRNVVWLTKKNDAYPTIKKSYNNTNQEDLLVLWGIHHPNDA
AEQTRLYQNPTTYISVGTSTLNQRLVPKIATRSKVNGQSGRMEFFWTILKSNDAINFESNGNFIAPENA
YKIVKKGDSTIMKSELEYSNCNTKCQTPIGAINSSMPFHNIHPLTIGECPKYVKSNRLVLATGLRNSPQ
GEKRRKKRGLFGAIAGFIEGGWQGMVDGWYGYHHSNEQGSGYAADKESTQRAIDGVTNKVNSIIDKMNT
QFEAVGREFNNLERRIENLNKKMEDGFLDVWTYNAELLVLMENERTLDFHDSNVKNLYDKVRLQLRDNA
KELGNGCFEFYHRCDNECMESVRNGTYDYPQYSEEARLKREEISGVKLESIGTYQILSIYSTVASSLAL
AIMVAGLSLWMCSNGSLQCRICI*

H5Egy(F392D).r (SEQ ID NO: 119)
CTTCCAACAGCCTCGTCCTGAGTGTTCATTTTGTCAATGATCGAATTGA

H5Egy(F392D).c (SEQ ID NO: 120)
CAAAATGAACACTCAGGACGAGGCTGTTGGAAGGGAATTTAATAACTTA

PDI-H5 Egypt-F392D DNA (SEQ ID NO: 121)
ATGGCGAAAAACGTTGCGATTTTCGGCTTATTGTTTTCTCTTCTTGTGTTGGTTCCTTCTCAGATCTTC
GCGGATCAGATTTGCATTGGTTACCATGCAAACAACTCGACAGAGCAGGTTGACACAATAATGGAAAAG
AATGTCACTGTTACACACGCCCAAGACATACTGGAAAAGACACACAACGGGAAACTCTGCAATCTAGAT
GGAGTGAAGCCTCTCATTTTGAGAGATTGTAGTGTAGCTGGATGGCTCCTCGGGAACCCAATGTGCGAT
GAATTCCTCAATGTGCCGGAATGGTCTTACATAGTGGAGAAAATCAATCCAGCCAATGACCTCTGTTAT
CCAGGGAATTTCAACGACTATGAAGAACTGAAACACCTATTGAGCAGAATAAACCATTTTGAGAAAATT
CAGATCATTCCCAAAGATTCTTGGTCAGATCATGAAGCCTCGGGAGTGAGCTCAGCATGCCCATACCAA
GGAAGATCCTCCTTTTTTAGAAATGTTGTATGGCTTACCAAAAAGAACGATGCATACCCAACAATAAAG
AAAAGTTACAATAATACTAACCAAGAAGATCTTTTGGTACTATGGGGGATTCACCATCCAAATGATGCT
GCAGAGCAGACAAGGCTTTATCAAACCCAACTACCTATATCTCCGTTGGGACATCAACACTAAACCAG
AGATTGGTACCCAAAATAGCTACTAGATCTAAGGTAAACGGGCAAAGTGGAAGGATGGAGTTCTTTTGG
ACAATTTTAAAATCGAATGATGCAATAAACTTTGAGAGCAATGGAAACTTCATTGCTCCAGAAAATGCA
TACAAAATTGTCAAGAAAGGAGATTCAACAATTATGAAAAGTGAGTTGGAATATAGTAACTGCAACACC
AAGTGTCAGACTCCAATAGGGGCGATAAACTCCAGTATGCCATTCCACAACATCCACCCTCTCACCATC
GGGGAATGCCCCAAATATGTGAAATCAAACAGATTAGTCCTTGCTACTGGGCTCAGGAATAGCCCTCAA
GGAGAGAAAAGAAGAAAAAAGAGAGGACTATTCGGAGCCATAGCAGGCTTTATAGAGGGAGGATGGCAG
GGAATGGTAGATGGTTGGTATGGGTACCACCATAGCAACGAGCAGGGGAGTGGGTACGCTGCAGACAAA
GAATCCACTCAAAGGGCTATAGATGGAGTCACCAATAAGGTCAATTCGATCATTGACAAAATGAACACT -continued CAGGACGAGGCTGTTGGAAGGGAATTTAATAACTTAGAAAGGAGAATAGAAAATTTAAACAAGAAGATG
GAAGACGGATTCCTAGATGTCTGGACTTATAATGCTGAACTTCTGGTTCTCATGGAAAATGAGAGAACT
CTAGACTTTCATGACTCAAATGTCAAGAATCTTTATGACAAGGTCCGACTACAGCTTAGGGATAATGCA
AAGGAGCTTGGTAACGGTTGTTTCGAGTTCTATCACAGATGTGATAATGAATGTATGGAAAGTGTAAGA
AACGGAACGTATGACTACCCTCAATATTCAGAAGAAGCAAGATTAAAAAGAGAGGAAATAAGTGGAGTA
AAATTGGAGTCAATAGGAACTTACCAAATACTGTCAATTTATTCAACAGTGGCGAGCTCCCTAGCACTG
GCAATCATGGTGGCTGGTCTATCTTTATGGATGTGCTCCAATGGATCGCTACAATGCAGAATTTGCATT
TAA PDI-H5 Egypt-F392D AA (SEQ ID NO: 122)
MAKNVAIFGLLFSLLVLVPSQIFADQICIGYHANNSTEQVDTIMEKNVTVTHAQDILEKTHNGKLCNLD
GVKPLILRDCSVAGWLLGNPMCDEFLNVPEWSYIVEKINPANDLCYPGNENDYEELKHLLSRINHFEKI
QIIPKDSWSDHEASGVSSACPYQGRSSFFRNVVWLTKKNDAYPTIKKSYNNTNQEDLLVLWGIHHPNDA
AEQTRLYQNPTTYISVGTSTLNQRLVPKIATRSKVNGQSGRMEFFWTILKSNDAINFESNGNFIAPENA
YKIVKKGDSTIMKSELEYSNCNTKCQTPIGAINSSMPFHNIHPLTIGECPKYVKSNRLVLATGLRNSPQ
GEKRRKKRGLFGAIAGFIEGGWQGMVDGWYGYHHSNEQGSGYAADKESTQRAIDGVTNKVNSIIDKMNT
QDEAVGREFNNLERRIENLNKKMEDGFLDVWTYNAELLVLMENERTLDFHDSNVKNLYDKVRLQLRDNA
KELGNGCFEFYHRCDNECMESVRNGTYDYPQYSEEARLKREEISGVKLESIGTYQILSIYSTVASSLAL
AIMVAGLSLWMCSNGSLQCRICI*

PDI-H1 Par-F390D + L429M (nt) (SEQ ID NO: 123)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAAACCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Par-F390D + L429M (aa) (SEQ ID NO: 124)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQTYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Par-K374E + F390D + L429M (nt) (SEQ ID NO: 125)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAAACCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC

TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGCAATCAGCTTCTGGATGTGCTCTAATGGGTCTCTACAGTGTAGAATATGTATTTAA

PDI-H1 Par-K374E + F390D + L429M (aa) (SEQ ID NO: 126)
MAKNVAIFGLLFSLLVVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQTYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Par-N97D + F390D + L429M (nt) (SEQ ID NO: 127)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAAACCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAGTAAATTCTGTTATTGAAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGCAATCAGCTTCTGGATGTGCTCTAATGGGTCTCTACAGTGTAGAATATGTATTTAA

PDI-H1 Par-N97D + F390D + L429M (aa) (SEQ ID NO: 128)
MAKNVAIFGLLFSLLVVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYPKLNQTYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Par-N97D + K374E + F390D + L429M (nt) (SEQ ID NO: 129)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAAACCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCACGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAGTAAATTCTGTTATTGAAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAATAGATGGGGTAAAGCTG

-continued

GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

A/California/7/09 (H1N1) (aa) (SEQ ID NO: 130) GenBank: FJ969540.1
DTLCIGYHANNSTDTVDTVLEKNVTVTHSVNLLEDKHNGKLCKLRGVAPLHLGKCNIAGWILGNPECES
LSTASSWSYIVETPSSDNGTCYPGDFIDYEELREQLSSVSSFERFEIFPKTSSWPNHDSNKGVTAACPH
AGAKSFYKNLIWLVKKGNSYPKLSKSYINDKGKEVLVLWGIHHPSTSADQQSLYQNADAYVFVGSSRYS
KKFKPETATRPKVRDQEGRMNYYWTLVEPGDKITFEATGNLVVPRYAFAMERNAGSGIIISDTPVHDCN
TTCQTPKGAINTSLPFQNIHPITIGKCPKYVKSTKLRLATGLRNIPSIQSRGLFGAIAGFIEGGWTGMV
DGWYGYHHQNEQGSGYAADLKSTQNAIDEITNKVNSVIEKMNTQFTAVGKEFNHLEKRIENLNKKVDDG
FLDIWTYNAELLVLLENERTLDYHDSNVKNLYEKVRSQLKNNAKEIGNGCFEFYHKCDNTCMESVKNGT
YDYPKYSEEAKLNREEIDGVKLESTRIYQILAIYSTVASSLVLVVSLGAISFWMCSNGSLQCRICI A/Honduras/17734/16 (H1N1) (aa) (SEQ ID NO: 131)
DTLCIGYHANNSTDTVDTVLEKNVTVTHSVNLLEDKHNGKLCKLRGVPPLHLGKCNIAGWILGNPECEP
LSTASSWSYIVETSSSDNGTCYPGDFINYEELREQLSSVSSFERFEIFPKTSSWPNHDSNKGVTAACPH
AGAKSFYKNLIWLVKKGNSYPKLSQSYINDKGKEVLVLWGIHHPSTTADQQSLYQNADAYVFVGTSRYS
KKFKPEIAIRPKVRDQEGRMNYYWTLVEPGDKITFEATGNLVVPRYAFTMERNAGSGIIISDTPVHDCN
TTCQTPEGAINTSLPFQNIHPITIGKCPKYVKSTKLRLATGLRNVPSIQSRGLFGAIAGFIEGGWTGMV
DGWYGYHHQNEQGSGYAADQKSTQSAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI A/Darwin/11/15 (H1N1) (aa) (SEQ ID NO: 132)
DTLCIGYHANNSTDTVDTVLEKNVTVTHSVNLLEDKHNGKLCKLRGVAPLHLGKCNIAGWILGNPECES
LSTASSWSYIVETSSSDNGTCYPGDFINYEELREQLSSVSSFERFEIFPKTSSWPNHDSNKGVTAACPH
AGAKSFYKNLIWLTKKGNSYPKLSQSYINDKGKEILVLWGIHHPSTTADQQSLYQNADAYVFVGTSRYS
KKFKPEIAIRPKVRDQEGRMNYYWTLVEPGDKITFEATGNLVVPRYAFTMERNAGSGIIISDTPVHDCN
TTCQTPEGAINTSLPFQNIHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSGEAKLNREKIEGVKLESTRIYQILAIYSTVASSLVLVVSLGAISFWMCSNGSLQCRICI A/Costa Rica/0513/16 (H1N1) (aa) (SEQ ID NO: 133)
DTLCIGYHANNSTDTVDTVLEKNVTVTHSVNLLEDKHNGKLCKLRGVAPLHLGKCNIAGWILGNPECES
LSTASSWSYIVETSNSDNGTCYPGDFINYEELREQLSSVSSFERFEIFPKTSSWPNHDSNKGVTAACPH
AGAKSFYKNLIWLVKKGNSYPKLNQSYVNDKGKEVLVLWGIHHPPTTADQQSLYQNADAYVFVGTSKYS
KKFKPEIATRPKVRDQEGRMNYYWTLVEPGDKITFEATGNLVVPRYAFTMERNAGSGIIISDTPVHDCN
TTCQTPEGAINTSLPFQNIHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI A/Michigan/45/15 (H1N1) (aa) (SEQ ID NO: 134) GenBank: KY117023.1
DTLCIGYHANNSTDTVDTVLEKNVTVTHSVNLLEDKHNGKLCKLRGVAPLHLGKCNIAGWILGNPECES
LSTASSWSYIVETSNSDNGTCYPGDFINYEELREQLSSVSSFERFEIFPKTSSWPNHDSNKGVTAACPH
AGAKSFYKNLIWLVKKGNSYPKLNQSYINDKGKEVLVLWGIHHPSTTADQQSLYQNADAYVFVGTSRYS
KKFKPEIATRPKVRDQEGRMNYYWTLVEPGDKITFEATGNLVVPRYAFTMERNAGSGIIISDTPVHDCN
TTCQTPEGAINTSLPFQNIHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI A/Massachusetts/06/17 (H1N1) (aa) (SEQ ID NO: 135)
DTLCIGYHANNSTDTVDTVLEKNVTVTHSVNLLEDKHNGKLCKLRGVAPLHLGKCNIAGWILGNPECES
LSTARSWSYIVETSNSDNGTCYPGDFINYEELREQLSSVSSFERFEIFPKTSSWPNHDSNKGVTAACPH
AGAKSFYKNLIWLVKKGNSYPKLNQSYINDKGKEVLVLWGIHHPSTTADQQSLYQNADAYVFVGTSRYS
KKFKPEIATRPKVRDQEGRMNYYWTLVEPGDKITFEATGNLVVPRYAFTMERNAGSGIIISDTPVHDCN
TTCQTPEGAINTSLPFQNVHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI A/Michigan/45/15 (H1N1) (nt) (SEQ ID NO: 136) GenBank: KY117023.1
ATGAAGGCAATACTAGTAGTTCTGCTATATACATTTACAACCGCAAATGCAGACACATTATGTATAGGT
TATCATGCGAACAATTCAACAGACACTGTAGACACAGTACTAGAAAAGAATGTAACAGTAACACACTCT
GTTAACCTTCTGGAAGACAAGCATAACGGAAAACTATGCAAACTAAGAGGGGTAGCCCCATTGCATTTG
GGTAAATGTAACATTGCTGGCTGGATCCTGGGAAATCCAGAGTGTGAATCACTCTCCACAGCAAGTTCA
TGGTCCTACATTGTGGAAACATCTAATTCAGACAATGGAACGTGTTACCCAGGAGATTTCATCAATTAT
GAGGAGCTAAGAGAGCAATTGAGCTCAGTGTCATCATTTGAAAGGTTTGAGATATTCCCCAAGACAAGT
TCATGGCCCAATCATGACTCGAACAAAGGTGTAACGGCAGCATGTCCTCACGCTGGAGCAAAAGCTTC
TACAAAAACTTGATATGGCTAGTTAAAAAGGAAATTCATACCCAAAGCTTAACCAATCCTACATTAAT
GATAAAGGGAAAGAAGTCCTCGTGCTGTGGGGCATTCACCATCCATCTACTACTGCTGACCAACAAGT
CTCTATCAGAATGCAGATGCATATGTTTTTGTGGGGACATCAAGATACAGCAAGAAGTTCAAGCCGGAA
ATAGCAACAAGACCCAAAGTGAGGGATCAAGAAGGGAGAATGAACTATTACTGGACACTAGTAGAGCCG
GGAGACAAAATAACATTCGAAGCAACTGGAAATCTAGTGGTACCGAGATATGCATTCACAATGGAAAGA
AATGCTGGATCTGGTATTATCATTTCAGATACACCAGTCCACGATTGCAATACAACTTGTCAGACACCC
GAGGGTGCTATAAACACCAGCCTCCCATTTCAGAATATACATCCGATCACAATTGGAAAATGTCCAAAG
TATGTAAAAAGCACAAAATTGAGACTGGCCACAGGATTGAGGAATGTTCCGTCTATTCAATCTAGAGGC

```
CTATTCGGGGCCATTGCCGGCTTCATTGAAGGGGGGTGGACAGGGATGGTAGATGGATGGTACGGTTAT
CACCATCAAAATGAGCAGGGGTCAGGATATGCAGCCGACCTGAAGAGCACACAAAATGCCATTGACAAG
ATTACTAACAAAGTAAATTCTGTTATTGAAAAGATGAATACACAGTTCACAGCAGTGGGTAAAGAGTTC
AACCACCTGGAAAAAAGAATAGAGAATCTAAATAAAAAAGTTGATGATGGTTTCCTGGACATTTGGACT
TACAATGCCGAACTGTTGGTTCTATTGGAAAATGAAAGAACTTTGGACTACCACGATTCAAATGTGAAG
AACTTGTATGAAAAGTAAGAAACCAGTTAAAAAACAATGCCAAGGAAATTGGAAACGGCTGCTTTGAA
TTTTACCACAAATGCGATAACACGTGCATGGAAAGTGTCAAAATGGGACTTATGACTACCCAAAATAC
TCAGAGGAAGCAAAATTAAACAGAGAAAAAATAGATGGGGTAAAGCTGGAATCAACAAGGATTTACCAG
ATTTTGGCGATCTATTCAACTGTCGCCAGTTCATTGGTACTGGTAGTCTCCCTGGGGGCAATCAGCTTC
TGGATGTGCTCTAATGGGTCTCTACAGTGTAGAATATGTATTTAA

A/California/7/09 (H1N1) (nt) (SEQ ID NO: 137) GenBank: FJ969540.1
ATGAAGGCAATACTAGTAGTTCTGCTATATACATTTGCAACCGCAAATGCAGACACATTATGTATAGGT
TATCATGCGAACAATTCAACAGACACTGTAGACACAGTACTAGAAAAGAATGTAACAGTAACACACTCT
GTTAACCTTCTAGAAGACAAGCATAACGGGAAACTATGCAAACTAAGAGGGGTAGCCCCATTGCATTTG
GGTAAATGTAACATTGCTGGCTGGATCCTGGGAAATCCAGAGTGTGAATCACTCTCCACAGCAAGCTCA
TGGTCCTACATTGTGGAAACACCTAGTTCAGACAATGGAACGTGTTACCCAGGAGATTTCATCGATTAT
GAGGAGCTAAGAGAGCAATTGAGCTCAGTGTCATCATTTGAAAGGTTTGAGATATTCCCAAGACAAGT
TCATGGCCCAATCATGACTCGAACAAAGGTGTAACGGCAGCATGTCCTCATGCTGGAGCAAAAGCTTC
TACAAAAATTTAATATGGCTAGTTAAAAAGGGAAATTCATACCCAAAGCTCAGCAAATCCTACATTAAT
GATAAAGGGAAAGAAGTCCTCGTGCTATGGGGCATTCACCATCCATCTACTAGTGCTGACCAACAAAGT
CTCTATCAGAATGCAGATGCATATGTTTTTGTGGGGTCATCAAGATACAGCAAGAAGTTCAAGCCGGAA
ATAGCAATAAGACCCAAAGTGAGGGRTCAGAAGGGAGAATGAACTATTACTGGACACTAGTAGAGCCG
GGGAGACAAAATAACATTCGAAGCAACTGGAAATCTAGTGGTACCGAGATATGCATTCGCAATGGAAGA
AATGCTGGATCTGGTATTATCATTTCAGATACACCAGTCCACGATTGCAATACAACTTGTCAAACACCC
AAGGGTGCTATAAACACCAGCCTCCCATTTCAGAATATACATCGATCACAATTGGAAAATGTCCAAAA
TATGTAAAAAGCACAAAATTGAGACTGGCCACAGGATTGAGGAATATCCCGTCTATTCAATCTAGAGGC
CTATTTGGGGCCATTGCCGGTTTCATTGAAGGGGGGTGGACAGGGATGGTAGATGGATGGTACGGTTAT
CACCATCAAAATGAGCAGGGGTCAGGATATGCAGCCGACCTGAAGAGCACACAGAATGCCATTGACGAG
ATTACTAACAAAGTAAATTCTGTTATTGAAAAGATGAATACACAGTTCACAGCAGTAGGTAAAGAGTTC
AACCACCTGGAAAAAAGAATAGAGAATTTAAATAAAAAAGTTGATGATGGTTTCCTGGACATTTGGACT
TACAATGCCGAACTGTTGGTTCTATTGGAAAATGAAAGAACTTTGGACTACCACGATTCAAATGTGAAG
AACTTATATGAAAAGGTAAGAAGCCAGCTAAAAAACAATGCCAAGGAAATTGGAAACGGCTGCTTTGAA
TTTTACCACAAATGCGATAACACGTGCATGGAAAGTGTCAAAATGGGACTTATGACTACCCAAAATAC
TCAGAGGAAGCAAAATTAAACAGAGAAGAAATAGATGGGGTAAAGCTGGAATCAACAAGGATTTACCAG
ATTTTGGCGATCTATTCAACTGTCGCCAGTTCATTGGTACTGGTAGTCTCCCTGGGGGCAATCAGTTTC
TGGATGTGCTCTAATGGGTCTCTACAGTGTAGAATATGTATTTAA A/Paris/1227/2017 (H1N1) (aa) (SEQ ID NO: 138)
DTLCIGYHANNSTDTVDTVLEKNVTVTHSVNLLEDKHNGKLCKLRGVAPLHLGKCNIAGWILGNPECES
LSTARSWSYIVETSNSDNGTCYPGDFINYEELREQLSSVSSFERFEIFPKTSSWPNHDSNKGVTAACPH
AGAKSFYKNLIWLVKKGNSYPKLNQTYINDKGKEVLVLWGIHHPSTTADQQSLYQNADAYVFVGTSRYS
KKFKPEIATRPKVRDQEGRMNYYWTLVEPGDKITFEATGNLVVPRYAFTMERNAGSGIIISDTPVHDCN
TTCQTPEGAINTSLPFQNVHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI A/Norway/2147/2017 (H1N1) (aa) (SEQ ID NO: 139)
DTLCIGYHANNSTDTVDTVLEKNVTVTHSVNLLEDKHNGKLCKLRGVAPLHLGKCNIAGWILGNPECES
LSTARSWSYIVETSNSDNGTCYPGDFINYEELREQLSSVSSFERFEIFPKTSSWPNHDSNKGVTAACPH
AGAKSFYKNLIWLVKKGNSYPKLNQSYINDKGKEVLVLWGIHHPSTTADQQSLYQNADAYVFVGTSRYS
KKFKPEIATRPKVRDQEGRMNYYWTLVEPGDKITFEATGNLVVPRYAFTMERNAGSGIIISDTPVQDCN
TTCQTPEGAINTSLPFQNVHPITIGKCPKYVKSTKLRLATGLRNVPSIQSRGLFGAIAGFIEGGWTGMV
DGWYGYHHQNEQGSGYAADLKSTQNAIDKITNKVNSVIEKMNTQFTAVGKEFNHLEKRIENLNKKVDDG
FLDIWTYNAELLVLLENERTLDYHDSNVKNLYEKVRNQLKNNAKEIGNGCFEFYHKCDNTCMESVKNGT
YDYPKYSEEAKLNREKIDGVKLESTRIYQILAIYSTVASSLVLVVSLGAISFWMCSNGSLQCRICI PDI-H1 Par-N97D + K374E + F390D + L429M (aa) (SEQ ID NO: 140)
MAKNVAIFGLLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYPKLNQTYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVHDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Nor-F390D + L429M (nt) (SEQ ID NO: 141)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGGAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAGCTTCTACAAAAACTTGATATGGCTAGTTAAAAAGGAAATTCATACCCAAAG
CTTAACCAATCCTACATTAATGATAAAGGGAAAGAAGTCCTCGTGCTGTGGGGCATTCACCATCCATCT
```

-continued

```
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCAGGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Nor-F390D + L429M (aa) (SEQ ID NO: 142)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVQDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Nor-K374E + F390D + L429M (nt) (SEQ ID NO: 143)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCAATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCAGGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGGAC
ACAGCAGTGGGTAAAGAGTTCAACCACCTGGAAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGGCAATCAGCTTCTGGATGTGCTCTAATGGGTCTCTACAGTGTAGAATATGTATTTAA

PDI-H1 Nor-K374E + F390D + L429M (aa) (SEQ ID NO: 144)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFINYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVQDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Nor-N97D + F390D + L429M (nt) (SEQ ID NO: 145)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
```

-continued

```
TATGCATTCACAATGGAAAGAAATGCTGGATCTGGTATTATCATTTCAGATACACCAGTCCAGGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACAAGATTACTAACAAAGTAAATTCTGTTATTGAAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGCAATCAGCTTCTGGATGTGCTCTAATGGGTCTCTACAGTGTAGAATATGTATTTAA

PDI-H1 Nor-N97D + F390D + L429M (aa)  (SEQ ID NO: 146)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYIPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVQDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDKITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*

PDI-H1 Nor-N97D + K374E + F390D + L429M (nt)  (SEQ ID NO: 147)
ATGGCGAAAAACGTTGCGATTTTCGGCTTATTGTTTTCTCTTCTTGTGTTGGTTCCTTCTCAGATCTTC
GCGGACACATTATGTATAGGTTATCATGCGAACAATTCAACAGACACTGTAGACACAGTACTAGAAAAG
AATGTAACAGTAACACACTCTGTTAACCTTCTGGAAGACAAGCATAACGGAAAACTATGCAAACTAAGA
GGGGTAGCCCCATTGCATTTGGGTAAATGTAACATTGCTGGCTGGATCCTGGGAAATCCAGAGTGTGAA
TCACTCTCCACAGCAAGATCATGGTCCTACATTGTGGAAACATCTAATTCAGACAATGGAACGTGTTAC
CCAGGAGATTTCATCGATTATGAGGAGCTAAGAGAGCAATTGAGCTCAGTGTCATCATTTGAAAGGTTT
GAGATATTCCCCAAGACAAGTTCATGGCCCAATCATGACTCGAACAAAGGTGTAACGGCAGCATGTCCT
CACGCTGGAGCAAAAAGCTTCTACAAAAACTTGATATGGCTAGTTAAAAAAGGAAATTCATACCCAAAG
CTTAACCAATCCTACATTAATGATAAAGGGAAAGAAGTCCTCGTGCTGTGGGGCATTCACCATCCATCT
ACTACTGCTGACCAACAAAGTCTCTATCAGAATGCAGATGCATATGTTTTTGTGGGGACATCAAGATAC
AGCAAGAAGTTCAAGCCGGAAATAGCAACAAGACCCAAAGTGAGGGATCAAGAAGGGAGAATGAACTAT
TACTGGACACTAGTAGAGCCGGGAGACAAAATAACATTCGAAGCAACTGGAAATCTAGTGGTACCGAGA
TATGCATTCACAATGGAAAGAAATGCTGGATCTGGTATTATCATTTCAGATACACCAGTCCAGGATTGC
AATACAACTTGTCAGACACCCGAGGGTGCTATAAACACCAGCCTCCCATTTCAGAATGTGCATCCGATC
ACAATTGGAAAATGTCCAAAGTATGTAAAAAGCACAAAATTGAGACTGGCCACAGGATTGAGGAATGTT
CCGTCTATTCAATCTAGAGGCCTATTCGGGGCCATTGCCGGCTTCATTGAAGGGGGGTGGACAGGGATG
GTAGATGGATGGTACGGTTATCACCATCAAAATGAGCAGGGGTCAGGATATGCAGCCGACCTGAAGAGC
ACACAAAATGCCATTGACGAGATTACTAACAAAGTAAATTCTGTTATTGAAAAGATGAATACACAGGAC
ACAGCAGTGGGTAAAGAGTTCAACCACCTGGAAAAAGAATAGAGAATCTAAATAAAAAAGTTGATGAT
GGTTTCCTGGACATTTGGACTTACAATGCCGAACTGTTGGTTCTAATGGAAAATGAAAGAACTTTGGAC
TATCACGATTCAAATGTGAAGAACTTGTATGAAAAAGTAAGAAACCAGTTAAAAAACAATGCCAAGGAA
ATTGGAAACGGCTGCTTTGAATTTTACCACAAATGCGATAACACGTGCATGGAAAGTGTCAAAAATGGG
ACTTATGACTACCCAAAATACTCAGAGGAAGCAAAATTAAACAGAGAAAAAATAGATGGGGTAAAGCTG
GAATCAACAAGGATTTACCAGATTTTGGCGATCTATTCAACTGTCGCCAGTTCATTGGTACTGGTAGTC
TCCCTGGGGCAATCAGCTTCTGGATGTGCTCTAATGGGTCTCTACAGTGTAGAATATGTATTTAA

PDI-H1 Nor-N97D + K374E + F390D + L429M (aa)  (SEQ ID NO: 148)
MAKNVAIFGLLFSLLVLVPSQIFADTLCIGYHANNSTDTVDTVLEKNVTVTHSVNLLEDKHNGKLCKLR
GVAPLHLGKCNIAGWILGNPECESLSTARSWSYIVETSNSDNGTCYPGDFIDYEELREQLSSVSSFERF
EIFPKTSSWPNHDSNKGVTAACPHAGAKSFYKNLIWLVKKGNSYPKLNQSYINDKGKEVLVLWGIHHPS
TTADQQSLYQNADAYVFVGTSRYSKKFKPEIATRPKVRDQEGRMNYYWTLVEPGDKITFEATGNLVVPR
YAFTMERNAGSGIIISDTPVQDCNTTCQTPEGAINTSLPFQNVHPITIGKCPKYVKSTKLRLATGLRNV
PSIQSRGLFGAIAGFIEGGWTGMVDGWYGYHHQNEQGSGYAADLKSTQNAIDEITNKVNSVIEKMNTQD
TAVGKEFNHLEKRIENLNKKVDDGFLDIWTYNAELLVLMENERTLDYHDSNVKNLYEKVRNQLKNNAKE
IGNGCFEFYHKCDNTCMESVKNGTYDYPKYSEEAKLNREKIDGVKLESTRIYQILAIYSTVASSLVLVV
SLGAISFWMCSNGSLQCRICI*
```

All citations are hereby incorporated by reference.

The present invention has been described with regard to one or more embodiments. However, it will be apparent to persons skilled in the art that a number of variations and modifications can be made without departing from the scope of the invention as defined in the claims.

The invention claimed is:

1. A modified influenza H1 hemagglutinin (HA) protein comprising an HA amino acid sequence of an influenza H1 strain, wherein the HA amino acid sequence comprises amino acid substitutions when compared to a wildtype HA amino acid sequence of the same influenza H1 strain, wherein the amino acid substitutions correspond to the following positions:
   i) positions 390 and 429 of reference sequence SEQ ID NO: 134;
   ii) positions 390, 429 and 97 of reference sequence SEQ ID NO: 134, wherein the wildtype HA amino acid sequence comprises any amino acid aside from aspartic acid (D) at position 97 and the substitution at position 97 converts the amino acid to any amino acid aside from asparagine (N) when the wildtype amino acid is N97;
   iii) positions 390, 429 and 374 of reference sequence SEQ ID NO: 134, wherein the wildtype HA amino acid sequence comprises any amino acid aside from glutamic acid (E) at position 374 and the substitution at position 374 converts the amino acid to any amino acid aside from lysine (K) when the wildtype amino acid is K374; and
   iv) positions 390, 429, 97 and 374 of reference sequence SEQ ID NO: 134, wherein the wildtype HA amino acid sequence comprises any amino acid aside from aspartic acid (D) at position 97 and the substitution at position 97 converts the amino acid to any amino acid aside from asparagine (N) when the wildtype amino acid is N97, and wherein the wildtype HA amino acid sequence comprises any amino acid aside from glutamic acid (E) at position 374 and the substitution at position 374 converts the amino acid to any amino acid aside from lysine (K) when the wildtype amino acid is K374.

2. A virus-like particle (VLP) comprising the modified influenza H1 hemagglutinin (HA) protein of claim 1.

3. A method of producing an antibody or antibody fragment comprising, administering the VLP of claim 2 to a subject, or a host animal, thereby producing the antibody or the antibody fragment.

4. An antibody produced by the method of claim 3.

5. A plant, portion of the plant, or plant cell comprising the VLP of claim 2.

6. A composition for inducing an immune response comprising, an effective dose of the VLP of claim 2, and a pharmaceutically acceptable carrier, adjuvant, vehicle or excipient.

7. A method for inducing immunity to an influenza infection in a subject, the method comprising administering the VLP of claim 2 to the subject, optionally wherein the VLP is administered to the subject orally, intranasally, intramuscularly, intraperitoneally, intravenously or subcutaneously.

8. The modified influenza H1 HA protein of claim 1, wherein the HA comprises plant-specific N-glycans, modified N-glycans or a combination thereof.

9. A virus-like particle (VLP) comprising the modified influenza H1 hemagglutinin (HA) protein of claim 8.

10. The modified influenza H1 HA protein of claim 1, wherein:
   the amino acid substitution corresponding to position 390 is selected from the group consisting of:
      aspartic acid, when the wildtype HA amino acid sequence of the influenza H1 strain does not comprise aspartic acid at position 390;
      glutamic acid, when the wildtype HA amino acid sequence of the influenza H1 strain does not comprise glutamic acid at position 390
      glutamine, when the wildtype HA amino acid sequence of the influenza H1 strain does not comprise glutamine at position 390; and serine, when the wildtype HA amino acid sequence of the influenza H1 strain does not comprise serine at position 390;

the amino acid substitution corresponding to position 429 is selected from the group consisting of:
methionine, when the wildtype HA amino acid sequence of the influenza H1 strain does not comprise methionine at position 429;
isoleucine, when the wildtype HA amino acid sequence of the influenza H1 strain does not comprise isoleucine at position 429;
glutamine, when the wildtype HA amino acid sequence of the influenza H1 strain does not comprise glutamine at position 429;
valine, when the wildtype HA amino acid sequence of the influenza H1 strain does not comprise valine at position 429; and
phenylalanine, when the wildtype HA amino acid sequence of the influenza H1 strain does not comprise phenylalanine at position 429;

the amino acid substitution corresponding to position 97 is selected from the group consisting of:
aspartic acid, when the wildtype HA amino acid sequence of the influenza H1 strain does not comprise aspartic acid at position 97;
glutamic acid, when the wildtype HA amino acid sequence of the influenza H1 strain does not comprise glutamic acid at position 97;
glutamine, when the wildtype HA amino acid sequence of the influenza H1 strain does not comprise glutamine at position 97; and
serine, when the wildtype HA amino acid sequence of the influenza H1 strain does not comprise serine at position 97; and the amino acid substitution corresponding to position 374 is selected from the group consisting of:
glutamic acid, when the wildtype HA amino acid sequence of the influenza H1 strain does not comprise glutamic acid at position 374;
aspartic acid, when the wildtype HA amino acid sequence of the influenza H1 strain does not comprise aspartic acid at position 374;
glutamine, when the wildtype HA amino acid sequence of the influenza H1 strain does not comprise glutamine at position 374;
arginine, when the wildtype HA amino acid sequence of the influenza H1 strain does not comprise arginine at position 374;
asparagine, when the wildtype HA amino acid sequence of the influenza H1 strain does not comprise asparagine at position 374;
histidine, when the wildtype HA amino acid sequence of the influenza H1 strain does not comprise histidine at position 374; and
serine, when the wildtype HA amino acid sequence of the influenza H1 strain does not comprise serine at position 374.

11. The modified influenza H1 HA protein of claim 1, wherein:
the amino acid substitution corresponding to position 390 is to an aspartic acid, when the wildtype HA amino acid sequence of the influenza H1 strain does not comprise aspartic acid at position 390;
the amino acid substitution corresponding to position 429 is to a methionine, when the wildtype HA amino acid sequence of the influenza H1 strain does not comprise methionine at position 429;
the amino acid substitution corresponding to position 97 is to an aspartic acid, when the wildtype HA amino acid sequence of the influenza H1 strain does not comprise aspartic acid at position 97; and
the amino acid substitution corresponding to position 374 is to a glutamic acid, when the wildtype HA amino acid sequence of the influenza H1 strain does not comprise glutamic acid at position 374.

12. A plant, portion of the plant, or plant cell comprising the H1 HA protein of claim 1.

13. A nucleic acid encoding the modified influenza H1 HA protein of claim 1.

14. A method of producing an influenza virus like particle (VLP) in a plant, portion of a plant, or a plant cell, comprising:
a)
i) introducing the nucleic acid of claim 13 into the plant, portion of the plant, or plant cell; or
ii) providing a plant, portion of a plant, or plant cell comprising the nucleic acid of claim 13; and
b) incubating the plant, portion of the plant, or plant cell under conditions that permit expression of the HA protein encoded by the nucleic acid, thereby producing the VLP; and
c) optionally harvesting the plant, portion of the plant, or plant cell, and purifying the VLP.

15. A VLP produced by the method of claim 14, the VLP optionally comprising one or more than one lipid derived from the plant, portion of the plant, or plant cell, plant-specific N-glycans, modified N-glycans or a combination thereof.

16. A method of increasing yield of production of an influenza virus like particle (VLP) in a plant, portion of a plant, or a plant cell, comprising:
a)
i) introducing the nucleic acid of claim 13 into the plant, portion of the plant, or plant cell; or ii) providing a plant, portion of a plant, or plant cell comprising the nucleic acid of claim 13; and
b) incubating the plant, portion of the plant, or plant cell under conditions that permit expression of the HA protein encoded by the nucleic acid, thereby producing the VLP at a higher yield compared to plant, portion of the plant, or plant cell expressing an unmodified HA protein; and
c) optionally harvesting the plant, portion of the plant, or plant cell, and purifying the VLP.

\* \* \* \* \*

SEQUENCE LISTING

<160> NUMBER OF SEQ ID NOS: 148

<210> SEQ ID NO 1
<211> LENGTH: 1722
<212> TYPE: DNA
<213> ORGANISM: Artificial Sequence
<220> FEATURE:
<223> OTHER INFORMATION: PDI-H1 Cal DNA

<400> SEQUENCE: 1

```
atggcgaaaa acgttgcgat tttcggctta ttgttttctc ttcttgtgtt ggttccttct    60
cagatcttcg ctgacacatt atgtataggt tatcatgcga acaattcaac agacactgta   120
gacacagtac tagaaaagaa tgtaacagta acacactctg ttaaccttct agaagacaag   180
cataacggga actatgcaa actaagaggg gtagccccat tgcatttggg taaatgtaac    240
attgctggct ggatcctggg aaatccagag tgtgaatcac tctccacagc aagctcatgg   300
tcctacattg tggaaacacc tagttcgac aatggaacgt gttacccagg agatttcatc    360
gattatgagg agctaagaga gcaattgagc tcagtgtcat catttgaaag gtttgagata   420
ttccccaaga caagttcatg gcccaatcat gactcgaaca aggtgtaac ggcagcatgt    480
cctcatgctg agcaaaaag cttctacaaa aatttaatat ggctagttaa aaaggaaat    540
tcatacccaa agctcagcaa atcctacatt aatgataaag ggaaagaagt cctcgtgcta   600
tgggcattc accatccatc tactagtgct gaccaacaaa gtctctatca gaatgcagat   660
gcatatgttt ttgtggggtc atcaagatac agcaagaagt tcaagccgga atagcaata   720
agacccaaag tgagggatca agaagggaga atgaactatt actggacact agtagagccg   780
ggagacaaaa taacattcga agcaactgga atctagtgg taccgagata tgcattcgca   840
atggaaagaa atgctggatc tggtattatc atttcagata caccagtcca cgattgcaat   900
acaacttgtc aaacacccaa gggtgctata acaccagcc tcccatttca gaatatacat   960
ccgatcacaa ttggaaaatg tccaaaatat gtaaaagca caaaattgag actggccaca  1020
ggattgagga atatcccgtc tattcaatct agaggactat ttggggccat tgccggtttc  1080
attgaagggg ggtggacagg gatggtagat ggatggtacg ttatcacca tcaaaatgag  1140
caggggtcag gatatgcagc cgacctgaag agcacacaga atgccattga cgagattact  1200
aacaaagtaa attctgttat tgaaaagatg aatacacagt tcacagcagt aggtaaagag  1260
ttcaaccacc tggaaaaaag aatagagaat ttaaataaaa aagttgatga tggtttcctg  1320
gacatttgga cttacaatgc cgaactgttg gttctattgg aaaatgaaag aactttggac  1380
taccacgatt caaatgtgaa gaacttatat gaaaaggtaa aagccagct aaaaaacaat  1440
gccaaggaaa ttgaaacgg ctgctttgaa ttttaccaca atgcgataa cacgtgcatg  1500
gaaagtgtca aaaatgggac ttatgactac ccaaaatact cagaggaagc aaaattaaac  1560
agagaagaaa tagatgggt aaagctggaa tcaacaagga tttaccagat tttggcgatc  1620
tattcaactg tcgccagttc attggtactg gtagtctccc tggggcaat cagtttctgg  1680
atgtgctcta tgggtctct acagtgtaga atatgtattt aa                      1722
```

<210> SEQ ID NO 2
<211> LENGTH: 573
<212> TYPE: PRT
<213> ORGANISM: Artificial Sequence
<220> FEATURE:
<223> OTHER INFORMATION: PDI-H1 Cal AA

<400> SEQUENCE: 2

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30
```

-continued

```
Ala Asn Asn Ser Thr Asp Thr Val Asp Thr Val Leu Glu Lys Asn Val
             35                  40                  45

Thr Val Thr His Ser Val Asn Leu Leu Glu Asp Lys His Asn Gly Lys
 50                  55                  60

Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
                 85                  90                  95

Ala Ser Ser Trp Ser Tyr Ile Val Glu Thr Pro Ser Ser Asp Asn Gly
                100                 105                 110

Thr Cys Tyr Pro Gly Asp Phe Ile Asp Tyr Glu Glu Leu Arg Glu Gln
            115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
                180                 185                 190

Lys Gly Lys Glu Val Leu Val Leu Trp Gly Ile His His Pro Ser Thr
            195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Ala Met Glu Arg Asn Ala Gly Ser Gly
            275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
    355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
    435                 440                 445

Leu Leu Val Leu Leu Glu Asn Glu Arg Thr Leu Asp Tyr His Asp Ser
```

```
                450              455              460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 3
<211> LENGTH: 1722
<212> TYPE: DNA
<213> ORGANISM: Artificial Sequence
<220> FEATURE:
<223> OTHER INFORMATION: PDI-H1 Mich DNA

<400> SEQUENCE: 3
atggcgaaaa acgttgcgat tttcggctta tgttttctc ttcttgtgtt ggttccttct      60
cagatcttcg cggacacatt atgtataggt tatcatgcga acaattcaac agacactgta    120
gacacagtac tagaaaagaa tgtaacagta acacactctg ttaaccttct ggaagacaag    180
cataacggaa aactatgcaa actaagaggg gtagccccat tgcatttggg taaatgtaac    240
attgctggct ggatcctggg aaatccagag tgtgaatcac tctccacagc aagttcatgg    300
tcctacattg tggaaacatc taattcagac aatggaacgt gttacccagg agatttcatc    360
aattatgagg agctaagaga gcaattgagc tcagtgtcat catttgaaag gtttgagata    420
ttccccaaga caagttcatg gcccaatcat gactcgaaca aggtgtaac ggcagcatgt    480 cctcacgctg gagcaaaaag cttctacaaa acttgatat ggctagttaa aaaggaaat    540 tcatacccaa agcttaacca atcctacatt aatgataaag ggaagaagt cctcgtgctg    600 tggggcattc accatccatc tactactgct gaccaacaaa gtctctatca gaatgcagat    660
gcatatgttt tgtgtgggac atcaagatac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatatacat    960
ccgatcacaa ttggaaaatg tccaaagtat gtaaaaagca caaaattgag actggccaca    1020
ggattgagga atgttccgtc tattcaatct agaggcctat cggggccat tgccggcttc    1080 attgaagggg gtggacagg atggtagat ggatggtacg ttatcacca tcaaaatgag    1140 caggggtcag gatatgcagc cgacctgaag agcacacaaa atgccattga caagattact    1200
aacaaagtaa attctgttat tgaaaagatg aatacacagt tcacagcagt gggtaaagag    1260
ttcaaccacc tggaaaaaag aatagagaat ctaaataaaa agttgatga tggtttcctg    1320 gacatttgga cttacaatgc cgaactgttg gttctattgg aaaatgaaag aactttggac    1380
```

```
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac    1560
agagaaaaaa tagatgggt aaagctgaaa tcaacaagga tttaccagat tttggcgatc    1620
tattcaactg tcgccagttc attggtactg gtagtctccc tgggggcaat cagcttctgg    1680
atgtgctcta tgggtctct acagtgtaga atatgtattt aa                       1722
```

```
<210> SEQ ID NO 4
<211> LENGTH: 573
<212> TYPE: PRT
<213> ORGANISM: Artificial Sequence
<220> FEATURE:
<223> OTHER INFORMATION: PDI-H1 Mich AA

<400> SEQUENCE: 4

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His Pro Ser Thr
        195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
        290                 295                 300
```

```
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
    370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Leu Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
        515                 520                 525
Leu Glu Ser Thr Arg Ile Tyr Gln Ile Leu Ala Ile Tyr Ser Thr Val
    530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 5
<211> LENGTH: 1722
<212> TYPE: DNA
<213> ORGANISM: Artificial Sequence
<220> FEATURE:
<223> OTHER INFORMATION: PDI-H1 Mass DNA

<400> SEQUENCE: 5
atggcgaaaa acgttgcgat tttcggctta ttgttttctc ttcttgtgtt ggttccttct    60
cagatcttcg cggacacatt atgtataggt tatcatgcga acaattcaac agacactgta   120
gacacagtac tagaaaagaa tgtaacagta acacactctg ttaaccttct ggaagacaag   180
cataacggaa aactatgcaa actaagaggg gtagccccat gcatttgggt aaatgtaac    240 attgctggct ggatcctggg aaatccagag tgtgaatcac tctccacagc aagatcatgg   300
tcctacattg tggaaacatc taattcagac aatggaacgt gttacccagg agatttcatc   360
aattatgagg agctaagaga gcaattgagc tcagtgtcat catttgaaag gtttgagata   420 ttcccccaaga caagttcatg gcccaatcat gactcgaaca aggtgtaac ggcagcatgt    480 cctcacgctg gagcaaaaag cttctacaaa aacttgatat ggctagttaa aaaaggaaat   540
```

```
tcatacccaa agcttaacca atcctacatt aatgataaag ggaaagaagt cctcgtgctg    600
tggggcattc accatccatc tactactgct gaccaacaaa gtctctatca gaatgcagat    660
gcatatgttt tgtggggac atcaagatac agcaagaagt tcaagccgga atagcaaca     720 agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatgtgcat    960
ccgatcacaa ttggaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg gttatcacca tcaaaatgag   1140 cagggggtcag gatatgcagc cgacctgaag agcacacaaa atgccattga caagattact   1200
aacaaagtaa attctgttat tgaaaagatg aatacacagt tcacagcagt gggtaaagag   1260
ttcaaccacc tggaaaaaag aatagagaat ctaaataaaa aagttgatga tggtttcctg   1320
gacatttgga cttacaatgc cgaactgttg gttctattgg aaaatgaaag aactttggac   1380
tatcacgatt caaatgtgaa gaacttgtat gaaaaagtaa gaaaccagtt aaaaaacaat   1440
gccaaggaaa ttggaaacgg ctgctttgaa ttttaccaca aatgcgataa cacgtgcatg   1500
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 6
<211> LENGTH: 573
<212> TYPE: PRT
<213> ORGANISM: Artificial Sequence
<220> FEATURE:
<223> OTHER INFORMATION: PDI-H1 Mass AA

<400> SEQUENCE: 6

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160
```

```
Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
        290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Leu Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 7
<211> LENGTH: 1722
<212> TYPE: DNA
<213> ORGANISM: Artificial Sequence
<220> FEATURE:
<223> OTHER INFORMATION: PDI-H1 CostaR DNA

<400> SEQUENCE: 7

| | | | | | |
|---|---|---|---|---|---|
| atggcgaaaa | acgttgcgat | tttcggctta | ttgttttctc | ttcttgtgtt | ggttccttct | 60 |
| cagatcttcg | cggacacatt | atgtataggt | tatcatgcga | acaattcaac | agacactgta | 120 |
| gacacagtac | tagaaaagaa | tgtaacagta | acacactctg | ttaaccttct | ggaagacaag | 180 |
| cataacggaa | aactatgcaa | actaagaggg | gtagccccat | gcatttggg | taaatgtaac | 240 |
| attgctggct | ggatcctggg | aaatccagag | tgtgaatcac | tctccacagc | aagttcatgg | 300 |
| tcctacattg | tggaaacatc | taattcagac | aatggaacgt | gttacccagg | agatttcatc | 360 |
| aattatgagg | agctaagaga | gcaattgagc | tcagtgtcat | catttgaaag | gtttgagata | 420 |
| ttccccaaga | caagttcatg | gcccaatcat | gactcgaaca | aaggtgtaac | ggcagcatgt | 480 |
| cctcacgctg | gagcaaaaag | cttctacaaa | aacttgatat | ggctagttaa | aaaaggaaat | 540 |
| tcatacccaa | agcttaacca | atcctacgtg | aatgataaag | gaaagaagt | cctcgtgctg | 600 |
| tggggcattc | accatccacc | cactactgct | gaccaacaaa | gtctctatca | gaatgcagat | 660 |
| gcatatgttt | ttgtggggac | atcaaagtac | agcaagaagt | tcaagccgga | aatagcaaca | 720 |
| agacccaaag | tgagggatca | agaagggaga | tgaactatt | actggacact | agtagagccg | 780 |
| ggagacaaaa | taacattcga | agcaactgga | aatctagtgg | taccgagata | tgcattcaca | 840 |
| atggaaagaa | atgctggatc | tggtattatc | atttcagata | caccagtcca | cgattgcaat | 900 |
| acaacttgtc | agacacccga | gggtgctata | aacaccagcc | tcccatttca | gaatatacat | 960 |
| ccgatcacaa | ttggaaaatg | tccaaagtat | gtaaaaagca | caaaattgag | actggccaca | 1020 |
| ggattgagga | atgttccgtc | tattcaatct | agaggcctat | tcggggccat | tgccggcttc | 1080 |
| attgaagggg | ggtggacagg | gatggtagat | ggatggtacg | gttatcacca | tcaaaatgag | 1140 |
| cagggggtcag | gatatgcagc | cgacctgaag | agcacacaaa | atgccattga | caagattact | 1200 |
| aacaaagtaa | attctgttat | tgaaaagatg | aatacacagt | tcacagcagt | gggtaaagag | 1260 |
| ttcaaccacc | tggaaaaaag | aatagagaat | ctaaataaaa | aagttgatga | tggtttcctg | 1320 |
| gacatttgga | cttacaatgc | cgaactgttg | gttctattgg | aaaatgaaag | aactttggac | 1380 |
| tatcacgatt | caaatgtgaa | gaacttgtat | gaaaaagtaa | gaaccagtt | aaaaaacaat | 1440 |
| gccaaggaaa | ttggaaacgg | ctgctttgaa | ttttaccaca | aatgcgataa | cacgtgcatg | 1500 |
| gaaagtgtca | aaaatgggac | ttatgactac | ccaaaatact | cagaggaagc | aaaattaaac | 1560 |
| agagaaaaaa | tagatggggt | aaagctggaa | tcaacaagga | tttaccagat | tttggcgatc | 1620 |
| tattcaactg | tcgccagttc | attggtactg | gtagtctccc | tgggggcaat | cagcttctgg | 1680 |
| atgtgctcta | atgggtctct | acagtgtaga | atatgtattt | aa | | 1722 |

<210> SEQ ID NO 8
<211> LENGTH: 573
<212> TYPE: PRT
<213> ORGANISM: Artificial Sequence
<220> FEATURE:
<223> OTHER INFORMATION: PDI-H1 CostaR AA

<400> SEQUENCE: 8

Met Ala Lys Asn Val Ala Ile Phe Gly Leu Leu Phe Ser Leu Leu Val

-continued

```
1               5                   10                  15
Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
                35                  40                  45

Thr Val Thr His Ser Val Asn Leu Leu Glu Asp Lys His Asn Gly Lys
50                  55                      60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
                100                 105                 110

Thr Cys Tyr Pro Gly Asp Phe Ile Asn Tyr Glu Glu Leu Arg Glu Gln
                115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Val Asn Asp
                180                 185                 190

Lys Gly Lys Glu Val Leu Val Leu Trp Gly Ile His His Pro Pro Thr
                195                 200                 205

Thr Ala Asp Gln Gln Ser Leu Tyr Gln Asn Ala Asp Ala Tyr Val Phe
210                 215                 220

Val Gly Thr Ser Lys Tyr Ser Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
                275                 280                 285

Ile Ile Ile Ser Asp Thr Pro Val His Asp Cys Asn Thr Thr Cys Gln
                290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
                370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
                420                 425                 430
```

```
Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 9
<211> LENGTH: 1722
<212> TYPE: DNA
<213> ORGANISM: Artificial Sequence
<220> FEATURE:
<223> OTHER INFORMATION: PDI-H1 Hond DNA

<400> SEQUENCE: 9

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cataacggga actatgcaa actaagaggg gtaccccat tgcatttggg taaatgtaac       240
attgctggct ggatcctggg aaatccagag tgtgaaccac tctccacagc aagttcatgg     300
tcctacattg tggaaacatc tagttcagac aatggaacgt gttacccagg agatttcatc     360
aattatgagg agctaaggga gcaattgagc tcagtgtcat catttgagag atttgagata     420
ttccccaaga caagttcatg gcccaatcat gactcgaaca aggtgtaac agcagcatgt     480
cctcacgctg ggcaaaaag cttctacaaa aatttaatat ggctagttaa aaaaggaaat     540
tcataccccaa agctcagcca atcctacatt aatgataaag aaaagaagt cctcgtgctg     600
tggggcattc accatccatc tactactgct gaccaacaaa gtctctatca gaatgcagat     660
gcatatgttt tgtggggac atcaagatac agcaagaagt tcaagccgga atagcaata     720
agacccaaag tgagggatca agaagggaga atgaactatt actggacact agtagagccg     780
ggagacaaaa taacattcga agcaactgga atctagtgg taccgagata tgcattcaca     840
atggaaagaa atgctggatc tggtattatc atttcagata caccagtcca cgattgcaat     900
acaacttgtc agacacccga gggtgctata aacaccagcc tcccatttca gaatatacat     960
ccgatcacaa ttgggaaatg tccaaagtat gtaaaaagca caaaattgag actggccaca    1020
ggattgagga atgtcccatc tattcaatct agaggcctat cggggcgat tgccggcttc    1080
attgaagggg gtggacagg gatggtagat ggatggtacg ttatcacca tcaaaatgag    1140
caggggtcag gatatgcagc cgaccagaag agcacacaaa gtgccattga caaaattact    1200
aacaaagtaa attctgttat tgaaaagatg aatacacagt tcacagcagt gggtaaagag    1260
```

-continued

```
ttcaaccact tggaaaaaag aatagagaat ttaaataaaa aagttgatga tggtttcctg   1320
gacatttgga cttacaatgc cgaactgctg gttctattgg aaaatgaaag aactttggac   1380
taccacgact caaatgtgaa gaacttgtat gaaaaggtaa gaaaccagtt aaaaaacaat   1440
gccaaggaaa ttggaaacgg ctgctttgaa ttttaccaca aatgcgataa cacgtgcatg   1500
gaaagtgtca aaatgggac ttatgactac ccaaaatact cagaggaagc aaaattaaac    1560
agagaaaaaa tagatggggt aaagctgaaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                     1722
```

<210> SEQ ID NO 10
<211> LENGTH: 573
<212> TYPE: PRT
<213> ORGANISM: Artificial Sequence
<220> FEATURE:
<223> OTHER INFORMATION: PDI-H1 Hond AA

<400> SEQUENCE: 10

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Pro Pro Leu His Leu Gly Lys Cys Asn
65                  70                  75                  80

Ile Ala Gly Trp Ile Leu Gly Asn Pro Glu Cys Glu Pro Leu Ser Thr
                85                  90                  95

Ala Ser Ser Trp Ser Tyr Ile Val Glu Thr Ser Ser Ser Asp Asn Gly
                100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
        130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Gln Ser Tyr Ile Asn Asp
                180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
        210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
```

```
            275                 280                 285
Ile Ile Ile Ser Asp Thr Pro Val His Asp Cys Asn Thr Thr Cys Gln
    290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
370                 375                 380
Tyr Ala Ala Asp Gln Lys Ser Thr Gln Ser Ala Ile Asp Lys Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
            435                 440                 445
Leu Leu Val Leu Leu Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
            515                 520                 525
Leu Glu Ser Thr Arg Ile Tyr Gln Ile Leu Ala Ile Tyr Ser Thr Val
            530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 11
<211> LENGTH: 1722
<212> TYPE: DNA
<213> ORGANISM: Artificial Sequence
<220> FEATURE:
<223> OTHER INFORMATION: PDI-H1 Darw DNA

<400> SEQUENCE: 11
atggcgaaaa acgttgcgat tttcggctta tgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cacaacggga actatgcaa actaagaggg gtagccccat tgcatttggg taaatgtaac     240
attgctggct ggatcctggg aaacccagag tgtgaatcac tctccacagc aagttcatgg     300
tcctacattg tggaaacatc tagttcagac aatggaacgt gttacccagg agatttcatc     360
aattatgagg agctaagaga gcaattgagc tcagtgtcat catttgaaag atttgagata     420
```

```
ttccccaaga caagttcatg gcccaatcat gactcgaaca aaggtgtaac ggcagcatgt    480
cctcacgctg gagcaaaaag cttctacaaa aatttaatat ggctaactaa aaaaggaaat    540
tcatacccaa agctcagcca atcctacatt aatgataaag ggaagaaat cctcgtgctg     600 tggggcattc accatccatc tactactgct gaccaacaaa gtctctatca gaatgcagat    660
gcatatgttt ttgtggggac atcaagatac agcaagaagt tcaagccgga aatagcaata    720
agacccaaag tgagggatca agaagggaga atgaactatt actggacact agtagagcca    780
ggtgacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata acaccagcc tcccatttca gaatatacat     960
ccgatcacaa ttggaaaatg tccaaagtat gtgaaaagca caaaattgag actggccaca   1020
ggattgagga atgtcccatc tattcaatct agaggcctat tcgggccat tgccggcttc    1080 attgaagggg ggtggacagg gatggtagat ggatggtacg gttatcacca tcaaaatgag   1140
caggggtcag ggtatgcagc cgacctgaag agcacacaaa atgccattga caaaattact   1200
aacaaagtaa attctgttat tgaaaagatg aatacacagt tcacagcagt gggtaaagag   1260
ttcaaccact tggaaaaaag aatagagaat ttaaataaaa aagttgatga tggtttcctg   1320
gacatttgga cttacaatgc cgaactgctg gttctattgg aaaatgaaag aactttggac   1380
taccacgatt caaatgtgaa gaacttgtat gaaaaggtaa gaaccagtt aaaaaacaat    1440 gccaaggaaa ttggaaatgg ttgctttgaa ttttaccaca aatgcgataa cacgtgcatg   1500
gaaagtgtca aaaatgggac ttatgactac ccaaaatact caggggaagc aaaattaaac   1560
agagaaaaaa tagaagggt aaagctggaa tcaacaagaa tttaccaaat tttggcgatc    1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 12
<211> LENGTH: 573
<212> TYPE: PRT
<213> ORGANISM: Artificial Sequence
<220> FEATURE:
<223> OTHER INFORMATION: PDI-H1 Darw AA

<400> SEQUENCE: 12

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Ser Asp Asn Gly
            100                 105                 110

Thr Cys Tyr Pro Gly Asp Phe Ile Asn Tyr Glu Glu Leu Arg Glu Gln
        115                 120                 125
```

```
Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Thr
                165                 170                 175

Lys Lys Gly Asn Ser Tyr Pro Lys Leu Ser Gln Ser Tyr Ile Asn Asp
                180                 185                 190

Lys Gly Lys Glu Ile Leu Val Leu Trp Gly Ile His His Pro Ser Thr
            195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
            435                 440                 445

Leu Leu Val Leu Leu Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510

Tyr Ser Glu Ala Lys Leu Asn Arg Glu Lys Ile Glu Gly Val Lys
            515                 520                 525

Leu Glu Ser Thr Arg Ile Tyr Gln Ile Leu Ala Ile Tyr Ser Thr Val
530                 535                 540

Ala Ser Ser Leu Val Leu Val Val Ser Leu Gly Ala Ile Ser Phe Trp
```

```
                545           550           555           560
Met Cys Ser Asn Gly Ser Leu Gln Cys Arg Ile Cys Ile
                  565           570
```

<210> SEQ ID NO 13
<211> LENGTH: 49
<212> TYPE: DNA
<213> ORGANISM: Artificial Sequence
<220> FEATURE:
<223> OTHER INFORMATION: Primer IF-CPMV(fl5'UTR)_SpPDI.c

<400> SEQUENCE: 13
tcgtgcttcg gcaccagtac aatggcgaaa aacgttgcga ttttcggct            49

<210> SEQ ID NO 14
<211> LENGTH: 46
<212> TYPE: DNA
<213> ORGANISM: Artificial Sequence
<220> FEATURE:
<223> OTHER INFORMATION: Primer IF-H1cTMCT.S1-4r

<400> SEQUENCE: 14
actaaagaaa ataggccttt aaatacatat tctacactgt agagac               46

<210> SEQ ID NO 15
<211> LENGTH: 53
<212> TYPE: DNA
<213> ORGANISM: Artificial Sequence
<220> FEATURE:
<223> OTHER INFORMATION: Primer H1Cal(F390D).r

<400> SEQUENCE: 15
ctctttacct actgctgtgt cctgtgtatt catcttttca ataacagaat tta       53

<210> SEQ ID NO 16
<211> LENGTH: 50
<212> TYPE: DNA
<213> ORGANISM: Artificial Sequence
<220> FEATURE:
<223> OTHER INFORMATION: Primer H1Cal(F390D).c

<400> SEQUENCE: 16
ttattgaaaa gatgaataca caggacacag cagtaggtaa agagttcaac            50

<210> SEQ ID NO 17
<211> LENGTH: 1722
<212> TYPE: DNA
<213> ORGANISM: Artificial Sequence
<220> FEATURE:
<223> OTHER INFORMATION: PDI-H1 Cal-F390D DNA sequence

<400> SEQUENCE: 17
atggcgaaaa acgttgcgat tttcggctta ttgttttctc ttcttgtgtt ggttccttct    60
cagatcttcg cggacacatt atgtataggt tatcatgcga caattcaac agacactgta    120 gacacagtac tagaaaagaa tgtaacagta acacactctg ttaaccttct agaagacaag   180
cataacggga actatgcaa actaagaggg tagcccccat tgcatttggg taaatgtaac    240
attgctggct ggatcctggg aaatccgag tgtgaatcac tctccacagc aagctcatgg   300
tcctacattg tggaaacacc tagttcagac aatggaacgt gttacccagg agatttcatc   360
gattatgagg agctaagaga gcaattgagc tcagtgtcat catttgaaag gtttgagata   420
ttccccaaga caagttcatg gcccaatcat gactcgaaca aggtgtaac ggcagcatgt   480

-continued

```
cctcatgctg gagcaaaaag cttctacaaa aatttaatat ggctagttaa aaaggaaat      540 tcatacccaa agctcagcaa atcctacatt aatgataaag ggaaagaagt cctcgtgcta     600
tggggcattc accatccatc tactagtgct gaccaacaaa gtctctatca gaatgcagat    660
gcatatgttt ttgtggggtc atcaagatac agcaagaagt tcaagccgga atagcaata    720 agacccaaag tgagggatca agaagggaga atgaactatt actggacact agtagagccg    780
ggagacaaaa taacattcga agcaactgga atctagtgg taccgagata tgcattcgca    840
atggaaagaa atgctggatc tggtattatc atttcagata caccagtcca cgattgcaat    900
acaacttgtc aaacacccaa gggtgctata acaccagcc tcccatttca gaatatacat    960
ccgatcacaa ttggaaaatg tccaaaatat gtaaaaagca caaaattgag actggccaca   1020
ggattgagga atatcccgtc tattcaatct agaggactat ttggggccat tgccggtttc   1080
attgaagggg ggtggacagg gatggtagat ggatggtacg ttatcacca tcaaaatgag    1140 caggggtcag gatatgcagc cgacctgaag agcacacaga tgccattga cgagattact    1200 aacaaagtaa attctgttat tgaaaagatg aatacacagg acacagcagt aggtaaagag   1260
ttcaaccacc tggaaaaaag aatagagaat ttaaataaaa aagttgatga tggtttcctg    1320
gacatttgga cttacaatgc cgaactgttg gttctattgg aaaatgaaag aactttggac    1380
taccacgatt caaatgtgaa gaacttatat gaaaaggtaa gaagccagct aaaaaacaat    1440
gccaaggaaa ttggaaacgg ctgctttgaa ttttaccaca atgcgataa cacgtgcatg    1500 gaaagtgtca aaatgggac ttatgactac ccaaaatact cagaggaagc aaaattaaac    1560
agagaagaaa tagatgggt aaagctggaa tcaacaagga tttaccagat tttggcgatc    1620
tattcaactg tcgccagttc attggtactg gtagtctccc tgggggcaat cagtttctgg    1680
atgtgctcta atgggtctct acagtgtaga atatgtattt aa                       1722
```

<210> SEQ ID NO 18
<211> LENGTH: 573
<212> TYPE: PRT
<213> ORGANISM: Artificial Sequence
<220> FEATURE:
<223> OTHER INFORMATION: PDI-H1 Cal-F390D AA sequence

<400> SEQUENCE: 18

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140
```

```
Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
```

<210> SEQ ID NO 19
<211> LENGTH: 48
<212> TYPE: DNA
<213> ORGANISM: Artificial Sequence
<220> FEATURE:
<223> OTHER INFORMATION: Primer H1Cal(L429M).r

<400> SEQUENCE: 19
gttctttcat tttccattag aaccaacagt tcggcattgt aagtccaa                    48

<210> SEQ ID NO 20
<211> LENGTH: 48
<212> TYPE: DNA
<213> ORGANISM: Artificial Sequence
<220> FEATURE:
<223> OTHER INFORMATION: Primer H1Cal(L429M).c

<400> SEQUENCE: 20
cgaactgttg gttctaatgg aaaatgaaag aactttggac taccacga                    48

<210> SEQ ID NO 21
<211> LENGTH: 1722
<212> TYPE: DNA
<213> ORGANISM: Artificial Sequence
<220> FEATURE:
<223> OTHER INFORMATION: PDI-H1 Cal-L429M DNA sequence

<400> SEQUENCE: 21

```
atggcgaaaa acgttgcgat tttcggctta ttgtttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cataacggga actatgcaa ctaagaggg gtagccccat tgcatttggg taaatgtaac       240
attgctggct ggatcctggg aaatccagag tgtgaatcac tctccacagc aagctcatgg     300
tcctacattg tggaaacacc tagttcagac aatggaacgt gttacccagg agatttcatc     360
gattatgagg agctaagaga gcaattgagc tcagtgtcat catttgaaag gtttgagata     420
ttccccaaga caagttcatg gcccaatcat gactcgaaca aggtgtaac ggcagcatgt      480
cctcatgctg agcaaaaag cttctacaaa aatttaatat ggctagttaa aaaggaaat      540
tcataccca agctcagcaa atcctacatt aatgataaag ggaagaagt cctcgtgcta      600
tggggcattc accatccatc tactagtgct gaccaacaaa gtctctatca gaatgcagat     660
gcatatgttt ttgtggggtc atcaagatac agcaagaagt tcaagccgga aatagcaata     720
agacccaaag tgagggatca agaagggaga tgaactatt actggacact agtagagccg      780
ggagacaaaa taacattcga agcaactgga aatctagtgg taccgagata tgcattcgca     840
atggaaagaa atgctggatc tggtattatc atttcagata caccagtcca cgattgcaat     900
acaacttgtc aaacacccaa gggtgctata aacaccagcc tcccattca gaatatacat      960
ccgatcacaa ttggaaaatg tccaaatat gtaaaaagca caaaattgag actggccaca    1020
ggattgagga atatcccgtc tattcaatct agaggactat tggggccat tgccggtttc    1080
attgaagggg ggtggacagg gatggtagat ggatggtacg gttatcacca tcaaaatgag    1140
caggggtcag gatatgcagc cgacctgaag agcacacaga atgccattga cgagattact    1200
aacaaagtaa attctgttat tgaaaagatg aatacacagt tcacagcagt aggtaaagag    1260
ttcaaccacc tggaaaaaag aatagagaat ttaaataaaa agttgatga tggtttcctg    1320
```

```
gacatttgga cttacaatgc cgaactgttg gttctaatgg aaaatgaaag aactttggac    1380
taccacgatt caaatgtgaa gaacttatat gaaaaggtaa gaagccagct aaaaaacaat    1440
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac    1560
agagaagaaa tagatggggt aaagctggaa tcaacaagga tttaccagat tttggcgatc    1620
tattcaactg tcgccagttc attggtactg gtagtctccc tgggggcaat cagtttctgg    1680
atgtgctcta atgggtctct acagtgtaga atatgtattt aa                      1722
```

<210> SEQ ID NO 22
<211> LENGTH: 573
<212> TYPE: PRT
<213> ORGANISM: Artificial Sequence
<220> FEATURE:
<223> OTHER INFORMATION: PDI-H1 Cal-L429M AA sequence

<400> SEQUENCE: 22

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285
```

```
Ile Ile Ile Ser Asp Thr Pro Val His Asp Cys Asn Thr Thr Cys Gln
        290             295                 300
Thr Pro Lys Gly Ala Ile Asn Thr Ser Leu Pro Phe Gln Asn Ile His
305             310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Ile Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Ser Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Glu Ile Asp Gly Val Lys
        515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 23
<211> LENGTH: 1722
<212> TYPE: DNA
<213> ORGANISM: Artificial Sequence
<220> FEATURE:
<223> OTHER INFORMATION: PDI-H1 Cal-F390D+L429M DNA sequence

<400> SEQUENCE: 23
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cataacggga actatgcaa actaagaggg gtagccccat tgcatttggg taaatgtaac     240
attgctggct ggatcctggg aaatccagag tgtgaatcac tctccacagc aagctcatgg     300
tcctacattg tggaaacacc tagttcagac aatggaacgt gttacccagg agatttcatc     360
gattatgagg agctaagaga gcaattgagc tcagtgtcat catttgaaag gtttgagata     420
ttccccaaga caagttcatg gcccaatcat gactcgaaca aaggtgtaac ggcagcatgt     480
```

-continued

```
cctcatgctg agcaaaaag cttctacaaa aatttaatat ggctagttaa aaaaggaaat    540
tcatacccaa agctcagcaa atcctacatt aatgataaag ggaaagaagt cctcgtgcta    600
tgggcattc accatccatc tactagtgct gaccaacaaa gtctctatca gaatgcagat    660
gcatatgttt ttgtggggtc atcaagatac agcaagaagt tcaagccgga atagcaata    720
agacccaaag tgagggatca agaagggaga atgaactatt actggacact agtagagccg    780
ggagacaaaa taacattcga agcaactgga atctagtgg taccgagata tgcattcgca    840
atggaaagaa atgctggatc tggtattatc atttcagata caccagtcca cgattgcaat    900
acaacttgtc aaacacccaa gggtgctata acaccagcc tcccatttca gaatatacat    960
ccgatcacaa ttggaaaatg tccaaaatat gtaaaagca caaaattgag actggccaca   1020
ggattgagga atatcccgtc tattcaatct agaggactat ttggggccat tgccggtttc   1080
attgaagggg ggtggacagg gatggtagat ggatggtacg gttatcacca tcaaaatgag   1140
cagggtcag atatgcagc cgacctgaag agcacacaga atgccattga cgagattact   1200
aacaaagtaa attctgttat tgaaaagatg aatacacagg acacagcagt aggtaaagag   1260
ttcaaccacc tggaaaaaag aatagagaat ttaaataaaa aagttgatga tggtttcctg   1320
gacatttgga cttacaatgc cgaactgttg gttctaatgg aaaatgaaag aactttggac   1380
taccacgatt caaatgtgaa gaacttatat gaaaaggtaa gaagccagct aaaaaacaat   1440
gccaaggaaa ttggaaacgg ctgctttgaa ttttaccaca aatgcgataa cacgtgcatg   1500
gaaagtgtca aaaatgggac ttatgactac ccaaaatact cagaggaagc aaaattaaac   1560
agagaagaaa tagatggggt aaagctggaa tcaacaagga tttaccagat tttggcgatc   1620
tattcaactg tcgccagttc attggtactg gtagtctccc tggggcaat cagtttctgg   1680
atgtgctcta atgggtctct acagtgtaga atatgtattt aa                     1722
```

<210> SEQ ID NO 24
<211> LENGTH: 573
<212> TYPE: PRT
<213> ORGANISM: Artificial Sequence
<220> FEATURE:
<223> OTHER INFORMATION: PDI-H1 Cal-F390D+L429M AA sequence

<400> SEQUENCE: 24

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
                100                 105                 110

Thr Cys Tyr Pro Gly Asp Phe Ile Asp Tyr Glu Glu Leu Arg Glu Gln
            115                 120                 125

Leu Ser Ser Val Ser Ser Phe Glu Arg Phe Glu Ile Phe Pro Lys Thr
        130                 135                 140
```

```
Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560
```

Met Cys Ser Asn Gly Ser Leu Gln Cys Arg Ile Cys Ile
            565                 570

<210> SEQ ID NO 25
<211> LENGTH: 52
<212> TYPE: DNA
<213> ORGANISM: Artificial Sequence
<220> FEATURE:
<223> OTHER INFORMATION: Primer H1Mich(N97D).r

<400> SEQUENCE: 25
tagctcctca taatcgatga aatctcctgg gtaacacgtt ccattgtctg aa          52

<210> SEQ ID NO 26
<211> LENGTH: 50
<212> TYPE: DNA
<213> ORGANISM: Artificial Sequence
<220> FEATURE:
<223> OTHER INFORMATION: H1Mich(N97D).c

<400> SEQUENCE: 26
cccaggagat tcatcgatt atgaggagct aagagagcaa ttgagctcag              50

<210> SEQ ID NO 27
<211> LENGTH: 1722
<212> TYPE: DNA
<213> ORGANISM: Artificial Sequence
<220> FEATURE:
<223> OTHER INFORMATION: PDI-H1 Mich-N97D DNA

<400> SEQUENCE: 27

| | |
|---|---|
| atggcgaaaa acgttgcgat tttcggctta tgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacgta acacactctg ttaaccttct ggaagacaag | 180 |
| cataacggaa aactatgcaa actaagaggg gtagccccat tgcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| gattatgagg agctaagaga gcaattgagc tcagtgtcat catttgaaag gtttgagata | 420 |
| ttccccaaga caagttcatg gcccaatcat gactcgaaca aggtgtaac ggcagcatgt | 480 |
| cctcacgctg agcaaaaag cttctacaaa aacttgatat ggctagttaa aaaggaaat | 540 |
| tcatacccaa agcttaacca atcctacatt aatgataaag ggaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata acaccagcc tcccatttca gaatatacat | 960 |
| ccgatcacaa ttggaaaatg tccaaagtat gtaaaaagca caaaattgag actggccaca | 1020 |
| ggattgagga atgttccgtc tattcaatct agaggcctat tcggggccat tgccggcttc | 1080 |
| attgaagggg ggtggacagg gatggtagat ggatggtacg ttatcacca tcaaaatgag | 1140 |
| caggggtcag gatatgcagc cgacctgaag agcacacaaa atgccattga caagattact | 1200 |
| aacaaagtaa attctgttat tgaaaagatg aatacacagt tcacagcagt gggtaaagag | 1260 |

-continued

```
ttcaaccacc tggaaaaaag aatagagaat ctaaataaaa aagttgatga tggtttcctg  1320
gacatttgga cttacaatgc cgaactgttg gttctattgg aaaatgaaag aactttggac  1380
tatcacgatt caaatgtgaa gaacttgtat gaaaaagtaa gaaaccagtt aaaaaacaat  1440
gccaaggaaa ttggaaacgg ctgctttgaa ttttaccaca aatgcgataa cacgtgcatg  1500
gaaagtgtca aaatgggac ttatgactac ccaaaatact cagaggaagc aaaattaaac  1560
agagaaaaaa tagatgggt aaagctgaaa tcaacaagga tttaccagat tttggcgatc  1620
tattcaactg tcgccagttc attggtactg gtagtctccc tggggggcaat cagcttctgg  1680 atgtgctcta atgggtctct acagtgtaga atatgtattt aa                     1722
```

<210> SEQ ID NO 28
<211> LENGTH: 573
<212> TYPE: PRT
<213> ORGANISM: Artificial Sequence
<220> FEATURE:
<223> OTHER INFORMATION: PDI-H1 Mich-N97D AA

<400> SEQUENCE: 28

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285
```

```
Ile Ile Ile Ser Asp Thr Pro Val His Asp Cys Asn Thr Thr Cys Gln
        290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Leu Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
        515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 29
<211> LENGTH: 57
<212> TYPE: DNA
<213> ORGANISM: Artificial Sequence
<220> FEATURE:
<223> OTHER INFORMATION: Primer H1Mich(K374E).r

<400> SEQUENCE: 29
tttgttagta atctcgtcaa tggcattttg tgtgctcttc aggtcggctg catatcc    57

<210> SEQ ID NO 30
<211> LENGTH: 50
<212> TYPE: DNA
<213> ORGANISM: Artificial Sequence
<220> FEATURE:
<223> OTHER INFORMATION: Primer H1Mich(K374E).c

<400> SEQUENCE: 30
acaaaatgcc attgacgaga ttactaacaa agtaaattct gttattgaaa    50

<210> SEQ ID NO 31
<211> LENGTH: 1722
<212> TYPE: DNA
<213> ORGANISM: Artificial Sequence
<220> FEATURE:
<223> OTHER INFORMATION: PDI-H1 Mich-K374E DNA

<400> SEQUENCE: 31

| | | | | | |
|---|---|---|---|---|---|
| atggcgaaaa | acgttgcgat | tttcggctta | ttgttttctc | ttcttgtgtt | ggttccttct | 60 |
| cagatcttcg | cggacacatt | atgtataggt | tatcatgcga | acaattcaac | agacactgta | 120 |
| gacacagtac | tagaaaagaa | tgtaacagta | acacactctg | ttaaccttct | ggaagacaag | 180 |
| cataacggaa | actatgcaa | actaagaggg | gtagccccat | gcatttggg | taaatgtaac | 240 |
| attgctggct | ggatcctggg | aaatccagag | tgtgaatcac | tctccacagc | aagttcatgg | 300 |
| tcctacattg | tggaaacatc | taattcagac | aatggaacgt | gttacccagg | agatttcatc | 360 |
| aattatgagg | agctaagaga | gcaattgagc | tcagtgtcat | catttgaaag | gtttgagata | 420 |
| ttccccaaga | caagttcatg | gcccaatcat | gactcgaaca | aggtgtaac | ggcagcatgt | 480 |
| cctcacgctg | agcaaaaag | cttctacaaa | aacttgatat | ggctagttaa | aaaaggaaat | 540 |
| tcatacccaa | agcttaacca | atcctacatt | aatgataaag | ggaagaagt | cctcgtgctg | 600 |
| tggggcattc | accatccatc | tactactgct | gaccaacaaa | gtctctatca | gaatgcagat | 660 |
| gcatatgttt | ttgtggggac | atcaagatac | agcaagaagt | tcaagccgga | aatagcaaca | 720 |
| agacccaaag | tgagggatca | agaagggaga | atgaactatt | actggacact | agtagagccg | 780 |
| ggagacaaaa | taacattcga | agcaactgga | aatctagtgg | taccgagata | tgcattcaca | 840 |
| atggaaagaa | atgctggatc | tggtattatc | atttcagata | caccagtcca | cgattgcaat | 900 |
| acaacttgtc | agacacccga | gggtgctata | acaccagcc | tcccatttca | gaatatacat | 960 |
| ccgatcacaa | ttggaaaatg | tccaaagtat | gtaaaagca | caaaattgag | actggccaca | 1020 |
| ggattgagga | atgttccgtc | tattcaatct | agaggcctat | tcgggggccat | tgccggcttc | 1080 |
| attgaagggg | ggtggacagg | gatggtagat | ggatggtacg | gttatcacca | tcaaaatgag | 1140 |
| caggggtcag | gatatgcagc | cgacctgaag | agcacacaaa | atgccattga | cgagattact | 1200 |
| aacaaagtaa | attctgttat | tgaaaagatg | aatacacagt | tcacagcagt | gggtaaagag | 1260 |
| ttcaaccacc | tggaaaaaag | aatagagaat | ctaaataaaa | aagttgatga | tggtttcctg | 1320 |
| gacatttgga | cttacaatgc | cgaactgttg | gttctattgg | aaaatgaaag | aactttggac | 1380 |
| tatcacgatt | caaatgtgaa | gaacttgtat | gaaaaagtaa | gaaccagtt | aaaaaacaat | 1440 |
| gccaaggaaa | ttggaaacgg | ctgctttgaa | ttttaccaca | aatgcgataa | cacgtgcatg | 1500 |
| gaaagtgtca | aaatgggac | ttatgactac | ccaaaatact | cagaggaagc | aaaattaaac | 1560 |
| agagaaaaaa | tagatggggt | aaagctggaa | tcaacaagga | tttaccagat | tttggcgatc | 1620 |
| tattcaactg | tcgccagttc | attggtactg | gtagtctccc | tgggggcaat | cagcttctgg | 1680 |
| atgtgctcta | atgggtctct | acagtgtaga | atatgtattt | aa | | 1722 |

<210> SEQ ID NO 32
<211> LENGTH: 573
<212> TYPE: PRT
<213> ORGANISM: Artificial Sequence
<220> FEATURE:
<223> OTHER INFORMATION: PDI-H1 Mich-K374E AA

<400> SEQUENCE: 32

Met Ala Lys Asn Val Ala Ile Phe Gly Leu Leu Phe Ser Leu Leu Val

```
1               5                   10                  15
Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
 50                  55                  60

Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
            85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
            130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
            165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
            245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
            290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
            325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
            405                 410                 415

Val Gly Lys Glu Phe Asn His Leu Glu Lys Arg Ile Glu Asn Leu Asn
            420                 425                 430
```

```
Lys Lys Val Asp Asp Gly Phe Leu Asp Ile Trp Thr Tyr Asn Ala Glu
        435                 440                 445

Leu Leu Val Leu Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
                515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 33
<211> LENGTH: 49
<212> TYPE: DNA
<213> ORGANISM: Artificial Sequence
<220> FEATURE:
<223> OTHER INFORMATION: Primer H1Mich(F390D).r

<400> SEQUENCE: 33
cccactgctg tgtcctgtgt attcatcttt tcaataacag aatttactt                49

<210> SEQ ID NO 34
<211> LENGTH: 49
<212> TYPE: DNA
<213> ORGANISM: Artificial Sequence
<220> FEATURE:
<223> OTHER INFORMATION: Primer H1Mich(F390D).c

<400> SEQUENCE: 34
aaagatgaat acacaggaca cagcagtggg taaagagttc aaccacctg                49

<210> SEQ ID NO 35
<211> LENGTH: 1722
<212> TYPE: DNA
<213> ORGANISM: Artificial Sequence
<220> FEATURE:
<223> OTHER INFORMATION: PDI-H1 Mich-F390D DNA

<400> SEQUENCE: 35
atggcgaaaa acgttgcgat tttcggctta ttgtttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat gcatttggg taaatgtaac      240 attgctggct ggatcctggg aaatccagag tgtgaatcac tctccacagc aagttcatgg     300
tcctacattg tggaaacatc taattcagac aatggaacgt gttacccagg agatttcatc     360
aattatgagg agctaagaga gcaattgagc tcagtgtcat catttgaaag gtttgagata     420
ttccccaaga caagttcatg gcccaatcat gactcgaaca aggtgtgtaac ggcagcatgt     480 cctcacgctg agcaaaaag cttctacaaa aacttgatat ggctagttaa aaaaggaaat     540
```

```
tcatacccaa agcttaacca atcctacatt aatgataaag ggaaagaagt cctcgtgctg    600
tggggcattc accatccatc tactactgct gaccaacaaa gtctctatca gaatgcagat    660
gcatatgttt ttgtggggac atcaagatac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatatacat    960
ccgatcacaa ttgaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg ttatcacca tcaaaatgag   1140
caggggtcag gatatgcagc cgacctgaag agcacacaaa atgccattga caagattact   1200
aacaaagtaa attctgttat tgaaaagatg aatacacagg acacagcagt gggtaaagag   1260
ttcaaccacc tggaaaaaag aatagagaat ctaaataaaa aagttgatga tggtttcctg   1320
gacatttgga cttacaatgc cgaactgttg gttctattgg aaaatgaaag aactttggac   1380
tatcacgatt caaatgtgaa gaacttgtat gaaaaagtaa gaaccagtt aaaaaacaat   1440
gccaaggaaa ttggaaacgg ctgctttgaa ttttaccaca aatgcgataa cacgtgcatg   1500
gaaagtgtca aaaatgggac ttatgactac ccaaaatact cagaggaagc aaaattaaac   1560
agagaaaaaa tagatggggt aaagctgaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                     1722
```

<210> SEQ ID NO 36
<211> LENGTH: 573
<212> TYPE: PRT
<213> ORGANISM: Artificial Sequence
<220> FEATURE:
<223> OTHER INFORMATION: PDI-H1 Mich-F390D AA

<400> SEQUENCE: 36

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
```

-continued

```
            145                 150                 155                 160
Pro His Ala Gly Ala Lys Ser Phe Tyr Lys Asn Leu Ile Trp Leu Val
                    165                 170                 175
Lys Lys Gly Asn Ser Tyr Pro Lys Leu Asn Gln Ser Tyr Ile Asn Asp
                    180                 185                 190
Lys Gly Lys Glu Val Leu Val Leu Trp Gly Ile His Pro Ser Thr
                195                 200                 205
Thr Ala Asp Gln Gln Ser Leu Tyr Gln Asn Ala Asp Ala Tyr Val Phe
    210                 215                 220
Val Gly Thr Ser Arg Tyr Ser Lys Lys Phe Lys Pro Glu Ile Ala Thr
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
                260                 265                 270
Val Val Pro Arg Tyr Ala Phe Thr Met Glu Arg Asn Ala Gly Ser Gly
                275                 280                 285
Ile Ile Ile Ser Asp Thr Pro Val His Asp Cys Asn Thr Thr Cys Gln
            290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
                340                 345                 350
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
            370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
                420                 425                 430
Lys Lys Val Asp Asp Gly Phe Leu Asp Ile Trp Thr Tyr Asn Ala Glu
                435                 440                 445
Leu Leu Val Leu Leu Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
                515                 520                 525
Leu Glu Ser Thr Arg Ile Tyr Gln Ile Leu Ala Ile Tyr Ser Thr Val
            530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 37
<211> LENGTH: 54
<212> TYPE: DNA
<213> ORGANISM: Artificial Sequence
<220> FEATURE:
<223> OTHER INFORMATION: Primer H1Mich(L429M).c

<400> SEQUENCE: 37

| | |
|---|---|
| cgaactgttg gttctaatgg aaaatgaaag aactttggac tatcacgatt caaa | 54 |

<210> SEQ ID NO 38
<211> LENGTH: 1722
<212> TYPE: DNA
<213> ORGANISM: Artificial Sequence
<220> FEATURE:
<223> OTHER INFORMATION: PDI-H1 Mich-L429M DNA

<400> SEQUENCE: 38

| | |
|---|---|
| atggcgaaaa acgttgcgat tttcggctta ttgtttttctc ttcttgtgtt ggttccttct | 60 |
| cagatcttcg cggacacatt atgtataggt tatcatgcga caattcaac agacactgta | 120 |
| gacacagtac tagaaaagaa tgtaacagta acacactctg ttaaccttct ggaagacaag | 180 |
| cataacggaa aactatgcaa actaagaggg gtagccccat tgcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| aattatgagg agctaagaga gcaattgagc tcagtgtcat catttgaaag gtttgagata | 420 |
| ttccccaaga caagttcatg gcccaatcat gactcgaaca aaggtgtaac ggcagcatgt | 480 |
| cctcacgctg agcaaaaag cttctacaaa aacttgatat ggctagttaa aaaggaaat | 540 |
| tcatacccaa agcttaacca atcctacatt aatgataaag ggaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata acaccagcc tcccatttca gaatatacat | 960 |
| ccgatcacaa ttggaaaatg tccaaagtat gtaaaaagca caaaattgag actggccaca | 1020 |
| ggattgagga atgttccgtc tattcaatct agaggcctat tcggggccat tgccggcttc | 1080 |
| attgaagggg ggtggacagg atggtagat ggatggtacg gttatcacca tcaaaatgag | 1140 |
| cagggtcag atatgcagc cgacctgaag agcacacaaa atgccattga caagattact | 1200 |
| aacaaagtaa attctgttat tgaaaagatg aatacacagt tcacagcagt gggtaaagag | 1260 |
| ttcaaccacc tggaaaaag aatagagaat ctaaataaaa aagttgatga tggtttcctg | 1320 |
| gacatttgga cttacaatgc cgaactgttg gttctaatgg aaaatgaaag aactttggac | 1380 |
| tatcacgatt caaatgtgaa gaacttgtat gaaaaagtaa gaaccagtt aaaaaacaat | 1440 |
| gccaaggaaa ttggaaacgg ctgctttgaa ttttaccaca atgcgataa cacgtgcatg | 1500 |
| gaaagtgtca aaaatgggac ttatgactac ccaaaatact cagaggaagc aaaattaaac | 1560 |
| agagaaaaaa tagatgggt aaagctgaa tcaacaagga tttaccagat tttggcgatc | 1620 |
| tattcaactg tcgccagttc attggtactg gtagtctccc tgggggcaat cagcttctgg | 1680 | atgtgctcta atgggtctct acagtgtaga atatgtattt aa                1722

<210> SEQ ID NO 39
<211> LENGTH: 573
<212> TYPE: PRT
<213> ORGANISM: Artificial Sequence
<220> FEATURE:
<223> OTHER INFORMATION: PDI-H1 Mich-L429M AA

<400> SEQUENCE: 39

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
```

Val Asp Gly Trp Tyr Gly Tyr His His Gln Asn Glu Gln Gly Ser Gly
355                 360                 365
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
                420                 425                 430
Lys Lys Val Asp Asp Gly Phe Leu Asp Ile Trp Thr Tyr Asn Ala Glu
                435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
                515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 40
<211> LENGTH: 1722
<212> TYPE: DNA
<213> ORGANISM: Artificial Sequence
<220> FEATURE:
<223> OTHER INFORMATION: PDI-H1 Mich-N97D+K374E DNA

<400> SEQUENCE: 40

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga caattcaac agacactgta | 120 |
| gacacagtac tagaaaagaa tgtaacagta acacactctg ttaaccttct ggaagacaag | 180 |
| cataacggaa aactatgcaa actaagaggg gtagccccat tgcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| gattatgagg agctaagaga gcaattgagc tcagtgtcat catttgaaag gtttgagata | 420 |
| ttccccaaga caagttcatg gcccaatcat gactcgaaca aggtgtaac ggcagcatgt | 480 |
| cctcacgctg agcaaaaag cttctacaaa aacttgatat ggctagttaa aaaggaaat | 540 |
| tcatacccaa agcttaacca atcctacatt aatgataaag ggaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt caagccgga aatagcaaca | 720 |
| agacccaaag tgagggatca agaagggaga atgaactatt actggacact agtagagccg | 780 |
| ggagacaaaa taacattcga agcaactgga atctagtgg taccgagata tgcattcaca | 840 |

```
atggaaagaa atgctggatc tggtattatc atttcagata caccagtcca cgattgcaat    900
acaacttgtc agacacccga gggtgctata acaccagcc tcccatttca gaatatacat    960
ccgatcacaa ttggaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg gttatcacca tcaaaatgag   1140
cagggggtcag atatgcagc cgacctgaag agcacacaaa tgccattga cgagattact   1200
aacaaagtaa attctgttat tgaaaagatg aatacacagt tcacagcagt gggtaaagag   1260
ttcaaccacc tggaaaaaag aatagagaat ctaaataaaa aagttgatga tggtttcctg   1320
gacatttgga cttacaatgc cgaactgttg gttctattgg aaaatgaaag aactttggac   1380
tatcacgatt caaatgtgaa gaacttgtat gaaaaagtaa gaaccagtt aaaaaacaat   1440
gccaaggaaa ttggaaacgg ctgctttgaa ttttaccaca atgcgataa cacgtgcatg   1500
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 41
<211> LENGTH: 573
<212> TYPE: PRT
<213> ORGANISM: Artificial Sequence
<220> FEATURE:
<223> OTHER INFORMATION: PDI-H1 Mich-N97D+K374E AA

<400> SEQUENCE: 41

```
Met Ala Lys Asn Val Ala Ile Phe Gly Leu Leu Phe Ser Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His Pro Ser Thr
        195                 200                 205
```

```
Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 42
<211> LENGTH: 1722
<212> TYPE: DNA
<213> ORGANISM: Artificial Sequence
<220> FEATURE:
<223> OTHER INFORMATION: PDI-H1 Mich-F390D+L429M DNA

<400> SEQUENCE: 42
```

```
atggcgaaaa acgttgcgat tttcggctta ttgttttctc ttcttgtgtt ggttccttct    60
cagatcttcg cggacacatt atgtataggt tatcatgcga acaattcaac agacactgta   120
gacacagtac tagaaaagaa tgtaacagta acacactctg ttaaccttct ggaagacaag   180
cataacggaa aactatgcaa actaagaggg gtagccccat tgcatttggg taaatgtaac   240
attgctggct ggatcctggg aaatccagag tgtgaatcac tctccacagc aagttcatgg   300
tcctacattg tggaaacatc taattcagac aatggaacgt gttacccagg agatttcatc   360
aattatgagg agctaagaga gcaattgagc tcagtgtcat catttgaaag gtttgagata   420
ttccccaaga caagttcatg gcccaatcat gactcgaaca aggtgtaac ggcagcatgt    480
cctcacgctg gagcaaaaag cttctacaaa aacttgatat ggctagttaa aaaggaaat   540
tcatacccaa agcttaacca atcctacatt aatgataaag ggaaagaagt cctcgtgctg   600
tggggcattc accatccatc tactactgct gaccaacaaa gtctctatca gaatgcagat   660
gcatatgttt ttgtggggac atcaagatac agcaagaagt tcaagccgga aatagcaaca   720
agacccaaag tgagggatca agaagggaga atgaactatt actggacact agtagagccg   780
ggagacaaaa taacattcga agcaactgga aatctagtgg taccgagata tgcattcaca   840
atggaaagaa atgctggatc tggtattatc atttcagata caccagtcca cgattgcaat   900
acaacttgtc agacacccga gggtgctata aacaccagcc tcccatttca gaatatacat   960
ccgatcacaa ttggaaaatg tccaaagtat gtaaaaagca caaaattgag actggcacca  1020
ggattgagga atgttccgtc tattcaatct agaggcctat tcggggccat tgccggcttc  1080
attgaagggg gtggacagg atggtagat ggatggtacg ttatcacca tcaaaatgag    1140
caggggtcag gatatgcagc cgacctgaag agcacacaaa atgccattga caagattact   1200
aacaaagtaa attctgttat tgaaaagatg aatacagg acacagcagt gggtaaagag    1260
ttcaaccacc tggaaaaag aatagagaat ctaaataaaa aagttgatga tggtttcctg   1320
gacatttgga cttacaatgc cgaactgttg gttctaatgg aaaatgaaag aactttggac   1380
tatcacgatt caaatgtgaa gaacttgtat gaaaagtaa gaaccagtt aaaaaacaat    1440
gccaaggaaa ttggaaacgg ctgctttgaa ttttaccaca atgcgataaa cacgtgcatg   1500
gaaagtgtca aaaatgggac ttatgactac ccaaaatact cagaggaagc aaaattaaac   1560
agagaaaaaa tagatgggt aaagctgaa tcaacaagga tttaccagat tttggcgatc    1620
tattcaactg tcgccagttc attggtactg gtagtctccc tgggggcaat cagcttctgg   1680
atgtgctcta tgggtctct acagtgtaga atatgtattt aa                     1722
```

<210> SEQ ID NO 43
<211> LENGTH: 573
<212> TYPE: PRT
<213> ORGANISM: Artificial Sequence
<220> FEATURE:
<223> OTHER INFORMATION: PDI-H1 Mich-F390D+L429M AA

<400> SEQUENCE: 43

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60
```

```
Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
            130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
                275                 280                 285

Ile Ile Ile Ser Asp Thr Pro Val His Asp Cys Asn Thr Thr Cys Gln
            290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
            450                 455                 460

Asn Val Lys Asn Leu Tyr Glu Lys Val Arg Asn Gln Leu Lys Asn Asn
465                 470                 475                 480
```

```
Ala Lys Glu Ile Gly Asn Gly Cys Phe Glu Phe Tyr His Lys Cys Asp
            485                 490                 495

Asn Thr Cys Met Glu Ser Val Lys Asn Gly Tyr Asp Tyr Pro Lys
        500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 44
<211> LENGTH: 1722
<212> TYPE: DNA
<213> ORGANISM: Artificial Sequence
<220> FEATURE:
<223> OTHER INFORMATION: PDI-H1 Mich-N97D+F390D+L429M DNA

<400> SEQUENCE: 44

| | | | |
|---|---|---|---|
| atggcgaaaa acgttgcgat tttcggctta ttgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct ggaagacaag | 180 |
| cataacggaa actatgcaa actaagaggg gtagccccat gcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| gattatgagg agctaagaga gcaattgagc tcagtgtcat catttgaaag gtttgagata | 420 |
| ttccccaaga caagttcatg gcccaatcat gactcgaaca aaggtgtaac ggcagcatgt | 480 |
| cctcacgctg gagcaaaaag cttctacaaa aacttgatat ggctagttaa aaaggaaat | 540 |
| tcatacccaa agcttaacca atcctacatt aatgataaag ggaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata aacaccagcc tcccatttca gaatatacat | 960 |
| ccgatcacaa ttggaaaatg tccaaagtat gtaaaaagca caaaattgag actggccaca | 1020 |
| ggattgagga atgttccgtc tattcaatct agaggcctat tcggggccat tgccggcttc | 1080 |
| attgaagggg ggtggacagg gatggtagat ggatggtacg gttatcacca tcaaaatgag | 1140 |
| cagggggtcag gatatgcagc cgacctgaag agcacacaaa atgccattga caagattact | 1200 |
| aacaaagtaa attctgttat tgaaaagatg aatacacagg acacagcagt gggtaaagag | 1260 |
| ttcaaccacc tggaaaaaag aatagagaat ctaaataaaa aagttgatga tggtttcctg | 1320 |
| gacatttgga cttacaatgc cgaactgttg gttctaatgg aaaatgaaag aactttggac | 1380 |
| tatcacgatt caaatgtgaa gaacttgtat gaaaaagtaa gaaccagtt aaaaaacaat | 1440 |
| gccaaggaaa ttggaaacgg ctgctttgaa ttttaccaca atgcgataa cacgtgcatg | 1500 |
| gaaagtgtca aaaatgggac ttatgactac ccaaaatact cagaggaagc aaaattaaac | 1560 |

```
agagaaaaaa tagatggggt aaagctggaa tcaacaagga tttaccagat tttggcgatc    1620
tattcaactg tcgccagttc attggtactg gtagtctccc tggggggcaat cagcttctgg    1680 atgtgctcta atgggtctct acagtgtaga atatgtattt aa                        1722
```

<210> SEQ ID NO 45
<211> LENGTH: 573
<212> TYPE: PRT
<213> ORGANISM: Artificial Sequence
<220> FEATURE:
<223> OTHER INFORMATION: PDI-H1 Mich-N97D+F390D+L429M AA

<400> SEQUENCE: 45

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335
```

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
                435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510

Tyr Ser Glu Glu Ala Lys Leu Asn Arg Glu Lys Ile Asp Gly Val Lys
                515                 520                 525

Leu Glu Ser Thr Arg Ile Tyr Gln Ile Leu Ala Ile Tyr Ser Thr Val
                530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 46
<211> LENGTH: 1722
<212> TYPE: DNA
<213> ORGANISM: Artificial Sequence
<220> FEATURE:
<223> OTHER INFORMATION: PDI-H1 Mich-K374E+F390D+L429M DNA

<400> SEQUENCE: 46

| | | |
|---|---|---|
| atggcgaaaa acgttgcgat ttcggctta ttgttttctc ttcttgtgtt ggttccttct | 60 |
| cagatcttcg cggacacatt atgtataggt tatcatgcga caattcaac agacactgta | 120 |
| gacacagtac tagaaaagaa tgtaacagta acacactctg ttaaccttct ggaagacaag | 180 |
| cataacggaa actatgcaa actaagaggg gtagccccat gcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| aattatgagg agctaagaga gcaattgagc tcagtgtcat catttgaaag gtttgagata | 420 |
| ttccccaaga caagttcatg gcccaatcat gactcgaaca aggtgtaac ggcagcatgt | 480 |
| cctcacgctg gagcaaaaag cttctacaaa aacttgatat ggctagttaa aaaggaaat | 540 |
| tcatacccaa agcttaacca atcctacatt aatgataaag ggaagaagt cctcgtgctg | 600 |
| tggggcattc accatccatc tactactgct gaccaacaaa gtctctatca gaatgcagat | 660 |
| gcatatgttt tgtggggac atcaagatac agcaagaagt tcaagccgga aatagcaaca | 720 |

```
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata acaccagcc tcccatttca gaatatacat     960
ccgatcacaa ttggaaaatg tccaaagtat gtaaaagca caaaattgag actggccaca    1020
ggattgagga atgttccgtc tattcaatct agaggcctat tcggggccat tgccggcttc    1080
attgaagggg ggtggacagg gatggtagat ggatggtacg ttatcacca tcaaaatgag    1140
caggggtcag gatatgcagc cgacctgaag agcacacaaa atgccattga cgagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                      1722
```

<210> SEQ ID NO 47
<211> LENGTH: 573
<212> TYPE: PRT
<213> ORGANISM: Artificial Sequence
<220> FEATURE:
<223> OTHER INFORMATION: PDI-H1 Mich-K374E+F390D+L429M AA

<400> SEQUENCE: 47

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
```

```
            180                 185                 190
Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 48
<211> LENGTH: 1722
<212> TYPE: DNA
<213> ORGANISM: Artificial Sequence
```

<220> FEATURE:
<223> OTHER INFORMATION: PDI-H1 Mich-N97D+K374E+F390D+L429M DNA

<400> SEQUENCE: 48

| | | | | | |
|---|---|---|---|---|---|
| atggcgaaaa | acgttgcgat | tttcggctta | ttgttttctc | ttcttgtgtt | ggttccttct | 60 |
| cagatcttcg | cggacacatt | atgtataggt | tatcatgcga | acaattcaac | agacactgta | 120 |
| gacacagtac | tagaaaagaa | tgtaacagta | acacactctg | ttaaccttct | ggaagacaag | 180 |
| cataacggaa | actatgcaa | actaagaggg | gtagccccat | tgcatttggg | taatgtaac | 240 |
| attgctggct | ggatcctggg | aaatccagag | tgtgaatcac | tctccacagc | aagttcatgg | 300 |
| tcctacattg | tggaaacatc | taattcagac | aatggaacgt | gttacccagg | agatttcatc | 360 |
| gattatgagg | agctaagaga | gcaattgagc | tcagtgtcat | catttgaaag | gtttgagata | 420 |
| ttccccaaga | caagttcatg | gcccaatcat | gactcgaaca | aggtgtaac | ggcagcatgt | 480 |
| cctcacgctg | agcaaaaag | cttctacaaa | aacttgatat | ggctagttaa | aaaggaaat | 540 |
| tcatacccaa | agcttaacca | atcctacatt | aatgataaag | ggaaagaagt | cctcgtgctg | 600 |
| tggggcattc | accatccatc | tactactgct | gaccaacaaa | gtctctatca | gaatgcagat | 660 |
| gcatatgtt | ttgtggggac | atcaagatac | agcaagaagt | tcaagccgga | aatagcaaca | 720 |
| agacccaaag | tgagggatca | agaagggaga | atgaactatt | actggacact | agtagagccg | 780 |
| ggagacaaaa | taacattcga | agcaactgga | aatctagtgg | taccgagata | tgcattcaca | 840 |
| atggaaagaa | atgctggatc | tggtattatc | atttcagata | caccagtcca | cgattgcaat | 900 |
| acaacttgtc | agacacccga | gggtgctata | aacaccagcc | tcccatttca | gaatatacat | 960 |
| ccgatcacaa | ttggaaaatg | tccaaagtat | gtaaaaagca | caaaattgag | actggccaca | 1020 |
| ggattgagga | atgttccgtc | tattcaatct | agaggcctat | tcggggccat | tgccggcttc | 1080 |
| attgaagggg | ggtggacagg | gatggtagat | ggatggtacg | gttatcacca | tcaaaatgag | 1140 |
| cagggggtcag | gatatgcagc | cgacctgaag | agcacacaaa | atgccattga | cgagattact | 1200 |
| aacaaagtaa | attctgttat | tgaaaagatg | aatacacagg | acacagcagt | gggtaaagag | 1260 |
| ttcaaccacc | tggaaaaaag | aatagagaat | ctaaataaaa | aagttgatga | tggtttcctg | 1320 |
| gacatttgga | cttacaatgc | cgaactgttg | gttctaatgg | aaaatgaaag | aactttggac | 1380 |
| tatcacgatt | caaatgtgaa | gaacttgtat | gaaaaagtaa | gaaccagtt | aaaaaacaat | 1440 |
| gccaaggaaa | ttgaaacgg | ctgctttgaa | ttttaccaca | aatgcgataa | cacgtgcatg | 1500 |
| gaaagtgtca | aaaatgggac | ttatgactac | ccaaaatact | cagaggaagc | aaaattaaac | 1560 |
| agagaaaaa | tagatgggt | aaagctggaa | tcaacaagga | tttaccagat | tttggcgatc | 1620 |
| tattcaactg | tcgccagttc | attggtactg | gtagtctccc | tggggcaat | cagcttctgg | 1680 |
| atgtgctcta | atgggtctct | acagtgtaga | atatgtattt | aa | | 1722 |

<210> SEQ ID NO 49
<211> LENGTH: 573
<212> TYPE: PRT
<213> ORGANISM: Artificial Sequence
<220> FEATURE:
<223> OTHER INFORMATION: PDI-H1 Mich-N97D+K374E+F390D+L429M AA

<400> SEQUENCE: 49

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

```
Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
 50                  55                  60

Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
                 85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
            115                 120                 125

Leu Ser Ser Val Ser Ser Phe Glu Arg Phe Glu Ile Phe Pro Lys Thr
            130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
            210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
```

```
                450                 455                 460
Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 50
<211> LENGTH: 1722
<212> TYPE: DNA
<213> ORGANISM: Artificial Sequence
<220> FEATURE:
<223> OTHER INFORMATION: PDI-H1 Mass-F390D+L429M DNA

<400> SEQUENCE: 50
atggcgaaaa acgttgcgat tttcggctta ttgtttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat tgcatttggg taaatgtaac     240
attgctggct ggatcctggg aaatccagag tgtgaatcac tctccacagc aagatcatgg     300
tcctacattg tggaaacatc taattcagac aatggaacgt gttacccagg agatttcatc     360
aattatgagg agctaagaga gcaattgagc tcagtgtcat catttgaaag gtttgagata     420
ttccccaaga caagttcatg gcccaatcat gactcgaaca aggtgtaac ggcagcatgt     480 cctcacgctg gagcaaaaag cttctacaaa aacttgatat ggctagttaa aaaggaaat     540 tcatacccaa agcttaacca atcctacatt aatgataaag ggaagaagt cctcgtgctg     600 tggggcattc accatccatc tactactgct gaccaacaaa gtctctatca gaatgcagat     660
gcatatgttt tgtgtgggac atcaagatac agcaagaagt tcaagccgga aatagcaaca     720
agacccaaag tgagggatca agaagggaga atgaactatt actggacact agtagagccg     780
ggagacaaaa taacattcga agcaactgga aatctagtgg taccgagata tgcattcaca     840
atggaaagaa atgctggatc tggtattatc atttcagata caccagtcca cgattgcaat     900
acaacttgtc agacacccga gggtgctata aacaccagcc tcccatttca gaatgtgcat     960
ccgatcacaa ttggaaaatg tccaaagtat gtaaaaagca caaaattgag actggccaca    1020
ggattgagga atgttccgtc tattcaatct agaggcctat tcggggccat tgccggcttc    1080
attgaagggg ggtggacagg gatggtagat ggatggtacg ttatcaccat caaaatgag    1140 caggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
```

-continued

```
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac     1560
agagaaaaaa tagatggggt aaagctgaaa tcaacaagga tttaccagat tttggcgatc    1620
tattcaactg tcgccagttc attggtactg gtagtctccc tgggggcaat cagcttctgg    1680
atgtgctcta tgggtctct acagtgtaga atatgtattt aa                        1722
```

<210> SEQ ID NO 51
<211> LENGTH: 573
<212> TYPE: PRT
<213> ORGANISM: Artificial Sequence
<220> FEATURE:
<223> OTHER INFORMATION: PDI-H1 Mass-F390D+L429M AA

<400> SEQUENCE: 51

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300
```

```
Thr Pro Glu Gly Ala Ile Asn Thr Ser Leu Pro Phe Gln Asn Val His
305                 310                 315                 320
Pro Ile Thr Ile Gly Lys Cys Pro Lys Tyr Val Lys Ser Thr Lys Leu
            325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
    370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
            435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
            515                 520                 525
Leu Glu Ser Thr Arg Ile Tyr Gln Ile Leu Ala Ile Tyr Ser Thr Val
        530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 52
<211> LENGTH: 1722
<212> TYPE: DNA
<213> ORGANISM: Artificial Sequence
<220> FEATURE:
<223> OTHER INFORMATION: PDI-H1 Mass-N97D+F390D+L429M DNA

<400> SEQUENCE: 52
atggcgaaaa acgttgcgat ttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat tgcatttggg taaatgtaac     240
attgctggct ggatcctggg aaatccagag tgtgaatcac tctccacagc aagatcatgg     300
tcctacattg tggaaacatc taattcagac aatggaacgt gttacccagg agatttcatc     360
gattatgagg agctaagaga gcaattgagc tcagtgtcat catttgaaag gtttgagata     420
ttccccaaga caagttcatg gcccaatcat gactcgaaca aggtgtaac ggcagcatgt     480
cctcacgctg gagcaaaaag cttctacaaa aacttgatat ggctagttaa aaaaggaaat    540
```

```
tcatacccaa agcttaacca atcctacatt aatgataaag ggaaagaagt cctcgtgctg    600
tggggcattc accatccatc tactactgct gaccaacaaa gtctctatca gaatgcagat    660
gcatatgttt ttgtggggac atcaagatac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatgtgcat    960
ccgatcacaa ttggaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg gttatcacca tcaaaatgag   1140
caggggtcag gatatgcagc cgacctgaag agcacacaaa atgccattga caagattact   1200
aacaaagtaa attctgttat tgaaaagatg aatacacagg acacagcagt gggtaaagag   1260
ttcaaccacc tggaaaaaag aatagagaat ctaaataaaa aagttgatga tggtttcctg   1320
gacatttgga cttacaatgc cgaactgttg gttctaatgg aaaatgaaag aactttggac   1380
tatcacgatt caaatgtgaa gaacttgtat gaaaaagtaa gaaaccagtt aaaaaacaat   1440
gccaaggaaa ttggaaacgg ctgctttgaa ttttaccaca atgcgataaa cacgtgcatg   1500
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tggggggcaat cagcttctgg   1680
atgtgctcta atgggtctct acagtgtaga atatgtattt aa                      1722
```

<210> SEQ ID NO 53
<211> LENGTH: 573
<212> TYPE: PRT
<213> ORGANISM: Artificial Sequence
<220> FEATURE:
<223> OTHER INFORMATION: PDI-H1 Mass-N97D+F390D+L429M AA

<400> SEQUENCE: 53

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160
```

Pro His Ala Gly Ala Lys Ser Phe Tyr Lys Asn Leu Ile Trp Leu Val
            165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
            245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
            290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
            325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
            405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
            485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
            530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
            565                 570

<210> SEQ ID NO 54
<211> LENGTH: 1722
<212> TYPE: DNA
<213> ORGANISM: Artificial Sequence
<220> FEATURE:
<223> OTHER INFORMATION: PDI-H1 Mass-K374E+F390D+L429M DNA

<400> SEQUENCE: 54

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat gcatttgggt aaatgtaac      240
attgctggct ggatcctggg aaatccagag tgtgaatcac tctccacagc aagatcatgg     300
tcctacattg tggaaacatc taattcagac aatggaacgt gttacccagg agatttcatc     360
aattatgagg agctaagaga gcaattgagc tcagtgtcat catttgaaag gtttgagata     420
ttccccaaga caagttcatg gcccaatcat gactcgaaca aggtgtaac ggcagcatgt      480
cctcacgctg agcaaaaag cttctacaaa aacttgatat ggctagttaa aaaaggaaat     540
tcatacccaa agcttaacca atcctacatt aatgataaag ggaaagaagt cctcgtgctg     600
tggggcattc accatccatc tactactgct gaccaacaaa gtctctatca gaatgcagat     660
gcatatgttt tgtgtgggac atcaagatac agcaagaagt tcaagccgga aatagcaaca     720
agacccaaag tgagggatca agaagggaga tgaactatt actggacact agtagagccg      780
ggagacaaaa taacattcga agcaactgga atctagtgg taccgagata tgcattcaca     840
atggaaagaa atgctggatc tggtattatc atttcagata caccagtcca cgattgcaat     900
acaacttgtc agacacccga gggtgctata acaccagcc tcccatttca gaatgtgcat     960
ccgatcacaa ttggaaaatg tccaaagtat gtaaaaagca caaaattgag actggccaca    1020
ggattgagga atgttccgtc tattcaatct agaggcctat tcgggccat tgccggcttc     1080
attgaagggg ggtggacagg gatggtagat ggatggtacg ttatcacca tcaaaatgag     1140
caggggtcag gatatgcagc cgacctgaag agcacacaaa atgccattga cgagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta tgggtctct acagtgtaga atatgtattt aa                        1722
```

<210> SEQ ID NO 55
<211> LENGTH: 573
<212> TYPE: PRT
<213> ORGANISM: Artificial Sequence
<220> FEATURE:
<223> OTHER INFORMATION: PDI-H1 Mass-K374E+F390D+L429M AA

<400> SEQUENCE: 55

Met Ala Lys Asn Val Ala Ile Phe Gly Leu Leu Phe Ser Leu Leu Val

-continued

```
1               5                   10                  15
Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
 50                  55                  60

Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
 130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
 210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
 290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
 370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430
```

```
Lys Lys Val Asp Asp Gly Phe Leu Asp Ile Trp Thr Tyr Asn Ala Glu
        435                 440                 445
Leu Leu Val Leu Met Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
                515                 520                 525
Leu Glu Ser Thr Arg Ile Tyr Gln Ile Leu Ala Ile Tyr Ser Thr Val
        530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 56
<211> LENGTH: 1722
<212> TYPE: DNA
<213> ORGANISM: Artificial Sequence
<220> FEATURE:
<223> OTHER INFORMATION: PDI-H1 Mass-N97D+K374E+F390D+L429M DNA

<400> SEQUENCE: 56

```
atggcgaaaa acgttgcgat tttcggctta ttgttttctc ttcttgtgtt ggttccttct    60
cagatcttcg cggacacatt atgtataggt tatcatgcga acaattcaac agacactgta   120
gacacagtac tagaaaagaa tgtaacagta acacactctg ttaaccttct ggaagacaag   180
cataacggaa actatgcaa actaagaggg gtagccccat tgcatttggg taaatgtaac   240
attgctggct ggatcctggg aaatccagag tgtgaatcac tctccacagc aagatcatgg   300
tcctacattg tggaaacatc taattcagac aatggaacgt gttacccagg agatttcatc   360
gattatgagg agctaagaga gcaattgagc tcagtgtcat catttgaaag gtttgagata   420
ttccccaaga caagttcatg gcccaatcat gactcgaaca aggtgtaac ggcagcatgt   480
cctcacgctg agcaaaaag cttctacaaa aacttgatat ggctagttaa aaaaggaaat   540
tcatacccaa agcttaacca atcctacatt aatgataaag ggaaagaagt cctcgtgctg   600
tggggcattc accatccatc tactactgct gaccaacaaa gtctctatca gaatgcagat   660
gcatatgttt tgtggggac atcaagatac agcaagaagt tcaagccgga aatagcaaca   720
agacccaaag tgagggatca agaagggaga atgaactatt actggacact agtagagccg   780
ggagacaaaa taacattcga agcaactgga aatctagtgg taccgagata tgcattcaca   840
atggaaagaa atgctggatc tggtattatc atttcagata caccagtcca cgattgcaat   900
acaacttgtc agacacccga gggtgctata aacaccagcc tcccatttca gaatgtgcat   960
ccgatcacaa ttggaaaatg tccaaagtat gtaaaaagca caaaattgag actggccaca  1020
ggattgagga atgttccgtc tattcaatct agaggcctat tcggggccat tgccggcttc  1080
attgaagggg ggtggacagg gatggtagat ggatggtacg ttatcacca tcaaaatgag  1140
cagggggtcag gatatgcagc cgacctgaag agcacacaaa atgccattga cgagattact  1200
aacaaagtaa attctgttat tgaaaagatg aatacacagg acacagcagt gggtaaagag  1260
```

```
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac    1560
agagaaaaaa tagatgggt aaagctgaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                      1722
```

<210> SEQ ID NO 57
<211> LENGTH: 573
<212> TYPE: PRT
<213> ORGANISM: Artificial Sequence
<220> FEATURE:
<223> OTHER INFORMATION: PDI-H1 Mass-N97D+K374E+F390D+L429M AA

<400> SEQUENCE: 57

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
```

```
         275                 280                 285
Ile Ile Ile Ser Asp Thr Pro Val His Asp Cys Asn Thr Thr Cys Gln
        290                 295                 300
Thr Pro Glu Gly Ala Ile Asn Thr Ser Leu Pro Phe Gln Asn Val His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
            515                 520                 525
Leu Glu Ser Thr Arg Ile Tyr Gln Ile Leu Ala Ile Tyr Ser Thr Val
        530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 58
<211> LENGTH: 1722
<212> TYPE: DNA
<213> ORGANISM: Artificial Sequence
<220> FEATURE:
<223> OTHER INFORMATION: PDI-H1 CR-F390D+L429M DNA

<400> SEQUENCE: 58

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat tgcatttggg taaatgtaac     240
attgctggct ggatcctggg aaatccagag tgtgaatcac tctccacagc aagttcatgg     300
tcctacattg tggaaacatc taattcagac aatggaacgt gttacccagg agatttcatc     360
aattatgagg agctaagaga gcaattgagc tcagtgtcat catttgaaag gtttgagata     420
```

```
ttcccccaaga caagttcatg gcccaatcat gactcgaaca aaggtgtaac ggcagcatgt      480
cctcacgctg gagcaaaaag cttctacaaa aacttgatat ggctagttaa aaaaggaaat      540
tcatacccaa agcttaacca atcctacgtg aatgataaag ggaaagaagt cctcgtgctg      600
tggggcattc accatccacc cactactgct gaccaacaaa gtctctatca gaatgcagat      660
gcatatgttt ttgtggggac atcaaagtac agcaagaagt tcaagccgga aatagcaaca      720
agacccaaag tgagggatca agaagggaga atgaactatt actggacact agtagagccg      780
ggagacaaaa taacattcga agcaactgga aatctagtgg taccgagata tgcattcaca      840
atggaaagaa atgctggatc tggtattatc atttcagata caccagtcca cgattgcaat      900
acaacttgtc agacacccga gggtgctata aacaccagcc tcccatttca gaatatacat      960
ccgatcacaa ttgaaaaatg tccaaagtat gtaaaaagca caaaattgag actggccaca     1020
ggattgagga atgttccgtc tattcaatct agaggcctat tcggggccat tgccggcttc     1080
attgaagggg ggtggacagg gatggtagat ggatggtacg gttatcacca tcaaaatgag     1140
caggggtcag gatatgcagc cgacctgaag agcacacaaa atgccattga caagattact     1200
aacaaagtaa attctgttat tgaaaagatg aatacacagg acacagcagt gggtaaagag     1260
ttcaaccacc tggaaaaaag aatagagaat ctaaataaaa aagttgatga tggtttcctg     1320
gacatttgga cttacaatgc cgaactgttg gttctaatgg aaaatgaaag aactttggac     1380
tatcacgatt caaatgtgaa gaacttgtat gaaaagtaa gaaaccagtt aaaaaacaat      1440
gccaaggaaa ttggaaacgg ctgctttgaa ttttaccaca aatgcgataa cacgtgcatg     1500
gaaagtgtca aaaatgggac ttatgactac ccaaaatact cagaggaagc aaaattaaac     1560
agagaaaaaa tagatggggt aaagctggaa tcaacaagga tttaccagat tttggcgatc     1620
tattcaactg tcgccagttc attggtactg gtagtctccc tgggggcaat cagcttctgg     1680
atgtgctcta atgggtctct acagtgtaga atatgtattt aa                        1722
```

<210> SEQ ID NO 59  
<211> LENGTH: 573  
<212> TYPE: PRT  
<213> ORGANISM: Artificial Sequence  
<220> FEATURE:  
<223> OTHER INFORMATION: PDI-H1 CR-F390D+L429M AA

<400> SEQUENCE: 59

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
                100                 105                 110

Thr Cys Tyr Pro Gly Asp Phe Ile Asn Tyr Glu Glu Leu Arg Glu Gln
            115                 120                 125
```

-continued

```
Leu Ser Ser Val Ser Ser Phe Glu Arg Phe Glu Ile Phe Pro Lys Thr
130                 135                 140
Ser Ser Trp Pro Asn His Asp Ser Asn Lys Gly Val Thr Ala Ala Cys
145                 150                 155                 160
Pro His Ala Gly Ala Lys Ser Phe Tyr Lys Asn Leu Ile Trp Leu Val
                165                 170                 175
Lys Lys Gly Asn Ser Tyr Pro Lys Leu Asn Gln Ser Tyr Val Asn Asp
            180                 185                 190
Lys Gly Lys Glu Val Leu Val Leu Trp Gly Ile His His Pro Pro Thr
        195                 200                 205
Thr Ala Asp Gln Gln Ser Leu Tyr Gln Asn Ala Asp Ala Tyr Val Phe
210                 215                 220
Val Gly Thr Ser Lys Tyr Ser Lys Lys Phe Lys Pro Glu Ile Ala Thr
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
            260                 265                 270
Val Val Pro Arg Tyr Ala Phe Thr Met Glu Arg Asn Ala Gly Ser Gly
        275                 280                 285
Ile Ile Ile Ser Asp Thr Pro Val His Asp Cys Asn Thr Thr Cys Gln
290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
        515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
```

```
                545                 550                 555                 560
Met Cys Ser Asn Gly Ser Leu Gln Cys Arg Ile Cys Ile
                565                 570
```

<210> SEQ ID NO 60
<211> LENGTH: 1722
<212> TYPE: DNA
<213> ORGANISM: Artificial Sequence
<220> FEATURE:
<223> OTHER INFORMATION: PDI-H1 CR-N97D+F390D+L429M DNA

<400> SEQUENCE: 60

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct ggaagacaag | 180 |
| cataacggaa actatgcaa ctaagaggg gtagccccat tgcatttggg taaatgtaac | 240 |
| attgctggct ggatcctggg aaatccagag tgtgaatcac tctccacagc aagttcatgg | 300 |
| tcctacattg tggaaacatc taattcagac aatggaacgt gttacccagg agatttcatc | 360 |
| gattatgagg agctaagaga gcaattgagc tcagtgtcat catttgaaag gtttgagata | 420 |
| ttccccaaga caagttcatg gcccaatcat gactcgaaca aaggtgtaac ggcagcatgt | 480 |
| cctcacgctg agcaaaaag cttctacaaa aacttgatat ggctagttaa aaaggaaat | 540 |
| tcatacccaa agcttaacca atcctacgtg aatgataaag ggaagaagt cctcgtgctg | 600 |
| tggggcattc accatccacc cactactgct gaccaacaaa gtctctatca gaatgcagat | 660 |
| gcatatgttt ttgtggggac atcaaagtac agcaagaagt tcaagccgga atagcaaca | 720 |
| agacccaaag tgagggatca agaagggaga tgaactatt actggacact agtagagccg | 780 |
| ggagacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata acaccagcc tcccatttca gaatatacat | 960 |
| ccgatcacaa ttggaaatg tccaaagtat gtaaaaagca caaaattgag actggccaca | 1020 |
| ggattgagga atgttccgtc tattcaatct agaggcctat tcggggccat tgccggcttc | 1080 |
| attgaagggg gtggacagg gatggtagat ggatggtacg ttatcacca tcaaaatgag | 1140 |
| caggggtcag gatatgcagc cgacctgaag agcacacaaa atgccattga caagattact | 1200 |
| aacaaagtaa attctgttat tgaaaagatg aatacacagg acacagcagt gggtaaagag | 1260 |
| ttcaaccacc tggaaaaaag aatagagaat ctaaataaaa agttgatga tggtttcctg | 1320 |
| gacatttgga cttacaatgc cgaactgttg gttctaatgg aaaatgaaag aactttggac | 1380 |
| tatcacgatt caaatgtgaa gaacttgtat gaaaaagtaa gaaccagtt aaaaaacaat | 1440 |
| gccaaggaaa ttggaaacgg ctgctttgaa ttttaccaca aatgcgataa cacgtgcatg | 1500 |
| gaaagtgtca aaatgggac ttatgactac ccaaaatact cagaggaagc aaaattaaac | 1560 |
| agagaaaaaa tagatggggt aaagctggaa tcaacaagga tttaccagat tttggcgatc | 1620 |
| tattcaactg tcgccagttc attggtactg gtagtctccc tgggggcaat cagcttctgg | 1680 |
| atgtgctcta tgggtctct acagtgtaga atatgtattt aa | 1722 |

<210> SEQ ID NO 61
<211> LENGTH: 573
<212> TYPE: PRT
<213> ORGANISM: Artificial Sequence
<220> FEATURE:

<223> OTHER INFORMATION: PDI-H1 CR-N97D+F390D+L429M AA

<400> SEQUENCE: 61

```

```
Asn Lys Val Asn Ser Val Ile Glu Lys Met Asn Thr Gln Asp Thr Ala
            405                 410                 415
Val Gly Lys Glu Phe Asn His Leu Glu Lys Arg Ile Glu Asn Leu Asn
        420                 425                 430
Lys Lys Val Asp Asp Gly Phe Leu Asp Ile Trp Thr Tyr Asn Ala Glu
    435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
            485                 490                 495
Asn Thr Cys Met Glu Ser Val Lys Asn Gly Thr Tyr Asp Tyr Pro Lys
        500                 505                 510
Tyr Ser Glu Glu Ala Lys Leu Asn Arg Glu Lys Ile Asp Gly Val Lys
    515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
            565                 570
```

<210> SEQ ID NO 62
<211> LENGTH: 1722
<212> TYPE: DNA
<213> ORGANISM: Artificial Sequence
<220> FEATURE:
<223> OTHER INFORMATION: PDI-H1 CR-K374E+F390D+L429M DNA

<400> SEQUENCE: 62

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat gcatttggg taaatgtaac      240
attgctggct ggatcctggg aaatccagag tgtgaatcac tctccacagc aagttcatgg     300
tcctacattg tggaaacatc taattcagac aatggaacgt gttacccagg agatttcatc     360
aattatgagg agctaagaga gcaattgagc tcagtgtcat catttgaaag gtttgagata     420
ttccccaaga caagttcatg gcccaatcat gactcgaaca aggtgtaac ggcagcatgt      480
cctcacgctg agcaaaaag cttctacaaa aacttgatat ggctagttaa aaaaggaaat     540
tcatacccaa agcttaacca atcctacgtg aatgataaag ggaaagaagt cctcgtgctg     600
tggggcattc accatccacc cactactgct gaccaacaaa gtctctatca gaatgcagat     660
gcatatgttt tgtgtgggac atcaaagtac agcaagaagt tcaagccgga aatagcaaca     720
agacccaaag tgagggatca agaagggaga atgaactatt actggacact agtagagccg     780
ggagacaaaa taacattcga agcaactgga aatctagtgg taccgagata tgcattcaca     840
atggaaagaa atgctggatc tggtattatc atttcagata caccagtcca cgattgcaat     900
acaacttgtc agacacccga gggtgctata aacaccagcc tcccatttca gaatatacat     960
ccgatcacaa ttggaaaatg tccaaagtat gtaaaaagca caaaattgag actggccaca    1020
ggattgagga atgttccgtc tattcaatct agaggcctat tcggggccat tgccggcttc    1080
```

-continued

```
attgaagggg ggtggacagg gatggtagat ggatggtacg gttatcacca tcaaaatgag    1140
caggggtcag gatatgcagc cgacctgaag agcacacaaa atgccattga cgagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaccagtt  aaaaaacaat    1440 gccaaggaaa ttgaaacgg ctgctttgaa ttttaccaca aatgcgataa cacgtgcatg     1500
gaaagtgtca aaatgggac ttatgactac ccaaaatact cagaggaagc aaaattaaac     1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                      1722
```

<210> SEQ ID NO 63
<211> LENGTH: 573
<212> TYPE: PRT
<213> ORGANISM: Artificial Sequence
<220> FEATURE:
<223> OTHER INFORMATION: PDI-H1 CR-K374E+F390D+L429M AA

<400> SEQUENCE: 63

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Val Asn Asp
            180                 185                 190

Lys Gly Lys Glu Val Leu Val Leu Trp Gly Ile His His Pro Pro Thr
        195                 200                 205

Thr Ala Asp Gln Gln Ser Leu Tyr Gln Asn Ala Asp Ala Tyr Val Phe
    210                 215                 220

Val Gly Thr Ser Lys Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255
```

Leu Val Glu Pro Gly Asp Lys Ile Thr Phe Glu Ala Thr Gly Asn Leu
        260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
        340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
        370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
        420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
        485                 490                 495

Asn Thr Cys Met Glu Ser Val Lys Asn Gly Thr Tyr Asp Tyr Pro Lys
        500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 64
<211> LENGTH: 1722
<212> TYPE: DNA
<213> ORGANISM: Artificial Sequence
<220> FEATURE:
<223> OTHER INFORMATION: PDI-H1 CR-N97D+K374E+F390D+L429M DNA

<400> SEQUENCE: 64
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa aactatgcaa actaagaggg gtagccccat tgcatttggg taaatgtaac     240

```
attgctggct ggatcctggg aaatccagag tgtgaatcac tctccacagc aagttcatgg    300
tcctacattg tggaaacatc taattcagac aatggaacgt gttacccagg agatttcatc    360
gattatgagg agctaagaga gcaattgagc tcagtgtcat catttgaaag gtttgagata    420
ttccccaaga caagttcatg gcccaatcat gactcgaaca aggtgtaac ggcagcatgt     480
cctcacgctg agcaaaaag cttctacaaa aacttgatat ggctagttaa aaaggaaat    540
tcatacccaa agcttaacca atcctacgtg aatgataaag ggaaagaagt cctcgtgctg    600
tggggcattc accatccacc cactactgct gaccaacaaa gtctctatca gaatgcagat    660
gcatatgttt ttgtggggac atcaaagtac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata acaccagcc tcccatttca gaatatacat     960
ccgatcacaa ttggaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg ttatcacca tcaaaatgag    1140
caggggtcag gatatgcagc cgacctgaag agcacacaaa atgccattga cgagattact   1200
aacaaagtaa attctgttat tgaaaagatg aatacacagg acacagcagt gggtaaagag   1260
ttcaaccacc tggaaaaaag aatagagaat ctaaataaaa aagttgatga tggtttcctg   1320
gacatttgga cttacaatgc cgaactgttg gttctaatgg aaaatgaaag aactttggac   1380
tatcacgatt caaatgtgaa gaacttgtat gaaaaagtaa gaaaccagtt aaaaaacaat   1440
gccaaggaaa ttggaaacgg ctgctttgaa tttaccaca aatgcgataa cacgtgcatg    1500
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 65
<211> LENGTH: 573
<212> TYPE: PRT
<213> ORGANISM: Artificial Sequence
<220> FEATURE:
<223> OTHER INFORMATION: PDI-H1 CR-N97D+K374E+F390D+L429M AA

<400> SEQUENCE: 65

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
```

-continued

```
                100             105               110
Thr Cys Tyr Pro Gly Asp Phe Ile Asp Tyr Glu Glu Leu Arg Glu Gln
            115                 120                 125
Leu Ser Ser Val Ser Ser Phe Glu Arg Phe Glu Ile Phe Pro Lys Thr
            130                 135                 140
Ser Ser Trp Pro Asn His Asp Ser Asn Lys Gly Val Thr Ala Ala Cys
145                 150                 155                 160
Pro His Ala Gly Ala Lys Ser Phe Tyr Lys Asn Leu Ile Trp Leu Val
                165                 170                 175
Lys Lys Gly Asn Ser Tyr Pro Lys Leu Asn Gln Ser Tyr Val Asn Asp
            180                 185                 190
Lys Gly Lys Glu Val Leu Val Leu Trp Gly Ile His His Pro Pro Thr
            195                 200                 205
Thr Ala Asp Gln Gln Ser Leu Tyr Gln Asn Ala Asp Ala Tyr Val Phe
            210                 215                 220
Val Gly Thr Ser Lys Tyr Ser Lys Lys Phe Lys Pro Glu Ile Ala Thr
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
            260                 265                 270
Val Val Pro Arg Tyr Ala Phe Thr Met Glu Arg Asn Ala Gly Ser Gly
            275                 280                 285
Ile Ile Ile Ser Asp Thr Pro Val His Asp Cys Asn Thr Thr Cys Gln
            290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
            370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
            435                 440                 445
Leu Leu Val Leu Met Glu Asn Glu Arg Thr Leu Asp Tyr His Asp Ser
            450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Glu Glu Ala Lys Leu Asn Arg Glu Lys Ile Asp Gly Val Lys
            515                 520                 525
```

```
Leu Glu Ser Thr Arg Ile Tyr Gln Ile Leu Ala Ile Tyr Ser Thr Val
    530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 66
<211> LENGTH: 50
<212> TYPE: DNA
<213> ORGANISM: Artificial Sequence
<220> FEATURE:
<223> OTHER INFORMATION: Primer H1Hond(N97D).c

<400> SEQUENCE: 66

| | | |
|---|---|---|
| cccaggagat tcatcgatt atgaggagct aagggagcaa ttgagctcag | | 50 |

<210> SEQ ID NO 67
<211> LENGTH: 1722
<212> TYPE: DNA
<213> ORGANISM: Artificial Sequence
<220> FEATURE:
<223> OTHER INFORMATION: PDI-H1 Hond-N97D DNA

<400> SEQUENCE: 67

| | |
|---|---|
| atggcgaaaa acgttgcgat tttcggctta ttgtttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct agaagacaag | 180 |
| cataacggga actatgcaa ctaagaggg gtaccccat tgcatttggg taaatgtaac | 240 |
| attgctggct ggatcctggg aaatccgag tgtgaaccac tctccacagc aagttcatgg | 300 |
| tcctacattg tggaaacatc tagttcagac aatggaacgt gttacccagg agatttcatc | 360 |
| gattatgagg agctaaggga gcaattgagc tcagtgtcat catttgagag atttgagata | 420 |
| ttccccaaga caagttcatg gcccaatcat gactcgaaca aaggtgtaac agcagcatgt | 480 |
| cctcacgctg gggcaaaaag cttctacaaa aatttaatat ggctagttaa aaaggaaat | 540 |
| tcatacccaa agctcagcca atcctacatt aatgataaag gaaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaata | 720 |
| agacccaaag tgagggatca agaagggaga atgaactatt actggacact agtagagccg | 780 |
| ggagacaaaa taacattcga agcaactgga aatctagtgg taccgagata tgcattcaca | 840 |
| atggaaagaa atgctggatc tggtattatc atttcagata caccagtcca cgattgcaat | 900 |
| acaacttgtc agacacccga gggtgctata acaccagcc tcccatttca gaatatacat | 960 |
| ccgatcacaa ttgggaaatg tccaaagtat gtaaaaagca caaaattgag actggccaca | 1020 |
| ggattgagga atgtcccatc tattcaatct agaggcctat tcggggcgat tgccggcttc | 1080 |
| attgaagggg ggtggacagg gatggtagat ggatggtacg ttatcacca tcaaaatgag | 1140 |
| caggggtcag gatatgcagc cgaccagaag agcacacaaa gtgccattga caaaattact | 1200 |
| aacaaagtaa attctgttat tgaaaagatg aatacacagt tcacagcagt gggtaaagag | 1260 |
| ttcaaccact ggaaaaaag aatagagaat ttaaataaaa agttgatga tggtttcctg | 1320 |
| gacatttgga cttacaatgc cgaactgctg gttctattgg aaaatgaaag aactttggac | 1380 |
| taccacgact caaatgtgaa gaacttgtat gaaaaggtaa gaaaccagtt aaaaaacaat | 1440 |

```
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                       1722
```

<210> SEQ ID NO 68
<211> LENGTH: 573
<212> TYPE: PRT
<213> ORGANISM: Artificial Sequence
<220> FEATURE:
<223> OTHER INFORMATION: PDI-H1 Hond-N97D AA

<400> SEQUENCE: 68

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Pro Leu His Leu Gly Lys Cys Asn
65                  70                  75                  80

Ile Ala Gly Trp Ile Leu Gly Asn Pro Glu Cys Glu Pro Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
```

```
            305                 310                 315                 320
    Pro Ile Thr Ile Gly Lys Cys Pro Lys Tyr Val Lys Ser Thr Lys Leu
                    325                 330                 335

Arg Leu Ala Thr Gly Leu Arg Asn Val Pro Ser Ile Gln Ser Arg Gly
                    340                 345                 350

Leu Phe Gly Ala Ile Ala Gly Phe Ile Glu Gly Gly Trp Thr Gly Met
                    355                 360                 365

Val Asp Gly Trp Tyr Gly Tyr His His Gln Asn Glu Gln Gly Ser Gly
                    370                 375                 380

Tyr Ala Ala Asp Gln Lys Ser Thr Gln Ser Ala Ile Asp Lys Ile Thr
    385                 390                 395                 400

Asn Lys Val Asn Ser Val Ile Glu Lys Met Asn Thr Gln Phe Thr Ala
                    405                 410                 415

Val Gly Lys Glu Phe Asn His Leu Glu Lys Arg Ile Glu Asn Leu Asn
                    420                 425                 430

Lys Lys Val Asp Asp Gly Phe Leu Asp Ile Trp Thr Tyr Asn Ala Glu
                    435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
    465                 470                 475                 480

Ala Lys Glu Ile Gly Asn Gly Cys Phe Glu Phe Tyr His Lys Cys Asp
                    485                 490                 495

Asn Thr Cys Met Glu Ser Val Lys Asn Gly Thr Tyr Asp Tyr Pro Lys
                    500                 505                 510

Tyr Ser Glu Glu Ala Lys Leu Asn Arg Glu Lys Ile Asp Gly Val Lys
                    515                 520                 525

Leu Glu Ser Thr Arg Ile Tyr Gln Ile Leu Ala Ile Tyr Ser Thr Val
                    530                 535                 540

Ala Ser Ser Leu Val Leu Val Val Ser Leu Gly Ala Ile Ser Phe Trp
    545                 550                 555                 560

Met Cys Ser Asn Gly Ser Leu Gln Cys Arg Ile Cys Ile
                    565                 570

<210> SEQ ID NO 69
<211> LENGTH: 57
<212> TYPE: DNA
<213> ORGANISM: Artificial Sequence
<220> FEATURE:
<223> OTHER INFORMATION: Primer H1Hond(K374E).r

<400> SEQUENCE: 69
tttgttagta atctcgtcaa tggcactttg tgtgctcttc tggtcggctg catatcc      57

<210> SEQ ID NO 70
<211> LENGTH: 50
<212> TYPE: DNA
<213> ORGANISM: Artificial Sequence
<220> FEATURE:
<223> OTHER INFORMATION: Primer H1Hond(K374E).c

<400> SEQUENCE: 70
acaaagtgcc attgacgaga ttactaacaa agtaaattct gttattgaaa              50

<210> SEQ ID NO 71
<211> LENGTH: 1722
<212> TYPE: DNA
<213> ORGANISM: Artificial Sequence
```

<220> FEATURE:
<223> OTHER INFORMATION: PDI-H1 Hond-K374E DNA

<400> SEQUENCE: 71

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cataacggga actatgcaa actaagaggg gtaccccccat tgcatttggg taaatgtaac     240
attgctggct ggatcctggg aaatccagag tgtgaaccac tctccacagc aagttcatgg     300
tcctacattg tggaaacatc tagttcagac aatggaacgt gttacccagg agatttcatc     360
aattatgagg agctaaggga gcaattgagc tcagtgtcat catttgagag atttgagata     420
ttccccaaga caagttcatg gcccaatcat gactcgaaca aaggtgtaac agcagcatgt     480
cctcacgctg gggcaaaaag cttctacaaa aatttaatat ggctagttaa aaaggaaat      540
tcataccccaa agctcagcca atcctacatt aatgataaag aaaagaagt cctcgtgctg     600
tggggcattc accatccatc tactactgct gaccaacaaa gtctctatca gaatgcagat     660
gcatatgttt tgtggggac atcaagatac agcaagaagt tcaagccgga atagcaata      720
agacccaaag tgagggatca agaagggaga tgaactatt actggacact agtagagccg     780
ggagacaaaa taacattcga agcaactgga atctagtgg taccgagata tgcattcaca     840
atggaaagaa atgctggatc tggtattatc atttcagata caccagtcca cgattgcaat     900
acaacttgtc agacacccga gggtgctata acaccagcc tcccattttca gaatatacat     960
ccgatcacaa ttgggaaatg tccaaagtat gtaaaaagca caaaattgag actggccaca    1020
ggattgagga atgtccccatc tattcaatct agaggcctat tcggggcgat tgccggcttc    1080
attgaagggg ggtggacagg gatggtagat ggatggtacg gttatcacca tcaaaatgag    1140
caggggtcag gatatgcagc cgaccagaag agcacacaaa gtgccattga cgagattact    1200
aacaaagtaa attctgttat tgaaaagatg aatacacagt tcacagcagt gggtaaagag    1260
ttcaaccact tggaaaaaag aatagagaat ttaaataaaa aagttgatga tggtttcctg    1320
gacatttgga cttacaatgc cgaactgctg gttctattgg aaaatgaaag aactttggac    1380
taccacgact caaatgtgaa gaacttgtat gaaaaggtaa gaaccagtt aaaaaacaat    1440
gccaaggaaa ttggaaacgg ctgctttgaa ttttaccaca atgcgataa cacgtgcatg    1500
gaaagtgtca aaaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                       1722
```

<210> SEQ ID NO 72
<211> LENGTH: 573
<212> TYPE: PRT
<213> ORGANISM: Artificial Sequence
<220> FEATURE:
<223> OTHER INFORMATION: PDI-H1 Hond-K374E AA

<400> SEQUENCE: 72

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

-continued

Ala Asn Asn Ser Thr Asp Thr Val Asp Thr Val Leu Glu Lys Asn Val
         35                  40                  45

Thr Val Thr His Ser Val Asn Leu Leu Glu Asp Lys His Asn Gly Lys
 50                  55                  60

Leu Cys Lys Leu Arg Gly Val Pro Pro Leu His Leu Gly Lys Cys Asn
 65                  70                  75                  80

Ile Ala Gly Trp Ile Leu Gly Asn Pro Glu Cys Glu Pro Leu Ser Thr
                 85                  90                  95

Ala Ser Ser Trp Ser Tyr Ile Val Glu Thr Ser Ser Asp Asn Gly
                100                 105                 110

Thr Cys Tyr Pro Gly Asp Phe Ile Asn Tyr Glu Glu Leu Arg Glu Gln
                115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Gln Ser Tyr Ile Asn Asp
                180                 185                 190

Lys Gly Lys Glu Val Leu Val Leu Trp Gly Ile His His Pro Ser Thr
    195                 200                 205

Thr Ala Asp Gln Gln Ser Leu Tyr Gln Asn Ala Asp Ala Tyr Val Phe
                210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
                275                 280                 285

Ile Ile Ile Ser Asp Thr Pro Val His Asp Cys Asn Thr Thr Cys Gln
                290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
    370                 375                 380

Tyr Ala Ala Asp Gln Lys Ser Thr Gln Ser Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
    435                 440                 445

Leu Leu Val Leu Leu Glu Asn Glu Arg Thr Leu Asp Tyr His Asp Ser

```
        450                 455                 460
Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 73
<211> LENGTH: 50
<212> TYPE: DNA
<213> ORGANISM: Artificial Sequence
<220> FEATURE:
<223> OTHER INFORMATION: Primer H1Hond(F390D).r

<400> SEQUENCE: 73
acccactgct gtgtcctgtg tattcatctt ttcaataaca gaatttactt         50

<210> SEQ ID NO 74
<211> LENGTH: 50
<212> TYPE: DNA
<213> ORGANISM: Artificial Sequence
<220> FEATURE:
<223> OTHER INFORMATION: H1Hond(F390D).c

<400> SEQUENCE: 74
aaagatgaat acacaggaca cagcagtggg taaagagttc aaccacttgg         50

<210> SEQ ID NO 75
<211> LENGTH: 1722
<212> TYPE: DNA
<213> ORGANISM: Artificial Sequence
<220> FEATURE:
<223> OTHER INFORMATION: PDI-H1 Hond-F390D DNA

<400> SEQUENCE: 75
atggcgaaaa acgttgcgat ttcggctta ttgttttctc ttcttgtgtt ggttccttct    60
cagatcttcg cggacacatt atgtataggt tatcatgcga acaattcaac agacactgta   120
gacacagtac tagaaaagaa tgtaacagta acacactctg ttaaccttct agaagacaag   180
cataacggga actatgcaa actaagaggg gtaccccat tgcatttggg taaatgtaac    240
attgctggct ggatcctggg aaatccagag tgtgaaccac tctccacagc aagttcatgg   300
tcctacattg tggaaacatc tagttcagac aatggaacgt gttacccagg agatttcatc   360
aattatgagg agctaaggga gcaattgagc tcagtgtcat catttgagag atttgagata   420
ttccccaaga caagttcatg gcccaatcat gactcgaaca aggtgtaac agcagcatgt   480 cctcacgctg ggcaaaaag cttctacaaa aatttaatat ggctagttaa aaaaggaaat   540
tcatacccaa agctcagcca atcctacatt aatgataaag aaaagaagt cctcgtgctg   600 tggggcattc accatccatc tactactgct gaccaacaaa gtctctatca gaatgcagat   660

```
gcatatgttt tgtggggac atcaagatac agcaagaagt tcaagccgga aatagcaata    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatatacat    960
ccgatcacaa ttgggaaatg tccaaagtat gtaaaaagca caaaattgag actggccaca   1020
ggattgagga atgtcccatc tattcaatct agaggcctat tcggggcgat tgccggcttc   1080
attgaagggg ggtggacagg gatggtagat ggatggtacg gttatcacca tcaaaatgag   1140
caggggtcag gatatgcagc cgaccagaag agcacacaaa gtgccattga caaaattact   1200
aacaaagtaa attctgttat tgaaaagatg aatacacagg acacagcagt gggtaaagag   1260
ttcaaccact tggaaaaaag aatagagaat ttaaataaaa aagttgatga tggtttcctg   1320
gacatttgga cttacaatgc cgaactgctg gttctattgg aaaatgaaag aactttggac   1380
taccacgact caaatgtgaa gaacttgtat gaaaaggtaa gaaccagttt aaaaaacaat   1440
gccaaggaaa ttggaaacgg ctgctttgaa ttttaccaca aatgcgataa cacgtgcatg   1500
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tggggggcaat cagcttctgg   1680
atgtgctcta atgggtctct acagtgtaga atatgtattt aa                       1722
```

<210> SEQ ID NO 76
<211> LENGTH: 573
<212> TYPE: PRT
<213> ORGANISM: Artificial Sequence
<220> FEATURE:
<223> OTHER INFORMATION: PDI-H1 Hond-F390D AA

<400> SEQUENCE: 76

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Pro Leu His Leu Gly Lys Cys Asn
65                  70                  75                  80

Ile Ala Gly Trp Ile Leu Gly Asn Pro Glu Cys Glu Pro Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175
```

```
Lys Lys Gly Asn Ser Tyr Pro Lys Leu Ser Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
        260                 265                 270

Val Val Pro Arg Tyr Ala Phe Thr Met Glu Arg Asn Ala Gly Ser Gly
    275                 280                 285

Ile Ile Ile Ser Asp Thr Pro Val His Asp Cys Asn Thr Thr Cys Gln
        290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
370                 375                 380

Tyr Ala Ala Asp Gln Lys Ser Thr Gln Ser Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 77
<211> LENGTH: 55
<212> TYPE: DNA
```

<210> SEQ ID NO 77
<211> LENGTH: 55
<212> TYPE: DNA
<213> ORGANISM: Artificial Sequence
<220> FEATURE:
<223> OTHER INFORMATION: Primer H1Hond(L429M).r

<400> SEQUENCE: 77

```
tctttcattt tccattagaa ccagcagttc ggcattgtaa gtccaaatgt ccagg        55
```

<210> SEQ ID NO 78
<211> LENGTH: 48
<212> TYPE: DNA
<213> ORGANISM: Artificial Sequence
<220> FEATURE:
<223> OTHER INFORMATION: Primer H1Hond(L429M).c

<400> SEQUENCE: 78

```
cgaactgctg gttctaatgg aaaatgaaag aactttggac taccacga             48
```

<210> SEQ ID NO 79
<211> LENGTH: 1722
<212> TYPE: DNA
<213> ORGANISM: Artificial Sequence
<220> FEATURE:
<223> OTHER INFORMATION: PDI-H1 Hond-L429M DNA

<400> SEQUENCE: 79

```
atggcgaaaa acgttgcgat tttcggctta ttgttttctc ttcttgtgtt ggttccttct     60
cagatcttcg cggacacatt atgtataggt tatcatgcga acaattcaac agacactgta    120
gacacagtac tagaaaagaa tgtaacagta acacactctg ttaaccttct agaagacaag    180
cataacggga actatgcaac taaggggta cccccat gcatttggg taaatgtaac         240
attgctggct ggatcctggg aaatccagag tgtgaaccac tctccacagc aagttcatgg    300
tcctacattg tggaaacatc tagttcagac aatggaacgt gttacccagg agatttcatc    360
aattatgagg agctaaggga gcaattgagc tcagtgtcat catttgagag atttgagata    420
ttccccaaga caagttcatg gcccaatcat gactcgaaca aggtgtaac agcagcatgt    480
cctcacgctg gggcaaaaag cttctacaaa aatttaatat ggctagttaa aaaaggaaat    540
tcatacccaa agctcagcca atcctacatt aatgataaag aaaagaagt cctcgtgctg    600
tggggcattc accatccatc tactactgct gaccaacaaa gtctctatca gaatgcagat    660
gcatatgttt ttgtggggac atcaagatac agcaagaagt tcaagccgga aatagcaata    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatatacat    960
ccgatcacaa ttgggaaatg tccaaagtat gtaaaaagca caaaattgag actggccaca   1020
ggattgagga atgtcccatc tattcaatct agaggcctat tcggggcgat gccggcttc    1080
attgaagggg ggtggacagg gatggtagat ggatggtacg gttatcacca tcaaaatgag   1140
caggggtcag gatatgcagc cgaccagaag agcacacaaa gtgccattga caaattact   1200
aacaaagtaa attctgttat tgaaaagatg aatacacagt tcacagcagt gggtaaagag   1260
ttcaaccact tggaaaaaag aatagagaat ttaaataaaa aagttgatga tggtttcctg   1320
gacatttgga cttacaatgc cgaactgctg gttctaatgg aaaatgaaag aactttggac   1380
taccacgact caaatgtgaa gaacttgtat gaaaaggtaa gaaccagtt aaaaaacaat   1440
gccaaggaaa ttggaaacgg ctgctttgaa ttttaccaca atgcgataaa cacgtgcatg   1500
```

```
gaaagtgtca aaaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                     1722
```

<210> SEQ ID NO 80
<211> LENGTH: 573
<212> TYPE: PRT
<213> ORGANISM: Artificial Sequence
<220> FEATURE:
<223> OTHER INFORMATION: PDI-H1 Hond-L429M AA

<400> SEQUENCE: 80

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Pro Pro Leu His Leu Gly Lys Cys Asn
65                  70                  75                  80

Ile Ala Gly Trp Ile Leu Gly Asn Pro Glu Cys Glu Pro Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320
```

```
Pro Ile Thr Ile Gly Lys Cys Pro Lys Tyr Val Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Gln Lys Ser Thr Gln Ser Ala Ile Asp Lys Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 81
<211> LENGTH: 1722
<212> TYPE: DNA
<213> ORGANISM: Artificial Sequence
<220> FEATURE:
<223> OTHER INFORMATION: PDI-H1 Hond-F390D+L429M DNA

<400> SEQUENCE: 81

```
atggcgaaaa acgttgcgat tttcggctta tgttttctc ttcttgtgtt ggttccttct     60
cagatcttcg cggacacatt atgtataggt tatcatgcga acaattcaac agacactgta    120
gacacagtac tagaaaagaa tgtaacagta acacactctg ttaaccttct agaagacaag    180
cataacggga actatgcaa actaagaggg tacccccat tgcatttggg taaatgtaac      240
attgctggct ggatcctggg aaatccagag tgtgaaccac tctccacagc aagttcatgg    300
tcctacattg tggaaacatc tagttcagac aatggaacgt gttacccagg agatttcatc    360
aattatgagg agctaaggga gcaattgagc tcagtgtcat catttgagag atttgagata    420
ttccccaaga caagttcatg gcccaatcat gactcgaaca aaggtgtaac agcagcatgt    480
cctcacgctg gggcaaaaag cttctacaaa aatttaatat ggctagttaa aaaaggaaat    540 tcataccca agctcagcca atcctacatt aatgataaag aaaagaagt cctcgtgctg      600 tggggcattc accatccatc tactactgct gaccaacaaa gtctctatca gaatgcagat    660
```

```
gcatatgttt tgtggggac atcaagatac agcaagaagt tcaagccgga aatagcaata    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata acaccagcc tcccatttca gaatatacat    960
ccgatcacaa ttgggaaatg tccaaagtat gtaaaaagca caaaattgag actgccaca    1020 ggattgagga atgtcccatc tattcaatct agaggcctat tcggggcgat tgccggcttc    1080
attgaagggg ggtggacagg gatggtagat ggatggtacg ttatcacca tcaaaatgag    1140 caggggtcag gatatgcagc cgaccagaag agcacacaaa gtgccattga caaaattact    1200
aacaaagtaa attctgttat tgaaaagatg aatacacagg acacagcagt gggtaaagag    1260
ttcaaccact tggaaaaaag aatagagaat ttaaataaaa aagttgatga tggtttcctg    1320
gacatttgga cttacaatgc cgaactgctg gttctaatgg aaaatgaaag aactttggac    1380
taccacgact caaatgtgaa gaacttgtat gaaaaggtaa gaaccagtt aaaaaacaat    1440 gccaaggaaa ttgaaacgg ctgctttgaa ttttaccaca aatgcgataa cacgtgcatg    1500
gaaagtgtca aaaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                      1722
```

<210> SEQ ID NO 82
<211> LENGTH: 573
<212> TYPE: PRT
<213> ORGANISM: Artificial Sequence
<220> FEATURE:
<223> OTHER INFORMATION: PDI-H1 Hond-F390D+L429M AA

<400> SEQUENCE: 82

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Pro Leu His Leu Gly Lys Cys Asn
65                  70                  75                  80

Ile Ala Gly Trp Ile Leu Gly Asn Pro Glu Cys Glu Pro Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175
```

```
Lys Lys Gly Asn Ser Tyr Pro Lys Leu Ser Gln Ser Tyr Ile Asn Asp
                180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
        210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
        290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
370                 375                 380

Tyr Ala Ala Asp Gln Lys Ser Thr Gln Ser Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 83
<211> LENGTH: 1722
```

<212> TYPE: DNA
<213> ORGANISM: Artificial Sequence
<220> FEATURE:
<223> OTHER INFORMATION: PDI-H1 Hond-N97D+F390D+L429M DNA

<400> SEQUENCE: 83

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cataacggga aactatgcaa actaagaggg gtaccccat tgcatttggg taaatgtaac      240
attgctggct ggatcctggg aaatccgag tgtgaaccac tctccacagc aagttcatgg      300
tcctacattg tggaaacatc tagttcagac aatggaacgt gttacccagg agatttcatc     360
gattatgagg agctaaggga gcaattgagc tcagtgtcat catttgagag atttgagata     420
ttccccaaga caagttcatg gcccaatcat gactcgaaca aaggtgtaac agcagcatgt     480
cctcacgctg gggcaaaaag cttctacaaa aatttaatat ggctagttaa aaaaggaaat     540
tcatacccaa agctcagcca atcctacatt aatgataaag gaaagaaagt cctcgtgctg     600
tgggcattc accatccatc tactactgct gaccaacaaa gtctctatca gaatgcagat      660
gcatatgttt tgtggggac atcaagatac agcaagaagt tcaagccgga aatagcaata      720
agacccaaag tgagggatca agaagggaga tgaactatt actggacact agtagagccg      780
ggagacaaaa taacattcga agcaactgga aatctagtgg taccgagata tgcattcaca     840
atggaaagaa atgctggatc tggtattatc atttcagata caccagtcca cgattgcaat     900
acaacttgtc agacacccga gggtgctata aacaccagcc tcccatttca gaatatacat     960
ccgatcacaa ttgggaaatg tccaaagtat gtaaaaagca caaattgag actggccaca    1020
ggattgagga atgtcccatc tattcaatct agaggcctat cggggcgat tgccggcttc     1080
attgaagggg gtggacagg gatggtagat ggatggtacg ttatcacca tcaaaatgag     1140
cagggtcag gatatgcagc cgaccagaag agcacacaaa gtgccattga caaaattact    1200
aacaaagtaa attctgttat tgaaaagatg aatacacagg acacagcagt gggtaaagag    1260
ttcaaccact tggaaaaaag aatagagaat ttaaataaaa aagttgatga tggtttcctg    1320
gacatttgga cttacaatgc cgaactgctg gttctaatgg aaaatgaaag aactttggac    1380
taccacgact caaatgtgaa gaacttgtat gaaaaggtaa gaaccagtt aaaaaacaat    1440
gccaaggaaa ttggaaacgg ctgctttgaa ttttaccaca atgcgataaa cacgtgcatg    1500
gaaagtgtca aaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                      1722
```

<210> SEQ ID NO 84
<211> LENGTH: 573
<212> TYPE: PRT
<213> ORGANISM: Artificial Sequence
<220> FEATURE:
<223> OTHER INFORMATION: PDI-H1 Hond-N97D+F390D+L429M AA

<400

```
            20                  25                  30
Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
 50                  55                  60

Leu Cys Lys Leu Arg Gly Val Pro Leu His Leu Gly Lys Cys Asn
 65                  70                  75                  80

Ile Ala Gly Trp Ile Leu Gly Asn Pro Glu Cys Glu Pro Leu Ser Thr
                     85                  90                  95

Ala Ser Ser Trp Ser Tyr Ile Val Glu Thr Ser Ser Asp Asn Gly
                100                 105                 110

Thr Cys Tyr Pro Gly Asp Phe Ile Asp Tyr Glu Glu Leu Arg Glu Gln
            115                 120                 125

Leu Ser Ser Val Ser Ser Phe Glu Arg Phe Glu Ile Phe Pro Lys Thr
            130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Gln Ser Tyr Ile Asn Asp
                180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
            210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
            290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Gln Lys Ser Thr Gln Ser Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445
```

```
Leu Leu Val Leu Met Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
        515                 520                 525
Leu Glu Ser Thr Arg Ile Tyr Gln Ile Leu Ala Ile Tyr Ser Thr Val
    530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 85
<211> LENGTH: 1722
<212> TYPE: DNA
<213> ORGANISM: Artificial Sequence
<220> FEATURE:
<223> OTHER INFORMATION: PDI-H1 Darw-N97D DNA

<400> SEQUENCE: 85
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cacaacggga actatgcaa actaagaggg gtagccccat gcatttggg taaatgtaac       240
attgctggct ggatcctggg aaacccagag tgtgaatcac tctccacagc aagttcatgg     300
tcctacattg tggaaacatc tagttcagac aatggaacgt gttacccagg agatttcatc     360
gattatgagg agctaagaga gcaattgagc tcagtgtcat catttgaaag atttgagata     420
ttccccaaga caagttcatg gcccaatcat gactcgaaca aaggtgtaac ggcagcatgt     480
cctcacgctg agcaaaaag cttctacaaa aatttaatat ggctaactaa aaaaggaaat     540
tcatacccaa agctcagcca atcctacatt aatgataaag ggaaagaaat cctcgtgctg     600
tggggcattc accatccatc tactactgct gaccaacaaa gtctctatca gaatgcagat     660
gcatatgttt ttgtggggac atcaagatac agcaagaagt tcaagccgga aatagcaata     720
agacccaaag tgagggatca agaagggaga atgaactatt actggacact agtagagcca     780
ggtgacaaaa taacattcga agcaactgga aatctagtgg taccgagata tgcattcaca     840
atggaaagaa atgctggatc tggtattatc atttcagata caccagtcca cgattgcaat     900
acaacttgtc agacacccga gggtgctata aacaccagcc tcccatttca gaatatacat     960
ccgatcacaa ttggaaaatg tccaaagtat gtgaaaagca caaaattgag actggccaca    1020
ggattgagga atgtcccatc tattcaatct agaggcctat tcgggccat tgccggcttc    1080
attgaagggg ggtggacagg gatggtagat ggatggtacg ttatcacca tcaaaatgag     1140
caggggtcag ggtatgcagc cgacctgaag agcacacaaa atgccattga caaaattact    1200
aacaaagtaa attctgttat tgaaaagatg aatacacagt tcacagcagt gggtaaagag    1260
ttcaaccact tggaaaaaag aatagagaat ttaaataaaa aagttgatga tggtttcctg    1320
```

```
gacatttgga cttacaatgc cgaactgctg gttctattgg aaaatgaaag aactttggac  1380
taccacgatt caaatgtgaa gaacttgtat gaaaaggtaa gaaaccagtt aaaaaacaat  1440
gccaaggaaa ttgaaatgg ttgctttgaa ttttaccaca aatgcgataa cacgtgcatg  1500
gaaagtgtca aaatgggac ttatgactac ccaaaatact caggggaagc aaaattaaac  1560
agagaaaaaa tagaaggggt aaagctggaa tcaacaagaa tttaccaaat tttggcgatc  1620
tattcaactg tcgccagttc attggtactg gtagtctccc tgggggcaat cagcttctgg  1680
atgtgctcta atgggtctct acagtgtaga atatgtattt aa                    1722
```

<210> SEQ ID NO 86
<211> LENGTH: 573
<212> TYPE: PRT
<213> ORGANISM: Artificial Sequence
<220> FEATURE:
<223> OTHER INFORMATION: PDI-H1 Darw-N97D AA

<400> SEQUENCE: 86

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Thr
                165                 170                 175

Lys Lys Gly Asn Ser Tyr Pro Lys Leu Ser Gln Ser Tyr Ile Asn Asp
            180                 185                 190

Lys Gly Lys Glu Ile Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
```

```
                290                 295                 300
Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
                435                 440                 445

Leu Leu Val Leu Leu Glu Asn Glu Arg Thr Leu Asp Tyr His Asp Ser
                450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510

Tyr Ser Gly Glu Ala Lys Leu Asn Arg Glu Lys Ile Glu Gly Val Lys
                515                 520                 525

Leu Glu Ser Thr Arg Ile Tyr Gln Ile Leu Ala Ile Tyr Ser Thr Val
                530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 87
<211> LENGTH: 56
<212> TYPE: DNA
<213> ORGANISM: Artificial Sequence
<220> FEATURE:
<223> OTHER INFORMATION: Primer H1Darw(K374E).r

<400> SEQUENCE: 87
tttgttagta atctcgtcaa tggcattttg tgtgctcttc aggtcggctg catacc      56

<210> SEQ ID NO 88
<211> LENGTH: 1722
<212> TYPE: DNA
<213> ORGANISM: Artificial Sequence
<220> FEATURE:
<223> OTHER INFORMATION: PDI-H1 Darw-K374E DNA

<400> SEQUENCE: 88
atggcgaaaa acgttgcgat ttcggctta ttgttttctc ttcttgtgtt ggttccttct      60
cagatcttcg cggacacatt atgtataggt tatcatgcga caaattcaac agacactgta    120
```

```
gacacagtac tagaaaagaa tgtaacagta acacactctg ttaaccttct agaagacaag    180
cacaacggga aactatgcaa actaagaggg gtagccccat tgcatttggg taaatgtaac    240
attgctggct ggatcctggg aaacccagag tgtgaatcac tctccacagc aagttcatgg    300
tcctacattg tggaaacatc tagttcagac aatggaacgt gttacccagg agatttcatc    360
aattatgagg agctaagaga gcaattgagc tcagtgtcat catttgaaag atttgagata    420
ttccccaaga caagttcatg gcccaatcat gactcgaaca aaggtgtaac ggcagcatgt    480
cctcacgctg gagcaaaaag cttctacaaa aatttaatat ggctaactaa aaaaggaaat    540
tcatacccaa agctcagcca atcctacatt aatgataaag ggaaagaaat cctcgtgctg    600
tggggcattc accatccatc tactactgct gaccaacaaa gtctctatca gaatgcagat    660
gcatatgttt ttgtggggac atcaagatac agcaagaagt tcaagccgga aatagcaata    720
agacccaaag tgagggatca agaagggaga atgaactatt actggacact agtagagcca    780
ggtgacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatatacat    960
ccgatcacaa ttggaaaatg tccaaagtat gtgaaaagca caaaattgag actggccaca   1020
ggattgagga atgtcccatc tattcaatct agaggcctat tcggggccat tgccggcttc   1080
attgaagggg ggtggacagg gatggtagat ggatggtacg gttatcacca tcaaaatgag   1140
caggggtcag ggtatgcagc cgacctgaag agcacacaaa atgccattga cgagattact   1200
aacaaagtaa attctgttat tgaaaagatg aatacacagt tcacagcagt gggtaaagag   1260
ttcaaccact ggaaaaaag aatagagaat ttaaataaaa aagttgatga tggtttcctg   1320
gacatttgga cttacaatgc cgaactgctg gttctattgg aaaatgaaag aactttggac   1380
taccacgatt caaatgtgaa gaacttgtat gaaaaggtaa gaaaccagtt aaaaaacaat   1440
gccaaggaaa ttggaaatgg ttgctttgaa ttttaccaca aatgcgataa cacgtgcatg   1500
gaaagtgtca aaaatgggac ttatgactac ccaaaatact caggggaagc aaaattaaac   1560
agagaaaaaa tagaagggt aaagctgaa tcaacaagaa tttaccaaat tttggcgatc   1620
tattcaactg tcgccagttc attggtactg gtagtctccc tgggggcaat cagcttctgg   1680
atgtgctcta tgggtctct acagtgtaga atatgtattt aa                       1722
```

<210> SEQ ID NO 89
<211> LENGTH: 573
<212> TYPE: PRT
<213> ORGANISM: Artificial Sequence
<220> FEATURE:
<223> OTHER INFORMATION: PDI-H1 Darw-K374E AA

<400> SEQUENCE: 89

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

-continued

```
Ile Ala Gly Trp Ile Leu Gly Asn Pro Glu Cys Glu Ser Leu Ser Thr
                85                  90                  95
Ala Ser Ser Trp Ser Tyr Ile Val Glu Thr Ser Ser Ser Asp Asn Gly
            100                 105                 110
Thr Cys Tyr Pro Gly Asp Phe Ile Asn Tyr Glu Glu Leu Arg Glu Gln
        115                 120                 125
Leu Ser Ser Val Ser Ser Phe Glu Arg Phe Glu Ile Phe Pro Lys Thr
    130                 135                 140
Ser Ser Trp Pro Asn His Asp Ser Asn Lys Gly Val Thr Ala Ala Cys
145                 150                 155                 160
Pro His Ala Gly Ala Lys Ser Phe Tyr Lys Asn Leu Ile Trp Leu Thr
                165                 170                 175
Lys Lys Gly Asn Ser Tyr Pro Lys Leu Ser Gln Ser Tyr Ile Asn Asp
            180                 185                 190
Lys Gly Lys Glu Ile Leu Val Leu Trp Gly Ile His His Pro Ser Thr
        195                 200                 205
Thr Ala Asp Gln Gln Ser Leu Tyr Gln Asn Ala Asp Ala Tyr Val Phe
    210                 215                 220
Val Gly Thr Ser Arg Tyr Ser Lys Lys Phe Lys Pro Glu Ile Ala Ile
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
            260                 265                 270
Val Val Pro Arg Tyr Ala Phe Thr Met Glu Arg Asn Ala Gly Ser Gly
        275                 280                 285
Ile Ile Ile Ser Asp Thr Pro Val His Asp Cys Asn Thr Thr Cys Gln
    290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
    370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Leu Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
```

```
              500             505             510
Tyr Ser Gly Glu Ala Lys Leu Asn Arg Glu Lys Ile Glu Gly Val Lys
            515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 90
<211> LENGTH: 1722
<212> TYPE: DNA
<213> ORGANISM: Artificial Sequence
<220> FEATURE:
<223> OTHER INFORMATION: PDI-H1 Darw-F390D DNA

<400> SEQUENCE: 90
```

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct agaagacaag | 180 |
| cacaacggga actatgcaa actaagaggg gtagccccat tgcatttggg taaatgtaac | 240 |
| attgctggct ggatcctggg aaacccagag tgtaatcac tctccacagc aagttcatgg | 300 |
| tcctacattg tggaaacatc tagttcagac aatggaacgt gttacccagg agatttcatc | 360 |
| aattatgagg agctaagaga gcaattgagc tcagtgtcat catttgaaag atttgagata | 420 |
| ttccccaaga caagttcatg gcccaatcat gactcgaaca aggtgtaac ggcagcatgt | 480 |
| cctcacgctg gagcaaaaag cttctacaaa aatttaatat ggctaactaa aaaggaaat | 540 |
| tcatacccaa agctcagcca atcctacatt aatgataaag ggaagaaat cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaata | 720 |
| agacccaaag tgagggatca agaagggaga atgaactatt actggacact agtagagcca | 780 |
| ggtgacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata acaccagcc tcccatttca gaatatacat | 960 |
| ccgatcacaa ttggaaatg tccaaagtat gtgaaaagca caaaattgag actggccaca | 1020 |
| ggattgagga atgtcccatc tattcaatct agaggcctat tcggggccat tgccggcttc | 1080 |
| attgaagggg gtggacagg atggtagat ggatggtacg ttatcacca tcaaaatgag | 1140 |
| caggggtcag ggtatgcagc cgacctgaag agcacacaaa atgccattga caaaattact | 1200 |
| aacaaagtaa attctgttat tgaaaagatg aatacacagg acacagcagt gggtaaagag | 1260 |
| ttcaaccact tggaaaaag aatagagaat ttaaataaaa aagttgatga tggtttcctg | 1320 |
| gacatttgga cttacaatgc cgaactgctg gttctattgg aaaatgaaag aactttggac | 1380 |
| taccacgatt caaatgtgaa gaacttgtat gaaaaagtaa gaaccagtt aaaaaacaat | 1440 |
| gccaaggaaa ttggaaatgg ttgctttgaa ttttaccaca atgcgataa cacgtgcatg | 1500 |
| gaaagtgtca aaaatgggac ttatgactac ccaaaatact caggggaagc aaaattaaac | 1560 |
| agagaaaaaa tagaagggt aaagctgaa tcaacaagaa tttaccaaat tttggcgatc | 1620 |
| tattcaactg tcgccagttc attggtactg gtagtctccc tggggcaat cagcttctgg | 1680 |

```
atgtgctcta atgggtctct acagtgtaga atatgtattt aa                    1722
```

<210> SEQ ID NO 91
<211> LENGTH: 573
<212> TYPE: PRT
<213> ORGANISM: Artificial Sequence
<220> FEATURE:
<223> OTHER INFORMATION: PDI-H1 Darw-F390D AA

<400> SEQUENCE: 91

| | | | | | | | | | | | | | | |
|---|---|---|---|---|---|---|---|---|---|---|---|---|---|---|
| Met | Ala | Lys | Asn | Val | Ala | Ile | Phe | Gly | Leu | Leu | Phe | Ser | Leu | Val |
| 1 | | | | 5 | | | | | 10 | | | | | 15 |
| Leu | Val | Pro | Ser | Gln | Ile | Phe | Ala | Asp | Thr | Leu | Cys | Ile | Gly | Tyr | His |
| | | | 20 | | | | | 25 | | | | | 30 | | |
| Ala | Asn | Asn | Ser | Thr | Asp | Thr | Val | Asp | Thr | Val | Leu | Glu | Lys | Asn | Val |
| | | 35 | | | | | 40 | | | | | 45 | | | |
| Thr | Val | Thr | His | Ser | Val | Asn | Leu | Leu | Glu | Asp | Lys | His | Asn | Gly | Lys |
| | 50 | | | | | 55 | | | | | 60 | | | | |
| Leu | Cys | Lys | Leu | Arg | Gly | Val | Ala | Pro | Leu | His | Leu | Gly | Lys | Cys | Asn |
| 65 | | | | | 70 | | | | | 75 | | | | | 80 |
| Ile | Ala | Gly | Trp | Ile | Leu | Gly | Asn | Pro | Glu | Cys | Glu | Ser | Leu | Ser | Thr |
| | | | | 85 | | | | | 90 | | | | | 95 | |
| Ala | Ser | Ser | Trp | Ser | Tyr | Ile | Val | Glu | Thr | Ser | Ser | Asp | Asn | Gly |
| | | | 100 | | | | | 105 | | | | | 110 | | |
| Thr | Cys | Tyr | Pro | Gly | Asp | Phe | Ile | Asn | Tyr | Glu | Glu | Leu | Arg | Glu | Gln |
| | | 115 | | | | | 120 | | | | | 125 | | | |
| Leu | Ser | Ser | Val | Ser | Ser | Phe | Glu | Arg | Phe | Glu | Ile | Phe | Pro | Lys | Thr |
| | 130 | | | | | 135 | | | | | 140 | | | | |
| Ser | Ser | Trp | Pro | Asn | His | Asp | Ser | Asn | Lys | Gly | Val | Thr | Ala | Ala | Cys |
| 145 | | | | | 150 | | | | | 155 | | | | | 160 |
| Pro | His | Ala | Gly | Ala | Lys | Ser | Phe | Tyr | Lys | Asn | Leu | Ile | Trp | Leu | Thr |
| | | | | 165 | | | | | 170 | | | | | 175 | |
| Lys | Lys | Gly | Asn | Ser | Tyr | Pro | Lys | Leu | Ser | Gln | Ser | Tyr | Ile | Asn | Asp |
| | | | 180 | | | | | 185 | | | | | 190 | | |
| Lys | Gly | Lys | Glu | Ile | Leu | Val | Leu | Trp | Gly | Ile | His | His | Pro | Ser | Thr |
| | | 195 | | | | | 200 | | | | | 205 | | | |
| Thr | Ala | Asp | Gln | Gln | Ser | Leu | Tyr | Gln | Asn | Ala | Asp | Ala | Tyr | Val | Phe |
| | 210 | | | | | 215 | | | | | 220 | | | | |
| Val | Gly | Thr | Ser | Arg | Tyr | Ser | Lys | Lys | Phe | Lys | Pro | Glu | Ile | Ala | Ile |
| 225 | | | | | 230 | | | | | 235 | | | | | 240 |
| Arg | Pro | Lys | Val | Arg | Asp | Gln | Glu | Gly | Arg | Met | Asn | Tyr | Tyr | Trp | Thr |
| | | | | 245 | | | | | 250 | | | | | 255 | |
| Leu | Val | Glu | Pro | Gly | Asp | Lys | Ile | Thr | Phe | Glu | Ala | Thr | Gly | Asn | Leu |
| | | | 260 | | | | | 265 | | | | | 270 | | |
| Val | Val | Pro | Arg | Tyr | Ala | Phe | Thr | Met | Glu | Arg | Asn | Ala | Gly | Ser | Gly |
| | | 275 | | | | | 280 | | | | | 285 | | | |
| Ile | Ile | Ile | Ser | Asp | Thr | Pro | Val | His | Asp | Cys | Asn | Thr | Thr | Cys | Gln |
| | 290 | | | | | 295 | | | | | 300 | | | | |
| Thr | Pro | Glu | Gly | Ala | Ile | Asn | Thr | Ser | Leu | Pro | Phe | Gln | Asn | Ile | His |
| 305 | | | | | 310 | | | | | 315 | | | | | 320 |
| Pro | Ile | Thr | Ile | Gly | Lys | Cys | Pro | Lys | Tyr | Val | Lys | Ser | Thr | Lys | Leu |
| | | | | 325 | | | | | 330 | | | | | 335 | |
| Arg | Leu | Ala | Thr | Gly | Leu | Arg | Asn | Val | Pro | Ser | Ile | Gln | Ser | Arg | Gly |
| | | | 340 | | | | | 345 | | | | | 350 | | |

```
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
    370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Leu Glu Asn Glu Arg Thr Leu Asp Tyr His Asp Ser
    450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Gly Glu Ala Lys Leu Asn Arg Glu Lys Ile Glu Gly Val Lys
        515                 520                 525
Leu Glu Ser Thr Arg Ile Tyr Gln Ile Leu Ala Ile Tyr Ser Thr Val
    530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 92
<211> LENGTH: 1722
<212> TYPE: DNA
<213> ORGANISM: Artificial Sequence
<220> FEATURE:
<223> OTHER INFORMATION: PDI-H1 Darw-L429M DNA

<400> SEQUENCE: 92
atggcgaaaa acgttgcgat tttcggctta ttgtttttctc ttcttgtgtt ggttccttct    60
cagatcttcg cggacacatt atgtataggt tatcatgcga acaattcaac agacactgta   120
gacacagtac tagaaaagaa tgtaacagta acacactctg ttaaccttct agaagacaag   180
cacaacggga actatgcaa actaagaggg gtagccccat gcatttggg taaatgtaac    240
attgctggct ggatcctggg aaacccagag tgtgaatcac tctccacagc aagttcatgg   300
tcctacattg tggaaacatc tagttcagac aatggaacgt gttacccagg agatttcatc   360
aattatgagg agctaagaga gcaattgagc tcagtgtcat catttgaaag atttgagata   420
ttccccaaga caagttcatg gcccaatcat gactcgaaca aaggtgtaac ggcagcatgt   480
cctcacgctg agcaaaaag cttctacaaa aatttaatat ggctaactaa aaaggaaat    540
tcatacccaa agctcagcca atcctacatt aatgataaag ggaaagaaat cctcgtgctg   600
tggggcattc accatccatc tactactgct gaccaacaaa gtctctatca gaatgcagat   660
gcatatgttt ttgtggggac atcaagatac agcaagaagt tcaagccgga aatagcaata   720
agacccaaag tgagggatca agaagggaga atgaactatt actggacact agtagagcca   780
ggtgacaaaa taacattcga agcaactgga aatctagtgg taccgagata tgcattcaca   840
```

```
atggaaagaa atgctggatc tggtattatc atttcagata caccagtcca cgattgcaat    900
acaacttgtc agacacccga gggtgctata acaccagcc tcccatttca gaatatacat    960
ccgatcacaa ttggaaaatg tccaaagtat gtgaaaagca caaaattgag actggccaca   1020
ggattgagga atgtcccatc tattcaatct agaggcctat tcggggccat tgccggcttc   1080
attgaagggg ggtggacagg gatggtagat ggatggtacg gttatcacca tcaaaatgag   1140
cagggggtcag ggtatgcagc cgacctgaag agcacacaaa atgccattga caaaattact   1200
aacaaagtaa attctgttat tgaaagatg aatacacagt tcacagcagt gggtaaagag   1260
ttcaaccact tggaaaaaag aatagagaat ttaaataaaa aagttgatga tggtttcctg   1320
gacatttgga cttacaatgc cgaactgctg gttctaatgg aaaatgaaag aactttggac   1380
taccacgatt caaatgtgaa gaacttgtat gaaaaggtaa gaaccagtt aaaaaacaat   1440
gccaaggaaa ttggaaatgg ttgctttgaa ttttaccaca aatgcgataa cacgtgcatg   1500
gaaagtgtca aaatgggac ttatgactac ccaaaatact caggggaagc aaaattaaac   1560
agagaaaaaa tagaaggggt aaagctggaa tcaacaagaa tttaccaaat tttggcgatc   1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 93
<211> LENGTH: 573
<212> TYPE: PRT
<213> ORGANISM: Artificial Sequence
<220> FEATURE:
<223> OTHER INFORMATION: PDI-H1 Darw-L429M AA

<400> SEQUENCE: 93

```
Met Ala Lys Asn Val Ala Ile Phe Gly Leu Leu Phe Ser Leu Leu Val
1               5                  10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Thr
                165                 170                 175

Lys Lys Gly Asn Ser Tyr Pro Lys Leu Ser Gln Ser Tyr Ile Asn Asp
            180                 185                 190

Lys Gly Lys Glu Ile Leu Val Leu Trp Gly Ile His His Pro Ser Thr
        195                 200                 205
```

Thr Ala Asp Gln Gln Ser Leu Tyr Gln Asn Ala Asp Ala Tyr Val Phe
    210                 215                 220
Val Gly Thr Ser Arg Tyr Ser Lys Lys Phe Lys Pro Glu Ile Ala Ile
225                 230                 235                 240
Arg Pro Lys Val Arg Asp Gln Glu Gly Arg Met Asn Tyr Tyr Trp Thr
                245                 250                 255
Leu Val Glu Pro Gly Asp Lys Ile Thr Phe Glu Ala Thr Gly Asn Leu
            260                 265                 270
Val Val Pro Arg Tyr Ala Phe Thr Met Glu Arg Asn Ala Gly Ser Gly
        275                 280                 285
Ile Ile Ile Ser Asp Thr Pro Val His Asp Cys Asn Thr Thr Cys Gln
290                 295                 300
Thr Pro Glu Gly Ala Ile Asn Thr Ser Leu Pro Phe Gln Asn Ile His
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
        355                 360                 365
Val Asp Gly Trp Tyr Gly Tyr His His Gln Asn Glu Gln Gly Ser Gly
370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
        435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Gly Glu Ala Lys Leu Asn Arg Glu Lys Ile Glu Gly Val Lys
        515                 520                 525
Leu Glu Ser Thr Arg Ile Tyr Gln Ile Leu Ala Ile Tyr Ser Thr Val
530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 94
<211> LENGTH: 1722
<212> TYPE: DNA
<213> ORGANISM: Artificial Sequence
<220> FEATURE:
<223> OTHER INFORMATION: PDI-H1 Darw-F390D+L429M DNA

<400> SEQUENCE: 94

-continued

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct agaagacaag     180
cacaacggga actatgcaa actaagaggg gtagccccat tgcatttggg taaatgtaac      240
attgctggct ggatcctggg aaacccagag tgtgaatcac tctccacagc aagttcatgg     300
tcctacattg tggaaacatc tagttcagac aatggaacgt gttacccagg agatttcatc     360
aattatgagg agctaagaga gcaattgagc tcagtgtcat catttgaaag atttgagata     420
ttccccaaga caagttcatg gcccaatcat gactcgaaca aggtgtaac ggcagcatgt      480
cctcacgctg agcaaaaag cttctacaaa aatttaatat ggctaactaa aaaaggaaat     540
tcatacccaa agctcagcca atcctacatt aatgataaag ggaaagaaat cctcgtgctg     600
tggggcattc accatccatc tactactgct gaccaacaaa gtctctatca gaatgcagat     660
gcatatgttt tgtggggac atcaagatac agcaagaagt tcaagccgga atagcaata      720
agacccaaag tgagggatca agaagggaga tgaactatt actggacact agtagagcca     780
ggtgacaaaa taacattcga agcaactgga atctagtgg taccgagata tgcattcaca     840
atggaaagaa atgctggatc tggtattatc atttcagata caccagtcca cgattgcaat     900
acaacttgtc agacacccga gggtgctata acaccagcc tcccatttca gaatatacat     960
ccgatcacaa ttggaaaatg tccaaagtat gtgaaaagca caaaattgag actggccaca    1020
ggattgagga atgtcccatc tattcaatct agaggcctat tcggggccat tgccggcttc    1080
attgaagggg ggtggacagg gatggtagat ggatggtacg ttatcacca tcaaaatgag     1140
cagggggtcag gtatgcagc cgacctgaag agcacacaaa atgccattga caaaattact    1200
aacaaagtaa attctgttat tgaaaagatg aatacacagg acacagcagt gggtaaagag    1260
ttcaaccact tggaaaaaag aatagagaat ttaaataaaa aagttgatga tggtttcctg    1320
gacatttgga cttacaatgc cgaactgctg gttctaatgg aaaatgaaag aactttggac    1380
taccacgatt caaatgtgaa gaacttgtat gaaaaggtaa gaaaccagtt aaaaaacaat    1440
gccaaggaaa ttggaaatgg ttgctttgaa ttttaccaca atgcgataa cacgtgcatg     1500
gaaagtgtca aaaatgggac ttatgactac ccaaaatact caggggaagc aaaattaaac    1560
agagaaaaaa tagaagggt aaagctggaa tcaacaagaa tttaccaaat tttggcgatc    1620
tattcaactg tcgccagttc attggtactg gtagtctccc tggggggcaat cagcttctgg    1680
atgtgctcta tgggtctct acagtgtaga atatgtattt aa                         1722
```

<210> SEQ ID NO 95
<211> LENGTH: 573
<212> TYPE: PRT
<213> ORGANISM: Artificial Sequence
<220> FEATURE:
<223> OTHER INFORMATION: PDI-H1 Darw-F390D+L429M AA

<400> SEQUENCE: 95

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
```

```
                50                  55                  60
Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
                     85                  90                  95

Ala Ser Ser Trp Ser Tyr Ile Val Glu Thr Ser Ser Ser Asp Asn Gly
                100                 105                 110

Thr Cys Tyr Pro Gly Asp Phe Ile Asn Tyr Glu Glu Leu Arg Glu Gln
                115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Thr
                165                 170                 175

Lys Lys Gly Asn Ser Tyr Pro Lys Leu Ser Gln Ser Tyr Ile Asn Asp
                180                 185                 190

Lys Gly Lys Glu Ile Leu Val Leu Trp Gly Ile His His Pro Ser Thr
                195                 200                 205

Thr Ala Asp Gln Gln Ser Leu Tyr Gln Asn Ala Asp Ala Tyr Val Phe
                210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
                275                 280                 285

Ile Ile Ile Ser Asp Thr Pro Val His Asp Cys Asn Thr Thr Cys Gln
                290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
                370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
                435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480
```

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Gly Glu Ala Lys Leu Asn Arg Glu Lys Ile Glu Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
            565                 570

<210> SEQ ID NO 96
<211> LENGTH: 1722
<212> TYPE: DNA
<213> ORGANISM: Artificial Sequence
<220> FEATURE:
<223> OTHER INFORMATION: PDI-H1 Darw-N97D+F390D+L429M DNA

<400> SEQUENCE: 96

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct agaagacaag | 180 |
| cacaacggga actatgcaa actaagaggg gtagccccat tgcatttggg taaatgtaac | 240 |
| attgctggct ggatcctggg aaacccagag tgtgaatcac tctccacagc aagttcatgg | 300 |
| tcctacattg tggaaacatc tagttcagac aatggaacgt gttacccagg agatttcatc | 360 |
| gattatgagg agctaagaga gcaattgagc tcagtgtcat catttgaaag atttgagata | 420 |
| ttccccaaga caagttcatg gcccaatcat gactcgaaca aggtgtaac ggcagcatgt | 480 |
| cctcacgctg agcaaaaag cttctacaaa aatttaatat ggctaactaa aaaaggaaat | 540 |
| tcatacccaa agctcagcca atcctacatt aatgataaag ggaagaaat cctcgtgctg | 600 |
| tggggcattc accatccatc tactactgct gaccaacaaa gtctctatca gaatgcagat | 660 |
| gcatatgttt tgtggggac atcaagatac agcaagaagt tcaagccgga aatagcaata | 720 |
| agacccaaag tgagggatca agaagggaga atgaactatt actggacact agtagagcca | 780 |
| ggtgacaaaa taacattcga agcaactgga atctagtgg taccgagata tgcattcaca | 840 |
| atggaaagaa atgctggatc tggtattatc atttcagata caccagtcca cgattgcaat | 900 |
| acaacttgtc agacacccga gggtgctata aacaccagcc tcccatttca gaatatacat | 960 |
| ccgatcacaa ttgaaaaatg tccaaagtat gtgaaaagca caaaattgag actggccaca | 1020 |
| ggattgagga atgtcccatc tattcaatct agaggcctat tcggggccat tgccggcttc | 1080 |
| attgaagggg gtggacagg gatggtagat ggatggtacg ttatcacca tcaaaatgag | 1140 |
| caggggtcag ggtatgcagc cgacctgaag agcacacaaa atgccattga caaaattact | 1200 |
| aacaaagtaa attctgttat tgaaaagatg aatacacagg acacagcagt gggtaaagag | 1260 |
| ttcaaccact ggaaaaaag aatagagaat ttaaataaaa agttgatga tggtttcctg | 1320 |
| gacatttgga cttacaatgc cgaactgctg gttctaatgg aaaatgaaag aactttggac | 1380 |
| taccacgatt caaatgtgaa gaacttgtat gaaaaggtaa gaaccagtt aaaaaacaat | 1440 |
| gccaaggaaa ttggaaatgg ttgctttgaa ttttaccaca aatgcgataa cacgtgcatg | 1500 |

-continued

```
gaaagtgtca aaaatgggac ttatgactac ccaaaatact caggggaagc aaaattaaac    1560
agagaaaaaa tagaaggggt aaagctggaa tcaacaagaa tttaccaaat tttggcgatc    1620
tattcaactg tcgccagttc attggtactg gtagtctccc tgggggcaat cagcttctgg    1680
atgtgctcta tgggtctct acagtgtaga atatgtattt aa                       1722
```

<210> SEQ ID NO 97
<211> LENGTH: 573
<212> TYPE: PRT
<213> ORGANISM: Artificial Sequence
<220> FEATURE:
<223> OTHER INFORMATION: PDI-H1 Darw-N97D+F390D+L429M AA

<400> SEQUENCE: 97

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Thr
                165                 170                 175

Lys Lys Gly Asn Ser Tyr Pro Lys Leu Ser Gln Ser Tyr Ile Asn Asp
            180                 185                 190

Lys Gly Lys Glu Ile Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
```

```
                    325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
            370                 375                 380
Tyr Ala Ala Asp Leu Lys Ser Thr Gln Asn Ala Ile Asp Lys Ile Thr
385                 390                 395                 400
Asn Lys Val Asn Ser Val Ile Glu Lys Met Asn Thr Gln Asp Thr Ala
                405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
            435                 440                 445
Leu Leu Val Leu Met Glu Asn Glu Arg Thr Leu Asp Tyr His Asp Ser
            450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
            500                 505                 510
Tyr Ser Gly Glu Ala Lys Leu Asn Arg Glu Lys Ile Glu Gly Val Lys
            515                 520                 525
Leu Glu Ser Thr Arg Ile Tyr Gln Ile Leu Ala Ile Tyr Ser Thr Val
            530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570

<210> SEQ ID NO 98
<211> LENGTH: 4540
<212> TYPE: DNA
<213> ORGANISM: Artificial Sequence
<220> FEATURE:
<223> OTHER INFORMATION: Cloning vector 1190 from left to right T-DNA

<400> SEQUENCE: 98
tggcaggata tattgtggtg taaacaaatt gacgcttaga caacttaata acacattgcg      60
gacgttttta atgtactgaa ttaacgccga atcccgggct ggtatattta tatgttgtca     120 ataactcaa aaaccataaa agtttaagtt agcaagtgtg tacatttta cttgaacaaa      180 aatattcacc tactactgtt ataaatcatt attaaacatt agagtaaaga aatatggatg     240
ataagaacaa gagtagtgat atttgacaa caatttgtt gcaacatttg agaaaatttt      300
gttgttctct cttttcattg gtcaaaaaca atagagagag aaaaggaag agggagaata      360 aaaacataat gtgagtatga gagagaaagt tgtacaaaag ttgtaccaaa atagttgtac     420
aaatatcatt gaggaatttg acaaaagcta cacaataag ggttaattgc tgtaaataaa      480
taaggatgac gcattagaga gatgtaccat tagagaattt ttggcaagtc attaaaaga      540 aagaataaat tatttttaaa attaaaagtt gagtcatttg attaaacatg tgattattta     600
atgaattgat gaaagagttg gattaaagtt gtattagtaa ttagaatttg gtgtcaaatt     660
```

```
taatttgaca tttgatcttt tcctatatat tgccccatag agtcagttaa ctcatttttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacactt    1020
gattcccttc aaacacatac aaagagaaga gactaattaa ttaattaatc atcttgagag    1080
aaaatggaac gagctataca aggaaacgac gctagggaac aagctaacag tgaacgttgg    1140
gatggaggat caggaggtac cacttctccc ttcaaacttc ctgacgaaag tccgagttgg    1200
actgagtggc ggctacataa cgatgagacg aattcgaatc aagataatcc ccttggtttc    1260
aaggaaagct ggggtttcgg gaaagttgta tttaagagat atctcagata cgacaggacg    1320
gaagcttcac tgcacagagt ccttggatct tggacgggag attcggttaa ctatgcagca    1380
tctcgatttt tcggtttcga ccagatcgga tgtacctata gtattcggtt tcgaggagtt    1440
agtatcaccg tttctggagg gtcgcgaact cttcagcatc tctgtgagat ggcaattcgg    1500
tctaagcaag aactgctaca gcttgcccca atcgaagtgg aaagtaatgt atcaagagga    1560
tgccctgaag gtactcaaac cttcgaaaaa gaaagcgagt aagttaaaat gcttcttcgt    1620
ctcctattta taatatggtt tgttattgtt aattttgttc ttgtagaaga gcttaattaa    1680
tcgttgttgt tatgaaatac tatttgtatg agatgaactg gtgtaatgta attcatttac    1740
ataagtggag tcagaatcag aatgtttcct ccataactaa ctagacatga agacctgccg    1800
cgtacaattg tcttatattt gaacaactaa aattgaacat cttttgccac aactttataa    1860
gtggttaata tagctcaaat atatggtcaa gttcaataga ttaataatgg aaatatcagt    1920
tatcgaaatt cattaacaat caacttaacg ttattaacta ctaattttat atcatcccct    1980
ttgataaatg atagtacacc aattaggaag gagcatgctc gcctaggaga ttgtcgtttc    2040
ccgccttcag tttgcaagct gctctagccg tgtagccaat acgcaaaccg cctctccccg    2100
cgcgttggga attactagcg cgtgtcgaca agcttgcatg ccggtcaaca tggtggagca    2160
cgacacactt gtctactcca aaaatatcaa agatacagtc tcagaagacc aaagggcaat    2220
tgagactttt caacaaaggg taatatccgg aaacctcctc ggattccatt gcccagctat    2280
ctgtcacttt attgtgaaga tagtggaaaa ggaaggtggc tcctacaaat gccatcattg    2340
cgataaagga aaggccatcg ttgaagatgc ctctgccgac agtggtccca agatggacc    2400
cccacccacg aggagcatcg tggaaaaaga agacgttcca accacgtctt caaagcaagt    2460
ggattgatgt gataacatgg tggagcacga cacacttgtc tactccaaaa atatcaaaga    2520
tacagtctca gaagaccaaa gggcaattga acttttcaa caaagggtaa tatccggaaa    2580
cctcctcgga ttccattgcc cagctatctg tcactttatt gtgaagatag tggaaaagga    2640
aggtggctcc tacaaatgcc atcattgcga taaaggaaag gccatcgttg aagatgcctc    2700
tgccgacagt ggtcccaaag atggaccccc acccacgagg agcatcgtgg aaaagaaga    2760
cgttccaacc acgtcttcaa agcaagtgga ttgatgtgat atctccactg acgtaaggga    2820
tgacgcacaa tcccactatc cttcgcaaga cccttcctct ataaggaa gttcatttca    2880
tttggagagg tattaaaatc ttaataggtt ttgataaaag cgaacgtggg gaaacccgaa    2940
ccaaaccttc ttctaaactc tctctcatct ctccttaaag caaacttctct cttgtctttc    3000
ttgcgtgagc gatcttcaac gttgtcagat cgtgcttcgg caccgcggat ggcgaaaaac    3060
```

```
gttgcgattt tcggcttatt gttttctctt cttgtgttgg ttccttctca gatcttcgcc    3120
tgcaggctcc tcagccaaaa cgacaccccc atctgtctat ccactggccc ctggatctgc    3180
tgcccaaact aactccatgg tgaccctggg atgcctggtc aagggctatt tccctgagcc    3240
agtgacagtg acctggaact ctggatccct gtccagcggt gtgcacacct cccagctgt    3300 cctgcagtct gacctctaca ctctgagcag ctcagtgact gtcccctcca gcacctggcc    3360
cagcgagacc gtcacctgca acgttgccca cccggccagc agcaccaagg tggacaagaa    3420
aattgtgccc agggattgtg gttgtaagcc ttgcatatgt acagtcccag aagtatcatc    3480
tgtcttcatc ttccccccaa agcccaagga tgtgctcacc attactctga ctcctaaggt    3540
cacgtgtgtt gtggtagaca tcagcaagga tgatcccgag gtccagttca gctggtttgt    3600
agatgatgtg gaggtgcaca cagctcagac gcaaccccgg gaggagcagt tcaacagcac    3660
tttccgctca gtcagtgaac ttcccatcat gcaccaggac tggctcaatg caaggagcg    3720 atcgctcacc atcaccatca ccatcaccat caccattaaa ggcctatttt ctttagtttg    3780
aatttactgt tattcggtgt gcatttctat gtttggtgag cggttttctg tgctcagagt    3840
gtgtttattt tatgtaattt aatttctttg tgagctcctg tttagcaggt cgtcccttca    3900
gcaaggacac aaaaagattt taattttatt aaaaaaaaaa aaaaaaaaga ccgggaattc    3960
gatatcaagc ttatcgacct gcagatcgtt caaacatttg gcaataaagt tcttaagat    4020 tgaatcctgt tgccggtctt gcgatgatta tcatataatt tctgttgaat tacgttaagc    4080
atgtaataat taacatgtaa tgcatgacgt tatttatgag atgggttttt atgattagag    4140
tcccgcaatt atacatttaa tacgcgatag aaaacaaaat atagcgcgca aactaggata    4200
aattatcgcg cgcggtgtca tctatgttac tagatctcta gagtctcaag cttggcgcgc    4260
ccacgtgact agtggcactg gccgtcgttt tacaacgtcg tgactgggaa aaccctggcg    4320
ttacccaact taatcgcctt gcagcacatc cccctttcgc cagctggcgt aatagcgaag    4380
aggcccgcac cgatcgccct tcccaacagt tgcgcagcct gaatggcgaa tgctagagca    4440
gcttgagctt ggatcagatt gtcgtttccc gccttcagtt taaactatca gtgtttgaca    4500
ggatatattg gcgggtaaac ctaagagaaa agagcgttta                          4540
```

<210> SEQ ID NO 99
<211> LENGTH: 3105
<212> TYPE: DNA
<213> ORGANISM: Artificial Sequence
<220> FEATURE:
<223> OTHER INFORMATION: Construct 1314 from 2X35S prom to NOS term

<400> SEQUENCE: 99

```
gtcaacatgg tggagcacga cacacttgtc tactccaaaa atatcaaaga tacagtctca     60
gaagaccaaa gggcaattga acttttcaa caaagggtaa tatccggaaa cctcctcgga    120
ttccattgcc cagctatctg tcactttatt gtgaagatag tggaaaagga aggtggctcc    180
tacaaatgcc atcattgcga taaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
```

```
atcgttgaag atgcctctgc cgacagtggt cccaaagatg acccccacc cacgaggagc   600
atcgtggaaa aagaagacgt tccaaccacg tcttcaaagc aagtggattg atgtgatatc   660
tccactgacg taagggatga cgcacaatcc cactatcctt cgcaagaccc ttcctctata   720
taaggaagtt catttcattt ggagaggtat aaaatctta ataggttttg ataaaagcga   780
acgtggggaa acccgaacca aaccttcttc taaactctct ctcatctctc ttaaagcaaa   840
cttctctctt gtctttcttg cgtgagcgat cttcaacgtt gtcagatcgt gcttcggcac   900
cagtacaatg gcgaaaaacg ttgcgatttt cggcttattg ttttctcttc ttgtgttggt   960
tccttctcag atcttcgctg acacattatg tataggttat catgcgaaca attcaacaga  1020
cactgtagac acagtactag aaaagaatgt aacagtaaca cactctgtta accttctaga  1080
agacaagcat aacgggaaac tatgcaaact aagaggggta gccccattgc atttgggtaa  1140
atgtaacatt gctggctgga tcctgggaaa tccagagtgt gaatcactct ccacagcaag  1200
ctcatggtcc tacattgtgg aaacacctag ttcagacaat ggaacgtgtt acccaggaga  1260
tttcatcgat tatgaggagc taagagagca attgagctca gtgtcatcat ttgaaaggtt  1320
tgagatattc cccaagacaa gttcatggcc caatcatgac tcgaacaaag gtgtaacggc  1380
agcatgtcct catgctggag caaaaagctt ctacaaaaat ttaatatggc tagttaaaaa  1440
aggaaattca tacccaaagc tcagcaaatc ctacattaat gataaaggga aagaagtcct  1500
cgtgctatgg ggcattcacc atccatctac tagtgctgac caacaaagtc tctatcagaa  1560
tgcagatgca tatgttttg tggggtcatc aagatacagc aagaagttca gccggaaat  1620
agcaataaga cccaaagtga gggatcaaga agggagaatg aactattact ggacactagt  1680
agagccggga gacaaaataa cattcgaagc aactggaaat ctagtggtac cgagatatgc  1740
attcgcaatg gaaagaaatg ctggatctgg tattatcatt tcagatacac cagtccacga  1800
ttgcaataca acttgtcaaa cacccaaggg tgctataaac accagcctcc catttcagaa  1860
tatacatccg atcacaattg gaaaatgtcc aaaatatgta aaaagcacaa aattgagact  1920
ggccacagga ttgaggaata tcccgtctat tcaatctaga ggactatttg ggccattgc  1980
cggtttcatt gaaggggggt ggacaggat ggtagatgaa tggtacggtt atcaccatca  2040
aaatgagcag gggtcaggat atgcagccga cctgaagagc acacagaatg ccattgacga  2100
gattactaac aaagtaaatt ctgttattga aaagatgaat acacagttca cagcagtagg  2160
taaagagttc aaccacctgg aaaaaagaat agagaattta aataaaaaag ttgatgatgg  2220
tttcctggac atttggactt acaatgccga actgttggtt ctattggaaa atgaaagaac  2280
tttggactac cacgattcaa atgtgaagaa cttatatgaa aaggtaagaa gccagctaaa  2340
aaacaatgcc aaggaaattg gaacggctg ctttgaattt taccacaaat gcgataacac  2400
gtgcatggaa agtgtcaaaa atgggactta tgactaccca aaatactcag aggaagcaaa  2460
attaaacaga gaagaaatag atggggtaaa gctggaatca acaaggattt accagatttt  2520
ggcgatctat tcaactgtcg ccagttcatt ggtactggta gtctccctgg gggcaatcag  2580
tttctggatg tgctctaatg ggtctctaca gtgtagaata tgtatttaaa ggcctatttt  2640
ctttagtttg aatttactgt tattcggtgt gcatttctat gtttggtgag cggttttctg  2700
tgctcagagt gtgtttattt tatgtaattt aatttctttg tgagctcctg tttagcaggt  2760
cgtcccttca gcaaggacac aaaaagattt taatttttatt aaaaaaaaaa aaaaaaaga  2820
ccgggaattc gatatcaagc ttatcgacct gcagatcgtt caaacatttg gcaataaagt  2880
ttcttaagat tgaatcctgt tgccggtctt gcgatgatta tcatataatt tctgttgaat  2940
```

```
tacgttaagc atgtaataat taacatgtaa tgcatgacgt tatttatgag atgggttttt   3000
atgattagag tcccgcaatt atacatttaa tacgcgatag aaaacaaaat atagcgcgca   3060
aactaggata aattatcgcg cgcggtgtca tctatgttac tagat                  3105
```

<210> SEQ ID NO 100
<211> LENGTH: 3105
<212> TYPE: DNA
<213> ORGANISM: Artificial Sequence
<220> FEATURE:
<223> OTHER INFORMATION: Construct 2980 from 2X35S prom to NOS term

<400> SEQUENCE: 100

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaggaaag gccatcgttg aagatgcctc tgccgacagt     240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gaccccacc cacgaggagc     600 atcgtggaaa agaagacgt tccaaccacg tcttcaaagc aagtggattg atgtgatatc     660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgg acacattatg tataggttat catgcgaaca attcaacaga   1020
cactgtagac acagtactag aaaagaatgt aacagtaaca cactctgtta accttctaga   1080
agacaagcat aacgggaaac tatgcaaact aagagggta gccccattgc atttgggtaa    1140
atgtaacatt gctggctgga tcctgggaaa tccagagtgt gaatcactct ccacagcaag   1200
ctcatggtcc tacattgtgg aaacacctag ttcagacaat ggaacgtgtt acccaggaga   1260
tttcatcgat tatgaggagc taagagagca attgagctca gtgtcatcat ttgaaaggtt   1320
tgagatattc cccaagacaa gttcatggcc caatcatgac tcgaacaaag gtgtaacggc   1380
agcatgtcct catgctggag caaaaagctt ctacaaaaat ttaatatggc tagttaaaaa   1440
aggaaattca tacccaaagc tcagcaaatc ctacattaat gataaaggga agaagtcct    1500 cgtgctatgg ggcattcacc atccatctac tagtgctgac caacaaagtc tctatcagaa   1560
tgcagatgca tatgttttg tggggtcatc aagatacagc aagaagttca gccggaaat    1620 agcaataaga cccaaagtga gggatcaaga agggagaatg aactattact ggacactagt   1680
agagccggga gacaaaataa cattcgaagc aactggaaat ctagtggtac cgagatatgc   1740
attcgcaatg gaaagaaatg ctggatctgg tattatcatt tcagatacac cagtccacga   1800
ttgcaataca acttgtcaaa cacccaaggg tgctataaac accagcctcc catttcagaa   1860
```

```
tatacatccg atcacaattg gaaaatgtcc aaaatatgta aaaagcacaa aattgagact    1920
ggccacagga ttgaggaata tcccgtctat tcaatctaga ggactatttg gggccattgc    1980
cggtttcatt gaaggggggt ggacagggat ggtagatgga tggtacggtt atcaccatca    2040
aaatgagcag gggtcaggat atgcagccga cctgaagagc acacagaatg ccattgacga    2100
gattactaac aaagtaaatt ctgttattga aaagatgaat acacaggaca cagcagtagg    2160
taaagagttc aaccacctgg aaaaaagaat agagaattta ataaaaaag ttgatgatgg     2220 tttcctggac atttggactt acaatgccga actgttggtt ctattggaaa atgaaagaac    2280
tttggactac cacgattcaa atgtgaagaa cttatatgaa aaggtaagaa gccagctaaa    2340
aaacaatgcc aaggaaattg gaaacggctg ctttgaattt taccacaaat gcgataacac    2400
gtgcatggaa agtgtcaaaa atgggactta tgactaccca aaatactcag aggaagcaaa    2460
attaaacaga gaagaaatag atggggtaaa gctggaatca acaaggattt accagatttt    2520
ggcgatctat tcaactgtcg ccagttcatt ggtactggta gtctccctgg gggcaatcag    2580
tttctggatg tgctctaatg ggtctctaca gtgtagaata tgtatttaaa ggcctatttt    2640
ctttagtttg aatttactgt tattcggtgt gcatttctat gtttggtgag cggttttctg    2700
tgctcagagt gtgtttattt tatgtaattt aatttctttg tgagctcctg tttagcaggt    2760
cgtcccttca gcaaggacac aaaaagattt taattttatt aaaaaaaaaa aaaaaaaga    2820 ccgggaattc gatatcaagc ttatcgacct gcagatcgtt caaacatttg gcaataaagt    2880
ttcttaagat tgaatcctgt tgccggtctt gcgatgatta tcatataatt tctgttgaat    2940
tacgttaagc atgtaataat taacatgtaa tgcatgacgt tatttatgag atgggttttt    3000
atgattagag tcccgcaatt atacatttaa tacgcgatag aaaacaaaat atagcgcgca    3060
aactaggata aattatcgcg cgcggtgtca tctatgttac tagat                    3105
```

<210> SEQ ID NO 101
<211> LENGTH: 3105
<212> TYPE: DNA
<213> ORGANISM: Artificial Sequence
<220> FEATURE:
<223> OTHER INFORMATION: Construct 2995 from 2X35S prom to NOS term

<400> SEQUENCE: 101

```
gtcaacatgg tggagcacga cacacttgtc tactccaaaa atatcaaaga tacagtctca      60
gaagaccaaa gggcaattga acttttcaa caaagggtaa tatccggaaa cctcctcgga     120
ttccattgcc cagctatctg tcactttatt gtgaagatag tggaaaagga aggtggctcc    180
tacaaatgcc atcattgcga taaggaaag gccatcgttg aagatgcctc tgccgacagt     240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaagatac agtctcagaa gaccaaaggg caattgagac ttttcaacaa     420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gaccccacc cacgaggagc     600 atcgtggaaa agaagacgt tccaaccacg tcttcaaagc aagtggattg atgtgatatc     660
tccactgacg taaggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
```

-continued

```
cttctctctt gtctttcttg cgtgagcgat cttcaacgtt gtcagatcgt gcttcggcac    900
cagtacaatg gcgaaaaacg ttgcgatttt cggcttattg ttttctcttc ttgtgttggt    960
tccttctcag atcttcgcgg acacattatg tataggttat catgcgaaca attcaacaga   1020
cactgtagac acagtactag aaaagaatgt aacagtaaca cactctgtta accttctaga   1080
agacaagcat aacgggaaac tatgcaaact aagagdggta gccccattgc atttgggtaa   1140
atgtaacatt gctggctgga tcctgggaaa tccagagtgt gaatcactct ccacagcaag   1200
ctcatggtcc tacattgtgg aaacacctag ttcagacaat ggaacgtgtt acccaggaga   1260
tttcatcgat tatgaggagc taagagagca attgagctca gtgtcatcat ttgaaaggtt   1320
tgagatattc cccaagacaa gttcatggcc caatcatgac tcgaacaaag gtgtaacggc   1380
agcatgtcct catgctggag caaaaagctt ctacaaaaat ttaatatggc tagttaaaaa   1440
aggaaattca tacccaaagc tcagcaaatc ctacattaat gataaaggga aagaagtcct   1500
cgtgctatgg ggcattcacc atccatctac tagtgctgac caacaaagtc tctatcagaa   1560
tgcagatgca tatgtttttg tggggtcatc aagatacagc aagaagttca gccggaaat    1620
agcaataaga cccaaagtga gggatcaaga agggagaatg aactattact ggacactagt   1680
agagccggga gacaaaataa cattcgaagc aactggaaat ctagtggtac cgagatatgc   1740
attcgcaatg gaaagaaatg ctggatctgg tattatcatt tcagatacac cagtccacga   1800
ttgcaataca acttgtcaaa cacccaaggg tgctataaac accagcctcc catttcagaa   1860
tatacatccg atcacaattg gaaaatgtcc aaaatatgta aaaagcacaa aattgagact   1920
ggccacagga ttgaggaata tcccgtctat tcaatctaga ggactatttg gggccattgc   1980
cggtttcatt gaaggggggt ggacaggdat ggtagatgga tggtacggtt atcaccatca   2040
aaatgagcag gggtcaggat atgcagccga cctgaagagc acacagaatg ccattgacga   2100
gattactaac aaagtaaatt ctgttattga aagatgaat acacaggaca cagcagtagg   2160
taaagagttc aaccacctgg aaaaaagaat agagaattta aataaaaaag ttgatgatgg   2220
tttcctggac atttggactt acaatgccga actgttggtt ctaatggaaa atgaaagaac   2280
tttggactac cacgattcaa atgtgaagaa cttatatgaa aaggtaagaa gccagctaaa   2340
aaacaatgcc aaggaaattg gaaacggctg ctttgaattt taccacaaat gcgataacac   2400
gtgcatggaa agtgtcaaaa atgggactta tgactaccca aaatactcag aggaagcaaa   2460
attaaacaga gaagaaatag atggggtaaa gctggaatca acaaggattt accagatttt   2520
ggcgatctat tcaactgtcg ccagttcatt ggtactggta gtctccctgg ggcaatcag    2580
tttctggatg tgctctaatg ggtctctaca gtgtagaata tgtatttaaa ggcctatttt   2640
ctttagtttg aatttactgt tattcggtgt gcatttctat gtttggtgag cggttttctg   2700
tgctcagagt gtgtttattt tatgtaattt aatttctttg tgagctcctg tttagcaggt   2760
cgtcccttca gcaaggacac aaaaagattt taatttttatt aaaaaaaaaa aaaaaaaga   2820
ccgggaattc gatatcaagc ttatcgacct gcagatcgt caaacatttg gcaataaagt    2880
ttcttaagat tgaatcctgt tgccggtctt gcgatgatta tcatataatt tctgttgaat   2940
tacgttaagc atgtaataat taacatgtaa tgcatgacgt tatttatgag atgggttttt   3000
atgattagag tcccgcaatt atacatttaa tacgcgatag aaaacaaaat atagcgcgca   3060
aactaggata aattatcgcg cgcggtgtca tctatgttac tagat                   3105
```

<210> SEQ ID NO 102

```
<211> LENGTH: 49
<212> TYPE: DNA
<213> ORGANISM: Artificial Sequence
<220> FEATURE:
<223> OTHER INFORMATION: Primer H1Mich(N380A).r

<400> SEQUENCE: 102
ttcaataaca gaagctactt tgttagtaat cttgtcaatg gcattttgt                49

<210> SEQ ID NO 103
<211> LENGTH: 48
<212> TYPE: DNA
<213> ORGANISM: Artificial Sequence
<220> FEATURE:
<223> OTHER INFORMATION: Primer H1Cal(N380A).c

<400> SEQUENCE: 103
gattactaac aaagtagctt ctgttattga aagatgaat acacagtt                 48

<210> SEQ ID NO 104
<211> LENGTH: 1722
<212> TYPE: DNA
<213> ORGANISM: Artificial Sequence
<220> FEATURE:
<223> OTHER INFORMATION: PDI-H1 Mich-N380A DNA

<400> SEQUENCE: 104
atggcgaaaa acgttgcgat tttcggctta ttgttttctc ttcttgtgtt ggttccttct   60
cagatcttcg cggacacatt atgtataggt tatcatgcga acaattcaac agacactgta  120
gacacagtac tagaaaagaa tgtaacagta acacactctg ttaaccttct ggaagacaag  180
cataacggaa aactatgcaa actaagaggg gtagccccat gcatttggg  taaatgtaac  240 attgctggct ggatcctggg aaatccagag tgtgaatcac tctccacagc aagttcatgg  300
tcctacattg tggaaacatc taattcagac aatggaacgt gttacccagg agatttcatc  360
aattatgagg agctaagaga gcaattgagc tcagtgtcat catttgaaag gtttgagata  420
ttccccaaga caagttcatg gcccaatcat gactcgaaca aggtgtaac  ggcagcatgt  480 cctcacgctg agcaaaaag  cttctacaaa aacttgatat ggctagttaa aaaggaaat   540 tcatacccaa agcttaacca atcctacatt aatgataaag ggaagaagt  cctcgtgctg  600 tggggcattc accatccatc tactactgct gaccaacaaa gtctctatca gaatgcagat  660
gcatatgttt ttgtggggac atcaagatac agcaagaagt tcaagccgga aatagcaaca  720
agacccaaag tgagggatca agaagggaga atgaactatt actggacact agtagagccg  780
ggagacaaaa taacattcga agcaactgga aatctagtgg taccgagata tgcattcaca  840
atggaaagaa atgctggatc tggtattatc atttcagata caccagtcca cgattgcaat  900
acaacttgtc agacacccga gggtgctata aacaccagcc tcccatttca gaatatacat  960
ccgatcacaa ttggaaaatg tccaaagtat gtaaaaagca caaaattgag actggccaca 1020
ggattgagga atgttccgtc tattcaatct agaggcctat tcggggccat tgccggcttc 1080
attgaagggg ggtggacagg gatggtagat ggatggtacg ttatcaccac tcaaaatgag 1140
caggggtcag gatatgcagc cgacctgaag agcacacaaa atgccattga caagattact 1200
aacaaagtag cttctgttat tgaaaagatg aatacacagt tcacagcagt gggtaaagag 1260
ttcaaccacc tggaaaaaag aatagagaat ctaaataaaa agttgatga  tggtttcctg 1320 gacatttgga cttacaatgc cgaactgttg gttctattgg aaaatgaaag aactttggac 1380
tatcacgatt caaatgtgaa gaacttgtat gaaaaagtaa gaaccagtt  aaaaaacaat 1440
```

```
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac     1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                       1722
```

<210> SEQ ID NO 105
<211> LENGTH: 573
<212> TYPE: PRT
<213> ORGANISM: Artificial Sequence
<220> FEATURE:
<223> OTHER INFORMATION: PDI-H1 Mich-N380A AA

<400> SEQUENCE: 105

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Ile His
```

```
305                 310                 315                 320
Pro Ile Thr Ile Gly Lys Cys Pro Lys Tyr Val Lys Ser Thr Lys Leu
                325                 330                 335
Arg Leu Ala Thr Gly Leu Arg Asn Val Pro Ser Ile Gln Ser Arg Gly
                340                 345                 350
Leu Phe Gly Ala Ile Ala Gly Phe Ile Glu Gly Gly Trp Thr Gly Met
                355                 360                 365
Val Asp Gly Trp Tyr Gly Tyr His His Gln Asn Glu Gln Gly Ser Gly
                370                 375                 380
Tyr Ala Ala Asp Leu Lys Ser Thr Gln Asn Ala Ile Asp Lys Ile Thr
385                 390                 395                 400
Asn Lys Val Ala Ser Val Ile Glu Lys Met Asn Thr Gln Phe Thr Ala
                405                 410                 415
Val Gly Lys Glu Phe Asn His Leu Glu Lys Arg Ile Glu Asn Leu Asn
                420                 425                 430
Lys Lys Val Asp Asp Gly Phe Leu Asp Ile Trp Thr Tyr Asn Ala Glu
                435                 440                 445
Leu Leu Val Leu Leu Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
                485                 490                 495
Asn Thr Cys Met Glu Ser Val Lys Asn Gly Thr Tyr Asp Tyr Pro Lys
                500                 505                 510
Tyr Ser Glu Glu Ala Lys Leu Asn Arg Glu Lys Ile Asp Gly Val Lys
                515                 520                 525
Leu Glu Ser Thr Arg Ile Tyr Gln Ile Leu Ala Ile Tyr Ser Thr Val
                530                 535                 540
Ala Ser Ser Leu Val Leu Val Val Ser Leu Gly Ala Ile Ser Phe Trp
545                 550                 555                 560
Met Cys Ser Asn Gly Ser Leu Gln Cys Arg Ile Cys Ile
                565                 570
```

<210> SEQ ID NO 106  
<211> LENGTH: 49  
<212> TYPE: DNA  
<213> ORGANISM: Artificial Sequence  
<220> FEATURE:  
<223> OTHER INFORMATION: H1Mich(N380A+F390D).r

<400> SEQUENCE: 106
cccactgctg tgtcctgtgt attcatcttt tcaataacag aagctactt         49

<210> SEQ ID NO 107  
<211> LENGTH: 1722  
<212> TYPE: DNA  
<213> ORGANISM: Artificial Sequence  
<220> FEATURE:  
<223> OTHER INFORMATION: PDI-H1 Mich-F390D+N380A DNA

<400> SEQUENCE: 107
atggcgaaaa acgttgcgat tttcggctta tgttttctc ttcttgtgtt ggttccttct         60
cagatcttcg cggacacatt atgtataggt tatcatgcga acaattcaac agacactgta        120
gacacagtac tagaaaagaa tgtaacagta acacactctg ttaaccttct ggaagacaag        180
cataacggaa aactatgcaa actaagaggg gtagccccat tgcatttggg taaatgtaac        240

```
attgctggct ggatcctggg aaatccagag tgtgaatcac tctccacagc aagttcatgg    300
tcctacattg tggaaacatc taattcagac aatggaacgt gttacccagg agatttcatc    360
aattatgagg agctaagaga gcaattgagc tcagtgtcat catttgaaag gtttgagata    420
ttccccaaga caagttcatg gcccaatcat gactcgaaca aaggtgtaac ggcagcatgt    480
cctcacgctg gagcaaaaag cttctacaaa aacttgatat ggctagttaa aaaggaaat    540 tcatacccaa gcttaaccaa atcctacatt aatgataaag ggaaagaagt cctcgtgctg   600
tggggcattc accatccatc tactactgct gaccaacaaa gtctctatca gaatgcagat   660
gcatatgttt ttgtggggac atcaagatac agcaagaagt tcaagccgga aatagcaaca   720
agacccaaag tgagggatca agaagggaga atgaactatt actggacact agtagagccg   780
ggagacaaaa taacattcga agcaactgga aatctagtgg taccgagata tgcattcaca   840
atggaaagaa atgctggatc tggtattatc atttcagata caccagtcca cgattgcaat   900
acaacttgtc agacacccga gggtgctata aacaccagcc tcccatttca gaatatacat   960
ccgatcacaa ttggaaaatg tccaaagtat gtaaaaagca caaaattgag actggccaca  1020
ggattgagga atgttccgtc tattcaatct agaggcctat tcggggccat tgccggcttc  1080
attgaagggg ggtggacagg gatggtagat ggatggtacg gttatcacca tcaaaatgag  1140 cagggggtcag gatatgcagc cgacctgaag agcacacaaa atgccattga caagattact  1200
aacaaagtag cttctgttat tgaaaagatg aatacacagg acacagcagt gggtaaagag  1260
ttcaaccacc tggaaaaaag aatagagaat ctaaataaaa aagttgatga tggtttcctg  1320
gacatttgga cttacaatgc cgaactgttg gttctattgg aaaatgaaag aactttggac  1380
tatcacgatt caaatgtgaa gaacttgtat gaaaaagtaa gaaccagtt aaaaaacaat  1440 gccaaggaaa ttggaaacgg ctgctttgaa ttttaccaca atgcgataaa cacgtgcatg  1500
gaaagtgtca aaaatgggac ttatgactac ccaaaatact cagaggaagc aaaattaaac  1560
agagaaaaaa tagatggggt aaagctggaa tcaacaagga tttaccagat tttggcgatc  1620
tattcaactg tcgccagttc attggtactg gtagtctccc tgggggcaat cagcttctgg  1680
atgtgctcta tgggtctct acagtgtaga atatgtattt aa                      1722
```

<210> SEQ ID NO 108
<211> LENGTH: 573
<212> TYPE: PRT
<213> ORGANISM: Artificial Sequence
<220> FEATURE:
<223> OTHER INFORMATION: PDI-H1 Mich-F390D+N380A AA

<400> SEQUENCE: 108

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95
```

Ala Ser Ser Trp Ser Tyr Ile Val Glu Thr Ser Asn Ser Asp Asn Gly
                100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Ala Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys

```
        515                 520                 525
Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 109
<211> LENGTH: 50
<212> TYPE: DNA
<213> ORGANISM: Artificial Sequence
<220> FEATURE:
<223> OTHER INFORMATION: Primer IF-H5ITMCT.s1-4r

<400> SEQUENCE: 109
actaaagaaa ataggccttt aaatgcaaat tctgcattgt aacgatccat            50

<210> SEQ ID NO 110
<211> LENGTH: 1731
<212> TYPE: DNA
<213> ORGANISM: Artificial Sequence
<220> FEATURE:
<223> OTHER INFORMATION: PDI-H5 Indo DNA

<400> SEQUENCE: 110
atggcgaaaa acgttgcgat tttcggctta tgttttctc ttcttgtgtt ggttccttct   60
cagatcttcg ccgatcagat ttgcattggt taccatgcaa acaattcaac agagcaggtt  120
gacacaatca tggaaaagaa cgttactgtt acacatgccc aagacatact ggaaagaca  180 cacaacggga agctctgcga tctagatgga gtgaagcctc taattttaag agattgtagt  240
gtagctggat ggctcctcgg gaacccaatg tgtgacgaat catcaatgt accggaatgg  300 tcttacatag tggagaaggc caatccaacc aatgacctct gttacccagg agtttcaac  360 gactatgaag aactgaaaca cctattgagc agaataaacc attttgagaa aattcaaatc  420
atccccaaaa gttcttggtc cgatcatgaa gcctcatcag gagttagctc agcatgtcca  480
tacctgggaa gtccctcctt ttttagaaat gtggtatggc ttatcaaaaa gaacagtaca  540
tacccaacaa taagaaaag ctacaataat accaaccaag aggatctttt ggtactgtgg  600
ggaattcacc atcctaatga tgcggcagag cagacaaggc tatatcaaaa cccaaccacc  660
tatatttcca ttgggacatc aacactaaac cagagattgg taccaaaaat agctactaga  720
tccaaagtaa acgggcaaag tggaaggatg gagttcttct ggacaatttt aaaacctaat  780
gatgcaatca acttcgagag taatggaaat ttcattgctc cagaatatgc atacaaaatt  840
gtcaagaaag gggactcagc aattatgaaa agtgaattgg aatatggtaa ctgcaacacc  900
aagtgtcaaa ctccaatggg ggcgataaac tctagtatgc cattccacaa catacccct   960 ctcaccatcg ggaatgcccc aaatatgtg aaatcaaaca gattagtcct tgcaacaggg  1020
ctcagaaata gccctcaaag agagagcaga agaaaaaaga gaggactatt tggagctata  1080
gcaggtttta tagagggagg atggcaggga atggtagatg gttggtatgg gtaccaccat  1140
agcaatgagc aggggagtgg gtacgctgca gacaaagaat ccactcaaaa ggcaatagat  1200
ggagtcacca ataaggtcaa ctcaatcatt gacaaaatga acactcagtt tgaggccgtt  1260
ggaagggaat taataacttt agaaggagaa atagagaatt taaacaagaa gatggaagac  1320
gggtttctag atgtctggac ttataatgcc gaacttctgg ttctcatgga aaatgagaga  1380
```

-continued

```
actctagact ttcatgactc aaatgttaag aacctctacg acaaggtccg actacagctt    1440
agggataatg caaaggagct gggtaacggt tgtttcgagt tctatcacaa atgtgataat    1500
gaatgtatgg aaagtataag aaacggaacg tacaactatc cgcagtattc agaagaagca    1560
agattaaaaa gagaggaaat aagtggggta aaattggaat caataggaac ttaccaaata    1620
ctgtcaattt attcaacagt ggcgagttcc ctagcactgg caatcatgat ggctggtcta    1680
tctttatgga tgtgctccaa tggatcgtta caatgcagaa tttgcattta a             1731
```

<210> SEQ ID NO 111
<211> LENGTH: 576
<212> TYPE: PRT
<213> ORGANISM: Artificial Sequence
<220> FEATURE:
<223> OTHER INFORMATION: PDI-H5 Indo AA

<400> SEQUENCE: 111

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
                20                  25                  30

Ala Asn Asn Ser Thr Glu Gln Val Asp Thr Ile Met Glu Lys Asn Val
            35                  40                  45

Thr Val Thr His Ala Gln Asp Ile Leu Glu Lys Thr His Asn Gly Lys
        50                  55                  60

Leu Cys Asp Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Ile Asn
                85                  90                  95

Val Pro Glu Trp Ser Tyr Ile Val Glu Lys Ala Asn Pro Thr Asn Asp
            100                 105                 110

Leu Cys Tyr Pro Gly Ser Phe Asn Asp Tyr Glu Glu Leu Lys His Leu
        115                 120                 125

Leu Ser Arg Ile Asn His Phe Glu Lys Ile Gln Ile Ile Pro Lys Ser
    130                 135                 140

Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190

Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285

Met Lys Ser Glu Leu Glu Tyr Gly Asn Cys Asn Thr Lys Cys Gln Thr
    290                 295                 300
```

```
Pro Met Gly Ala Ile Asn Ser Ser Met Pro Phe His Asn Ile His Pro
305                 310                 315                 320

Leu Thr Ile Gly Glu Cys Pro Lys Tyr Val Lys Ser Asn Arg Leu Val
            325                 330                 335

Leu Ala Thr Gly Leu Arg Asn Ser Pro Gln Arg Glu Ser Arg Arg Lys
            340                 345                 350

Lys Arg Gly Leu Phe Gly Ala Ile Ala Gly Phe Ile Glu Gly Gly Trp
            355                 360                 365

Gln Gly Met Val Asp Gly Trp Tyr Gly Tyr His His Ser Asn Glu Gln
370                 375                 380

Gly Ser Gly Tyr Ala Ala Asp Lys Glu Ser Thr Gln Lys Ala Ile Asp
385                 390                 395                 400

Gly Val Thr Asn Lys Val Asn Ser Ile Ile Asp Lys Met Asn Thr Gln
                405                 410                 415

Phe Glu Ala Val Gly Arg Glu Phe Asn Asn Leu Glu Arg Arg Ile Glu
            420                 425                 430

Asn Leu Asn Lys Lys Met Glu Asp Gly Phe Leu Asp Val Trp Thr Tyr
            435                 440                 445

Asn Ala Glu Leu Leu Val Leu Met Glu Asn Glu Arg Thr Leu Asp Phe
450                 455                 460

His Asp Ser Asn Val Lys Asn Leu Tyr Asp Lys Val Arg Leu Gln Leu
465                 470                 475                 480

Arg Asp Asn Ala Lys Glu Leu Gly Asn Gly Cys Phe Glu Phe Tyr His
                485                 490                 495

Lys Cys Asp Asn Glu Cys Met Glu Ser Ile Arg Asn Gly Thr Tyr Asn
            500                 505                 510

Tyr Pro Gln Tyr Ser Glu Glu Ala Arg Leu Lys Arg Glu Glu Ile Ser
            515                 520                 525

Gly Val Lys Leu Glu Ser Ile Gly Thr Tyr Gln Ile Leu Ser Ile Tyr
            530                 535                 540

Ser Thr Val Ala Ser Ser Leu Ala Leu Ala Ile Met Met Ala Gly Leu
545                 550                 555                 560

Ser Leu Trp Met Cys Ser Asn Gly Ser Leu Gln Cys Arg Ile Cys Ile
                565                 570                 575

<210> SEQ ID NO 112
<211> LENGTH: 49
<212> TYPE: DNA
<213> ORGANISM: Artificial Sequence
<220> FEATURE:
<223> OTHER INFORMATION: Primer H5Ind(F393D).r

<400> SEQUENCE: 112
cttccaacgg cctcgtcctg agtgttcatt ttgtcaatga ttgagttga          49

<210> SEQ ID NO 113
<211> LENGTH: 49
<212> TYPE: DNA
<213> ORGANISM: Artificial Sequence
<220> FEATURE:
<223> OTHER INFORMATION: Primer H5Ind(F393D).c

<400> SEQUENCE: 113
caaaatgaac actcaggacg aggccgttgg aagggaattt aataactta          49

<210> SEQ ID NO 114
<211> LENGTH: 1731
<212> TYPE: DNA
```

<213> ORGANISM: Artificial Sequence
<220> FEATURE:
<223> OTHER INFORMATION: PDI-H5 Indo-F393D DNA

<400> SEQUENCE: 114

```
atggcgaaaa acgttgcgat tttcggctta ttgttttctc ttcttgtgtt ggttccttct    60
cagatcttcg cggatcagat ttgcattggt taccatgcaa acaattcaac agagcaggtt   120
gacacaatca tggaaaagaa cgttactgtt acacatgccc aagacatact ggaaaagaca   180
cacaacggga agctctgcga tctagatgga gtgaagcctc taattttaag agattgtagt   240
gtagctggat ggctcctcgg gaacccaatg tgtgacgaat tcatcaatgt accggaatgg   300
tcttacatag tggagaaggc caatccaacc aatgacctct gttacccagg agtttcaac    360
gactatgaag aactgaaaca cctattgagc agaataaacc attttgagaa aattcaaatc   420
atccccaaaa gttcttggtc cgatcatgaa gcctcatcag gagttagctc agcatgtcca   480
tacctgggaa gtccctcctt ttttagaaat gtggtatggc ttatcaaaaa gaacagtaca   540
tacccaacaa taagaaaaag ctacaataat accaaccaag aggatctttt ggtactgtgg   600
ggaattcacc atcctaatga tgcggcagag cagacaaggc tatatcaaaa cccaaccacc   660
tatatttcca ttgggacatc aacactaaac cagagattgg taccaaaaat agctactaga   720
tccaaagtaa acgggcaaag tggaaggatg gagttcttct ggacaatttt aaaacctaat   780
gatgcaatca acttcgagag taatggaaat ttcattgctc agaatatgc atacaaaatt    840
gtcaagaaag gggactcagc aattatgaaa agtgaattgg aatatggtaa ctgcaacacc   900
aagtgtcaaa ctccaatggg ggcgataaac tctagtatgc cattccacaa catacaccct   960
ctcaccatcg gggaatgccc caaatatgtg aaatcaaaca gattagtcct gcaacaggg   1020
ctcagaaata gccctcaaag agagagcaga agaaaaaaga gaggactatt tggagctata   1080
gcaggtttta tagagggagg atggcaggga atggtagatg gttggtatgg gtaccaccat   1140
agcaatgagc aggggagtgg gtacgctgca gacaaagaat ccactcaaaa ggcaatagat   1200
ggagtcacca ataaggtcaa ctcaatcatt gacaaaatga acactcagga cgaggccgtt   1260
ggaagggaat taataacttt agaaaggaga atagagaatt aaacaagaa gatgaagac    1320
gggtttctag atgtctggac ttataatgcc gaacttctgg ttctcatgga aaatgagaga   1380
actctagact tcatgactc aaatgttaag aacctacgt acaaggtccg actcagctt     1440
agggataatg caaggagct gggtaacggt tgtttcgagt ctatcacaa atgtgataat    1500
gaatgtatgg aaagtataag aaacggaacg tacaactatc cgcagtattc agaagaagca   1560
agattaaaaa gagaggaaat aagtgggta aaattggaat caataggaac ttaccaaata    1620
ctgtcaattt attcaacagt ggcgagttcc ctagcactgg caatcatgat ggctggtcta   1680
tctttatgga tgtgctccaa tggatcgtta caatgcagaa tttgcattta a           1731
```

<210> SEQ ID NO 115
<211> LENGTH: 576
<212> TYPE: PRT
<213> ORGANISM: Artificial Sequence
<220> FEATURE:
<223> OTHER INFORMATION: PDI-H5 Indo-F393D AA

<400> SEQUENCE: 115

```
Met Ala Lys Asn Val Ala Ile Phe Gly Leu Leu Phe Ser Leu Leu Val
1               5                   10                  15
Leu Val Pro Ser Gln Ile Phe Ala Asp Gln Ile Cys Ile Gly

```
Ala Asn Asn Ser Thr Glu Gln Val Asp Thr Ile Met Glu Lys Asn Val
         35                  40                  45

Thr Val Thr His Ala Gln Asp Ile Leu Glu Lys Thr His Asn Gly Lys
 50                  55                  60

Leu Cys Asp Leu Asp Gly Val Lys Pro Leu Ile Leu Arg Asp Cys Ser
 65                  70                  75                  80

Val Ala Gly Trp Leu Leu Gly Asn Pro Met Cys Asp Glu Phe Ile Asn
                 85                  90                  95

Val Pro Glu Trp Ser Tyr Ile Val Glu Lys Ala Asn Pro Thr Asn Asp
                100                 105                 110

Leu Cys Tyr Pro Gly Ser Phe Asn Asp Tyr Glu Glu Leu Lys His Leu
            115                 120                 125

Leu Ser Arg Ile Asn His Phe Glu Lys Ile Gln Ile Ile Pro Lys Ser
        130                 135                 140

Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190

Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285

Met Lys Ser Glu Leu Glu Tyr Gly Asn Cys Asn Thr Lys Cys Gln Thr
    290                 295                 300

Pro Met Gly Ala Ile Asn Ser Ser Met Pro Phe His Asn Ile His Pro
305                 310                 315                 320

Leu Thr Ile Gly Glu Cys Pro Lys Tyr Val Lys Ser Asn Arg Leu Val
                325                 330                 335

Leu Ala Thr Gly Leu Arg Asn Ser Pro Gln Arg Glu Ser Arg Arg Lys
            340                 345                 350

Lys Arg Gly Leu Phe Gly Ala Ile Ala Gly Phe Ile Glu Gly Gly Trp
        355                 360                 365

Gln Gly Met Val Asp Gly Trp Tyr Gly Tyr His His Ser Asn Glu Gln
    370                 375                 380

Gly Ser Gly Tyr Ala Ala Asp Lys Glu Ser Thr Gln Lys Ala Ile Asp
385                 390                 395                 400

Gly Val Thr Asn Lys Val Asn Ser Ile Ile Asp Lys Met Asn Thr Gln
                405                 410                 415

Asp Glu Ala Val Gly Arg Glu Phe Asn Asn Leu Glu Arg Arg Ile Glu
            420                 425                 430

Asn Leu Asn Lys Lys Met Glu Asp Gly Phe Leu Asp Val Trp Thr Tyr
        435                 440                 445
```

```
Asn Ala Glu Leu Leu Val Leu Met Glu Asn Glu Arg Thr Leu Asp Phe
    450                 455                 460

His Asp Ser Asn Val Lys Asn Leu Tyr Asp Lys Val Arg Leu Gln Leu
465                 470                 475                 480

Arg Asp Asn Ala Lys Glu Leu Gly Asn Gly Cys Phe Glu Phe Tyr His
                485                 490                 495

Lys Cys Asp Asn Glu Cys Met Glu Ser Ile Arg Asn Gly Thr Tyr Asn
                500                 505                 510

Tyr Pro Gln Tyr Ser Glu Glu Ala Arg Leu Lys Arg Glu Glu Ile Ser
            515                 520                 525

Gly Val Lys Leu Glu Ser Ile Gly Thr Tyr Gln Ile Leu Ser Ile Tyr
    530                 535                 540

Ser Thr Val Ala Ser Ser Leu Ala Leu Ala Ile Met Met Ala Gly Leu
545                 550                 555                 560

Ser Leu Trp Met Cys Ser Asn Gly Ser Leu Gln Cys Arg Ile Cys Ile
                565                 570                 575
```

<210> SEQ ID NO 116
<211> LENGTH: 51
<212> TYPE: DNA
<213> ORGANISM: Artificial Sequence
<220> FEATURE:
<223> OTHER INFORMATION: Primer IF-H5_Egy.r

<400> SEQUENCE: 116
actaaagaaa ataggccttt aaatgcaaat tctgcattgt agcgatccat t        51

<210> SEQ ID NO 117
<211> LENGTH: 1728
<212> TYPE: DNA
<213> ORGANISM: Artificial Sequence
<220> FEATURE:
<223> OTHER INFORMATION: PDI-H5 Egypt DNA

<400> SEQUENCE: 117
atggcgaaaa acgttgcgat tttcggctta tgttttctc ttcttgtgtt ggttccttct    60
cagatcttcg cggatcagat ttgcattggt taccatgcaa acaactcgac agagcaggtt   120
gacacaataa tggaaaagaa tgtcactgtt acacacgccc aagacatact ggaaaagaca   180
cacaacggga aactctgcaa tctagatgga gtgaagcctc tcattttgag agattgtagt   240
gtagctggat ggctcctcgg gaacccaatg tgcgatgaat cctcaatgt gccggaatgg   300 tcttacatag tggagaaaat caatccagcc aatgacctct gttatccagg gaatttcaac   360
gactatgaag aactgaaaca cctattgagc agaataaacc attttgagaa aattcagatc   420
attcccaaag attcttggtc agatcatgaa gcctcgggag tgagctcagc atgcccatac   480
caaggaagat cctccttttt tagaaatgtt gtatggctta ccaaaaagaa cgatgcatac   540
ccaacaataa agaaaagtta caataatact aaccaagaag tcttttggt actatggggg   600 attcaccatc caaatgatgc tgcagagcag acaaggcttt atcaaaaccc aactacctat   660
atctccgttg ggacatcaac actaaaccag agattggtac ccaaaatagc tactagatct   720
aaggtaaacg gcaaagtgg aaggatgag ttcttttgga caattttaaa atcgaatgat   780 gcaataaaact ttgagagcaa tggaaactc attgctccag aaaatgcata caaaattgtc   840
aagaaaggag attcaacaat tatgaaaagt gagttggaat atagtaactg caacaccaag   900
tgtcagactc caatagggc gataaactcc agtatgccat ccacaacat ccaccctctc   960 accatcgggg aatgcccaa atatgtgaaa tcaaacagat tagtccttgc tactgggctc  1020
```

```
aggaatagcc ctcaaggaga gaaaagaaga aaaaagagag gactattcgg agccatagca    1080
ggctttatag agggaggatg gcagggaatg gtagatggtt ggtatgggta ccaccatagc    1140
aacgagcagg ggagtgggta cgctgcagac aaagaatcca ctcaaagggc tatagatgga    1200
gtcaccaata aggtcaattc gatcattgac aaaatgaaca ctcagtttga ggctgttgga    1260
agggaattta ataacttaga aaggagaata gaaaatttaa acaagaagat ggaagacgga    1320
ttcctagatg tctggactta taatgctgaa cttctggttc tcatggaaaa tgagagaact    1380
ctagactttc atgactcaaa tgtcaagaat ctttatgaca aggtccgact acagcttagg    1440
gataatgcaa aggagcttgg taacggttgt ttcgagttct atcacagatg tgataatgaa    1500
tgtatggaaa gtgtaagaaa cggaacgtat gactaccctc aatattcaga agaagcaaga    1560
ttaaaaagag aggaaataag tggagtaaaa ttggagtcaa taggaactta ccaaatactg    1620
tcaatttatt caacagtggc gagctcccta gcactggcaa tcatggtggc tggtctatct    1680
ttatggatgt gctccaatgg atcgctacaa tgcagaattt gcatttaa              1728
```

<210> SEQ ID NO 118
<211> LENGTH: 575
<212> TYPE: PRT
<213> ORGANISM: Artificial Sequence
<220> FEATURE:
<223> OTHER INFORMATION: PDI-H5 Egypt AA

<400> SEQUENCE: 118

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
                20                  25                  30

Ala Asn Asn Ser Thr Glu Gln Val Asp Thr Ile Met Glu Lys Asn Val
            35                  40                  45

Thr Val Thr His Ala Gln Asp Ile Leu Glu Lys Thr His Asn Gly Lys
        50                  55                  60

Leu Cys Asn Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Leu Asn
                85                  90                  95

Val Pro Glu Trp Ser Tyr Ile Val Glu Lys Ile Asn Pro Ala Asn Asp
            100                 105                 110

Leu Cys Tyr Pro Gly Asn Phe Asn Asp Tyr Glu Glu Leu Lys His Leu
        115                 120                 125

Leu Ser Arg Ile Asn His Phe Glu Lys Ile Gln Ile Ile Pro Lys Asp
    130                 135                 140

Ser Trp Ser Asp His Glu Ala Ser Gly Val Ser Ala Cys Pro Tyr
145                 150                 155                 160

Gln Gly Arg Ser Ser Phe Phe Arg Asn Val Val Trp Leu Thr Lys Lys
                165                 170                 175

Asn Asp Ala Tyr Pro Thr Ile Lys Lys Ser Tyr Asn Asn Thr Asn Gln
            180                 185                 190

Glu Asp Leu Leu Val Leu Trp Gly Ile His His Pro Asn Asp Ala Ala
        195                 200                 205

Glu Gln Thr Arg Leu Tyr Gln Asn Pro Thr Thr Tyr Ile Ser Val Gly
    210                 215                 220

Thr Ser Thr Leu Asn Gln Arg Leu Val Pro Lys Ile Ala Thr Arg Ser
225                 230                 235                 240
```

Lys Val Asn Gly Gln Ser Gly Arg Met Glu Phe Phe Trp Thr Ile Leu
            245                 250                 255

Lys Ser Asn Asp Ala Ile Asn Phe Glu Ser Asn Gly Asn Phe Ile Ala
        260                 265                 270

Pro Glu Asn Ala Tyr Lys Ile Val Lys Lys Gly Asp Ser Thr Ile Met
            275                 280                 285

Lys Ser Glu Leu Glu Tyr Ser Asn Cys Asn Thr Lys Cys Gln Thr Pro
        290                 295                 300

Ile Gly Ala Ile Asn Ser Ser Met Pro Phe His Asn Ile His Pro Leu
305                 310                 315                 320

Thr Ile Gly Glu Cys Pro Lys Tyr Val Lys Ser Asn Arg Leu Val Leu
            325                 330                 335

Ala Thr Gly Leu Arg Asn Ser Pro Gln Gly Glu Lys Arg Arg Lys Lys
        340                 345                 350

Arg Gly Leu Phe Gly Ala Ile Ala Gly Phe Ile Glu Gly Gly Trp Gln
            355                 360                 365

Gly Met Val Asp Gly Trp Tyr Gly Tyr His His Ser Asn Glu Gln Gly
        370                 375                 380

Ser Gly Tyr Ala Ala Asp Lys Glu Ser Thr Gln Arg Ala Ile Asp Gly
385                 390                 395                 400

Val Thr Asn Lys Val Asn Ser Ile Ile Asp Lys Met Asn Thr Gln Phe
            405                 410                 415

Glu Ala Val Gly Arg Glu Phe Asn Asn Leu Glu Arg Arg Ile Glu Asn
        420                 425                 430

Leu Asn Lys Lys Met Glu Asp Gly Phe Leu Asp Val Trp Thr Tyr Asn
            435                 440                 445

Ala Glu Leu Leu Val Leu Met Glu Asn Glu Arg Thr Leu Asp Phe His
        450                 455                 460

Asp Ser Asn Val Lys Asn Leu Tyr Asp Lys Val Arg Leu Gln Leu Arg
465                 470                 475                 480

Asp Asn Ala Lys Glu Leu Gly Asn Gly Cys Phe Glu Phe Tyr His Arg
            485                 490                 495

Cys Asp Asn Glu Cys Met Glu Ser Val Arg Asn Gly Thr Tyr Asp Tyr
        500                 505                 510

Pro Gln Tyr Ser Glu Glu Ala Arg Leu Lys Arg Glu Glu Ile Ser Gly
            515                 520                 525

Val Lys Leu Glu Ser Ile Gly Thr Tyr Gln Ile Leu Ser Ile Tyr Ser
530                 535                 540

Thr Val Ala Ser Ser Leu Ala Leu Ala Ile Met Val Ala Gly Leu Ser
545                 550                 555                 560

Leu Trp Met Cys Ser Asn Gly Ser Leu Gln Cys Arg Ile Cys Ile
            565                 570                 575

<210> SEQ ID NO 119
<211> LENGTH: 49
<212> TYPE: DNA
<213> ORGANISM: Artificial Sequence
<220> FEATURE:
<223> OTHER INFORMATION: Primer H5Egy(F392D).r

<400> SEQUENCE: 119
cttccaacag cctcgtcctg agtgttcatt ttgtcaatga tcgaattga          49

<210> SEQ ID NO 120
<211> LENGTH: 49

<212> TYPE: DNA
<213> ORGANISM: Artificial Sequence
<220> FEATURE:
<223> OTHER INFORMATION: Primer H5Egy(F392D).c

<400> SEQUENCE: 120
caaaatgaac actcaggacg aggctgttgg aagggaattt aataactta         49

<210> SEQ ID NO 121
<211> LENGTH: 1728
<212> TYPE: DNA
<213> ORGANISM: Artificial Sequence
<220> FEATURE:
<223> OTHER INFORMATION: PDI-H5 Egypt-F392D DNA

<400> SEQUENCE: 121
atggcgaaaa acgttgcgat tttcggctta ttgttttctc ttcttgtgtt ggttccttct      60
cagatcttcg cggatcagat ttgcattggt taccatgcaa caactcgac agagcaggtt     120
gacacaataa tggaaaagaa tgtcactgtt acacacgccc aagacatact ggaaaagaca     180
cacaacggga aactctgcaa tctagatgga gtgaagcctc tcattttgag agattgtagt     240
gtagctggat ggctcctcgg aaacccaatg tgcgatgaat tcctcaatgt gccggaatgg     300
tcttacatag tggagaaaat caatccagcc aatgacctct gttatccagg aatttcaac     360
gactatgaag aactgaaaca cctattgagc agaataaacc attttgagaa aattcagatc     420
attcccaaag attcttggtc agatcatgaa gcctcgggag tgagctcagc atgcccatac     480
caaggaagat cctcctttt tagaaatgtt gtatggctta ccaaaaagaa cgatgcatac     540
ccaacaataa agaaaagtta caataatact aaccaagaag atcttttggt actatggggg     600
attcaccatc caaatgatgc tgcagagcag acaaggcttt atcaaaaccc aactacctat     660
atctccgttg gaacatcaac actaaccag agattggtac ccaaaatagc tactagatct     720
aaggtaaacg gcaaagtgg aaggatgag ttcttttgga caattttaaa atcgaatgat     780
gcaataaact ttgagagcaa tggaaacttc attgctccag aaaatgcata caaaattgtc     840
aagaaaggag attcaacaat tatgaaaagt gagttggaat atagtaactg caacaccaag     900
tgtcagactc caataggggc gataaaactcc agtatgccat tccacaacat ccaccctctc     960
accatcgggg aatgccccaa atatgtgaaa tcaaacagat tagtccttgc tactgggctc    1020
aggaatagcc ctcaaggaga gaaaagaaga aaaagagag gactattcgg agccatagca    1080
ggctttatag agggaggatg gcagggaatg gtagatggtt ggtatgggta ccaccatagc    1140
aacgagcagg gagtgggta cgctgcagac aaagaatcca ctcaaagggc tatagatgga    1200
gtcaccaata aggtcaattc gatcattgac aaaatgaaca ctcaggacga ggctgttgga    1260
agggaattta ataacttaga aaggagaata gaaaatttaa acaagaagat ggaagacgga    1320
ttcctagatg tctggactta taatgctgaa cttctggttc tcatggaaaa tgagagaact    1380
ctagactttc atgactcaaa tgtcaagaat ctttatgaca aggtccgact acagcttagg    1440
gataatgcaa aggagcttgg taacggttgt ttcgagttct atcacagatg tgataatgaa    1500
tgtatggaaa gtgtaagaaa cggaacgtat gactaccctc aatattcaga agaagcaaga    1560
ttaaaaagag aggaaataag tggagtaaaa ttggagtcaa taggaactta ccaaatactg    1620
tcaatttatt caacagtggc gagctcccta gcactggcaa tcatggtggc tggtctatct    1680
ttatggatgt gctccaatgg atcgctacaa tgcagaattt gcatttaa           1728

<210> SEQ ID NO 122

```
<211> LENGTH: 575
<212> TYPE: PRT
<213> ORGANISM: Artificial Sequence
<220> FEATURE:
<223> OTHER INFORMATION: PDI-H5 Egypt-F392D AA

<400> SEQUENCE: 122
```

| | | | | | | | | | | | | | | |
|---|---|---|---|---|---|---|---|---|---|---|---|---|---|---|
| Met | Ala | Lys | Asn | Val | Ala | Ile | Phe | Gly | Leu | Leu | Phe | Ser | Leu | Val |
| 1 | | | | 5 | | | | | 10 | | | | | 15 |
| Leu | Val | Pro | Ser | Gln | Ile | Phe | Ala | Asp | Gln | Ile | Cys | Ile | Gly | Tyr | His |
| | | | 20 | | | | | 25 | | | | | 30 | | |
| Ala | Asn | Asn | Ser | Thr | Glu | Gln | Val | Asp | Thr | Ile | Met | Glu | Lys | Asn | Val |
| | | 35 | | | | | 40 | | | | | 45 | | | |
| Thr | Val | Thr | His | Ala | Gln | Asp | Ile | Leu | Glu | Lys | Thr | His | Asn | Gly | Lys |
| | 50 | | | | | 55 | | | | | 60 | | | | |
| Leu | Cys | Asn | Leu | Asp | Gly | Val | Lys | Pro | Leu | Ile | Leu | Arg | Asp | Cys | Ser |
| 65 | | | | | 70 | | | | | 75 | | | | | 80 |
| Val | Ala | Gly | Trp | Leu | Leu | Gly | Asn | Pro | Met | Cys | Asp | Glu | Phe | Leu | Asn |
| | | | | 85 | | | | | 90 | | | | | 95 | |
| Val | Pro | Glu | Trp | Ser | Tyr | Ile | Val | Glu | Lys | Ile | Asn | Pro | Ala | Asn | Asp |
| | | | | 100 | | | | | 105 | | | | | 110 | |
| Leu | Cys | Tyr | Pro | Gly | Asn | Phe | Asn | Asp | Tyr | Glu | Glu | Leu | Lys | His | Leu |
| | | | 115 | | | | | 120 | | | | | 125 | | |
| Leu | Ser | Arg | Ile | Asn | His | Phe | Glu | Lys | Ile | Gln | Ile | Ile | Pro | Lys | Asp |
| | | 130 | | | | | 135 | | | | | 140 | | | |
| Ser | Trp | Ser | Asp | His | Glu | Ala | Ser | Gly | Val | Ser | Ser | Ala | Cys | Pro | Tyr |
| 145 | | | | | 150 | | | | | 155 | | | | | 160 |
| Gln | Gly | Arg | Ser | Ser | Phe | Phe | Arg | Asn | Val | Val | Trp | Leu | Thr | Lys | Lys |
| | | | | 165 | | | | | 170 | | | | | 175 | |
| Asn | Asp | Ala | Tyr | Pro | Thr | Ile | Lys | Lys | Ser | Tyr | Asn | Asn | Thr | Asn | Gln |
| | | | | 180 | | | | | 185 | | | | | 190 | |
| Glu | Asp | Leu | Leu | Val | Leu | Trp | Gly | Ile | His | His | Pro | Asn | Asp | Ala | Ala |
| | | | 195 | | | | | 200 | | | | | 205 | | |
| Glu | Gln | Thr | Arg | Leu | Tyr | Gln | Asn | Pro | Thr | Thr | Tyr | Ile | Ser | Val | Gly |
| | | 210 | | | | | 215 | | | | | 220 | | | |
| Thr | Ser | Thr | Leu | Asn | Gln | Arg | Leu | Val | Pro | Lys | Ile | Ala | Thr | Arg | Ser |
| 225 | | | | | 230 | | | | | 235 | | | | | 240 |
| Lys | Val | Asn | Gly | Gln | Ser | Gly | Arg | Met | Glu | Phe | Phe | Trp | Thr | Ile | Leu |
| | | | | 245 | | | | | 250 | | | | | 255 | |
| Lys | Ser | Asn | Asp | Ala | Ile | Asn | Phe | Glu | Ser | Asn | Gly | Asn | Phe | Ile | Ala |
| | | | | 260 | | | | | 265 | | | | | 270 | |
| Pro | Glu | Asn | Ala | Tyr | Lys | Ile | Val | Lys | Lys | Gly | Asp | Ser | Thr | Ile | Met |
| | | | 275 | | | | | 280 | | | | | 285 | | |
| Lys | Ser | Glu | Leu | Glu | Tyr | Ser | Asn | Cys | Asn | Thr | Lys | Cys | Gln | Thr | Pro |
| | | 290 | | | | | 295 | | | | | 300 | | | |
| Ile | Gly | Ala | Ile | Asn | Ser | Ser | Met | Pro | Phe | His | Asn | Ile | His | Pro | Leu |
| 305 | | | | | 310 | | | | | 315 | | | | | 320 |
| Thr | Ile | Gly | Glu | Cys | Pro | Lys | Tyr | Val | Lys | Ser | Asn | Arg | Leu | Val | Leu |
| | | | | 325 | | | | | 330 | | | | | 335 | |
| Ala | Thr | Gly | Leu | Arg | Asn | Ser | Pro | Gln | Gly | Lys | Arg | Lys | Lys |
| | | | | 340 | | | | | 345 | | | | | 350 |
| Arg | Gly | Leu | Phe | Gly | Ala | Ile | Ala | Gly | Phe | Ile | Glu | Gly | Gly | Trp | Gln |
| | | | | 355 | | | | | 360 | | | | | 365 | |
| Gly | Met | Val | Asp | Gly | Trp | Tyr | Gly | Tyr | His | His | Ser | Asn | Glu | Gln | Gly |
| | | | | 370 | | | | | 375 | | | | | 380 | |

```
Ser Gly Tyr Ala Ala Asp Lys Glu Ser Thr Gln Arg Ala Ile Asp Gly
385                 390                 395                 400

Val Thr Asn Lys Val Asn Ser Ile Ile Asp Lys Met Asn Thr Gln Asp
                405                 410                 415

Glu Ala Val Gly Arg Glu Phe Asn Asn Leu Glu Arg Arg Ile Glu Asn
            420                 425                 430

Leu Asn Lys Lys Met Glu Asp Gly Phe Leu Asp Val Trp Thr Tyr Asn
        435                 440                 445

Ala Glu Leu Leu Val Leu Met Glu Asn Glu Arg Thr Leu Asp Phe His
450                 455                 460

Asp Ser Asn Val Lys Asn Leu Tyr Asp Lys Val Arg Leu Gln Leu Arg
465                 470                 475                 480

Asp Asn Ala Lys Glu Leu Gly Asn Gly Cys Phe Glu Phe Tyr His Arg
                485                 490                 495

Cys Asp Asn Glu Cys Met Glu Ser Val Arg Asn Gly Thr Tyr Asp Tyr
            500                 505                 510

Pro Gln Tyr Ser Glu Glu Ala Arg Leu Lys Arg Glu Glu Ile Ser Gly
        515                 520                 525

Val Lys Leu Glu Ser Ile Gly Thr Tyr Gln Ile Leu Ser Ile Tyr Ser
530                 535                 540

Thr Val Ala Ser Ser Leu Ala Leu Ala Ile Met Val Ala Gly Leu Ser
545                 550                 555                 560

Leu Trp Met Cys Ser Asn Gly Ser Leu Gln Cys Arg Ile Cys Ile
                565                 570                 575

<210> SEQ ID NO 123
<211> LENGTH: 1722
<212> TYPE: DNA
<213> ORGANISM: Artificial Sequence
<220> FEATURE:
<223> OTHER INFORMATION: PDI-H1 Par-F390D+L429M (nt)

<400> SEQUENCE: 123
atggcgaaaa acgttgcgat tttcggctta ttgttttctc ttcttgtgtt ggttccttct      60
cagatcttcg cggacacatt atgtataggt tatcatgcga acaattcaac agacactgta    120
gacacagtac tagaaaagaa tgtaacagta acacactctg ttaaccttct ggaagacaag    180
cataacggaa aactatgcaa actaagaggg gtagccccat tgcatttggg taatgtaac     240 attgctggct ggatcctggg aaatccagag tgtgaatcac tctccacagc aagatcatgg    300
tcctacattt ggaaacatc taattcagac aatggaacgt gttacccagg agatttcatc     360
aattatgagg agctaagaga gcaattgagc tcagtgtcat catttgaaag gtttgagata    420
ttccccaaga caagttcatg gcccaatcat gactcgaaca aggtgtaac ggcagcatgt     480 cctcacgctg agcaaaaag cttctacaaa aacttgatat ggctagttaa aaaaggaaat    540
tcatacccaa agcttaacca aacctacatt aatgataaag ggaagaagt cctcgtgctg     600 tggggcattc accatccatc tactactgct gaccaacaaa gtctctatca gaatgcagat    660
gcatatgttt ttgtggggac atcaagatac agcaagaagt tcaagccgga aatagcaaca    720
agacccaaag tgagggatca agaagggaga atgaactatt actggacact agtagagccg    780
ggagacaaaa taacattcga agcaactgga aatctagtgg taccgagata tgcattcaca    840
atggaaagaa atgctggatc tggtattatc atttcagata caccagtcca cgattgcaat    900
acaacttgtc agacacccga gggtgctata aacaccagcc tcccatttca gaatgtgcat    960
```

-continued

```
ccgatcacaa ttggaaaatg tccaaagtat gtaaaaagca caaaattgag actggccaca    1020
ggattgagga atgttccgtc tattcaatct agaggcctat tcggggccat tgccggcttc    1080
attgaagggg ggtggacagg gatggtagat ggatggtacg gttatcacca tcaaaatgag    1140 cagggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaccagtt aaaaaacaat     1440 gccaaggaaa ttggaaacgg ctgctttgaa ttttaccaca aatgcgataa cacgtgcatg    1500
gaaagtgtca aaaatgggac ttatgactac ccaaaatact cagaggaagc aaaattaaac    1560
agagaaaaaa tagatggggt aaagctggaa tcaacaagga tttaccagat tttggcgatc    1620
tattcaactg tcgccagttc attggtactg gtagtctccc tgggggcaat cagcttctgg    1680
atgtgctcta tgggtctctc acagtgtaga atatgtattt aa                      1722
```

<210> SEQ ID NO 124
<211> LENGTH: 573
<212> TYPE: PRT
<213> ORGANISM: Artificial Sequence
<220> FEATURE:
<223> OTHER INFORMATION: PDI-H1 Par-F390D+L429M (aa)

<400> SEQUENCE: 124

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
                100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
        130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Thr Tyr Ile Asn Asp
                180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
        210                 215                 220

Val Gly Thr Ser Arg Tyr Ser Lys Lys Phe Lys Pro Glu Ile Ala Thr
```

```
                    225                 230                 235                 240
Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
                275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
                355                 360                 365

Val Asp Gly Trp Tyr Gly Tyr His His Gln Asn Glu Gln Gly Ser Gly
                370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
                435                 440                 445

Leu Leu Val Leu Met Glu Asn Glu Arg Thr Leu Asp Tyr His Asp Ser
                450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510

Tyr Ser Glu Glu Ala Lys Leu Asn Arg Glu Lys Ile Asp Gly Val Lys
                515                 520                 525

Leu Glu Ser Thr Arg Ile Tyr Gln Ile Leu Ala Ile Tyr Ser Thr Val
                530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 125
<211> LENGTH: 1722
<212> TYPE: DNA
<213> ORGANISM: Artificial Sequence
<220> FEATURE:
<223> OTHER INFORMATION: PDI-H1 Par-K374E+F390D+L429M (nt)

<400> SEQUENCE: 125

```
atggcgaaaa acgttgcgat tttcggctta ttgttttctc ttcttgtgtt ggttccttct      60
cagatcttcg cggacacatt atgtataggt tatcatgcga acaattcaac agacactgta     120
```

| | |
|---|---|
| gacacagtac tagaaaagaa tgtaacagta acacactctg ttaaccttct ggaagacaag | 180 |
| cataacggaa aactatgcaa actaagaggg gtagccccat tgcatttggg taaatgtaac | 240 |
| attgctggct ggatcctggg aaatccagag tgtgaatcac tctccacagc aagatcatgg | 300 |
| tcctacattg tggaaacatc taattcgac aatggaacgt gttacccagg agatttcatc | 360 |
| aattatgagg agctaagaga gcaattgagc tcagtgtcat catttgaaag gtttgagata | 420 |
| ttccccaaga caagttcatg gcccaatcat gactcgaaca aaggtgtaac ggcagcatgt | 480 |
| cctcacgctg gagcaaaaag cttctacaaa aacttgatat ggctagttaa aaaaggaaat | 540 |
| tcatacccaa agcttaacca aacctacatt aatgataaag ggaaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga aatctagtgg taccgagata tgcattcaca | 840 |
| atggaaagaa atgctggatc tggtattatc atttcagata caccagtcca cgattgcaat | 900 |
| acaacttgtc agacacccga gggtgctata aacaccagcc tcccatttca gaatgtgcat | 960 |
| ccgatcacaa ttggaaaatg tccaaagtat gtaaaagca caaaattgag actggccaca | 1020 |
| ggattgagga atgttccgtc tattcaatct agaggcctat tcggggccat tgccggcttc | 1080 |
| attgaagggg gtggacagg gatggtagat ggatggtacg gttatcacca tcaaaatgag | 1140 |
| cagggtcag gatatgcagc cgacctgaag agcacacaaa atgccattga cgagattact | 1200 |
| aacaaagtaa attctgttat tgaaaagatg aatacacagg acacagcagt gggtaaagag | 1260 |
| ttcaaccacc tggaaaaaag aatagagaat ctaaataaaa aagttgatga tggtttcctg | 1320 |
| gacatttgga cttacaatgc cgaactgttg gttctaatgg aaaatgaaag aactttggac | 1380 |
| tatcacgatt caaatgtgaa gaacttgtat gaaaaagtaa gaaaccagtt aaaaaacaat | 1440 |
| gccaaggaaa ttggaaacgg ctgctttgaa ttttaccaca aatgcgataa cacgtgcatg | 1500 |
| gaaagtgtca aaaatgggac ttatgactac ccaaaatact cagaggaagc aaaattaaac | 1560 |
| agagaaaaaa tagatggggt aaagctgaa tcaacaagga tttaccagat tttggcgatc | 1620 |
| tattcaactg tcgccagttc attggtactg gtagtctccc tgggggcaat cagcttctgg | 1680 |
| atgtgctcta atgggtctct acagtgtaga atatgtattt aa | 1722 |

```
<210> SEQ ID NO 126
<211> LENGTH: 573
<212> TYPE: PRT
<213> ORGANISM: Artificial Sequence
<220> FEATURE:
<223> OTHER INFORMATION: PDI-H1 Par-K374E+F390D+L429M (aa)

<400> SEQUENCE: 126

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80
```

```
Ile Ala Gly Trp Ile Leu Gly Asn Pro Glu Cys Glu Ser Leu Ser Thr
            85                  90                  95
Ala Arg Ser Trp Ser Tyr Ile Val Glu Thr Ser Asn Ser Asp Asn Gly
            100                 105                 110
Thr Cys Tyr Pro Gly Asp Phe Ile Asn Tyr Glu Glu Leu Arg Glu Gln
            115                 120                 125
Leu Ser Ser Val Ser Ser Phe Glu Arg Phe Glu Ile Phe Pro Lys Thr
            130                 135                 140
Ser Ser Trp Pro Asn His Asp Ser Asn Lys Gly Val Thr Ala Ala Cys
145                 150                 155                 160
Pro His Ala Gly Ala Lys Ser Phe Tyr Lys Asn Leu Ile Trp Leu Val
            165                 170                 175
Lys Lys Gly Asn Ser Tyr Pro Lys Leu Asn Gln Thr Tyr Ile Asn Asp
            180                 185                 190
Lys Gly Lys Glu Val Leu Val Leu Trp Gly Ile His His Pro Ser Thr
            195                 200                 205
Thr Ala Asp Gln Gln Ser Leu Tyr Gln Asn Ala Asp Ala Tyr Val Phe
            210                 215                 220
Val Gly Thr Ser Arg Tyr Ser Lys Lys Phe Lys Pro Glu Ile Ala Thr
225                 230                 235                 240
Arg Pro Lys Val Arg Asp Gln Glu Gly Arg Met Asn Tyr Tyr Trp Thr
            245                 250                 255
Leu Val Glu Pro Gly Asp Lys Ile Thr Phe Glu Ala Thr Gly Asn Leu
            260                 265                 270
Val Val Pro Arg Tyr Ala Phe Thr Met Glu Arg Asn Ala Gly Ser Gly
            275                 280                 285
Ile Ile Ile Ser Asp Thr Pro Val His Asp Cys Asn Thr Thr Cys Gln
            290                 295                 300
Thr Pro Glu Gly Ala Ile Asn Thr Ser Leu Pro Phe Gln Asn Val His
305                 310                 315                 320
Pro Ile Thr Ile Gly Lys Cys Pro Lys Tyr Val Lys Ser Thr Lys Leu
            325                 330                 335
Arg Leu Ala Thr Gly Leu Arg Asn Val Pro Ser Ile Gln Ser Arg Gly
            340                 345                 350
Leu Phe Gly Ala Ile Ala Gly Phe Ile Glu Gly Gly Trp Thr Gly Met
            355                 360                 365
Val Asp Gly Trp Tyr Gly Tyr His His Gln Asn Glu Gln Gly Ser Gly
            370                 375                 380
Tyr Ala Ala Asp Leu Lys Ser Thr Gln Asn Ala Ile Asp Glu Ile Thr
385                 390                 395                 400
Asn Lys Val Asn Ser Val Ile Glu Lys Met Asn Thr Gln Asp Thr Ala
            405                 410                 415
Val Gly Lys Glu Phe Asn His Leu Glu Lys Arg Ile Glu Asn Leu Asn
            420                 425                 430
Lys Lys Val Asp Asp Gly Phe Leu Asp Ile Trp Thr Tyr Asn Ala Glu
            435                 440                 445
Leu Leu Val Leu Met Glu Asn Glu Arg Thr Leu Asp Tyr His Asp Ser
450                 455                 460
Asn Val Lys Asn Leu Tyr Glu Lys Val Arg Asn Gln Leu Lys Asn Asn
465                 470                 475                 480
Ala Lys Glu Ile Gly Asn Gly Cys Phe Glu Phe Tyr His Lys Cys Asp
            485                 490                 495
Asn Thr Cys Met Glu Ser Val Lys Asn Gly Thr Tyr Asp Tyr Pro Lys
```

```
                    500             505             510
Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 127
<211> LENGTH: 1722
<212> TYPE: DNA
<213> ORGANISM: Artificial Sequence
<220> FEATURE:
<223> OTHER INFORMATION: PDI-H1 Par-N97D+F390D+L429M (nt)

<400> SEQUENCE: 127
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa actatgcaa actaagaggg gtagccccat gcatttggg taaatgtaac       240 attgctggct ggatcctggg aaatccagag tgtgaatcac tctccacagc aagatcatgg     300
tcctacattg tggaaacatc taattcagac aatggaacgt gttacccagg agatttcatc     360
gattatgagg agctaagaga gcaattgagc tcagtgtcat catttgaaag gtttgagata     420
ttccccaaga caagttcatg gcccaatcat gactcgaaca aggtgtaac ggcagcatgt      480 cctcacgctg agcaaaaag cttctacaaa aacttgatat ggctagttaa aaaaggaaat      540
tcatacccaa agcttaacca aacctacatt aatgataaag ggaagaagt cctcgtgctg     600 tggggcattc accatccatc tactactgct gaccaacaaa gtctctatca gaatgcagat     660
gcatatgttt tgtggggac atcaagatac agcaagaagt tcaagccgga aatagcaaca     720
agacccaaag tgagggatca agaagggaga atgaactatt actggacact agtagagccg     780
ggagacaaaa taacattcga agcaactgga atctagtgg taccgagata tgcattcaca     840
atggaaagaa atgctggatc tggtattatc atttcagata caccagtcca cgattgcaat     900
acaacttgtc agacacccga gggtgctata acaccagcc tcccatttca gaatgtgcat     960
ccgatcacaa ttggaaaatg tccaaagtat gtaaaaagca caaaattgag actggccaca    1020
ggattgagga atgttccgtc tattcaatct agaggcctat tcggggccat tgccggcttc    1080
attgaagggg gtggacagg gatggtagat ggatggtacg gttatcacca tcaaaatgag     1140
caggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa agttgatga tggtttcctg    1320 gacatttgga cttacaatgc cgaactgttg gttctaatgg aaaatgaaag aactttggac    1380
tatcacgatt caaatgtgaa gaacttgtat gaaaaagtaa gaaccagtt aaaaaacaat    1440 gccaaggaaa ttggaaacgg ctgctttgaa ttttaccaca atgcgataa cacgtgcatg    1500 gaaagtgtca aaatgggac ttatgactac ccaaaatact cagaggaagc aaaattaaac    1560
agagaaaaaa tagatgggggt aaagctgaa tcaacaagga tttaccagat tttggcgatc    1620
tattcaactg tcgccagttc attggtactg gtagtctccc tgggggcaat cagcttctgg    1680
```
atgtgctcta atgggtctct acagtgtaga atatgtattt aa　　　　　　　　　　　　　　1722

<210> SEQ ID NO 128
<211> LENGTH: 573
<212> TYPE: PRT
<213> ORGANISM: Artificial Sequence
<220> FEATURE:
<223> OTHER INFORMATION: PDI-H1 Par-N97D+F390D+L429M (aa)

<400> SEQUENCE: 128

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Thr Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
    515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 129
<211> LENGTH: 1722
<212> TYPE: DNA
<213> ORGANISM: Artificial Sequence
<220> FEATURE:
<223> OTHER INFORMATION: PDI-H1 Par-N97D+K374E+F390D+L429M (nt)

<400> SEQUENCE: 129

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga acaattcaac agacactgta | 120 |
| gacacagtac tagaaaagaa tgtaacagta acacactctg ttaaccttct ggaagacaag | 180 |
| cataacggaa actatgcaa actaagaggg gtagccccat gcatttggg taaatgtaac | 240 |
| attgctggct ggatcctggg aaatccagag tgtgaatcac tctccacagc aagatcatgg | 300 |
| tcctacattg tggaaacatc taattcagac aatggaacgt gttacccagg agatttcatc | 360 |
| gattatgagg agctaagaga gcaattgagc tcagtgtcat catttgaaag gtttgagata | 420 |
| ttccccaaga caagttcatg gcccaatcat gactcgaaca aaggtgtaac ggcagcatgt | 480 |
| cctcacgctg agcaaaaag cttctacaaa aacttgatat ggctagttaa aaaggaaat | 540 |
| tcatacccaa agcttaacca aacctacatt aatgataaag ggaagaagt cctcgtgctg | 600 |
| tggggcattc accatccatc tactactgct gaccaacaaa gtctctatca gaatgcagat | 660 |
| gcatatgttt ttgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga aatctagtgg taccgagata tgcattcaca | 840 |

```
atggaaagaa atgctggatc tggtattatc atttcagata caccagtcca cgattgcaat    900
acaacttgtc agacacccga gggtgctata acaccagcc tcccatttca gaatgtgcat     960
ccgatcacaa ttggaaaatg tccaaagtat gtaaaaagca caaaattgag actggccaca   1020
ggattgagga atgttccgtc tattcaatct agaggcctat tcggggccat tgccggcttc   1080
attgaagggg ggtggacagg gatggtagat ggatggtacg ttatcacca tcaaaatgag    1140
cagggggtcag atatgcagc cgacctgaag agcacacaaa atgccattga cgagattact   1200
aacaaagtaa attctgttat tgaaaagatg aatacacagg acacagcagt gggtaaagag   1260
ttcaaccacc tggaaaaaag aatagagaat ctaaataaaa aagttgatga tggtttcctg   1320
gacatttgga cttacaatgc cgaactgttg gttctaatgg aaaatgaaag aactttggac   1380
tatcacgatt caaatgtgaa gaacttgtat gaaaaagtaa gaaccagtt aaaaaacaat   1440
gccaaggaaa ttggaaacgg ctgctttgaa ttttaccaca aatgcgataa cacgtgcatg   1500
gaaagtgtca aaatgggac ttatgactac ccaaaatact cagaggaagc aaaattaaac   1560
agagaaaaaa tagatggggt aaagctggaa tcaacaagga tttaccagat tttggcgatc   1620
tattcaactg tcgccagttc attggtactg gtagtctccc tgggggcaat cagcttctgg   1680
atgtgctcta atgggtctct acagtgtaga atatgtattt aa                      1722
```

<210> SEQ ID NO 130
<211> LENGTH: 549
<212> TYPE: PRT
<213> ORGANISM: Alphainfluenza A virus

<400> SEQUENCE: 130

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
```

```
            210                 215                 220
Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ser Asp Thr Pro Val
                260                 265                 270

His Asp Cys Asn Thr Thr Cys Gln Thr Pro Lys Gly Ala Ile Asn Thr
            275                 280                 285

Ser Leu Pro Phe Gln Asn Ile His Pro Ile Thr Ile Gly Lys Cys Pro
        290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
                340                 345                 350

His Gln Asn Glu Gln Gly Ser Gly Tyr Ala Ala Asp Leu Lys Ser Thr
            355                 360                 365

Gln Asn Ala Ile Asp Glu Ile Thr Asn Lys Val Asn Ser Val Ile Glu
        370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Tyr His Asp Ser Asn Val Lys Asn Leu Tyr Glu Lys
            435                 440                 445

Val Arg Ser Gln Leu Lys Asn Asn Ala Lys Glu Ile Gly Asn Gly Cys
450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
        530                 535                 540

Cys Arg Ile Cys Ile
545

<210> SEQ ID NO 131
<211> LENGTH: 549
<212> TYPE: PRT
<213> ORGANISM: Alphainfluenza A virus

<400> SEQUENCE: 131

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30
```

```
Leu Glu Asp Lys His Asn Gly Lys Leu Cys Lys Leu Arg Gly Val Pro
         35                  40                  45

Pro Leu His Leu Gly Lys Cys Asn Ile Ala Gly Trp Ile Leu Gly Asn
 50                  55                  60

Pro Glu Cys Glu Pro Leu Ser Thr Ala Ser Ser Trp Ser Tyr Ile Val
 65              70                  75                  80

Glu Thr Ser Ser Ser Asp Asn Gly Thr Cys Tyr Pro Gly Asp Phe Ile
                 85                  90                  95

Asn Tyr Glu Glu Leu Arg Glu Gln Leu Ser Ser Val Ser Ser Phe Glu
             100                 105                 110

Arg Phe Glu Ile Phe Pro Lys Thr Ser Ser Trp Pro Asn His Asp Ser
         115                 120                 125

Asn Lys Gly Val Thr Ala Ala Cys Pro His Ala Gly Ala Lys Ser Phe
 130                 135                 140

Tyr Lys Asn Leu Ile Trp Leu Val Lys Lys Gly Asn Ser Tyr Pro Lys
 145                 150                 155                 160

Leu Ser Gln Ser Tyr Ile Asn Asp Lys Gly Lys Glu Val Leu Val Leu
                 165                 170                 175

Trp Gly Ile His His Pro Ser Thr Thr Ala Asp Gln Gln Ser Leu Tyr
             180                 185                 190

Gln Asn Ala Asp Ala Tyr Val Phe Val Gly Thr Ser Arg Tyr Ser Lys
         195                 200                 205

Lys Phe Lys Pro Glu Ile Ala Ile Arg Pro Lys Val Arg Asp Gln Glu
 210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                 245                 250                 255

Met Glu Arg Asn Ala Gly Ser Gly Ile Ile Ile Ser Asp Thr Pro Val
             260                 265                 270

His Asp Cys Asn Thr Thr Cys Gln Thr Pro Glu Gly Ala Ile Asn Thr
         275                 280                 285

Ser Leu Pro Phe Gln Asn Ile His Pro Ile Thr Ile Gly Lys Cys Pro
 290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                 325                 330                 335

Ile Glu Gly Gly Trp Thr Gly Met Val Asp Gly Trp Tyr Gly Tyr His
             340                 345                 350

His Gln Asn Glu Gln Gly Ser Gly Tyr Ala Ala Asp Gln Lys Ser Thr
         355                 360                 365

Gln Ser Ala Ile Asp Lys Ile Thr Asn Lys Val Asn Ser Val Ile Glu
 370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                 405                 410                 415

Asp Ile Trp Thr Tyr Asn Ala Glu Leu Leu Val Leu Leu Glu Asn Glu
             420                 425                 430

Arg Thr Leu Asp Tyr His Asp Ser Asn Val Lys Asn Leu Tyr Glu Lys
         435                 440                 445

Val Arg Asn Gln Leu Lys Asn Asn Ala Lys Glu Ile Gly Asn Gly Cys
```

```
            450                 455                 460
Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Ala Lys Leu Asn
                485                 490                 495

Arg Glu Lys Ile Asp Gly Val Lys Leu Glu Ser Thr Arg Ile Tyr Gln
                500                 505                 510

Ile Leu Ala Ile Tyr Ser Thr Val Ala Ser Ser Leu Val Leu Val Val
            515                 520                 525

Ser Leu Gly Ala Ile Ser Phe Trp Met Cys Ser Asn Gly Ser Leu Gln
            530                 535                 540

Cys Arg Ile Cys Ile
545

<210> SEQ ID NO 132
<211> LENGTH: 549
<212> TYPE: PRT
<213> ORGANISM: Alphainfluenza A virus

<400> SEQUENCE: 132

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
                35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Ser Ser Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
                100                 105                 110

Arg Phe Glu Ile Phe Pro Lys Thr Ser Ser Trp Pro Asn His Asp Ser
            115                 120                 125

Asn Lys Gly Val Thr Ala Ala Cys Pro His Ala Gly Ala Lys Ser Phe
130                 135                 140

Tyr Lys Asn Leu Ile Trp Leu Thr Lys Lys Gly Asn Ser Tyr Pro Lys
145                 150                 155                 160

Leu Ser Gln Ser Tyr Ile Asn Asp Lys Gly Lys Glu Ile Leu Val Leu
                165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Ile Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270
```

His Asp Cys Asn Thr Thr Cys Gln Thr Pro Glu Gly Ala Ile Asn Thr
            275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Asn Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Gly Glu Ala Lys Leu Asn
                485                 490                 495

Arg Glu Lys Ile Glu Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
    530                 535                 540

Cys Arg Ile Cys Ile
545

<210> SEQ ID NO 133
<211> LENGTH: 549
<212> TYPE: PRT
<213> ORGANISM: Alphainfluenza A virus

<400> SEQUENCE: 133

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

```
Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Asn Gln Ser Tyr Val Asn Asp Lys Gly Lys Glu Val Leu Val Leu
                165                 170                 175

Trp Gly Ile His His Pro Pro Thr Thr Ala Asp Gln Gln Ser Leu Tyr
            180                 185                 190

Gln Asn Ala Asp Ala Tyr Val Phe Val Gly Thr Ser Lys Tyr Ser Lys
        195                 200                 205

Lys Phe Lys Pro Glu Ile Ala Thr Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Glu Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Asn Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Lys Ile Asp Gly Val Lys Leu Glu Ser Thr Arg Ile Tyr Gln
            500                 505                 510
```

```
Ile Leu Ala Ile Tyr Ser Thr Val Ala Ser Ser Leu Val Val Val
            515                 520                 525

Ser Leu Gly Ala Ile Ser Phe Trp Met Cys Ser Asn Gly Ser Leu Gln
530                 535                 540

Cys Arg Ile Cys Ile
545

<210> SEQ ID NO 134
<211> LENGTH: 549
<212> TYPE: PRT
<213> ORGANISM: Alphainfluenza A virus

<400> SEQUENCE: 134

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys
145                 150                 155                 160

Leu Asn Gln Ser Tyr Ile Asn Asp Lys Gly Lys Glu Val Leu Val Leu
                165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Thr Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Glu Gly Ala Ile Asn Thr
        275                 280                 285

Ser Leu Pro Phe Gln Asn Ile His Pro Ile Thr Ile Gly Lys Cys Pro
290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335
```

Ile Glu Gly Gly Trp Thr Gly Met Val Asp Gly Trp Tyr Gly Tyr His
                340                 345                 350

His Gln Asn Glu Gln Gly Ser Gly Tyr Ala Ala Asp Leu Lys Ser Thr
                355                 360                 365

Gln Asn Ala Ile Asp Lys Ile Thr Asn Lys Val Asn Ser Val Ile Glu
370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Tyr His Asp Ser Asn Val Lys Asn Leu Tyr Glu Lys
                435                 440                 445

Val Arg Asn Gln Leu Lys Asn Asn Ala Lys Glu Ile Gly Asn Gly Cys
450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Lys Ile Asp Gly Val Lys Leu Glu Ser Thr Arg Ile Tyr Gln
                500                 505                 510

Ile Leu Ala Ile Tyr Ser Thr Val Ala Ser Ser Leu Val Leu Val Val
                515                 520                 525

Ser Leu Gly Ala Ile Ser Phe Trp Met Cys Ser Asn Gly Ser Leu Gln
530                 535                 540

Cys Arg Ile Cys Ile
545

<210> SEQ ID NO 135
<211> LENGTH: 549
<212> TYPE: PRT
<213> ORGANISM: Alphainfluenza A virus

<400> SEQUENCE: 135

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Arg Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
130                 135                 140

Tyr Lys Asn Leu Ile Trp Leu Val Lys Lys Gly Asn Ser Tyr Pro Lys

```
            145                 150                 155                 160
Leu Asn Gln Ser Tyr Ile Asn Asp Lys Gly Lys Glu Val Leu Val Leu
                    165                 170                 175

Trp Gly Ile His His Pro Ser Thr Thr Ala Asp Gln Gln Ser Leu Tyr
                    180                 185                 190

Gln Asn Ala Asp Ala Tyr Val Phe Val Gly Thr Ser Arg Tyr Ser Lys
                    195                 200                 205

Lys Phe Lys Pro Glu Ile Ala Thr Arg Pro Lys Val Arg Asp Gln Glu
            210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                    245                 250                 255

Met Glu Arg Asn Ala Gly Ser Gly Ile Ile Ile Ser Asp Thr Pro Val
                    260                 265                 270

His Asp Cys Asn Thr Thr Cys Gln Thr Pro Glu Gly Ala Ile Asn Thr
                    275                 280                 285

Ser Leu Pro Phe Gln Asn Val His Pro Ile Thr Ile Gly Lys Cys Pro
            290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                    325                 330                 335

Ile Glu Gly Gly Trp Thr Gly Met Val Asp Gly Trp Tyr Gly Tyr His
                    340                 345                 350

His Gln Asn Glu Gln Gly Ser Gly Tyr Ala Ala Asp Leu Lys Ser Thr
                    355                 360                 365

Gln Asn Ala Ile Asp Lys Ile Thr Asn Lys Val Asn Ser Val Ile Glu
            370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                    405                 410                 415

Asp Ile Trp Thr Tyr Asn Ala Glu Leu Leu Val Leu Leu Glu Asn Glu
                    420                 425                 430

Arg Thr Leu Asp Tyr His Asp Ser Asn Val Lys Asn Leu Tyr Glu Lys
                    435                 440                 445

Val Arg Asn Gln Leu Lys Asn Asn Ala Lys Glu Ile Gly Asn Gly Cys
            450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                    485                 490                 495

Arg Glu Lys Ile Asp Gly Val Lys Leu Glu Ser Thr Arg Ile Tyr Gln
                    500                 505                 510

Ile Leu Ala Ile Tyr Ser Thr Val Ala Ser Ser Leu Val Leu Val Val
                    515                 520                 525

Ser Leu Gly Ala Ile Ser Phe Trp Met Cys Ser Asn Gly Ser Leu Gln
            530                 535                 540

Cys Arg Ile Cys Ile
545

<210> SEQ ID NO 136
```

```
<211> LENGTH: 1701
<212> TYPE: DNA
<213> ORGANISM: Alphainfluenza A virus

<400> SEQUENCE: 136
atgaaggcaa tactagtagt tctgctatat acatttacaa ccgcaaatgc agacacatta      60
tgtataggtt atcatgcgaa caattcaaca gacactgtag acacagtact agaaaagaat     120
gtaacagtaa cacactctgt taaccttctg gaagacaagc ataacggaaa actatgcaaa     180
ctaagagggg tagccccatt gcatttgggt aaatgtaaca ttgctggctg gatcctggga     240
aatccagagt gtgaatcact ctccacagca agttcatggt cctacattgt ggaaacatct     300
aattcagaca atggaacgtg ttacccagga gatttcatca attatgagga gctaagagag     360
caattgagct cagtgtcatc atttgaaagg tttgagatat tccccaagac aagttcatgg     420
cccaatcatg actcgaacaa aggtgtaacg gcagcatgtc ctcacgctgg agcaaaaagc     480
ttctacaaaa acttgatatg gctagttaaa aaggaaatt cataccccaaa gcttaaccaa     540
tcctacatta tgataaagg gaagaagtc ctcgtgctgt ggggcattca ccatccatct     600
actactgctg accaacaaag tctctatcag aatgcagatg catatgtttt tgtggggaca     660
tcaagataca gcaagaagtt caagccggaa atagcaacaa acccaaagt gagggatcaa     720
gaagggagaa tgaactatta ctggacacta gtagagccgg agacaaaat aacattcgaa     780
gcaactgaa atcagtggt accgagatat gcattcacaa tggaaagaaa tgctggatct     840
ggtattatca tttcagatac accagtccac gattgcaata caacttgtca gacacccgag     900
ggtgctataa acaccagcct cccatttcag aatatacatc cgatcacaat ggaaaaatgt     960
ccaaagtatg taaaaagcac aaaattgaga ctggccacag gattgaggaa tgttccgtct    1020
attcaatcta gaggcctatt cggggccatt gccggcttca ttgaagggg gtggacaggg    1080
atggtagatg gatggtacgg ttatcaccat caaaatgagc aggggtcagg atatgcagcc    1140
gacctgaaga gcacacaaaa tgccattgac aagattacta caaagtaaa ttctgttatt    1200
gaaaagatga atacacagtt cacagcagtg gtaaagagt caaccacct ggaaaaaaga    1260
atagagaatc taaataaaaa agttgatgat ggtttcctgg acatttggac ttacaatgcc    1320
gaactgttgg ttctattgga aaatgaaaga actttggact atcacgattc aaatgtgaag    1380
aacttgtatg aaaaagtaag aaaccagtta aaaaacaatg ccaaggaaat tggaaacggc    1440
tgctttgaat tttaccacaa atgcgataac acgtgcatgg aaagtgtcaa aatgggact    1500
tatgactacc caaatactc agaggaagca aaattaaaca gagaaaaaat agatgggta    1560
aagctggaat caacaaggat ttaccagatt ttggcgatct attcaactgt cgccagttca    1620
ttggtactgg tagtctccct gggggcaatc agcttctgga tgtgctctaa tgggtctcta    1680
cagtgtagaa tatgtattta a                                              1701

<210> SEQ ID NO 137
<211> LENGTH: 1701
<212> TYPE: DNA
<213> ORGANISM: Alphainfluenza A virus

<400> SEQUENCE: 137
atgaaggcaa tactagtagt tctgctatat acatttgcaa ccgcaaatgc agacacatta      60
tgtataggtt atcatgcgaa caattcaaca gacactgtag acacagtact agaaaagaat     120
gtaacagtaa cacactctgt taaccttcta gaagacaagc ataacgggaa actatgcaaa     180
ctaagagggg tagccccatt gcatttgggt aaatgtaaca ttgctggctg gatcctggga     240
```

-continued

```
aatccagagt gtgaatcact ctccacagca agctcatggt cctacattgt ggaaacacct      300
agttcagaca atggaacgtg ttacccagga gatttcatcg attatgagga gctaagagag      360
caattgagct cagtgtcatc atttgaaagg tttgagatat tccccaagac aagttcatgg      420
cccaatcatg actcgaacaa aggtgtaacg gcagcatgtc ctcatgctgg agcaaaaagc      480
ttctacaaaa atttaatatg gctagttaaa aaaggaaatt catacccaaa gctcagcaaa      540
tcctacatta atgataaagg gaagaagtc ctcgtgctat ggggcattca ccatccatct       600
actagtgctg accaacaaag tctctatcag aatgcagatg catatgtttt tgtggggtca      660
tcaagataca gcaagaagtt caagccggaa atagcaataa gacccaaagt gagggrtcra     720
gaagggagaa tgaactatta ctggacacta gtagagccgg agacaaaat aacattcgaa       780
gcaactggaa atctagtggt accgagatat gcattcgcaa tggaaagaaa tgctggatct      840
ggtattatca tttcagatac accagtccac gattgcaata aacttgtca acacccaag       900
ggtgctataa acaccagcct cccatttcag aatatacatc cgatcacaat ggaaaatgt      960
ccaaaatatg taaaaagcac aaaattgaga ctggccacag gattgaggaa tatcccgtct     1020
attcaatcta gaggcctatt tggggccatt gccggtttca ttgaaggggg gtggacaggg     1080
atggtagatg gatggtacgg ttatcaccat caaaatgagc aggggtcagg atatgcagcc     1140
gacctgaaga gcacacagaa tgccattgac gagattacta caaagtaaa ttctgttatt     1200
gaaagatga atacacagtt cacagcagta ggtaaagagt caaccacct ggaaaaaaga      1260
atagagaatt taaataaaaa agttgatgat ggtttcctgg acatttggac ttacaatgcc     1320
gaactgttgg ttctattgga aaatgaaaga actttggact accacgattc aaatgtgaag     1380
aacttatatg aaaaggtaag aagccagcta aaaaacaatg ccaaggaaat tggaaacggc     1440
tgctttgaat tttaccacaa atgcgataac acgtgcatgg aaagtgtcaa aaatgggact     1500
tatgactacc caaaatactc agaggaagca aaattaaaca gagaagaaat agatggggta     1560
aagctggaat caacaaggat ttaccagatt ttggcgatct attcaactgt cgccagttca     1620
ttggtactgg tagtctccct gggggcaatc agtttctgga tgtgctctaa tgggtctcta     1680
cagtgtagaa tatgtattta a                                                1701
```

<210> SEQ ID NO 138
<211> LENGTH: 549
<212> TYPE: PRT
<213> ORGANISM: Alphainfluenza A virus

<400> SEQUENCE: 138

```
Asp Thr Leu Cys Ile Gly Tyr His Ala Asn Asn Ser Thr Asp Thr

```
Arg Phe Glu Ile Phe Pro Lys Thr Ser Ser Trp Pro Asn His Asp Ser
            115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Asn Gln Thr Tyr Ile Asn Asp Lys Gly Lys Glu Val Leu Val Leu
                165                 170                 175

Trp Gly Ile His His Pro Ser Thr Thr Ala Asp Gln Gln Ser Leu Tyr
                180                 185                 190

Gln Asn Ala Asp Ala Tyr Val Phe Val Gly Thr Ser Arg Tyr Ser Lys
        195                 200                 205

Lys Phe Lys Pro Glu Ile Ala Thr Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
                260                 265                 270

His Asp Cys Asn Thr Thr Cys Gln Thr Pro Glu Gly Ala Ile Asn Thr
                275                 280                 285

Ser Leu Pro Phe Gln Asn Val His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
                340                 345                 350

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Tyr His Asp Ser Asn Val Lys Asn Leu Tyr Glu Lys
        435                 440                 445

Val Arg Asn Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Lys Ile Asp Gly Val Lys Leu Glu Ser Thr Arg Ile Tyr Gln
                500                 505                 510

Ile Leu Ala Ile Tyr Ser Thr Val Ala Ser Ser Leu Val Leu Val Val
            515                 520                 525
```

```
Ser Leu Gly Ala Ile Ser Phe Trp Met Cys Ser Asn Gly Ser Leu Gln
    530                 535                 540
Cys Arg Ile Cys Ile
545

<210> SEQ ID NO 139
<211> LENGTH: 549
<212> TYPE: PRT
<213> ORGANISM: Alphainfluenza A virus

<400> SEQUENCE: 139

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Arg Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Asn Gln Ser Tyr Ile Asn Asp Lys Gly Lys Glu Val Leu Val Leu
                165                 170                 175

Trp Gly Ile His His Pro Ser Thr Thr Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Thr Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Thr
                245                 250                 255

Met Glu Arg Asn Ala Gly Ser Gly Ile Ile Ile Ser Asp Thr Pro Val
            260                 265                 270

Gln Asp Cys Asn Thr Thr Cys Gln Thr Pro Glu Gly Ala Ile Asn Thr
        275                 280                 285

Ser Leu Pro Phe Gln Asn Val His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350
```

His Gln Asn Glu Gln Gly Ser Gly Tyr Ala Ala Asp Leu Lys Ser Thr
        355                 360                 365

Gln Asn Ala Ile Asp Lys Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Asn Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Ala Lys Leu Asn
                485                 490                 495

Arg Glu Lys Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
    530                 535                 540

Cys Arg Ile Cys Ile
545

<210> SEQ ID NO 140
<211> LENGTH: 573
<212> TYPE: PRT
<213> ORGANISM: Artificial Sequence
<220> FEATURE:
<223> OTHER INFORMATION: PDI-H1 Par-N97D+K374E+F390D+L429M (aa)

<400> SEQUENCE: 140

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

-continued

Pro His Ala Gly Ala Lys Ser Phe Tyr Lys Asn Leu Ile Trp Leu Val
            165                 170                 175

Lys Lys Gly Asn Ser Tyr Pro Lys Leu Asn Gln Thr Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
            245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val His Asp Cys Asn Thr Thr Cys Gln
290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
            325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
            405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
            485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
            530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
            565                 570

<210> SEQ ID NO 141
<211> LENGTH: 1722
<212> TYPE: DNA
<213> ORGANISM: Artificial Sequence
<220> FEATURE:
<223> OTHER INFORMATION: PDI-H1 Nor-F390D+L429M (nt)

<400> SEQUENCE: 141

```
atggcgaaaa acgttgcgat tttcggctta ttgttttctc ttcttgtgtt ggttccttct      60
cagatcttcg cggacacatt atgtataggt tatcatgcga acaattcaac agacactgta     120
gacacagtac tagaaaagaa tgtaacagta acacactctg ttaaccttct ggaagacaag     180
cataacggaa actatgcaa actaagaggg gtagccccat gcatttggg taaatgtaac       240
attgctggct ggatcctggg aaatccagag tgtgaatcac tctccacagc aagatcatgg     300
tcctacattg tggaaacatc taattcagac aatggaacgt gttacccagg agatttcatc     360
aattatgagg agctaagaga gcaattgagc tcagtgtcat catttgaaag gtttgagata     420
ttccccaaga caagttcatg gcccaatcat gactcgaaca aggtgtaac ggcagcatgt      480
cctcacgctg agcaaaaag cttctacaaa aacttgatat ggctagttaa aaaaggaaat     540
tcatacccaa agcttaacca atcctacatt aatgataaag gaaagaagt cctcgtgctg     600
tggggcattc accatccatc tactactgct gaccaacaaa gtctctatca gaatgcagat     660
gcatatgttt tgtggggac atcaagatac agcaagaagt tcaagccgga atagcaaca     720
agacccaaag tgagggatca agaagggaga tgaactatt actggacact agtagagccg     780
ggagacaaaa taacattcga agcaactgga atctagtgg taccgagata tgcattcaca     840
atggaaagaa atgctggatc tggtattatc atttcagata caccagtcca ggattgcaat     900
acaacttgtc agacacccga gggtgctata acaccagcc tcccatttca gaatgtgcat     960
ccgatcacaa ttggaaaatg tccaaagtat gtaaaaagca caaaattgag actggccaca    1020
ggattgagga tgttccgtc tattcaatct agaggcctat tcggggccat tgccggcttc    1080
attgaagggg ggtggacagg gatggtagat ggatggtacg ttatcacca tcaaaatgag    1140
caggggtcag gatatgcagc cgacctgaag agcacacaaa atgccattga caagattact    1200
aacaaagtaa attctgttat tgaaaagatg aatacacagg acacagcagt gggtaaagag    1260
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaccagtt aaaaaacaat    1440
gccaaggaaa ttggaaacgg ctgctttgaa ttttaccaca atgcgataa cacgtgcatg    1500
gaaagtgtca aaatgggac ttatgactac ccaaaatact cagaggaagc aaaattaaac    1560
agagaaaaaa tagatgggt aaagctggaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                       1722
```

<210> SEQ ID NO 142
<211> LENGTH: 573
<212> TYPE: PRT
<213> ORGANISM: Artificial Sequence
<220> FEATURE:
<223> OTHER INFORMATION: PDI-H1 Nor-F390D+L429M (aa)

<400> SEQUENCE: 142

Met Ala Lys Asn Val Ala Ile Phe Gly Leu Leu Phe Ser Leu Leu Val

-continued

```
1               5                   10                  15
Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
 50                  55                  60

Leu Cys Lys Leu Arg Gly Val Ala Pro Leu His Leu Gly Lys Cys Asn
 65                  70                  75                  80

Ile Ala Gly Trp Ile Leu Gly Asn Pro Glu Cys Glu Ser Leu Ser Thr
            85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
            115                 120                 125

Leu Ser Ser Val Ser Ser Phe Glu Arg Phe Glu Ile Phe Pro Lys Thr
            130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
            165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
            195                 200                 205

Thr Ala Asp Gln Gln Ser Leu Tyr Gln Asn Ala Asp Ala Tyr Val Phe
 210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
            245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
            275                 280                 285

Ile Ile Ile Ser Asp Thr Pro Val Gln Asp Cys Asn Thr Thr Cys Gln
            290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
            325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
            370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
            405                 410                 415

Val Gly Lys Glu Phe Asn His Leu Glu Lys Arg Ile Glu Asn Leu Asn
            420                 425                 430
```

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
            485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
        530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
            565                 570

<210> SEQ ID NO 143
<211> LENGTH: 1722
<212> TYPE: DNA
<213> ORGANISM: Artificial Sequence
<220> FEATURE:
<223> OTHER INFORMATION: PDI-H1 Nor-K374E+F390D+L429M (nt)

<400> SEQUENCE: 143

| | | |
|---|---|---|
| atggcgaaaa acgttgcgat tttcggctta ttgttttctc ttcttgtgtt ggttccttct | 60 |
| cagatcttcg cggacacatt atgtataggt tatcatgcga caattcaac agacactgta | 120 |
| gacacagtac tagaaaagaa tgtaacagta acacactctg ttaaccttct ggaagacaag | 180 |
| cataacggaa actatgcaa ctaagagggg gtagccccat tgcatttggg taaatgtaac | 240 |
| attgctggct ggatcctggg aaatccagag tgtgaatcac tctccacagc aagatcatgg | 300 |
| tcctacattg tggaaacatc taattcagac aatggaacgt gttacccagg agatttcatc | 360 |
| aattatgagg agctaagaga gcaattgagc tcagtgtcat catttgaaag gtttgagata | 420 |
| ttccccaaga caagttcatg gcccaatcat gactcgaaca aggtgtaac ggcagcatgt | 480 |
| cctcacgctg agcaaaaag cttctacaaa aacttgatat ggctagttaa aaaaggaaat | 540 |
| tcatacccaa agcttaacca atcctacatt aatgataaag ggaaagaagt cctcgtgctg | 600 |
| tggggcattc accatccatc tactactgct gaccaacaaa gtctctatca gaatgcagat | 660 |
| gcatatgttt tgtggggac atcaagatac agcaagaagt tcaagccgga aatagcaaca | 720 |
| agacccaaag tgagggatca agaagggaga atgaactatt actggacact agtagagccg | 780 |
| ggagacaaaa taacattcga agcaactgga aatctagtgg taccgagata tgcattcaca | 840 |
| atggaaagaa atgctggatc tggtattatc atttcagata caccagtcca ggattgcaat | 900 |
| acaacttgtc agacacccga gggtgctata aacaccagcc tcccatttca gaatgtgcat | 960 |
| ccgatcacaa ttggaaaatg tccaaagtat gtaaaaagca caaaattgag actggccaca | 1020 |
| ggattgagga atgttccgtc tattcaatct agaggcctat tcggggccat tgccggcttc | 1080 |
| attgaagggg gtggacagg gatggtagat ggatggtacg ttatcacca tcaaaatgag | 1140 |
| caggggtcag gatatgcagc cgacctgaag agcacacaaa atgccattga cgagattact | 1200 |
| aacaaagtaa attctgttat tgaaaagatg aatacacagg acacagcagt gggtaaagag | 1260 |

```
ttcaaccacc tggaaaaaag aatagagaat ctaaataaaa aagttgatga tggtttcctg    1320
gacatttgga cttacaatgc cgaactgttg gttctaatgg aaaatgaaag aactttggac    1380
tatcacgatt caaatgtgaa gaacttgtat gaaaaagtaa gaaaccagtt aaaaaacaat    1440
gccaaggaaa ttggaaacgg ctgctttgaa ttttaccaca aatgcgataa cacgtgcatg    1500
gaaagtgtca aaatgggac ttatgactac ccaaaatact cagaggaagc aaaattaaac    1560
agagaaaaaa tagatgggt aaagctgaaa tcaacaagga tttaccagat tttggcgatc    1620
tattcaactg tcgccagttc attggtactg gtagtctccc tgggggcaat cagcttctgg    1680
atgtgctcta atgggtctct acagtgtaga atatgtattt aa                       1722
```

<210> SEQ ID NO 144
<211> LENGTH: 573
<212> TYPE: PRT
<213> ORGANISM: Artificial Sequence
<220> FEATURE:
<223> OTHER INFORMATION: PDI-H1 Nor-K374E+F390D+L429M (aa)

<400> SEQUENCE: 144

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asn Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
    210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
```

```
          275                 280                 285
Ile Ile Ile Ser Asp Thr Pro Val Gln Asp Cys Asn Thr Thr Cys Gln
            290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570

<210> SEQ ID NO 145
<211> LENGTH: 1722
<212> TYPE: DNA
<213> ORGANISM: Artificial Sequence
<220> FEATURE:
<223> OTHER INFORMATION: PDI-H1 Nor-N97D+F390D+L429M (nt)

<400> SEQUENCE: 145
atggcgaaaa acgttgcgat tttcggctta ttgttttctc ttcttgtgtt ggttccttct     60
cagatcttcg cggacacatt atgtataggt tatcatgcga acaattcaac agacactgta    120
gacacagtac tagaaaagaa tgtaacagta acacactctg ttaaccttct ggaagacaag    180
cataacggaa actatgcaa actaagaggg gtagccccat tgcatttggg taaatgtaac    240
attgctggct ggatcctggg aaatccagag tgtgaatcac tctccacagc aagatcatgg    300
tcctacattg tggaaacatc taattcagac aatggaacgt gttacccagg agatttcatc    360
gattatgagg agctaagaga gcaattgagc tcagtgtcat catttgaaag gtttgagata    420
```

```
ttccccaaga caagttcatg gcccaatcat gactcgaaca aaggtgtaac ggcagcatgt      480
cctcacgctg gagcaaaaag cttctacaaa aacttgatat ggctagttaa aaaaggaaat      540
tcatacccaa agcttaacca atcctacatt aatgataaag ggaagaagt cctcgtgctg       600 tggggcattc accatccatc tactactgct gaccaacaaa gtctctatca gaatgcagat      660
gcatatgttt ttgtggggac atcaagatac agcaagaagt tcaagccgga aatagcaaca      720
agacccaaag tgagggatca agaagggaga atgaactatt actggacact agtagagccg      780
ggagacaaaa taacattcga agcaactgga aatctagtgg taccgagata tgcattcaca      840
atggaaagaa atgctggatc tggtattatc atttcagata caccagtcca ggattgcaat      900
acaacttgtc agacacccga gggtgctata acaccagcc tcccatttca gaatgtgcat       960
ccgatcacaa ttgaaaaatg tccaaagtat gtaaaaagca caaattgag actggccaca      1020 ggattgagga atgttccgtc tattcaatct agaggcctat tcggggccat tgccggcttc     1080
attgaagggg ggtggacagg gatggtagat ggatggtacg gttatcacca tcaaaatgag     1140 cagggtcag gatatgcagc cgacctgaag agcacacaaa atgccattga caagattact       1200
aacaaagtaa attctgttat tgaaaagatg aatacacagg acacagcagt gggtaaagag     1260
ttcaaccacc tggaaaaaag aatagagaat ctaaataaaa aagttgatga tggtttcctg     1320
gacatttgga cttacaatgc cgaactgttg gttctaatgg aaaatgaaag aactttggac     1380
tatcacgatt caaatgtgaa gaacttgtat gaaaaagtaa gaaaccagtt aaaaaacaat     1440
gccaaggaaa ttggaaacgg ctgctttgaa ttttaccaca atgcgataaa cacgtgcatg     1500
gaaagtgtca aaaatgggac ttatgactac ccaaaatact cagaggaagc aaaattaaac     1560
agagaaaaaa tagatggggt aaagctggaa tcaacaagga tttaccagat tttggcgatc     1620
tattcaactg tcgccagttc attggtactg gtagtctccc tgggggcaat cagcttctgg     1680
atgtgctcta atgggtctct acagtgtaga atatgtattt aa                        1722
```

<210> SEQ ID NO 146
<211> LENGTH: 573
<212> TYPE: PRT
<213> ORGANISM: Artificial Sequence
<220> FEATURE:
<223> OTHER INFORMATION: PDI-H1 Nor-N97D+F390D+L429M (aa)

<400> SEQUENCE: 146

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Lys His Asn Gly Lys
        50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125
```

```
Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
                180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
                260                 265                 270

Val Val Pro Arg Tyr Ala Phe Thr Met Glu Arg Asn Ala Gly Ser Gly
        275                 280                 285

Ile Ile Ile Ser Asp Thr Pro Val Gln Asp Cys Asn Thr Thr Cys Gln
290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
                340                 345                 350

Leu Phe Gly Ala Ile Ala Gly Phe Ile Glu Gly Gly Trp Thr Gly Met
            355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Lys Ile Thr
385                 390                 395                 400

Asn Lys Val Asn Ser Val Ile Glu Lys Met Asn Thr Gln Asp Thr Ala
                405                 410                 415

Val Gly Lys Glu Phe Asn His Leu Glu Lys Arg Ile Glu Asn Leu Asn
                420                 425                 430

Lys Lys Val Asp Asp Gly Phe Leu Asp Ile Trp Thr Tyr Asn Ala Glu
        435                 440                 445

Leu Leu Val Leu Met Glu Asn Glu Arg Thr Leu Asp Tyr His Asp Ser
450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
                500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
530                 535                 540

Ala Ser Ser Leu Val Leu Val Val Ser Leu Gly Ala Ile Ser Phe Trp
```

545             550             555             560
Met Cys Ser Asn Gly Ser Leu Gln Cys Arg Ile Cys Ile
                565             570

<210> SEQ ID NO 147
<211> LENGTH: 1722
<212> TYPE: DNA
<213> ORGANISM: Artificial Sequence
<220> FEATURE:
<223> OTHER INFORMATION: PDI-H1 Nor-N97D+K374E+F390D+L429M (nt)

<400> SEQUENCE: 147

| | | | | | |
|---|---|---|---|---|---|
| atggcgaaaa | acgttgcgat | ttcggctta | ttgttttctc | ttcttgtgtt | ggttccttct | 60 |
| cagatcttcg | cggacacatt | atgtataggt | tatcatgcga | acaattcaac | agacactgta | 120 |
| gacacagtac | tagaaaagaa | tgtaacagta | acacactctg | ttaaccttct | ggaagacaag | 180 |
| cataacggaa | actatgcaa | actaagaggg | gtagccccat | tgcatttggg | taaatgtaac | 240 |
| attgctggct | ggatcctggg | aaatccagag | tgtgaatcac | tctccacagc | aagatcatgg | 300 |
| tcctacattg | tggaaacatc | taattcagac | aatggaacgt | gttacccagg | agatttcatc | 360 |
| gattatgagg | agctaagaga | gcaattgagc | tcagtgtcat | catttgaaag | gtttgagata | 420 |
| ttccccaaga | caagttcatg | gcccaatcat | gactcgaaca | aggtgtaac | ggcagcatgt | 480 |
| cctcacgctg | gagcaaaaag | cttctacaaa | aacttgatat | ggctagttaa | aaaggaaat | 540 |
| tcatacccaa | agcttaacca | atcctacatt | aatgataaag | ggaaagaagt | cctcgtgctg | 600 |
| tggggcattc | accatccatc | tactactgct | gaccaacaaa | gtctctatca | gaatgcagat | 660 |
| gcatatgttt | ttgtggggac | atcaagatac | agcaagaagt | tcaagccgga | aatagcaaca | 720 |
| agacccaaag | tgagggatca | agaagggaga | atgaactatt | actggacact | agtagagccg | 780 |
| ggagacaaaa | taacattcga | agcaactgga | aatctagtgg | taccgagata | tgcattcaca | 840 |
| atggaaagaa | atgctggatc | tggtattatc | atttcagata | caccagtcca | ggattgcaat | 900 |
| acaacttgtc | agacacccga | gggtgctata | acaccagcc | tcccatttca | gaatgtgcat | 960 |
| ccgatcacaa | ttggaaaatg | tccaaagtat | gtaaaaagca | caaaattgag | actggccaca | 1020 |
| ggattgagga | atgttccgtc | tattcaatct | agaggcctat | tcggggccat | tgccggcttc | 1080 |
| attgaagggg | ggtggacagg | gatggtagat | ggatggtacg | gttatcacca | tcaaaatgag | 1140 |
| caggggtcag | gatatgcagc | cgacctgaag | agcacacaaa | atgccattga | cgagattact | 1200 |
| aacaaagtaa | attctgttat | tgaaaagatg | aatacacagg | acacagcagt | gggtaaagag | 1260 |
| ttcaaccacc | tggaaaaaag | aatagagaat | ctaaataaaa | aagttgatga | tggtttcctg | 1320 |
| gacatttgga | cttacaatgc | cgaactgttg | gttctaatgg | aaaatgaaag | aactttggac | 1380 |
| tatcacgatt | caaatgtgaa | gaacttgtat | gaaaagtaa | gaaccagtt | aaaaaacaat | 1440 |
| gccaaggaaa | ttggaaacgg | ctgctttgaa | ttttaccaca | aatgcgataa | cacgtgcatg | 1500 |
| gaaagtgtca | aaaatgggac | ttatgactac | ccaaaatact | cagaggaagc | aaaattaaac | 1560 |
| agagaaaaaa | tagatggggt | aaagctggaa | tcaacaagga | tttaccagat | tttggcgatc | 1620 |
| tattcaactg | tcgccagttc | attggtactg | gtagtctccc | tgggggcaat | cagcttctgg | 1680 |
| atgtgctcta | atgggtctct | acagtgtaga | atatgtattt | aa | | 1722 |

<210> SEQ ID NO 148
<211> LENGTH: 573
<212> TYPE: PRT
<213> ORGANISM: Artificial Sequence
<220> FEATURE:

<223> OTHER INFORMATION: PDI-H1 Nor-N97D+K374E+F390D+L429M (aa)

<400> SEQUENCE: 148

```
Met Ala Lys Asn Val Ala Ile Phe Gly Leu Leu Phe Ser Leu Leu Val
 1               5                  10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Arg Ser Trp Ser Tyr Ile Val Glu Thr Ser Asn Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Asn Gln Ser Tyr Ile Asn Asp
            180                 185                 190

Lys Gly Lys Glu Val Leu Val Leu Trp Gly Ile His His Pro Ser Thr
        195                 200                 205

Thr Ala Asp Gln Gln Ser Leu Tyr Gln Asn Ala Asp Ala Tyr Val Phe
210                 215                 220

Val Gly Thr Ser Arg Tyr Ser Lys Lys Phe Lys Pro Glu Ile Ala Thr
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Thr Met Glu Arg Asn Ala Gly Ser Gly
        275                 280                 285

Ile Ile Ile Ser Asp Thr Pro Val Gln Asp Cys Asn Thr Thr Cys Gln
290                 295                 300

Thr Pro Glu Gly Ala Ile Asn Thr Ser Leu Pro Phe Gln Asn Val His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Val Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
370                 375                 380

Tyr Ala Ala Asp Leu Lys Ser Thr Gln Asn Ala Ile Asp Glu Ile Thr
385                 390                 395                 400
```

-continued

```
Asn Lys Val Asn Ser Val Ile Glu Lys Met Asn Thr Gln Asp Thr Ala
            405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
            435                 440                 445

Leu Leu Val Leu Met Glu Asn Glu Arg Thr Leu Asp Tyr His Asp Ser
    450                 455                 460

Asn Val Lys Asn Leu Tyr Glu Lys Val Arg Asn Gln Leu Lys Asn Asn
465                 470                 475                 480

Ala Lys Glu Ile Gly Asn Gly Cys Phe Glu Phe Tyr His Lys Cys Asp
            485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Lys Ile Asp Gly Val Lys
            515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
            565                 570
```